(12) United States Patent
Matos

(10) Patent No.: US 8,965,508 B2
(45) Date of Patent: Feb. 24, 2015

(54) CONTROLLING A PERSONAL MEDICAL DEVICE

(71) Applicant: Jeffrey A. Matos, New Rochelle, NY (US)

(72) Inventor: Jeffrey A. Matos, New Rochelle, NY (US)

(*) Notice: Subject to any disclaimer, the term of this patent is extended or adjusted under 35 U.S.C. 154(b) by 0 days.

(21) Appl. No.: 14/181,876

(22) Filed: Feb. 17, 2014

(65) Prior Publication Data

US 2014/0371816 A1 Dec. 18, 2014

Related U.S. Application Data

(62) Division of application No. 12/763,949, filed on Apr. 20, 2010, now Pat. No. 8,655,450.

(60) Provisional application No. 61/214,096, filed on Apr. 20, 2009.

(51) Int. Cl.
| | |
|---|---|
| *A61N 1/37* | (2006.01) |
| *A61N 1/372* | (2006.01) |
| *A61N 1/39* | (2006.01) |
| *G06F 19/00* | (2011.01) |

(52) U.S. Cl.
CPC .......... *A61N 1/3727* (2013.01); *A61N 1/3906* (2013.01); *A61N 1/37247* (2013.01); *A61N 1/3956* (2013.01); *G06F 19/3481* (2013.01); *G06F 19/3406* (2013.01)
USPC ............................................. 607/30

(58) Field of Classification Search
USPC ............................................. 607/60, 30, 32
See application file for complete search history.

*Primary Examiner* — Paula J Stice
(74) *Attorney, Agent, or Firm* — Karl F. Milde, Jr.; Eckert Seamans Cherin & Mellott, LLC

(57) ABSTRACT

Medical monitoring and treatment apparatus, which is controlled by a plurality of control sources, includes a "personal medical device" (PMD) or an "implantable medical device" (IMD), respectively carried by, or implanted in, a patient. The PMD/IMD is alternatively self-controlled or controlled by one or more local external control stations, at or near the location of the patient, and/or one or more remote external control stations, remote from the patient. Either or both of the local and remote stations may be operated by a person, such as the patient, a patient facilitator and/or a medical professional, or the stations may operate automatically. Since the device is controlled by multiple sources, hierarchies are used to select the source of control.

71 Claims, 91 Drawing Sheets

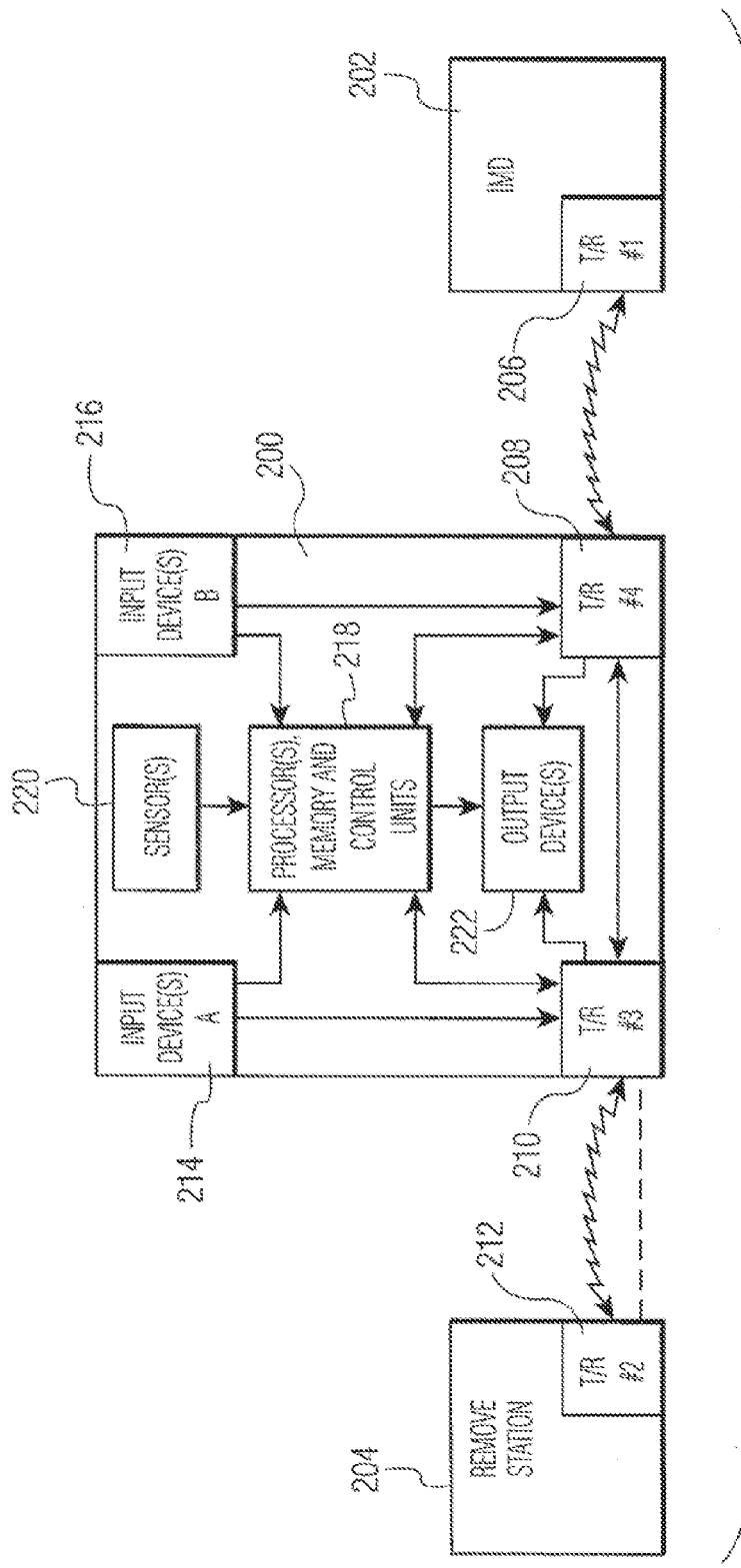

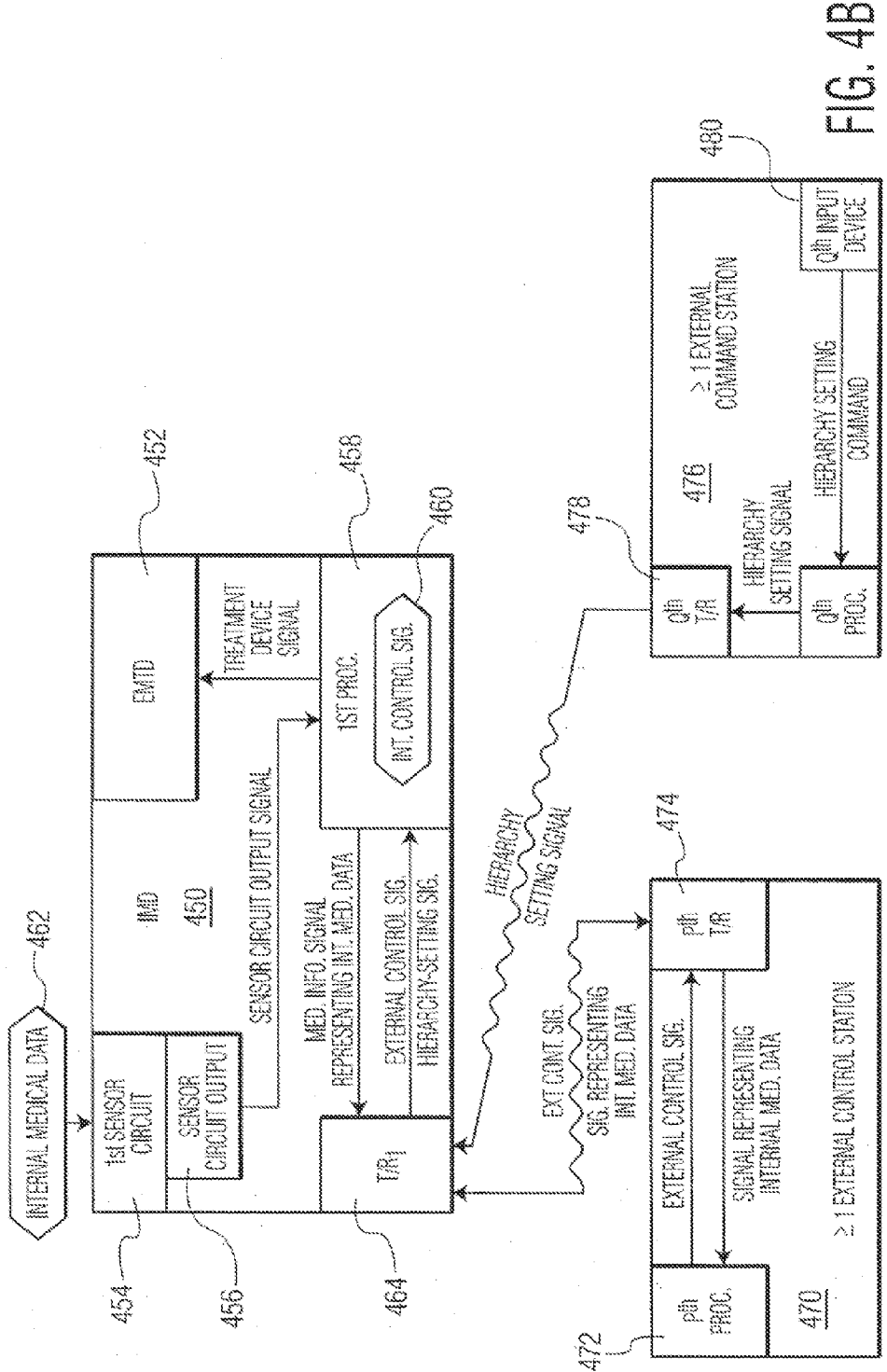

FIG. 15

ACCESS TO HIERARCHY CONTROL
SELECT ONE CHOICE IN EACH OF FIRST THREE ROWS.

1500

ROW 1: MP | MP WITH MD PERMISSION
ROW 2: MD | MD WITH MP PERMISSION | MD NOT ALLOWED
ROW 3: PATIENT | PATIENT WITH MP PERMISSION | PATIENT WITH MD PERMISSION | PATIENT NOT ALLOWED

ENTER MP PASSWORD | ENTER MD PASSWORD | ENTER PT PASSWORD

FIG. 20

NOTIFICATION EXAMPLES WITH SIMPLE FUNCTION*

| IMD = ICD | IMD = BLOOD SUGAR CONTROL DEVICE |
|---|---|
| FUNCTION* = HEART RATE (B.P.M.) | FUNCTION* = BLOOD GLUCOSE CONCENTRATION (MG./DL.) |
| ICD RX AND NOTIFY MP | BSD RX AND NOTIFY PT AND MP |
| ------- HR = 240 | ------- BS = 350 |
| ICD RX ONLY | BSD RX AND NOTIFY PT |
| ------- HR = 150 | ------- BS = 160 |
| NOTIFY PT ONLY | BSD RX ONLY |
| ------- HR = 125 | ------- BS = 120 |
| NORMAL RANGE | NORMAL RANGE |
| ------- HR = 80 | ------- BS = 65 |
| ICD RX ONLY | NOTIFY PT ONLY |
|  | ------- BS = 40 |
|  | NOTIFY PT AND MP |

FIG. 22A      FIG. 22B

EXAMPLE OF NOTIFICATION FOR ICD: NON-SIMPLE FUNCTION*

FUNCTION* FORMAT

FUNCTION* = A • (10+2B+C)
WHERE:  A = HEART RATE FOR RATES ≥ 180 B.P.M., AND
        A = 0 FOR RATES < 180 B.P.M.
        B = # OF ICD SHOCKS IN PAST 24 HOURS, AND
        C = # OF ICD SHOCKS IN PAST 20 MINUTES

| | FUNCTION* |
|---|---|
| ICD Rx AND NOTIFY MP | ≥ 2500 |
| ICD Rx ONLY | ≥ 1800 |
| NORMAL RANGE | |

2 DIMENSIONAL CONTINGENCY ARRAY FORMAT

| HEART RATE | B=0 AND C=0 | B=1 | B=2 OR C=1 | B=3 OR B=2 & C=1 | B≤4 OR B≤3 & C=1 OR C≤2 |
|---|---|---|---|---|---|
| <180 | NO Rx | NO Rx | NO Rx | NO Rx | NO Rx |
| 180-193 | Rx | Rx | Rx | Rx | Rx-NOT |
| 193-209 | Rx | Rx | Rx | Rx-NOT | Rx-NOT |
| 209-223 | Rx | Rx | Rx-NOT | Rx-NOT | Rx-NOT |
| 223-250 | Rx | Rx-NOT | Rx-NOT | Rx-NOT | Rx-NOT |
| >250 | Rx-NOT | | | | |

NOT = NOTIFY MP

FOR BOTH FORMATS, MP NOTIFICATION WILL BE TRIGGERED BY:

HR >250, WITHOUT A SHOCK WITHIN THE LAST 24 HR.

HR ≤ 223, WITH 1 SHOCK DELIVERED BETWEEN 20 MIN. AND 24 HR. IN THE PAST

HR ≤ 209, WITH EITHER (A) 2 SHOCKS, EACH DELIVERED BETWEEN 20 MIN. AND 24 HR. IN THE PAST, OR (B) 1 SHOCK DELIVERED WITHIN THE LAST 20 MIN.

HR ≤ 193, WITH EITHER (A) 3 SHOCKS, EACH DELIVERED BETWEEN 20 MIN. AND 24 HR. IN THE PAST, OR (B) 3 OR MORE SHOCKS DELIVERED BETWEEN 20 MIN. AND 24 HR. IN THE PAST AND 1 SHOCK DELIVERED WITHIN THE LAST 20 MIN.

HR > 180 WITH EITHER (A) 4 OR MORE SHOCKS DELIVERED BETWEEN 20 MIN. AND 24 HR. IN THE PAST, OR (B) 3 OR MORE SHOCKS DELIVERED BETWEEN 20 MIN. AND 24 HR. IN THE PAST AND 1 SHOCK DELIVERED WITHIN THE LAST 20 MIN. OR (C) 2 OR MORE SHOCKS DELIVERED WITHIN THE LAST 20 MIN.

FOR BOTH FORMATS, ICD THERAPY WILL BE TRIGGERED BY HEART RATE >180 B.P.M.

FIG. 23

EXAMPLE OF TRIGGERING OF PATIENT INTERROGATION AND OF MP NOTIFICATION FOR ICD; NON-SIMPLE FUNCTION*

FUNCTION* FORMAT

FUNCTION* = D + E

D = HEART RATE (B.P.M.) – 70
E = 80 X (SENSOR VALUE)[0.2 — 1]

SENSOR VALUE = 1 INDICATES NIL CHANCE OF PATIENT FALL
SENSOR VALUE = 2 INDICATES POSSIBLE PATIENT FALL
SENSOR VALUE = 3 INDICATES HIGH LIKELIHOOD OF PATIENT FALL
SENSOR VALUE = 4 INDICATES NEAR CERTAINTY OF PATIENT FALL

ICD Rx
AND NOTIFY MP ———————— FUNCTION* = 150

ICD Rx ONLY ———————— FUNCTION* = 95

INTERROGATE PT,
ICD Rx ONLY IF ———————— FUNCTION* = 76
APPROPRIATE

NORMAL RANGE

2 DIMENSIONAL CONTINGENCY ARRAY FORMAT

| HEART RATE | SENSOR VALUE | | | |
|---|---|---|---|---|
| | 1 | 2 | 3 | 4 |
| <120 | NO Rx | NO Rx | NO Rx | NO Rx |
| 120-126 | NO Rx | NO Rx | NO Rx | INT ± Rx |
| 126-134 | NO Rx | NO Rx | INT ± Rx | INT ± Rx |
| 134-140 | NO Rx | INT ± Rx | INT ± Rx | INT ± Rx |
| 140-146 | NO Rx | INT ± Rx | INT ± Rx | Rx |
| 146-154 | INT ± Rx | Rx | Rx | Rx |
| 154-166 | INT ± Rx | Rx | Rx | Rx |
| 166-200 | Rx | Rx | Rx | Rx+NOT |
| 200-206 | Rx | Rx | Rx+NOT | Rx+NOT |
| 206-214 | Rx | Rx+NOT | Rx+NOT | Rx+NOT |
| 214-226 | Rx+NOT | Rx+NOT | Rx+NOT | Rx+NOT |
| >226 | Rx+NOT | Rx+NOT | Rx+NOT | Rx+NOT |

INT = INTERROGATE PATIENT    NOT = NOTIFY MP

PATIENT INTERROGATION ± Rx
WILL BE TRIGGERED BY

HR 146-165 FOR SENSOR VALUE = 1
HR 134-154 FOR SENSOR VALUE = 2
HR 126-146 FOR SENSOR VALUE = 3
HR 120-140 FOR SENSOR VALUE = 4

Rx W/OUT PATIENT INTERROGATION
WILL BE TRIGGERED BY

HR 166-226 FOR SENSOR VALUE = 1
HR 154-214 FOR SENSOR VALUE = 2
HR 146-206 FOR SENSOR VALUE = 3
HR 140-200 FOR SENSOR VALUE = 4

Rx WITH MP NOTIFICATION
WILL BE TRIGGERED BY

HR>226 FOR SENSOR VALUE = 1
HR>214 FOR SENSOR VALUE = 2
HR>206 FOR SENSOR VALUE = 3
HR>200 FOR SENSOR VALUE = 4

FIG. 24

TABLE 1A: MULTI-ENTITY IMD CONTROL (1)

2 ENTITY SYSTEMS:

| ENTITY #1 | ENTITY #2 |
|---|---|
| IMD | MP |
| IMD | ME-DEVICE |
| IMD | PT |
| IMD | PT-DEVICE |
| IMD- ALGO #1 | IMD- ALGO #2 |

3 ENTITY SYSTEMS:

| ENTITY #1 | ENTITY #2 | ENTITY #3 |
|---|---|---|
| IMD | ME-DEVICE | MP |
| IMD | PT | MP |
| IMD | PT | ME-DEVICE |
| IMD | PT-DEVICE | MP |
| IMD | PT-DEVICE | ME-DEVICE |
| IMD | PT-DEVICE | PT |
| IMD- ALGO #1 | IMD- ALGO #2 | MP |
| IMD- ALGO #1 | IMD- ALGO #2 | ME-DEVICE |
| IMD- ALGO #1 | IMD- ALGO #2 | PT |
| IMD- ALGO #1 | IMD- ALGO #2 | PT-DEVICE |
| IMD- ALGO #1 | IMD- ALGO #2 | IMD- ALGO #3 |

4 ENTITY SYSTEMS:

| ENTITY #1 | ENTITY #2 | ENTITY #3 | ENTITY #4 |
|---|---|---|---|
| IMD | PT | ME-DEVICE | MP |
| IMD | PT-DEVICE | ME-DEVICE | MP |
| IMD | PT-DEVICE | PT | MP |
| IMD | PT-DEVICE | PT | ME-DEVICE |
| IMD- ALGO #1 | IMD- ALGO #2 | ME-DEVICE | MP |
| IMD- ALGO #1 | IMD- ALGO #2 | PT | MP |
| IMD- ALGO #1 | IMD- ALGO #2 | PT | ME-DEVICE |
| IMD- ALGO #1 | IMD- ALGO #2 | PT-DEVICE | MP |
| IMD- ALGO #1 | IMD- ALGO #2 | PT-DEVICE | ME-DEVICE |
| IMD- ALGO #1 | IMD- ALGO #2 | PT-DEVICE | PT |
| IMD- ALGO #1 | IMD- ALGO #2 | IMD- ALGO #3 | MP |
| IMD- ALGO #1 | IMD- ALGO #2 | IMD- ALGO #3 | ME-DEVICE |
| IMD- ALGO #1 | IMD- ALGO #2 | IMD- ALGO #3 | PT |
| IMD- ALGO #1 | IMD- ALGO #2 | IMD- ALGO #3 | PT-DEVICE |
| IMD- ALGO #1 | IMD- ALGO #2 | IMD- ALGO #3 | IMD- ALGO #4 |

FIG. 27A

TABLE 1B: MULTI-ENTITY IMD CONTROL (2)

5 ENTITY SYSTEMS:

| ENTITY #1 | ENTITY #2 | ENTITY #3 | ENTITY #4 | ENTITY #5 |
|---|---|---|---|---|
| IMD | PT-DEVICE | PT | ME-DEVICE | MP |
| IMD-ALGO #1 | IMD-ALGO #2 | PT | ME-DEVICE | MP |
| IMD-ALGO #1 | IMD-ALGO #2 | PT-DEVICE | ME-DEVICE | MP |
| IMD-ALGO #1 | IMD-ALGO #2 | PT-DEVICE | PT | MP |
| IMD-ALGO #1 | IMD-ALGO #2 | PT-DEVICE | PT | ME-DEVICE |
| IMD-ALGO #1 | IMD-ALGO #2 | IMD-ALGO #3 | ME-DEVICE | MP |
| IMD-ALGO #1 | IMD-ALGO #2 | IMD-ALGO #3 | PT | MP |
| IMD-ALGO #1 | IMD-ALGO #2 | IMD-ALGO #3 | PT | ME-DEVICE |
| IMD-ALGO #1 | IMD-ALGO #2 | IMD-ALGO #3 | PT-DEVICE | MP |
| IMD-ALGO #1 | IMD-ALGO #2 | IMD-ALGO #3 | PT-DEVICE | ME-DEVICE |
| IMD-ALGO #1 | IMD-ALGO #2 | IMD-ALGO #3 | PT-DEVICE | PT |

FIG. 27B

TABLE 2: CLASSIFICATION OF SOME POSSIBLE SYSTEM ALGORITHMS

| FIG. # | CONTROL ENTITIES | MONITOR @ | DETERMINE IF RX WARRANTED @ | DETERMINE WHICH ENTITY PROVIDES RX @ |
|---|---|---|---|---|
| 29 | 3: IMD/PT/MP | IMD | IMD | IMD |
| 30 | " " | IMD | PTDEV | PTDEV |
| 31 | " " | IMD | PT | PT |
| 32 | 3: IMD/PTDEV/PT | IMD | M.E.DEV | M.E.DEV |
| 33 | 3: IMD/PT/MP | IMD | MP | MP |
| 34 | " " | PTDEV | IMD | IMD |
| 35 | " " | PTDEV | PTDEV | PTDEV |
| 36 | " " | PTDEV | PT | PT |
| 37 | " " | PTDEV | MP | MP |
| 38 | 3: IMD/PTDEV/PT | IMD | IMD | IMD |
| 39 | " " | IMD | PTDEV | PTDEV |
| 40 | " " | IMD | PT | PT |
| 41 | " " | PTDEV | IMD | IMD |
| 42 | " " | PTDEV | PTDEV | PTDEV |
| 43 | " " | PTDEV | PT | PT |
| 44 | 3: ENTITY 1, ENTITY 2, ENTITY 3 | ENTITY 1 | ENTITY 1 | ENTITY 1 |
| 45 | " " | ENTITY 1 | ENTITY 2 | ENTITY 2 |
| 46 | 2: IMD/PT | IMD | IMD | IMD |
| 47 | " " | IMD | PT | PT |
| 48 | " " | PTDEV | IMD | IMD |
| 49 | " " | PTDEV | PT | PT |
| 50 | 5: IMD/PTDEV/PT/ M.E.DEV/MP | IMD | IMD | IMD |
| 51 | " " | PTDEV | PTDEV | PTDEV |
| 52 | " " | RS | RS | RS |
| 53 | 3: IMD/PT/MP | IMD &/OR PTDEV | 1) IMD & 2) PT OR MP, IF NOTIFIED | MP OR PT MAY MAY OVERRULE IMD |
| 54 | 3: IMD/PT/MP | IMD &/OR PTDEV | 1) IMD & 2) PT OR MP, IF NOTIFIED | MP>PT>IMD |
| 55 | " " | IMD &/OR PTDEV | 1) IMD & 2) PT OR MP, IF NOTIFIED | PT>MP>IMD |
| 56A | 5: IMD/PTDEV/PT/ M.E.DEV/MP | IMD &/OR PTDEV | 1) IMD & ANY OF 2) PTDEV, PT, M.E.DEV OR MP, IF NOTIFIED | MP>M.E.DEV>PT> PTDEV>IMD |
| 56B | 5: IMD/PTDEV/PT/ M.E.DEV/MP | IMD &/OR PTDEV | 1) IMD & ANY OF 2) PTDEV, PT, M.E.DEV OR MP, IF NOTIFIED | MP>M.E.DEV>PT> PTDEV>IMD |

FIG. 28

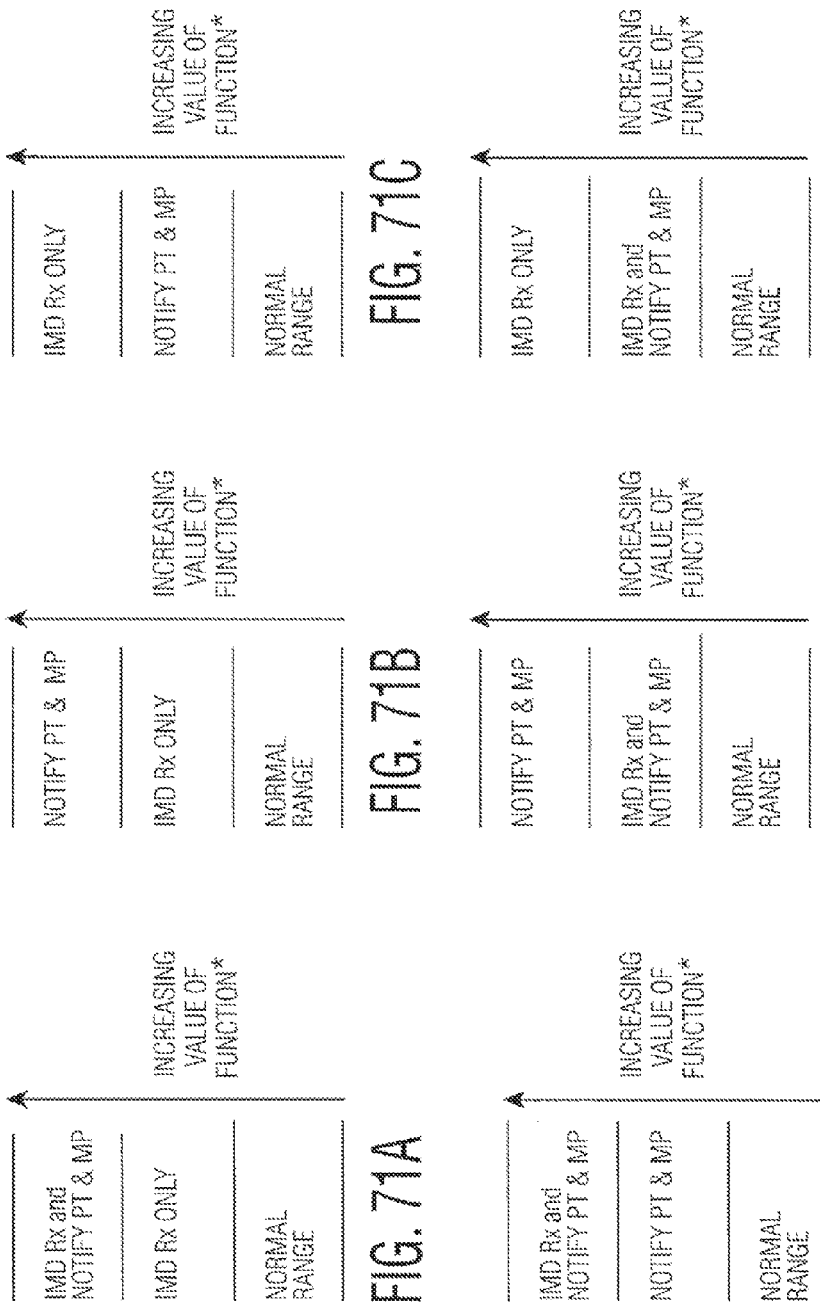

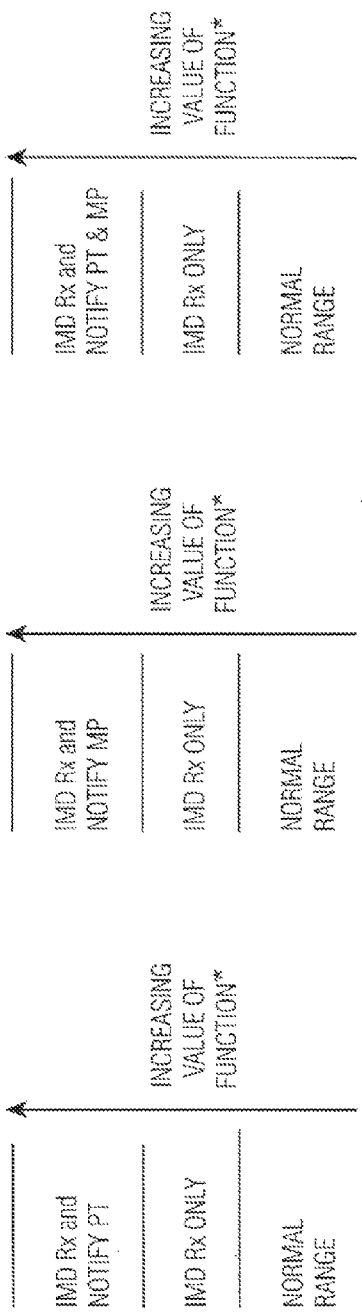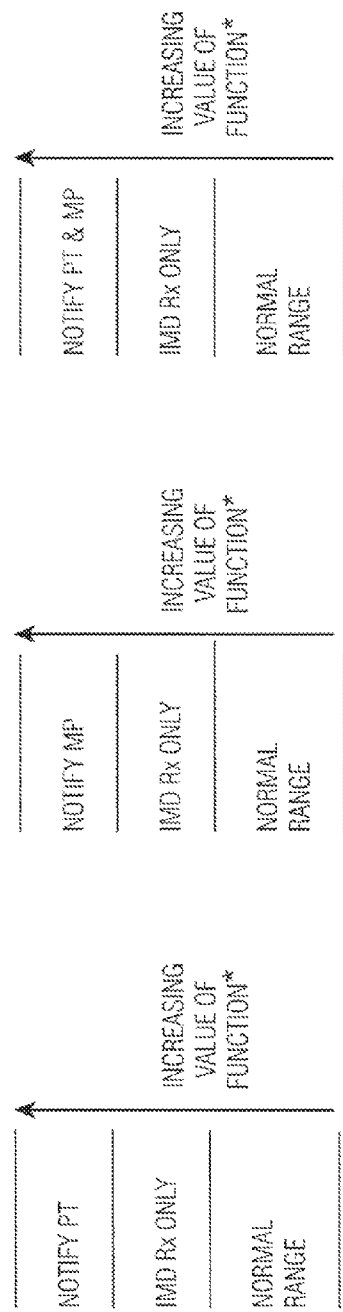

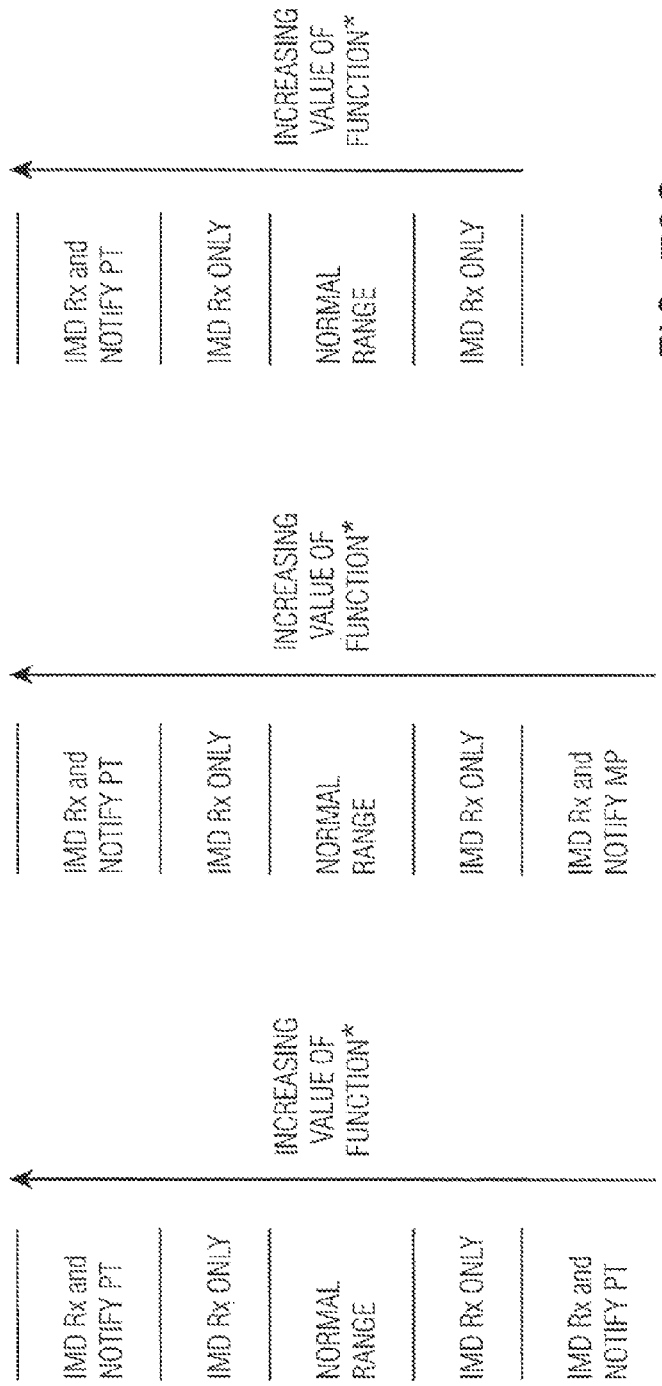

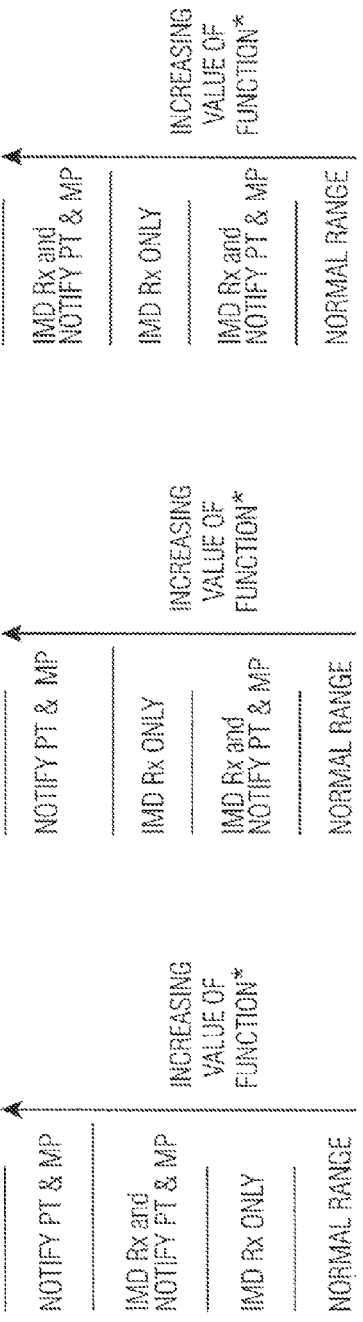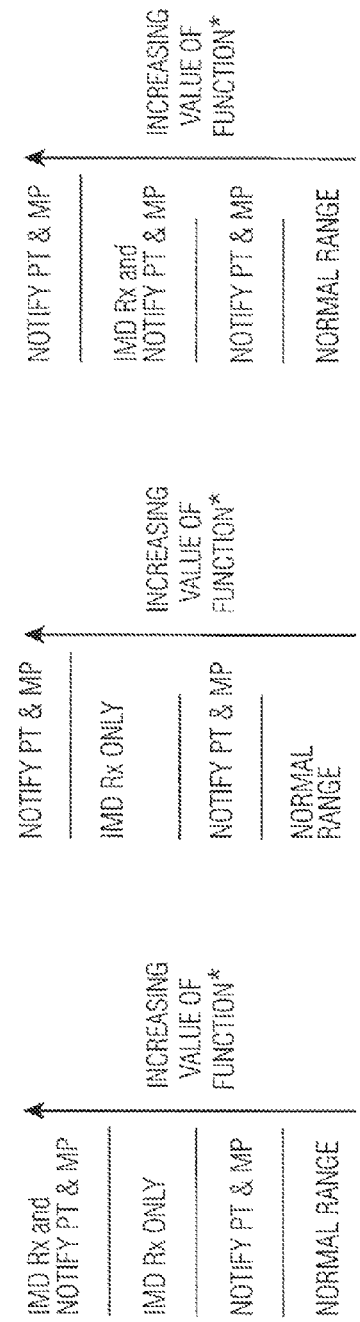

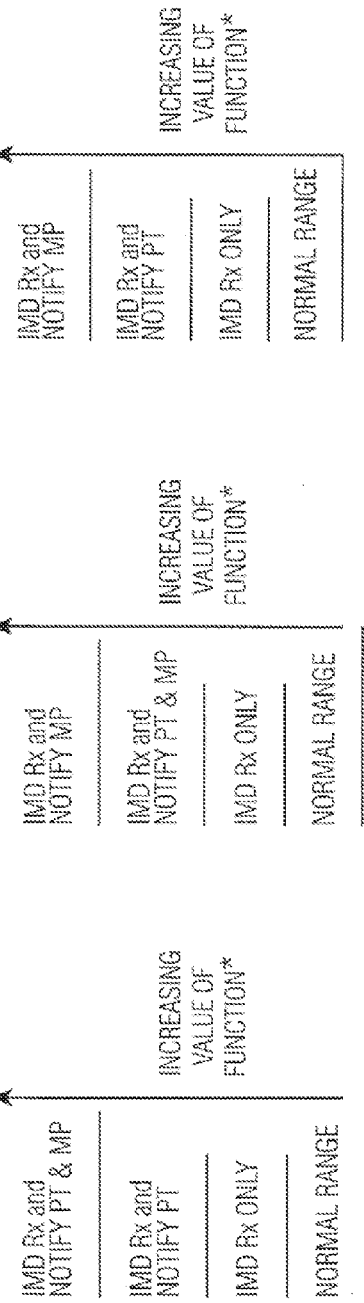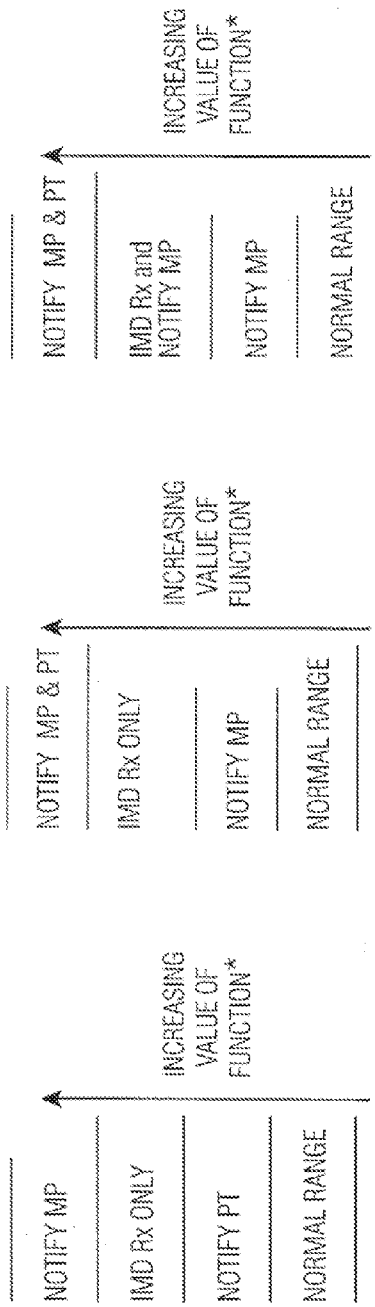

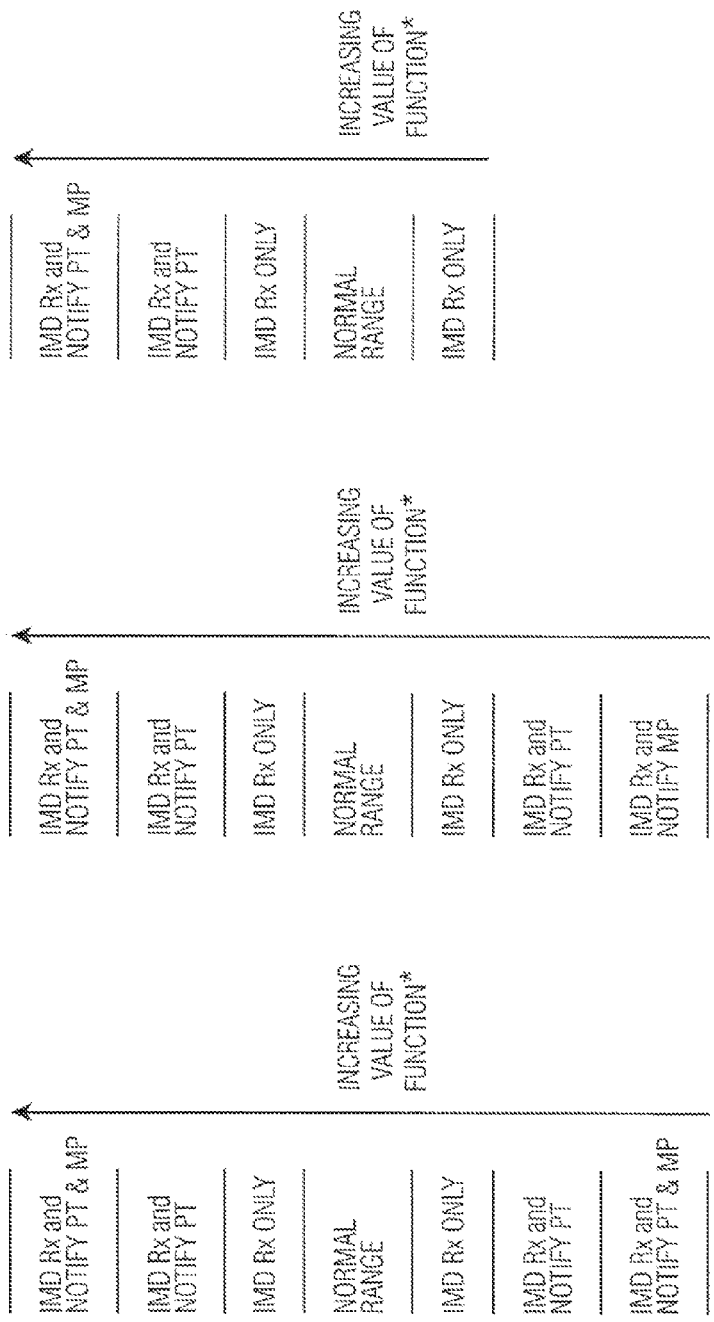

TABLE 3: SUMMARY OF CASE HISTORY EXAMPLES, AND CLASSIFICATION OF CONTROL TRANSFERS[1]

| FIGURE | EXAMPLE | SCENARIO | DEVICE>DEVICE PT DEV > IMD | DEVICE>DEVICE MD DEV > IMD | DEVICE>HUMAN PT DEV > PT | HUMAN>DEVICE PT > IMD | HUMAN>DEVICE MP > IMD | HUMAN>DEVICE MP > PT DEV | HUMAN>HUMAN MP > PT | ADDITIONAL FEATURES |
|---|---|---|---|---|---|---|---|---|---|---|
| FIG. 78 | A | BLOOD SUGAR MANAGEMENT | | | 2 | 1 | | 3 | | |
| | B | | | | | 1 | | | 2 | PT DEVICE (=PATIENT DEVICE = PT DEV) NOTIFIES MP, LEADING TO 2 |
| FIG. 79 | A | VT RATE < VT DETECT RATE | | | | | ** | | | PT DEVICE NOTIFIES IMD, LEADING TO IMD THERAPY   ** OPTIONAL MP CONTROL LATER |
| FIG. 80 | B | | | | | | 1 | | | PT DEVICE NOTIFIES MP, LEADING TO 1 |
| FIG. 81 | A | ICD LEAD FAILURE | | | | 1 | 1 | | | PT DEVICE NOTIFIES IMD, OPTIONAL IMD SELF-PROGRAMMING |
| | B | | 1 | 2 | | | 2 | | | |
| | C | | | 2 | | | 1 | | | |
| FIG. 82 | A | INAPPROPRIATE ICD SHOCKS FOR SVT | | | | 1 | 3 | 3 | | 1) PARALLEL IMD ALGORITHMS  2) TIME DEPENDENT 2ND AND 3RD NOTIFICATION  3) TIME DEPENDENT RETURN OF CONTROL  4) REMOTE REPROGRAMMING OF NOTIFICATION CRITERIA |
| | B | | 1 | 2 | | | 3 | | | |

[1] BOLDFACE NUMERALS REFER TO THE SEQUENCE OF STEPS IN EACH EXAMPLE. ">" SIGNS SHOULD BE READ AS "TAKES CONTROL FROM". THUS, IN THE LINE FOR FIG. 78 EXAMPLE A, THE "1" IN THE "PT > IMD" COLUMN INDICATES THAT THE FIRST CONTROL SHIFT IS THE PT TAKING CONTROL FROM THE IMD, THE "2" INDICATES THAT THE PT DEVICE THEN TAKES CONTROL FROM THE PT.

FIG. 77

CONTROLLING A PERSONAL MEDICAL DEVICE

CROSS-REFERENCE TO RELATED APPLICATIONS

This application is a division of U.S. patent application Ser. No. 12/763,949 now U.S. Pat. No. 8,655,450, filed Apr. 20, 2010.

The subject matter of this application is related to that of:

1) U.S. patent application Ser. No. 10/460,458, filed Jun. 11, 2003, published on Dec. 18, 2003 as U.S. Patent Publication No. US/2003/0233129, and now U.S. Pat. No. 7,277,752 [provisional application 60/387,990 filed on Jun. 11, 2002];

2) U.S. patent application Ser. No. 11/502,484, filed Aug. 10, 2006, and published on Feb. 2, 2007 as U.S. Patent Publication No. US/2007/0043585A1 [provisional application 60/709,078 filed on Aug. 17, 2005];

3) U.S. patent application Ser. No. 11/893,897, filed Aug. 18, 2007, and published on Dec. 27, 2007 as U.S. Patent Publication No. US/2007/0299473 and now U.S. Pat. No. 7,769,465 [divisional application of U.S. Pat. No. 7,277,752 cited above];

4) U.S. patent application Ser. No. 11/895,934, filed Aug. 28, 2007, and published on Mar. 6, 2008 as U.S. Patent Publication No. US/2008/0058884, and now U.S. Pat. No. 8,214,043 [provisional application 60/840,772 filed on Aug. 29, 2006, provisional application 60/928,567 filed on May 10, 2007, and provisional application 60/930,525 filed on May 17, 2007];

5) U.S. patent application Ser. No. 11/805,268, filed May 22, 2007, and published on May 29, 2008 as U.S. Patent Publication No. US/2008/0122636 and now U.S. Pat. No. 8,289,172 [a continuation in part of U.S. patent application Ser. No. 11/388,311, filed Jun. 24, 2006, and published on Oct. 5, 2006 as U.S. Patent Publication No. US/2006/0220883 (provisional application 60/664,997 filed on Mar. 24, 2005)];

6) U.S. patent application Ser. No. 12/154,079, filed May 19, 2008, and published on Dec. 4, 2008 as U.S. Patent Publication No. US/2008/0300659 and now U.S. Pat. No. 8,473,065 [provisional application 60/930,525 filed on May 17, 2007];

7) Provisional Patent Application 61/204,957, filed on Jan. 13, 2009;

8) Provisional Patent Application 61/214,096, filed Apr. 20, 2009;

9) U.S. patent application Ser. No. 12/657,155, filed Jan. 13, 2010, and published on Jul. 14, 2011 as U.S. Patent Publication No. US/2011/0172740;

10) U.S. patent application Ser. No. 13/537,318, filed Jun. 29, 2012, and published on Nov. 22, 2012 as U.S. Patent Publication No. US/2012/0296381 and now U.S. Pat. No. 8,565,882 [divisional application of U.S. Pat. No. 8,214,043 cited above];

11) U.S. patent application Ser. No. 13/840,021, filed Mar. 15, 2013, and published on Oct. 24, 2013 as U.S. Patent Publication No. US/2013/0282071 [continuation in part of U.S. Pat. No. 8,214,043 cited above], now allowed;

12) U.S. patent application Ser. No. 13/795,250, filed Mar. 12, 2013, and published on 8/29/13 as U.S. Patent Publication No. US/2013/0226265 and now U.S. Pat. No. 8,583,251 [divisional application of U.S. Pat. No. 8,473,065 cited above]; and 13) U.S. patent application Ser. No. 14/076,521, filed Nov. 11, 2013, [continuation of U.S. Pat. No. 8,473,065 cited above].

This application claims priority from the aforementioned U.S. Provisional Application No. 61/214,096 and the aforementioned Utility patent applications U.S. patent application Ser. No. 12/763,949, filed Apr. 20, 2010.

All of the aforementioned U.S. patent and published patent applications are incorporated herein by reference.

BACKGROUND OF THE INVENTION

Implantable medical devices, though they may have complex decision making algorithms do not always make medically optimal decisions. Some of the time, this is because they do not have access to enough clinical information. At other times, it may be because they are not optimally programmed. At still other times, it is because their operating algorithms are not capable of distinguishing between different conditions (e.g. electromagnetic interference vs. broken lead wire vs. life threatening tachycardia, in a patient with an ICD). At yet other times, it may be because of a device malfunction.

Outside input to the IMD, either in the form of additional data about the patient, or control signals which alter the functioning of the IMD, can address the aforementioned deficiencies of an IMD. The outside inputs may originate from an external device, from the patient himself/herself, or from a remotely located medical professional. The inventions described in the specification herein present IMD systems with such outside inputs.

The U.S. Pat. No. 7,277,752 describes an implantable defibrillator which may be controlled by a remote medical professional ("MP"). Two families of formats are discussed. In the first family of formats, the MP is the primary controller; the ICD takes control if communications with the MP are inadequate. In the second family of formats, the ICD is the primary controller; the MP may take control of the ICD if he/she determines that such control is necessary based on the analysis of iCD signals transmitted to the MP. The specification discusses (a) providing means for the MP to preview an ICD therapy decision, (b) having the MP communicate with the patient to determine the appropriate choice of therapy; and (c) ICD battery power conservation.

The U.S. patent application Ser. No. 11/502,484 discusses the remote control of other types of iMDs using the same two formats as presented in U.S. Pat. No. 7,277,752. Also discussed is (a) the filtering of implanted device information before it is presented to the MP; (b) sensor apparatus for external defibrillator devices; and (c) situating the MP in locations other than a central station—e.g. as a practitioner in a physician's office.

The U.S. patent application Ser. No. 11/893,897 presents the control of an external defibrillator which has three operating modalities: (a) control by a remotely located medical professional, (b) control by an on-scene person, and (c) control by the logic circuitry within the device. It also presents remotely controlling and implantable defibrillator with pacing capabilities.

The U.S. patent application Ser. No. 11/895,934 discusses the assembly of a remotely controllable defibrillator or pacemaker system by (a) using (i) an unmodified cellular telephone as the communications device, to work in conjunction with (ii) an implanted defibrillator or pacemaker which can communicate with the cellular telephone; (b) using (i) a modified cellular telephone as the communications device, to work in conjunction with (ii) an implanted defibrillator or pacemaker which has been adapted to communicate with the cellular telephone; or (c) using a three component system including (i) an adapter device; (ii) unmodified cellular telephone which communicates with the adapter device, and (iii) an implanted defibrillator or pacemaker which can communicate with the adapter.

The U.S. patent application Ser. No. 12/154,079 discusses four formats for the division of/sharing of control between an MP and an IMD's controlling circuits. It discusses a communications device which relays information between the IMD) and a central station, with the relay device having patient inputs. It discusses formats for central station notification in a two-agent IMD system (i.e. IMD and MP). It discusses a medical expert device which may be used in conjunction with the human medical professional. It also discusses (a) four different IMD battery power management arrangements; and (b) formats for limiting or terminating communications with a central station in the event of either (i) low IMD battery reserve; and/or (ii) non-dire treatment circumstances.

The U.S. Provisional Patent Application No. 61/204,957 presents a highly flexible communications system for an IMD environment which includes the IMD and a variety of repeater devices including a patient device. Techniques of communication security are discussed for an IMD system. The granting of permission by a patient, allowing remote reprogramming of the IMD) is presented.

The U.S. patent application Ser. No. 11/805,268, discusses the division of control of an aircraft among (a) an onboard pilot who may be impaired, (b) an autopilot/computerized flight management system, and (c) a remotely located pilot. The impaired pilot may be considered to be analogous to any device or person in the currently considered IMD system whose function is less than optimal—e.g. the IMD or the patient. The autopilot/computerized flight management system may be considered to be analogous to any of the devices in the IMD system including the patient device, the medical expert device or even the IMD. The remote pilot may be considered to be analogous to medical professional, since both are the system entities with the highest level of competence. Management algorithms and logic structures are presented in this patent application which examine the distribution of control among the aforementioned entities, and which pertain to aircraft in particular and other "mission critical devices" for which an imperfect performance by a controller may lead to a disaster.

The present application examines multi-entity control of an IMD, in which one of the entities is the IMD patient. Data from the patient potentially expands the breadth of information in a way that allows for better decision making than is the case when data originates solely from the IMD sensors.

SUMMARY OF THE INVENTION

The IMD system, according to the invention, comprises (i) an IMD, (ii) other outside agents which may control the IMD, one such agent being the IMD patient, and (iii) a device (the "patient device") through which the patient interacts with the IMD system. Examples of systems which include the patient include:

(a) a 2-agent system comprising the IMD and the patient (b) a 3-agent system comprising the IMD, the patient, and a patient device (c) a 3-agent system comprising the IMD the patient, and a medical professional (d) a 5-agent system comprising the IMD, the patient, a patient device, a medical expert device and a medical professional, and (e) a 7-agent system comprising an IMD with three control algorithms, the patient, a patient device, a medical expert device and a medical professional. The medical professional is a human expert who may remotely manage the IMD.

It is a principal object of the present invention to allow-in an IMD system that includes an IMD, a patient and a patient device-treatment decisions which can be based on inputs from the patient. In one format, the patient input is direct; The patient takes control of IMD:

(a) at his/her own initiative (b) at the invitation of a device which is part of the system; i.e., (i) the IMD (ii) the PT device, or (iii) the ME device; or (c) at the invitation of Medical Professional. In another format, the patient input is indirect; Information about the patient coming from a patient device is used to control or assist in the control of the IMD. The patient device assessment of the patient may be:

(a) cognitive, and/or (b) physiologic (i) via sensors attached to patient, and/or (ii) via sensors in the vicinity of the patient. Treatment decisions that may be made by the patient or by the patient device include:

(a) overriding an IMD recommendation for treatment, thereby withhold such treatment (b) overriding an IMD recommendation for no treatment, thereby causing such treatment (c) taking control away from the IMD entirely (d) returning control to the IMD (after having taken control away)

(e) changing the programming of the IMD:

(i) its detection parameters (ii) its treatment parameters, and/or (iii) its parameters for notifying each of one or more other devices or persons of a pre-specified medical state.

It is a further object of the present invention to back up patient control in an IMD system with a "safety net," i.e. having the patient's management decisions overseen, either by (a) a person—the MP, or (b) a device:

i) the patient device, and/or ii) the medical expert device. In a preferred embodiment of the invention, one or more of these entities may take control away from the patient, if the patient is not performing at a level that is deemed proper by the overseeing agent (i.e. the MP, the M.E. device, etc,).

In an IMD system in which control of the treatment administered by the IMD may issue from any one of two or more systems, a hierarchical approach which sets forth which entity is in control under which conditions is necessary. For example, in one operating modality, the patient may be able to overrule the decision of the IMD, and the MP may be able to overrule the decision of the patient. In more complex modalities:

(a) there may be more entities, and a control hierarchy which indicates which entity is in control under which conditions;

(b) the list of possible control entities (in addition to the IMD) may include:

(i) both persons and devices;

(ii) only devices, or (iii) three or more persons (e.g. the patient, the MP, and the patient's MD;

(c) one hierarchical structure may be in effect for certain conditions, and another hierarchical structure for others (e.g.

an ICD which (i) operates autonomously for tachycardia rates between 160 and 220, (ii) allows MP intervention for tachycardias with rates greater than 220, and (iii) allows either MP or patient intervention for tachycardias with rates between 140 and 160 (with the MP having priority over the patient). It is a further object of the present invention to institute such hierarchical structures.

The aforementioned logical structure addresses the question of which entity may dominate which other entity. Additional logical structure is required to address:

(a) What are the conditions which trigger the transfer?

(b) Does such transfer always occur when the conditions are met, or not always

If not always, what determines when transfer does occur?

(c) Can the rules be changed which specify the transfer conditions?

If yes, who can change them, and how is such a change executed? A structure which allows optional transfer of control involves notifying one entity (e.g. the patient) about the conditions observed by another entity (e.g. the IMD) only under certain circumstances. Thus such notification entails signaling the possible new control source about a patient condition, for which the new control source has the option of taking control. By limiting the conditions for which notification takes place, the patient, other persons and/or devices are not burdened with information about routine matters that the device may easily handle, and the device power supply is not wasted, transmitting unimportant information.

It is a further object of the present invention to provide a system of control sharing in an IMD system by utilizing selective notification of the non-iMD entities in the system.

The IMD system may be rendered more sophisticated by control structures in which not only notification depends on patient condition, but return of control (once it has been taken away), second notification (i.e. notification following return of control, which may have different criteria than [first] notification prior to return of control), and second return of control (i.e. return of control following second notification) also may occur and are also dependent on patient condition. These features (first and second notification and first and second return of control) may be time dependent, as well as patient condition dependent. It is a further object of the present invention to include such logical formats in the operating algorithms of its member devices.

It is a further object of the present invention to allow at least one person, at least one time, to determine the details of the aforementioned hierarchical structure, and information sharing structure. For example, the MP may initially set the system so that under certain circumstances, the patient is allowed to overrule certain IMD decisions; The MP may later determine that the patient should not have such access (either temporarily or permanently) and reprogram the hierarchy accordingly. The MP (or other authorized person [e.g. the patient's physician]) may, from time to time also reprogram:

(a) notification criteria (b) return of control criteria (c) second notification criteria, and (d) second return of control criteria.

It is a further object of the current invention to provide a method (a) of arithmetic blending of multiple types of parametric data of various types, related to patient condition, (b) of arithmetic blending of non parametric types of data of various types, related to patient condition, and (c) of arithmetic blending of both parametric and non-parametric data of various types; wherein the blending method generates a numerical value which may be used to estimate the severity of a patient condition. This numerical method to measure severity of a medical condition, referred to hereinbelow as "FUNCTION*" is used by the IMD to determine whether:

(a) treatment may be necessary; and/or (b) notification of one or more outside agents (e.g. the patient or the MP) may be desirable.

An arithmetic structure FUNCTION* facilitates (a) the arithmetic blending of diverse parametric information; (b) the arithmetic blending of diverse non-parametric information; and (c) the blending of parametric with non-parametric information.

It is a further object of the current invention to provide a system in which an IMD, a patient device with patient sensors, and a patient can pool their information, to allow for better decision making than would be the case with the use of information coming from only one of the aforementioned three sources. This pooling can be accomplished by:

(a) having the IMD send some or all relevant information to the patient device;

(b) having the patient device send some or all relevant information to the IMD;

(c) both (a) and (b); and/or (d) formats in which some or all of the IMD information and the patient device information is sent to a third entity which pools and integrates the information.

It is a further object of the current invention to provide a system in which multiple algorithms may be utilized in parallel fashion to simultaneously evaluate patient data. The algorithms may be non-identical because:

(a) there may be no unique best method of evaluating the necessity and type of treatment for a given patient situation; and/or (b) each algorithm may have access to only a subset of all relevant information needed to make the best decision or recommendation. The algorithms:

(a) may be all device based; or (b) may include both device based inputs and human inputs. Types of all device based algorithms include:

(a) multiple algorithms running on the microprocessor(s) of a single IMD;

(b) two or more of:

(i) at least one IMD algorithm, (ii) a patient device algorithm, and (iii) a medical expert device algorithm. In the algorithmic processing of information, one or more of the aforementioned devices may be replaced by, or augmented by a person, viz.:

(a) the patient (b) the medical professional and/or (c) the patient's physician. Algorithms are provided which allow for:

(a) automatic processing of information in device-only situations;

(b) processing of information in device-only situations in which there are automatic components and in which there is also person-based input (for selecting among non-agreeing algorithms);

(c) processing of information in which there are device inputs and one or more person inputs.

According to a particular feature of the present invention, a medical expert device is included in the IMD system, located remotely from the IMD, which may either take control of IMD function under certain circumstances, or function in an advisory capacity. The medical expert device may have an extensive database, which may be used to augment the functioning of the IMD, the patient device, the patient and/or the medical professional.

It is a further object of the invention to provide a patient device which not only communicates with the IMD, but may also:

(a) serve as a repeater/relay unit, linking the IMD and a remotely located medical professional, as described in U.S. patent application Ser. No. 12/154,079; and/or (b) serve as a cellular telephone device.

For a full understanding of the present invention, reference should now be made to the following detailed description of the preferred embodiments of the invention as illustrated in the following drawings.

BRIEF DESCRIPTION OF THE DRAWINGS

FIG. 2 is a representational diagram showing a system in which a communications relay unit which links an IMD to a remote station allows access to the system by a person at the site of the relay unit.

FIG. 4B is a block diagram showing system architecture for a system which includes an IMD, at least one external control station and at least one external command station, and which shows the exchange of information-carrying signals between these structures.

FIG. 15 illustrates a touch-sensitive programming and display screen for programming access to hierarch control within the IMD system.

Figure 20:
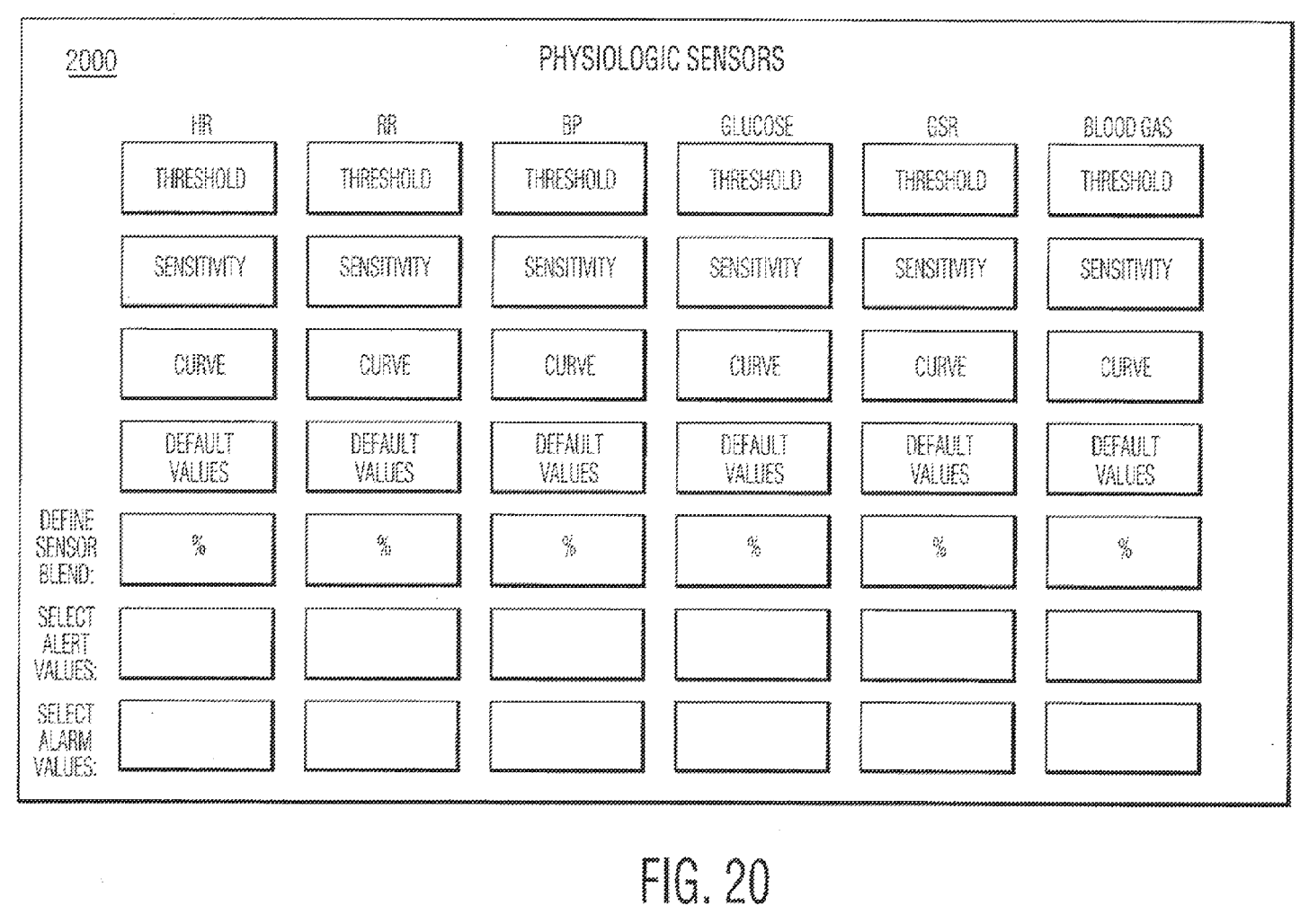

FIG. 20 illustrates a touch-sensitive programming and display screen for programming the management of data from individual sensors in a patient device.

FIGS. 22A and 22B illustrate the use of a mathematical entity which measures patient condition to determine when an IMD notifies the patient and when the IMD notifies a medical professional.

FIG. 23 illustrates another use of a mathematical entity which measures patient condition to determine when an IMD notifies a medical professional for a first time, and when it notifies the medical professional for a second time.

FIG. 24 illustrates yet another use of a mathematical entity which measures patient condition to determine when an IMD notifies the patient and when the IMD notifies a medical professional.

FIG. 27A is a table showing the elements in a variety of 2-, 3- and 4-entity IMD systems.

FIG. 27B is a table showing the elements in a variety of 5-entity IMD systems.

FIG. 28 is a table which shows a taxonomy of some 2, 3 and 5 entity IMD systems, classifying the algorithms shown in FIGS. 29 through 57, herein.

FIGS. 71A-71F show graphic representations of some arithmetic relationships illustrating possible formats for patient treatment, and patient and/or medical professional notification in a 3-entity IMD system.

FIGS. 72A-72F show additional graphic representations of some arithmetic relationships illustrating possible formats for patient treatment, and patient and/or medical professional notification in a 3-entity IMD system.

FIGS. 73A-73C show additional graphic representations of some arithmetic relationships illustrating possible formats for patient treatment, and patient and/or medical professional notification in a 3-entity IMD system.

FIGS. 74A-74F show additional graphic representations of some arithmetic relationships illustrating possible formats for patient treatment, and patient and/or medical professional notification in a 3-entity IMD system.

FIGS. 75A-75F show additional graphic representations of some arithmetic relationships illustrating possible formats for patient treatment, and patient and/or medical professional notification in a 3-entity IMD system.

FIGS. 76A-76C show additional graphic representations of some arithmetic relationships illustrating possible formats for patient treatment, and patient and/or medical professional notification in a 3-entity IMD system.

FIG. 77 is a table showing a summary of examples illustrating control transfer and entity interaction in the case histories illustrated in FIGS. 76-80.

DETAILED DESCRIPTION OF THE PREFERRED EMBODIMENT

Figure 25:
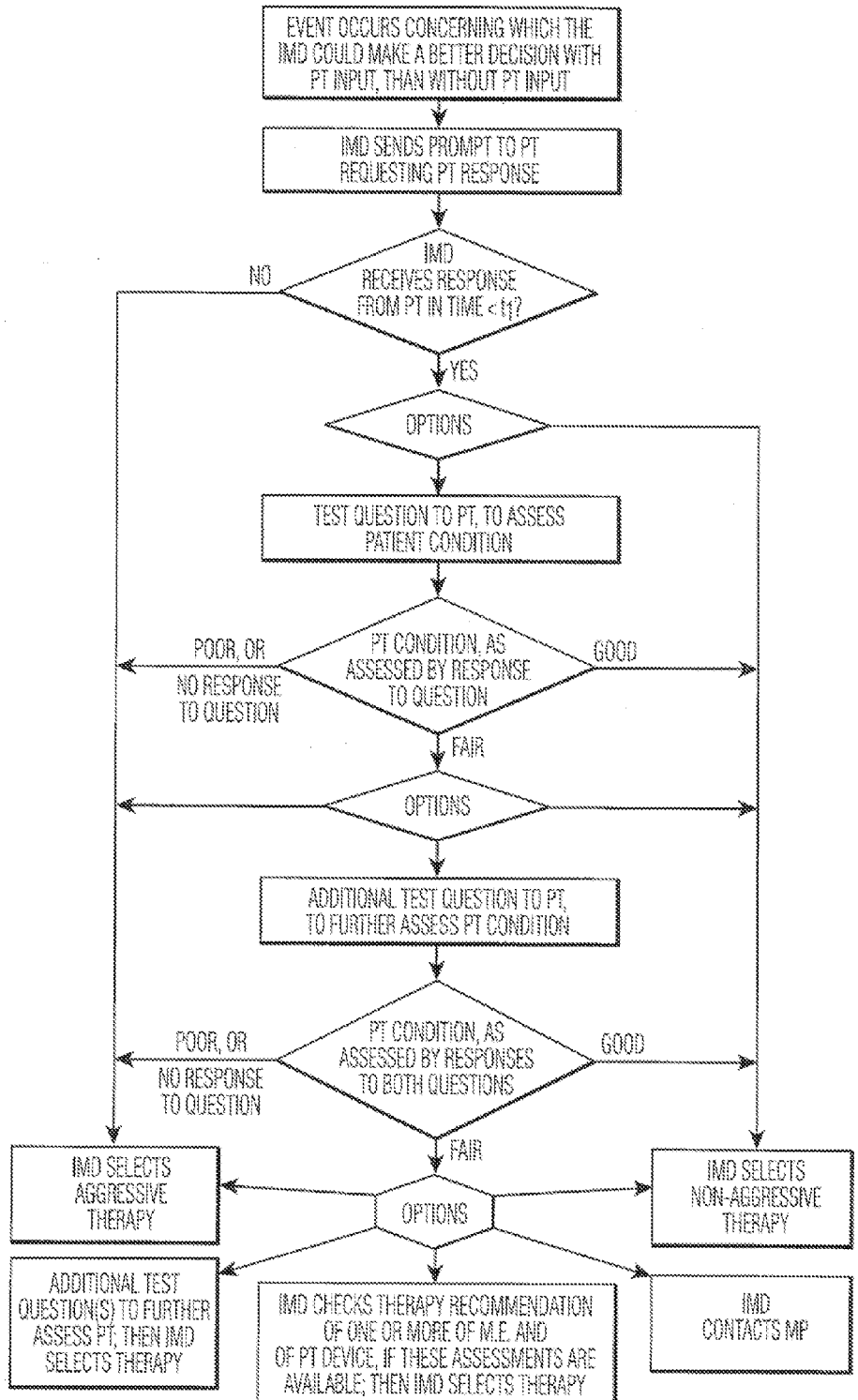
FIG. 25 is a flow diagram showing use of cognitive information about the patient by the IMD.
Figure 26:
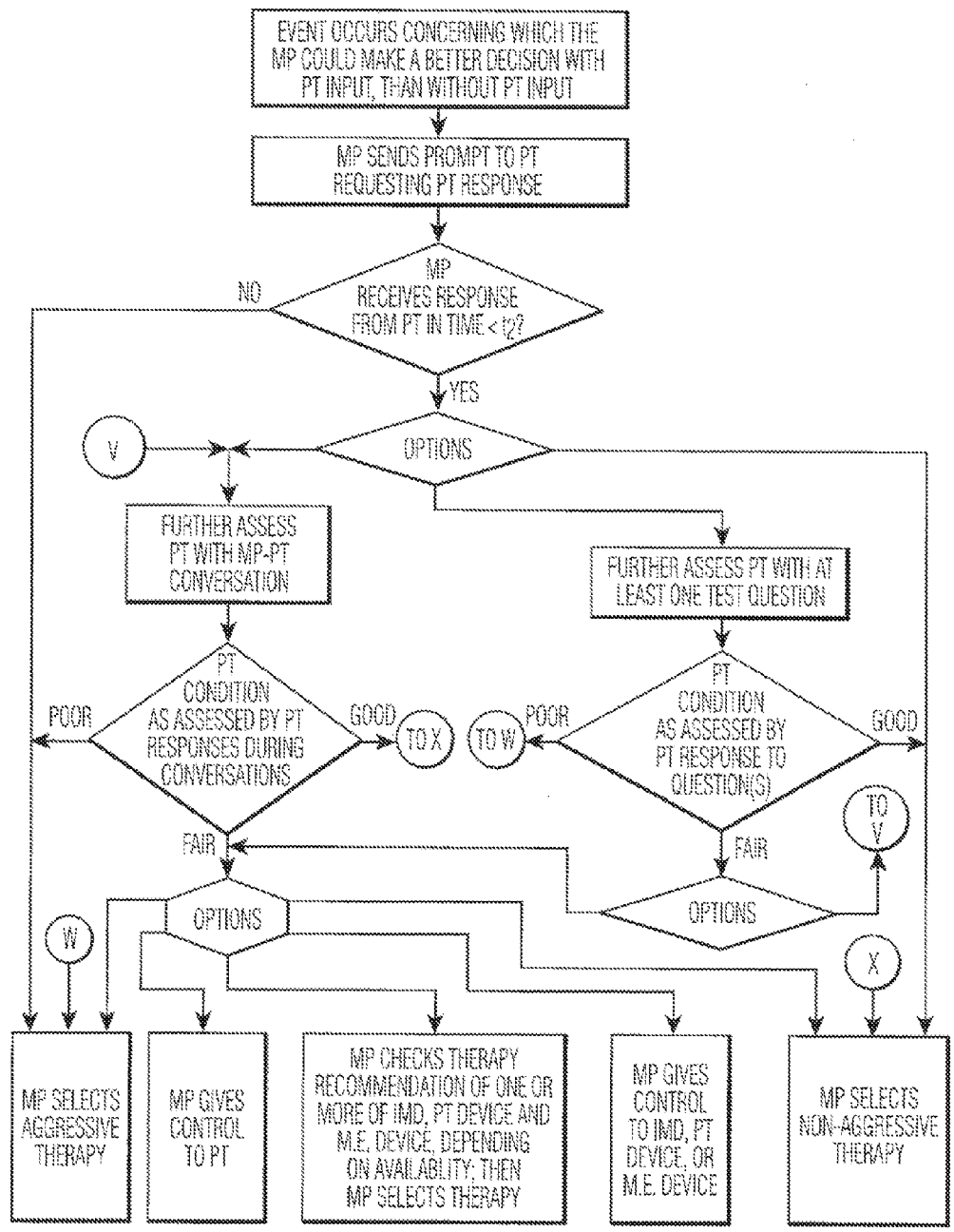
FIG. 26 is a flow diagram showing use of cognitive information about the patient by the medical professional.
Figure 27C:
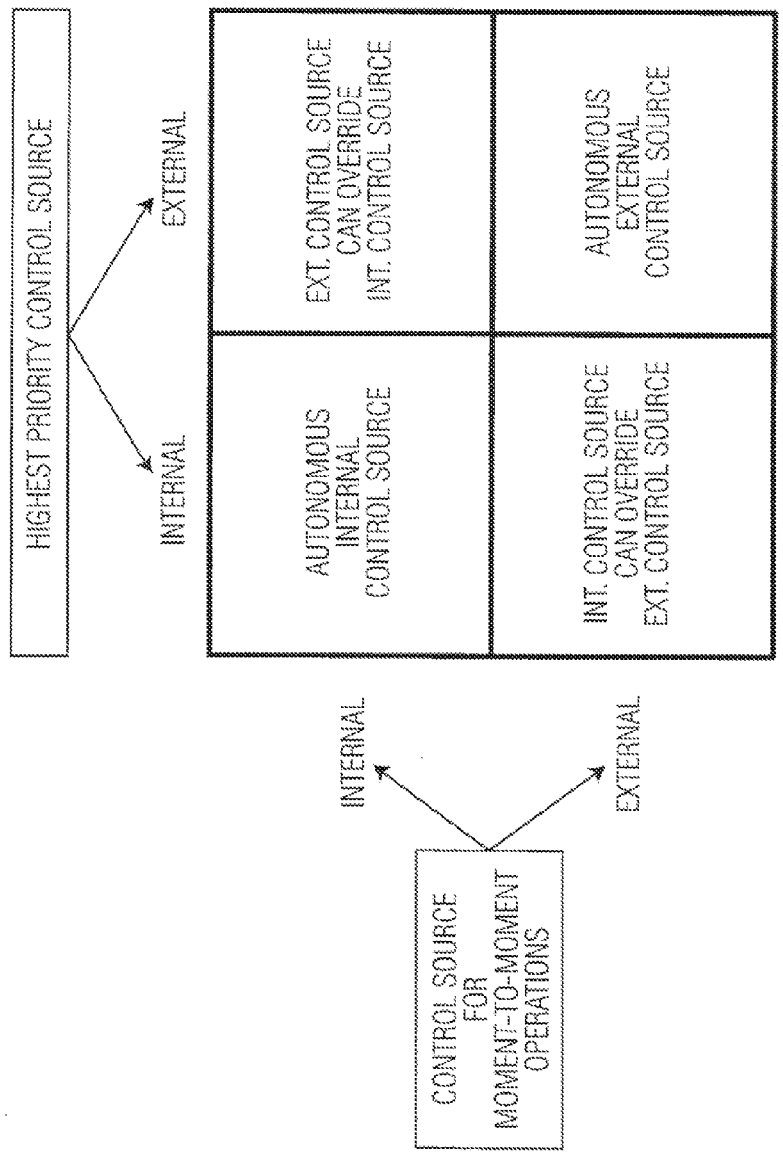
FIG. 27C is a 2×2 table showing the relationship of four operating states in an IMD which may be controlled both internally and externally.
Figure 42:
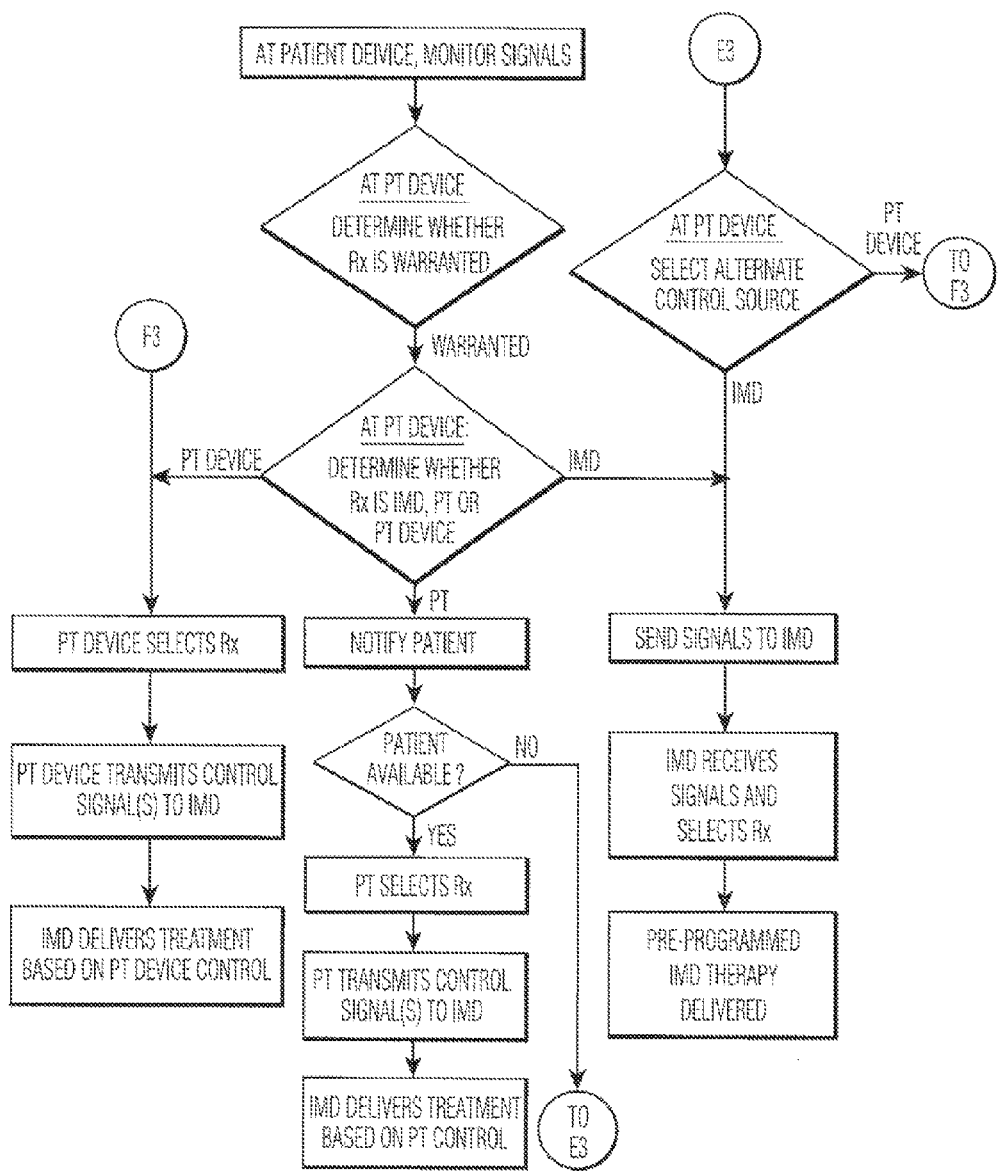
FIG. 42 is another flow diagram illustrating the control of a 3 entity IMD system, which may be controlled by each of an IMD, a patient device and a patient.
Figure 43:
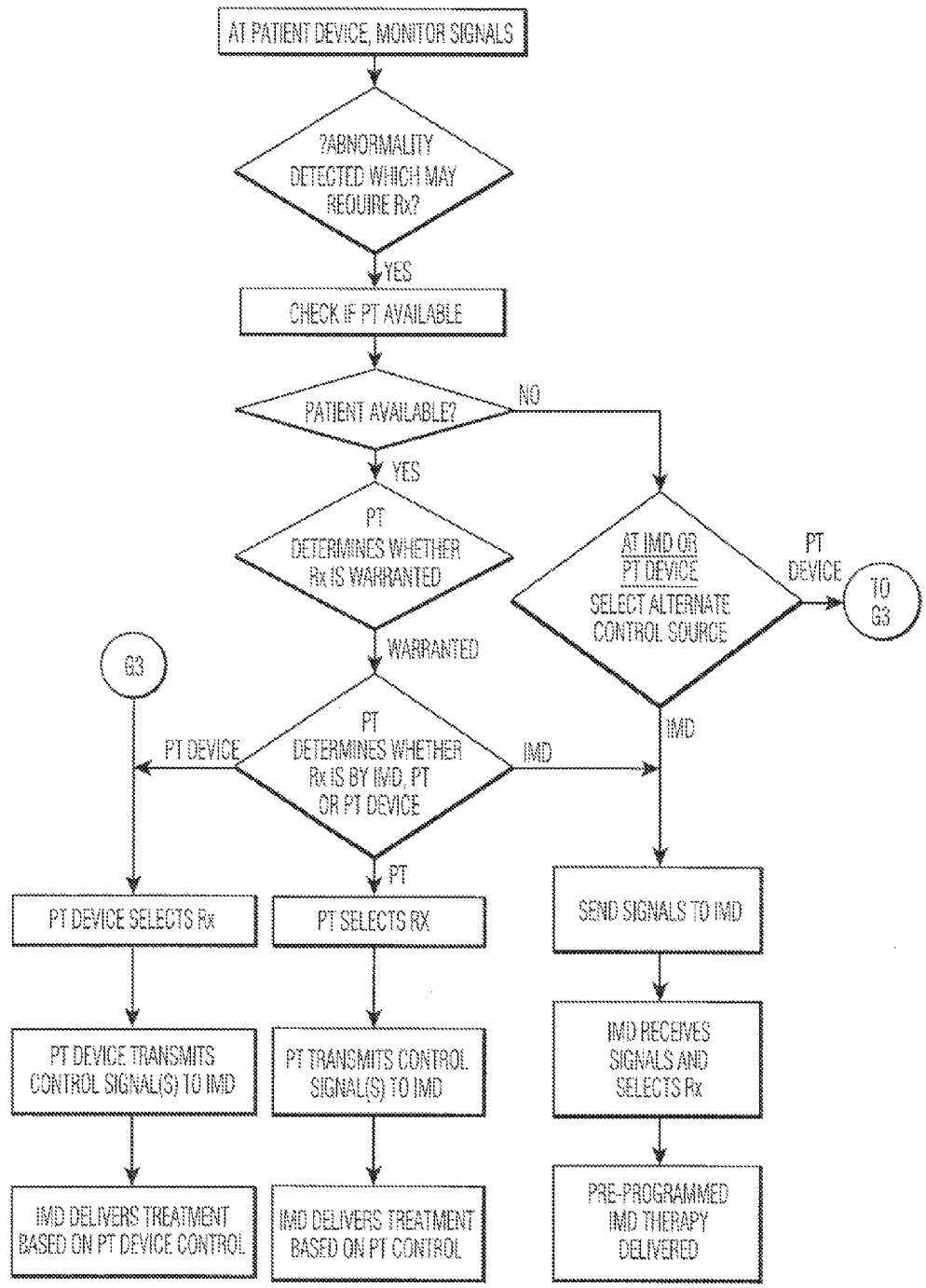
FIG. 43 is another flow diagram illustrating the control of a 3 entity IMD system, which may be controlled by each of an IMD, a patient device and a patient.
Figure 44:
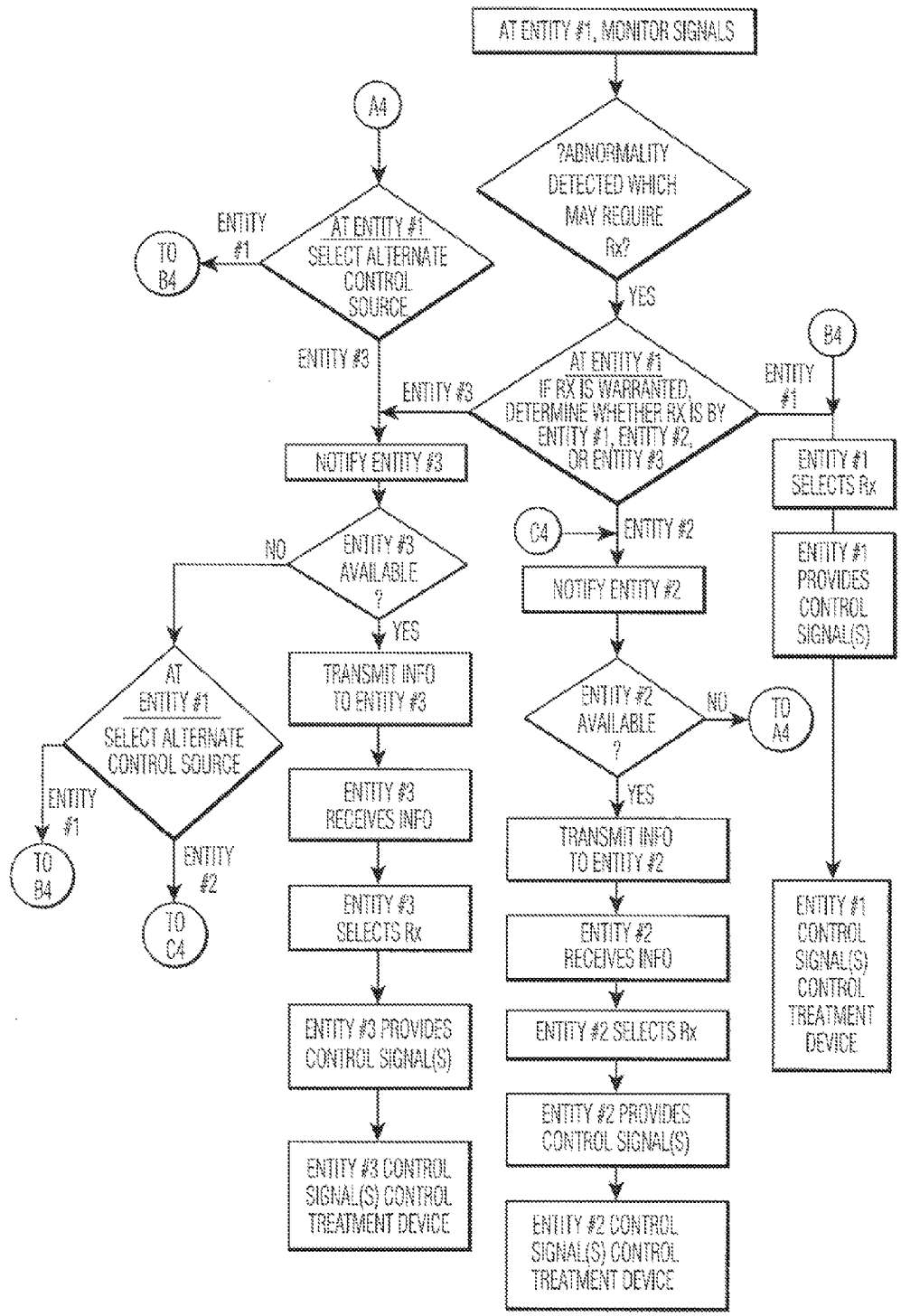
FIG. 44 is a flow diagram illustrating the control of a general 3 entity IMD system, which may be controlled by each of its entities.
Figure 45:
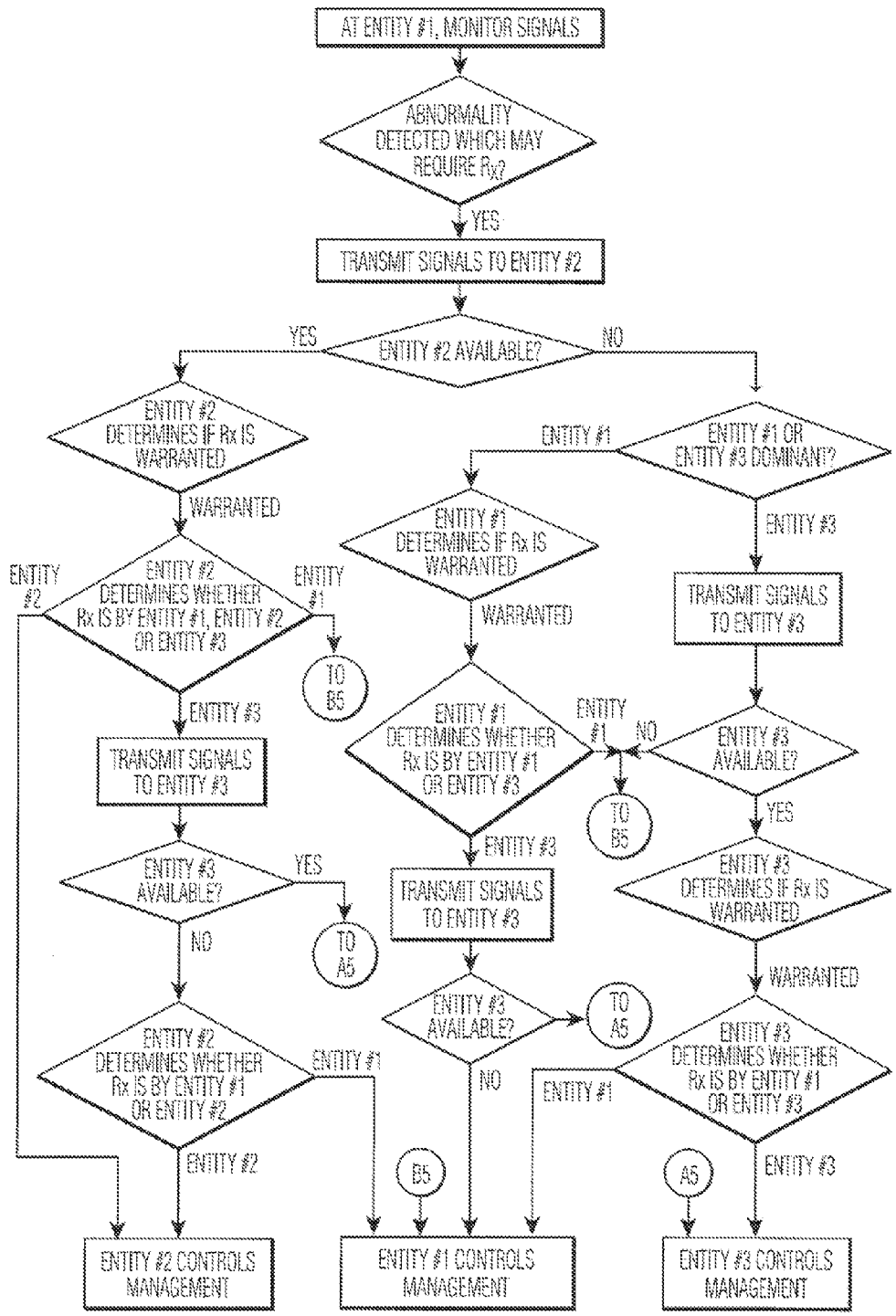
FIG. 45 is another flow diagram illustrating the control of a general 3 entity IMD system, which may be controlled by each of its entities.
Figure 48:
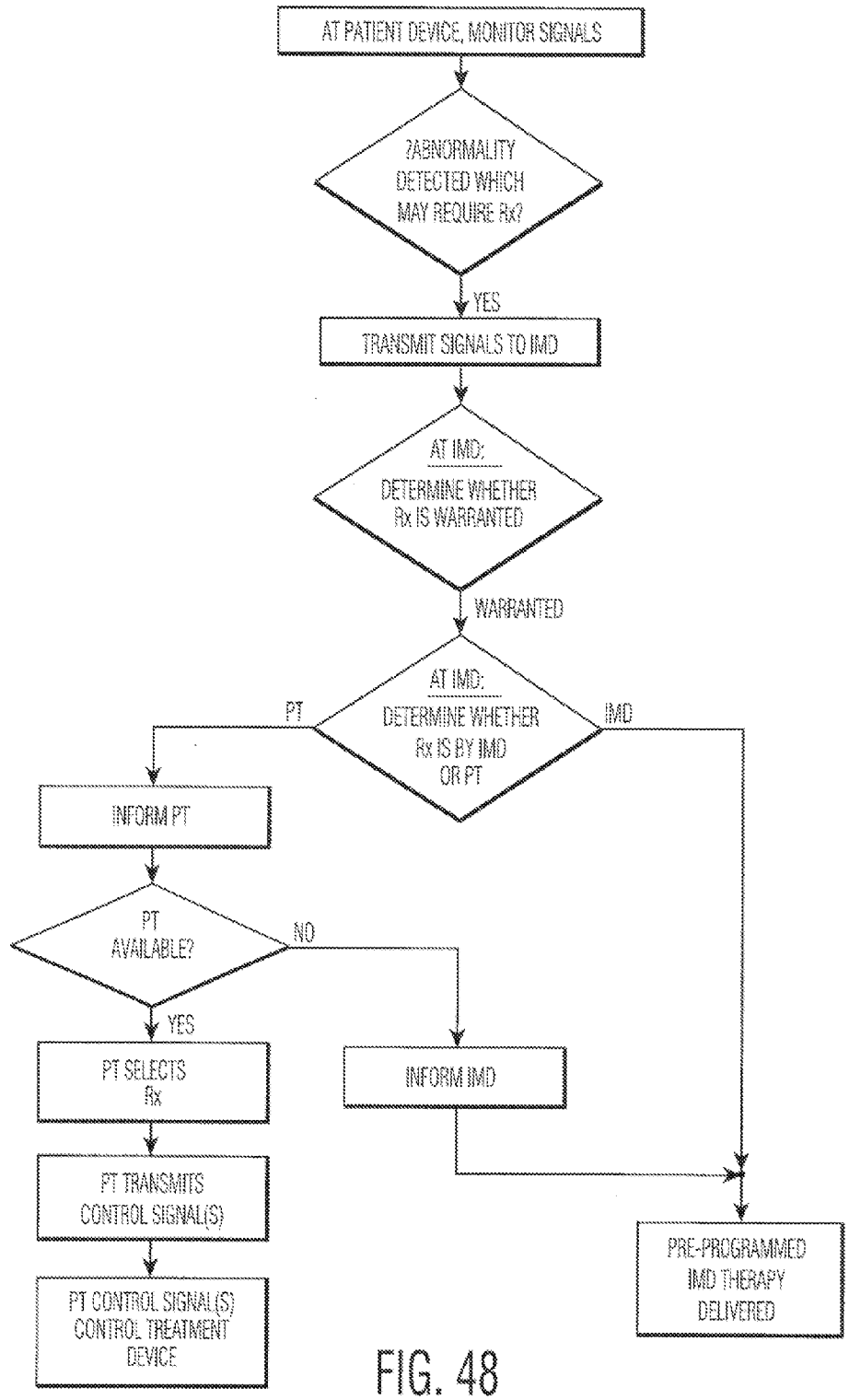
FIG. 48 is another flow diagram illustrating the control of a 2 entity IMD system, which may be controlled by each of an IMD and a patient.
Figure 49:
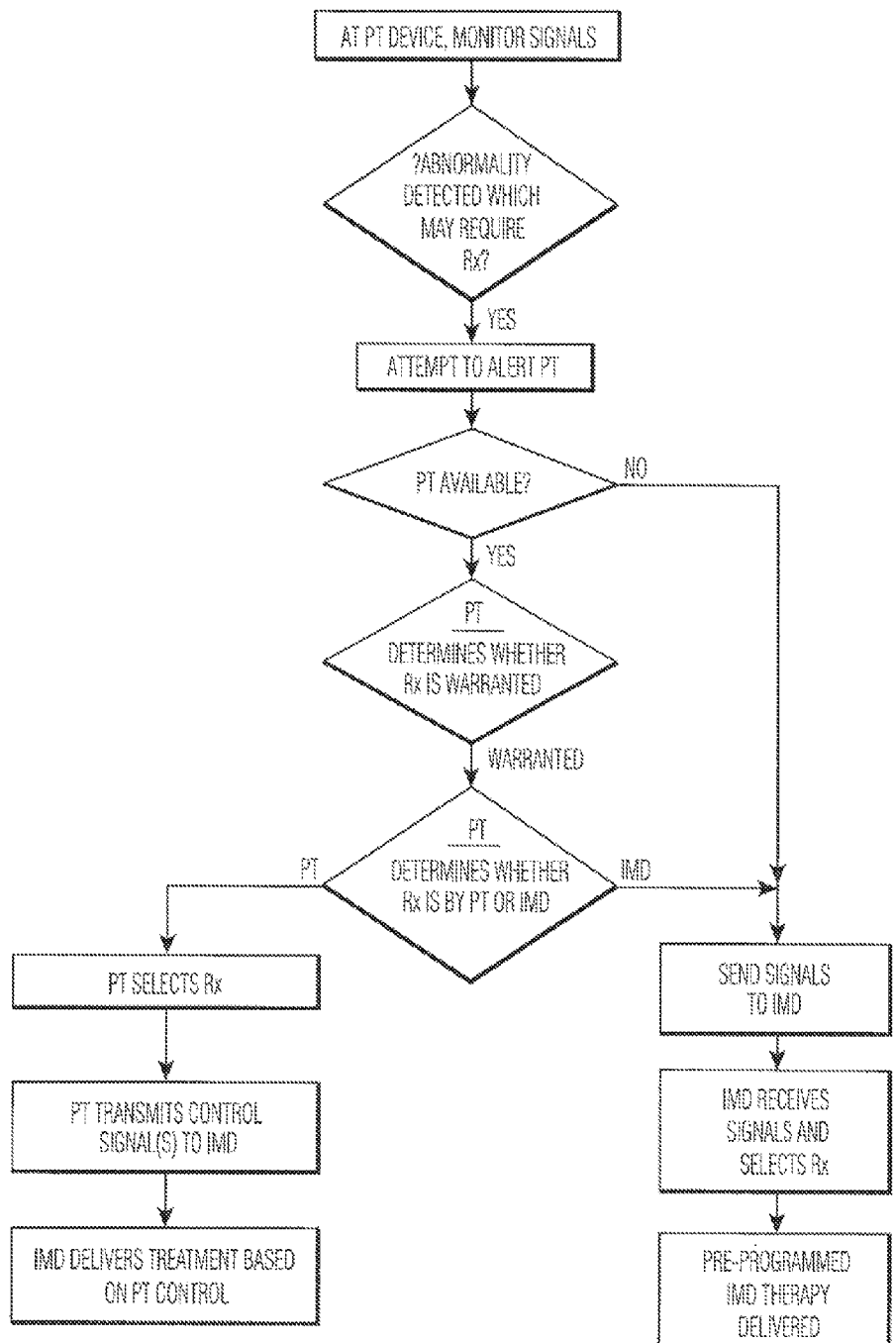
FIG. 49 is another flow diagram illustrating the control of a 2 entity IMD system, which may be controlled by each of an IMD and a patient.
Figure 50:
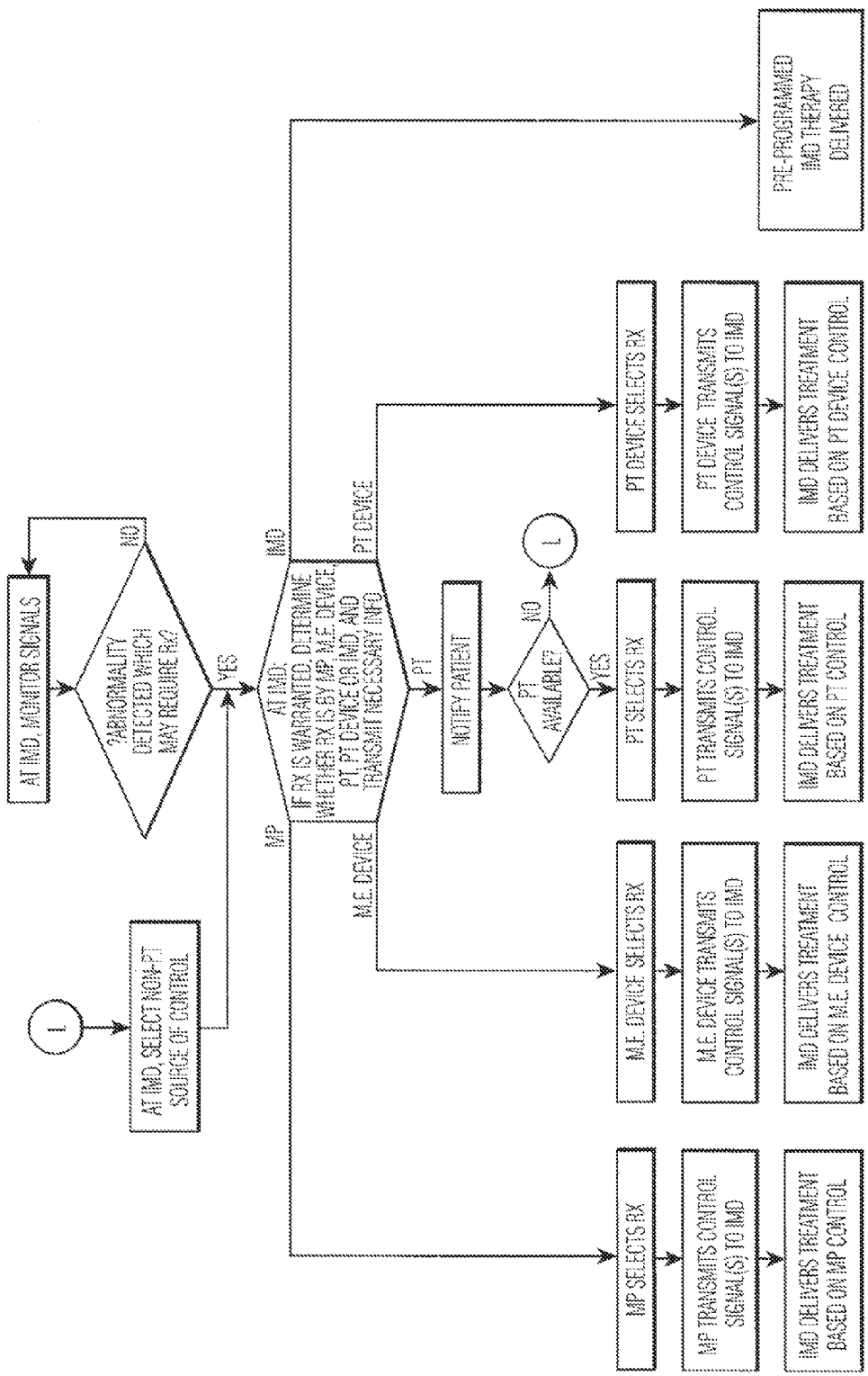
FIG. 50 is a flow diagram illustrating the control of a 5 entity IMD system, which may be controlled by each of an IMD, a patient device, a patient, a medical expert device and a medical professional.
Figure 51:
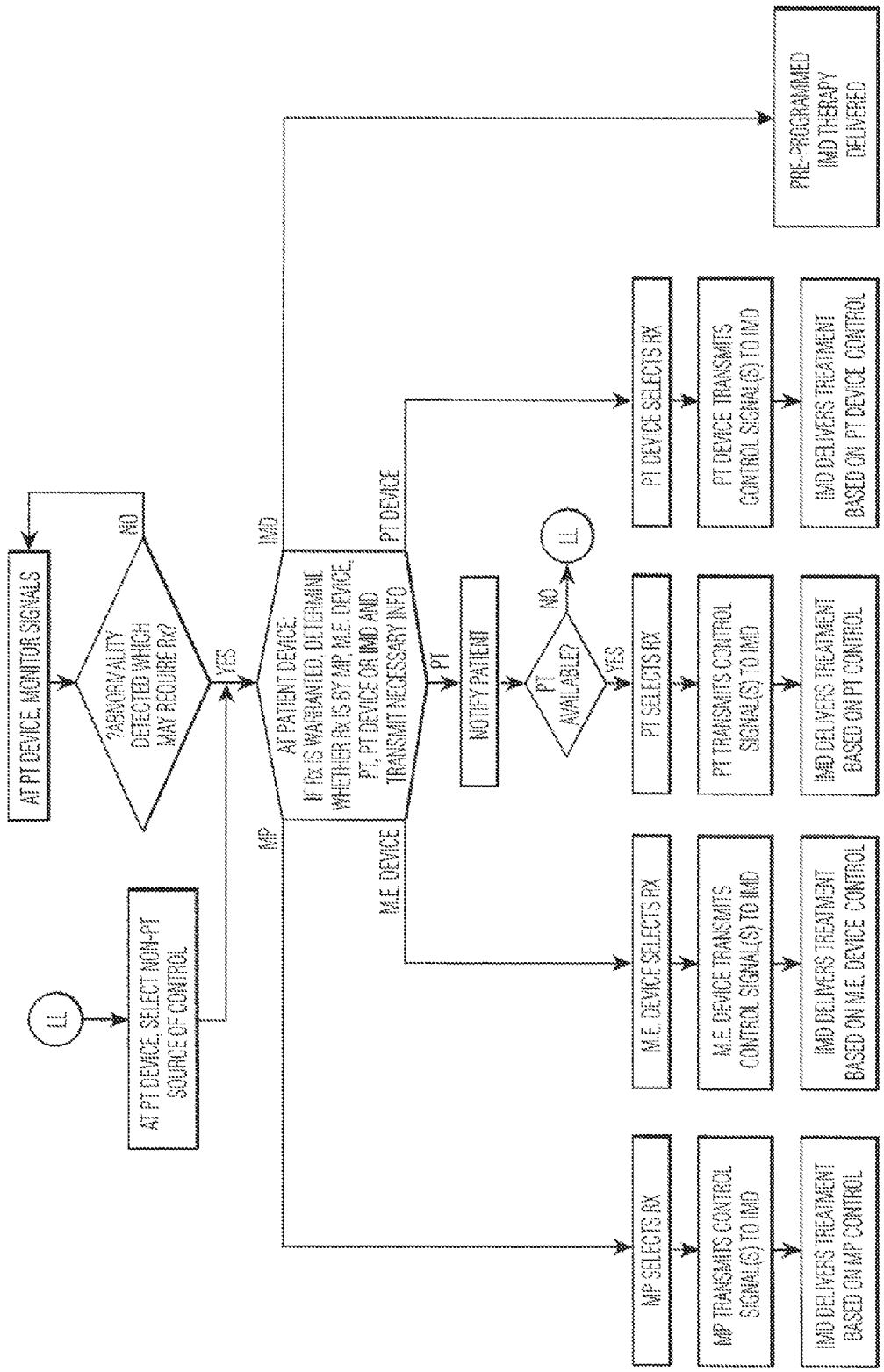
FIG. 51 is another flow diagram illustrating the control of a 5 entity IMD system, which may be controlled by each of an IMD, a patient device, a patient, a medical expert device and a medical professional.
Figure 52:
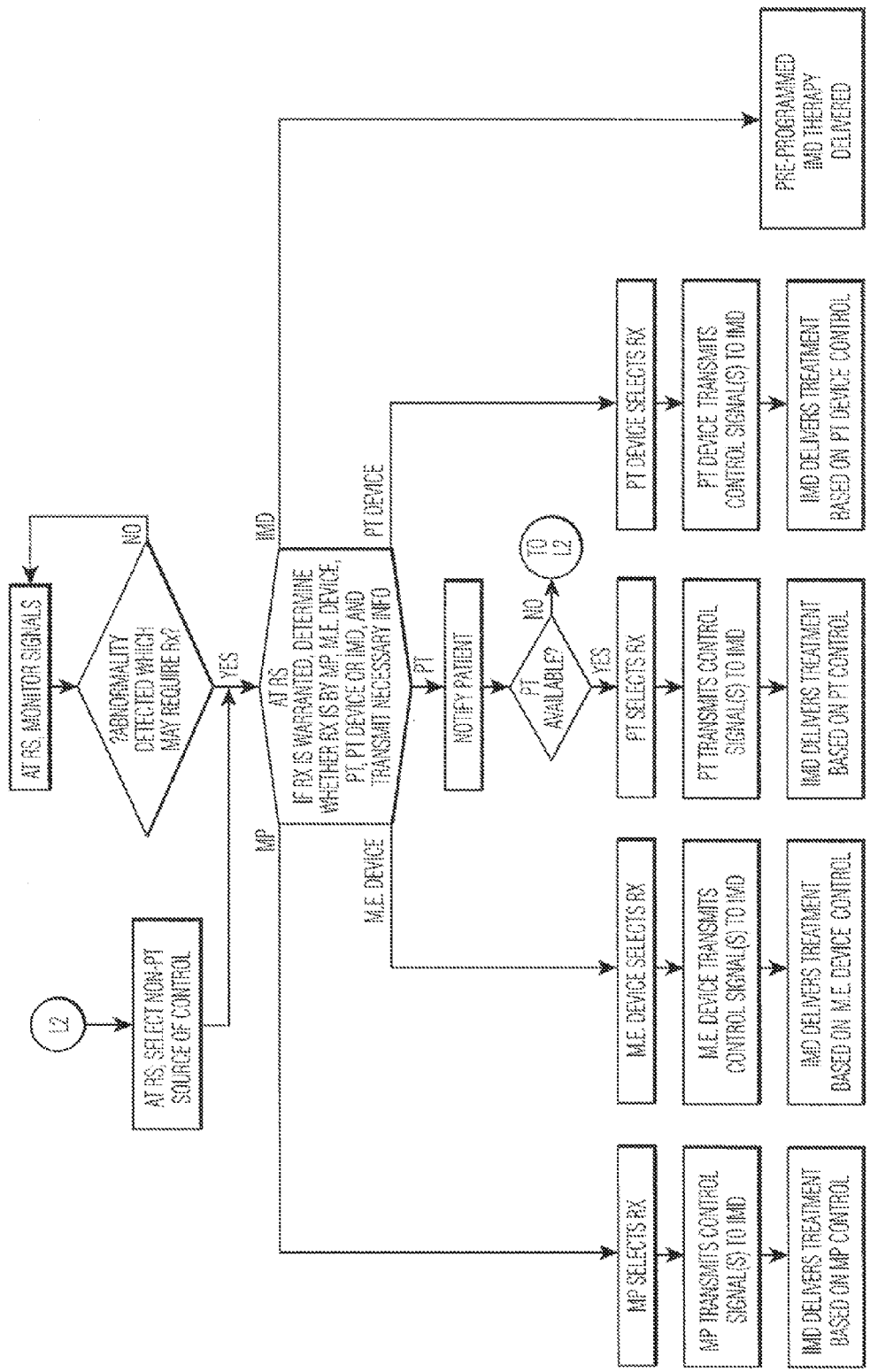
FIG. 52 is another flow diagram illustrating the control of a 5 entity IMD system, which may be controlled by each of an IMD, a patient device, a patient, a medical expert device and a medical professional.
Figure 53:
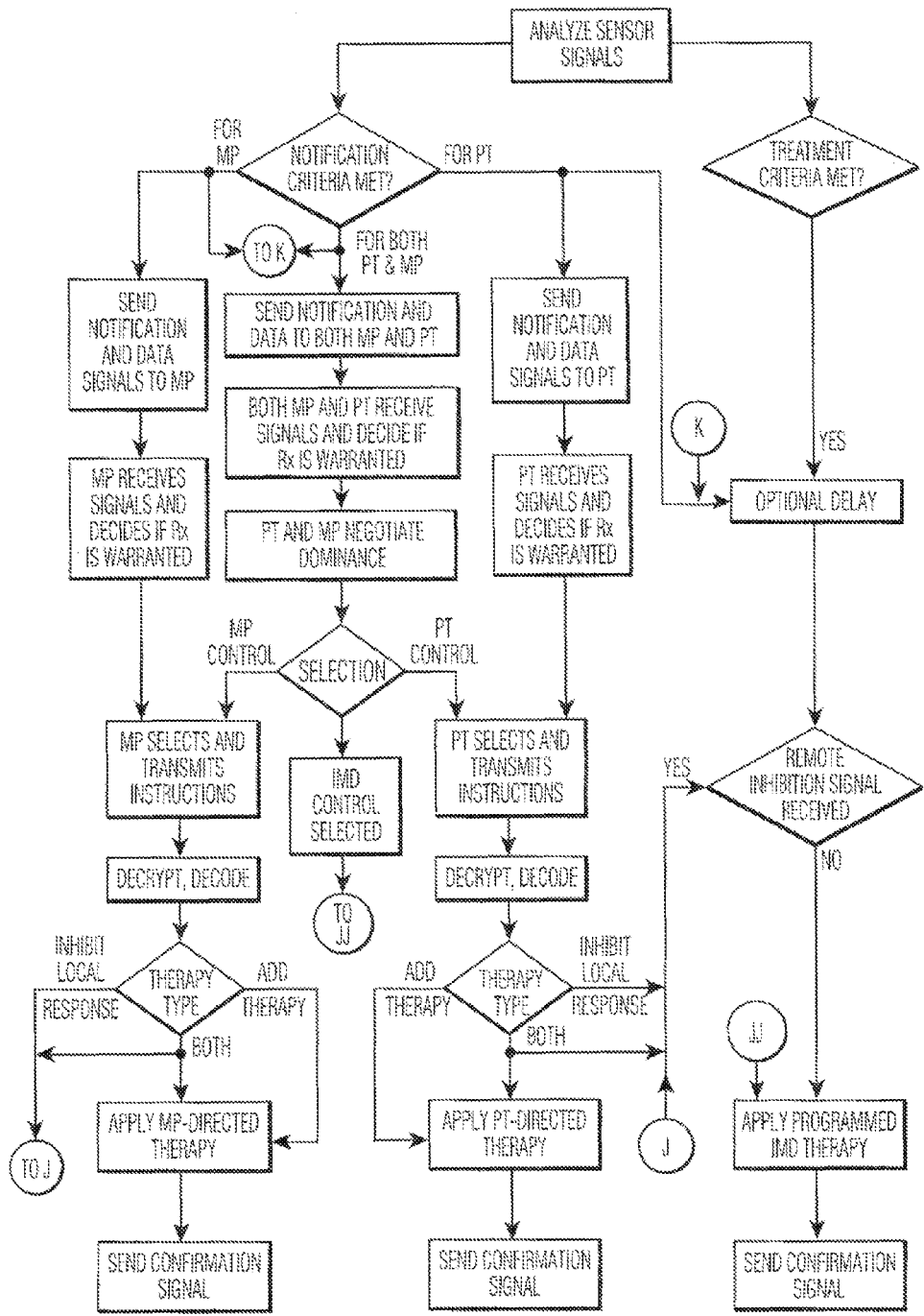
FIG. 53 is another flow diagram illustrating the control of a 3 entity IMD system, which may be controlled by each of an IMD, a patient and a medical professional.
Figure 54:
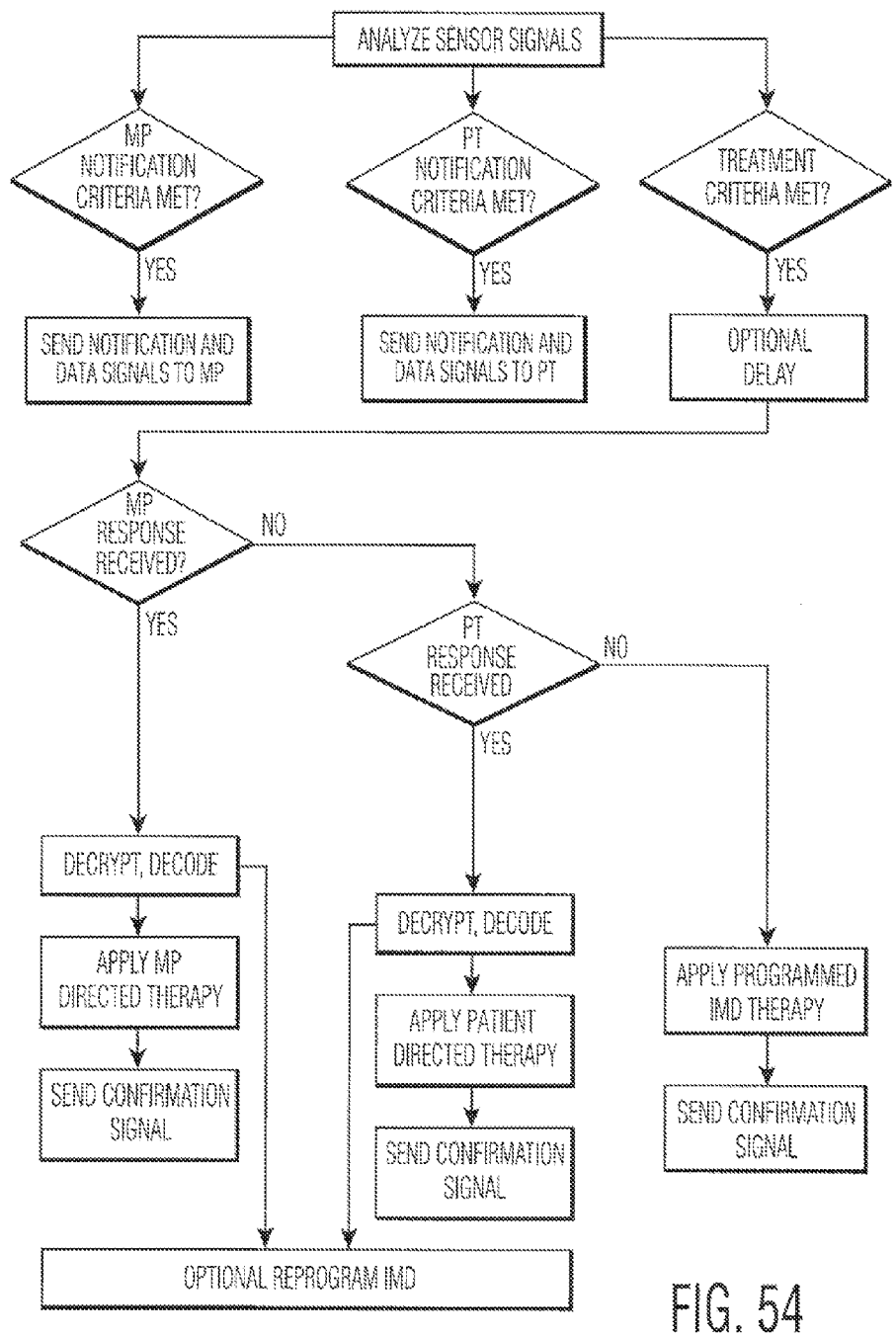
FIG. 54 is another flow diagram illustrating the control of a 3 entity IMD system, which may be controlled by each of an IMD, a patient and a medical professional.
Figure 55:
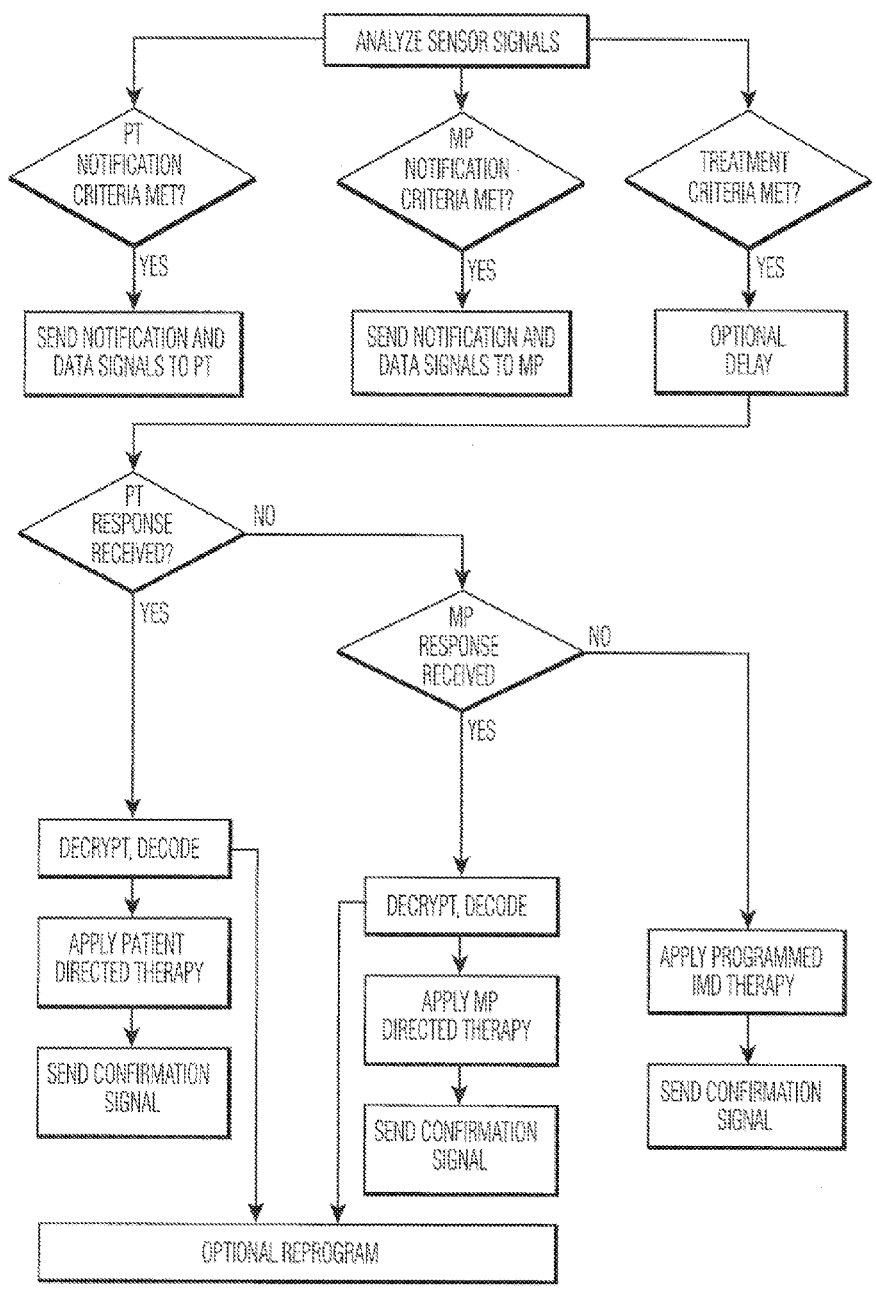
FIG. 55 is another flow diagram illustrating the control of a 3 entity IMD system, which may be controlled by each of an IMD, a patient and a medical professional.
Figure 56A:
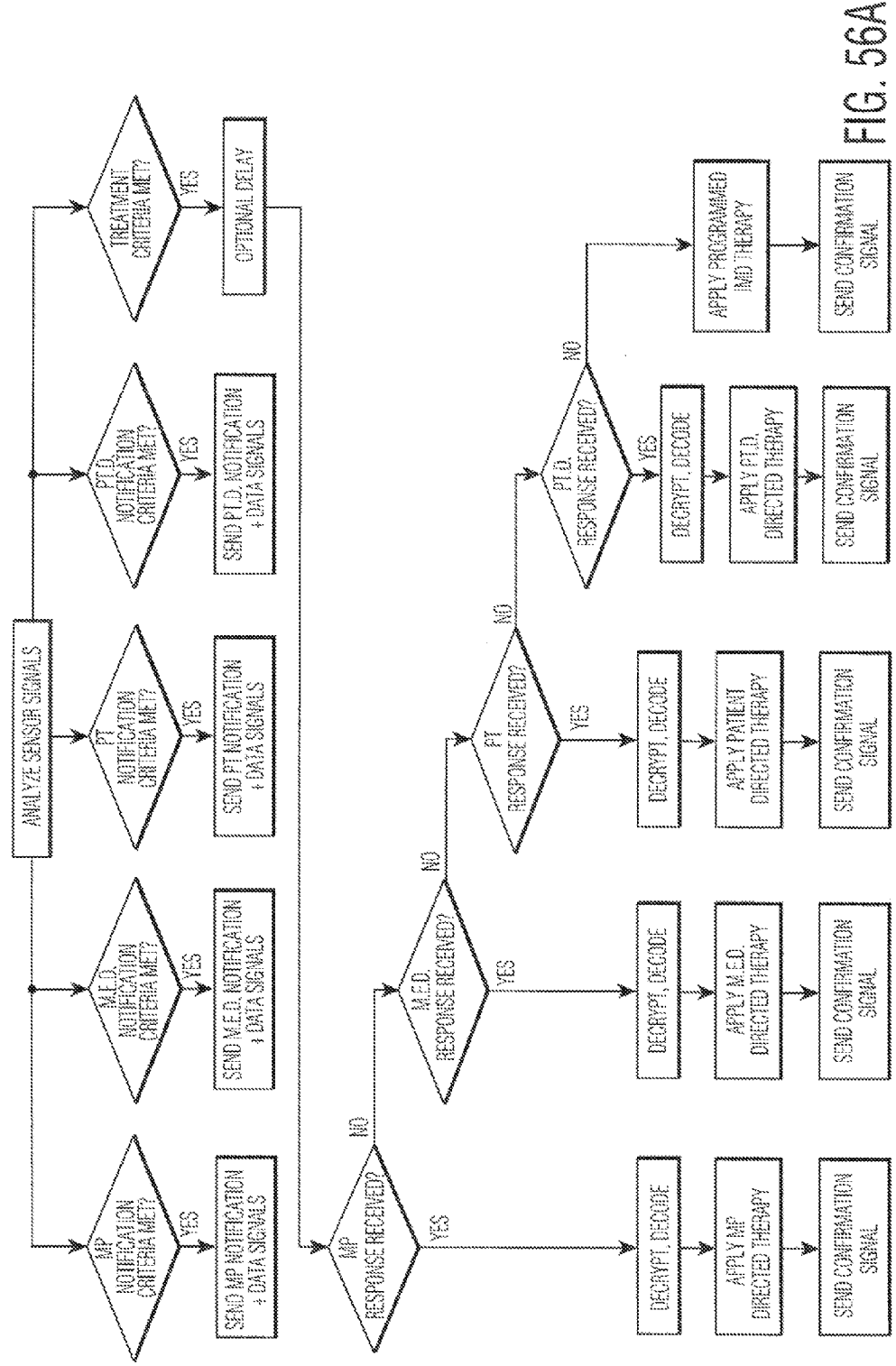
FIG. 56A is another flow diagram illustrating the control of a 5 entity IMD system, which may be controlled by each of an IMD, a patient device, a patient a medical expert device, and a medical professional.
Figure 56B:
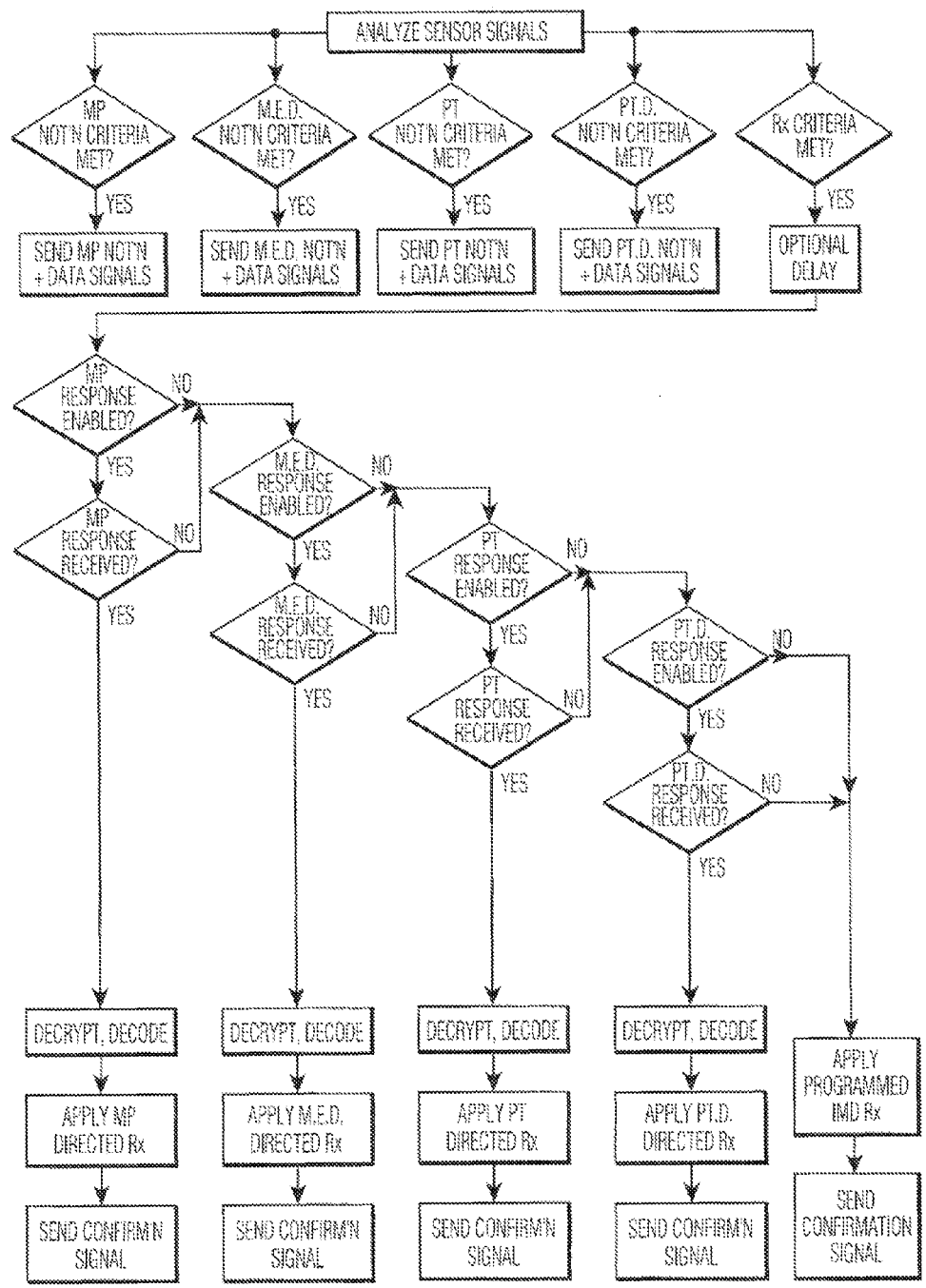
FIG. 56B is another flow diagram illustrating the control of a 5 entity IMD system, which may be controlled by each of an IMD, a patient device, a patient a medical expert device, and a medical professional.
Figure 56C:
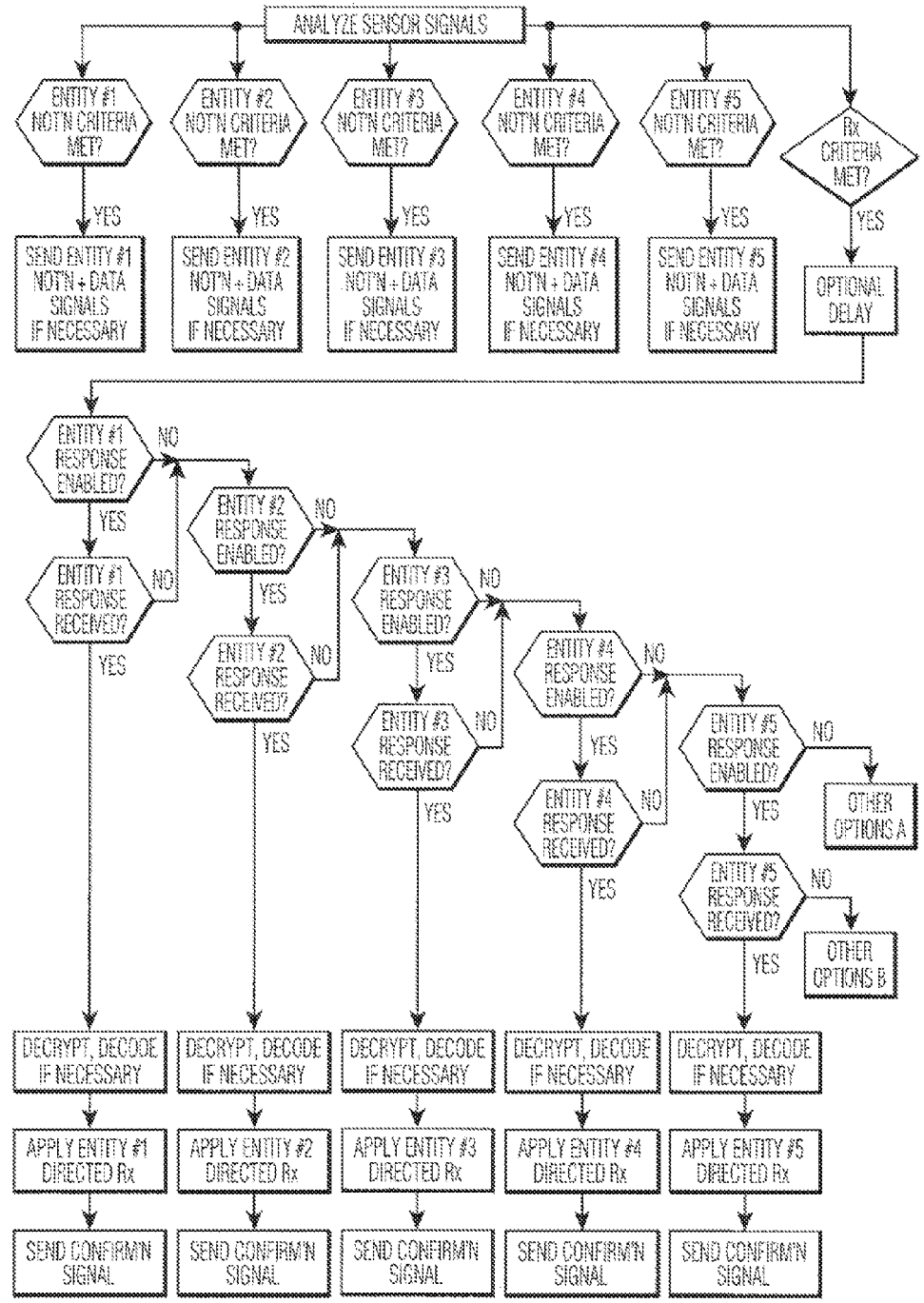
FIG. 56C is another flow diagram illustrating the control of a 5 entity system, which may be controlled by each of its five constituent entities.
Figure 56D:
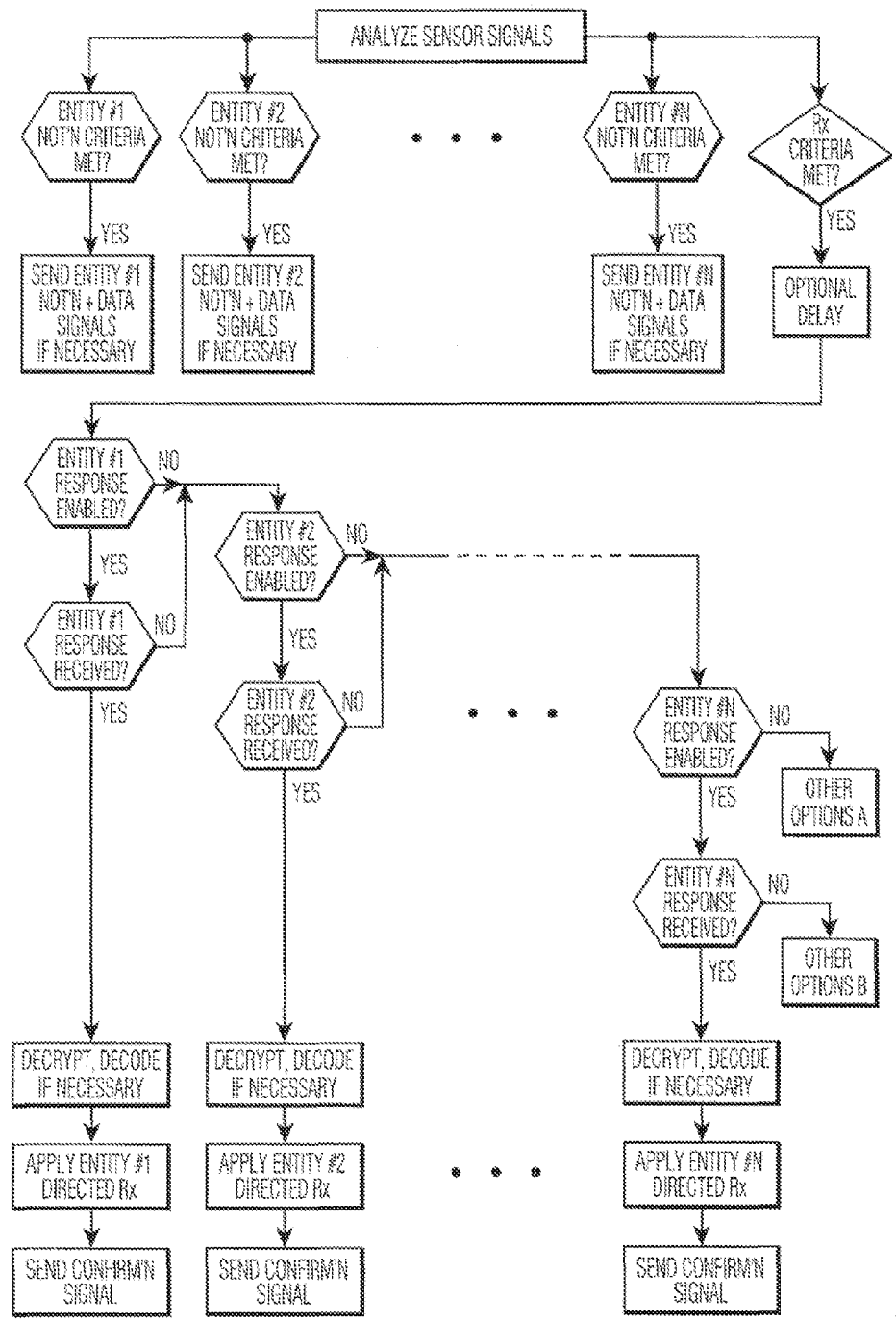
FIG. 56D is another flow diagram illustrating the control of an N entity system, which may be controlled by each of its N constituent entities.
Figure 57:
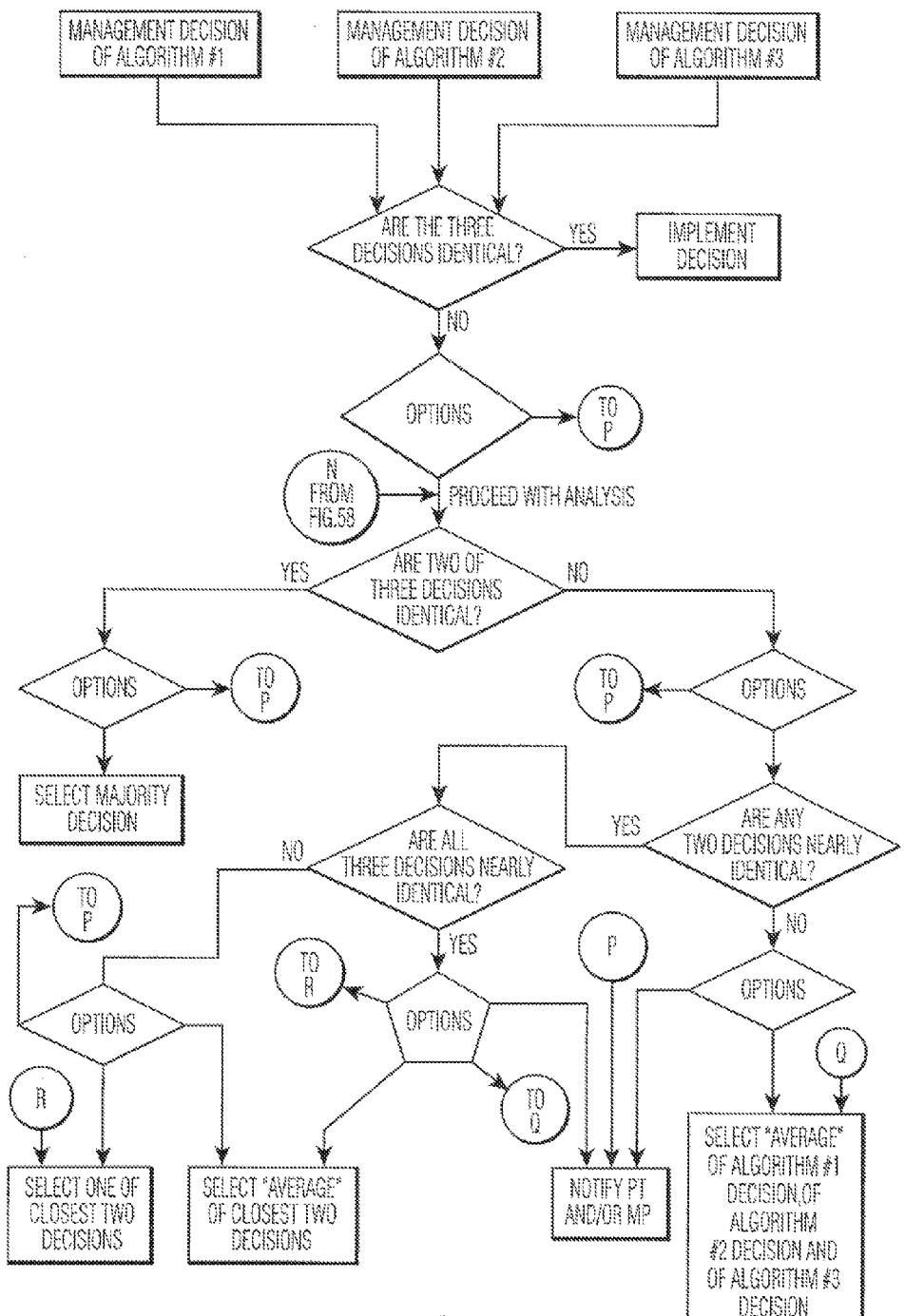
FIG. 57 is a flow diagram illustrating the operation of three parallel algorithms, for management of sensor information in an IMD system.
Figure 58:
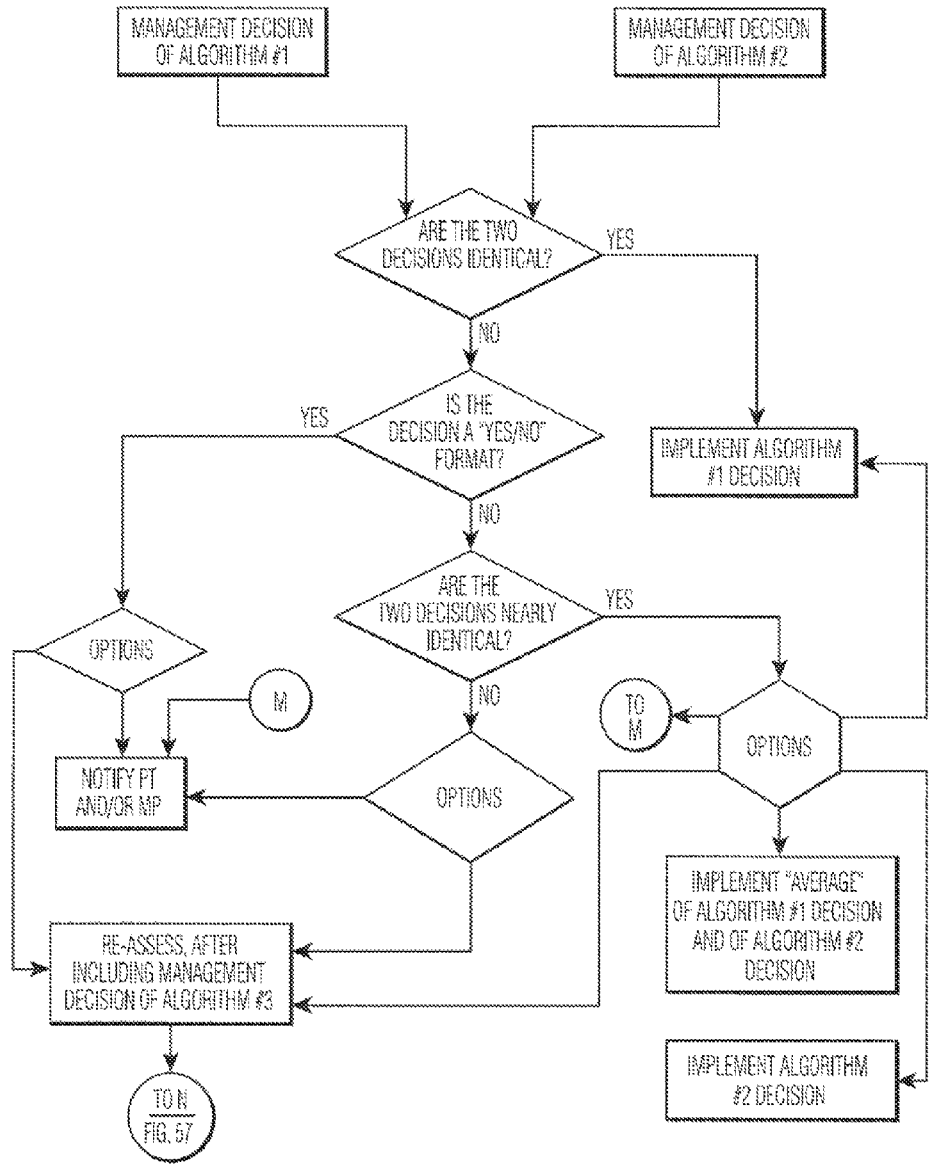
FIG. 58 is a flow diagram illustrating the operation of two parallel algorithms, for management of sensor information in an IMD) system.
Figure 61:
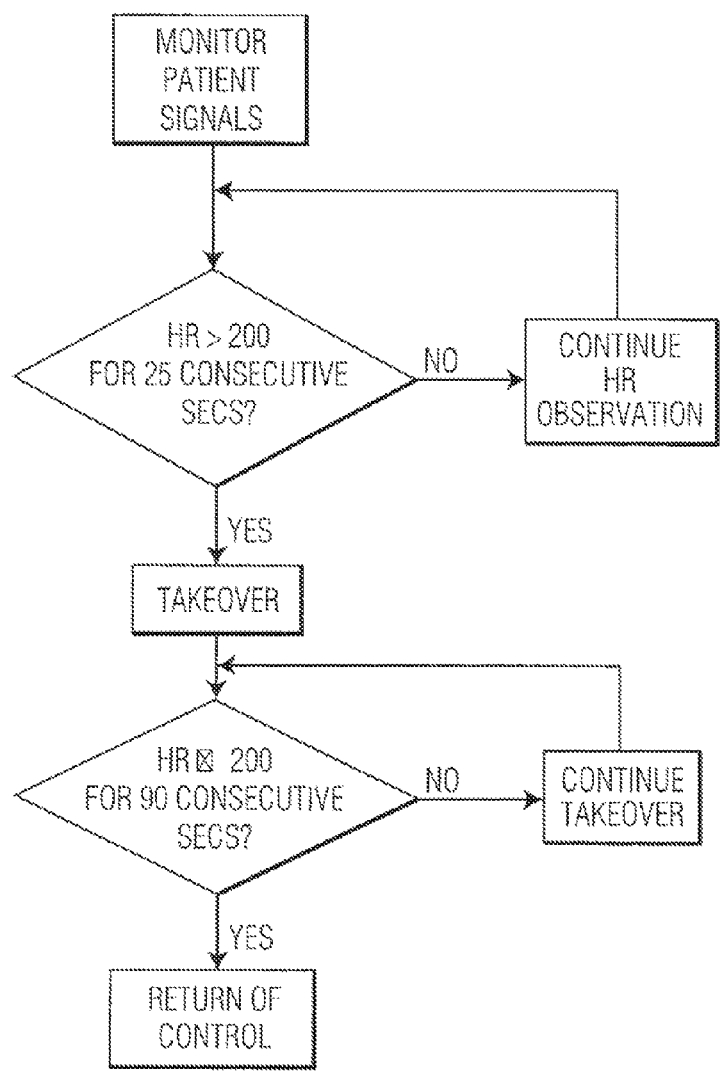
FIG. 61 is another flow diagram illustrating methods of shifting control of an IMD, in an IMD system.
Figure 62:
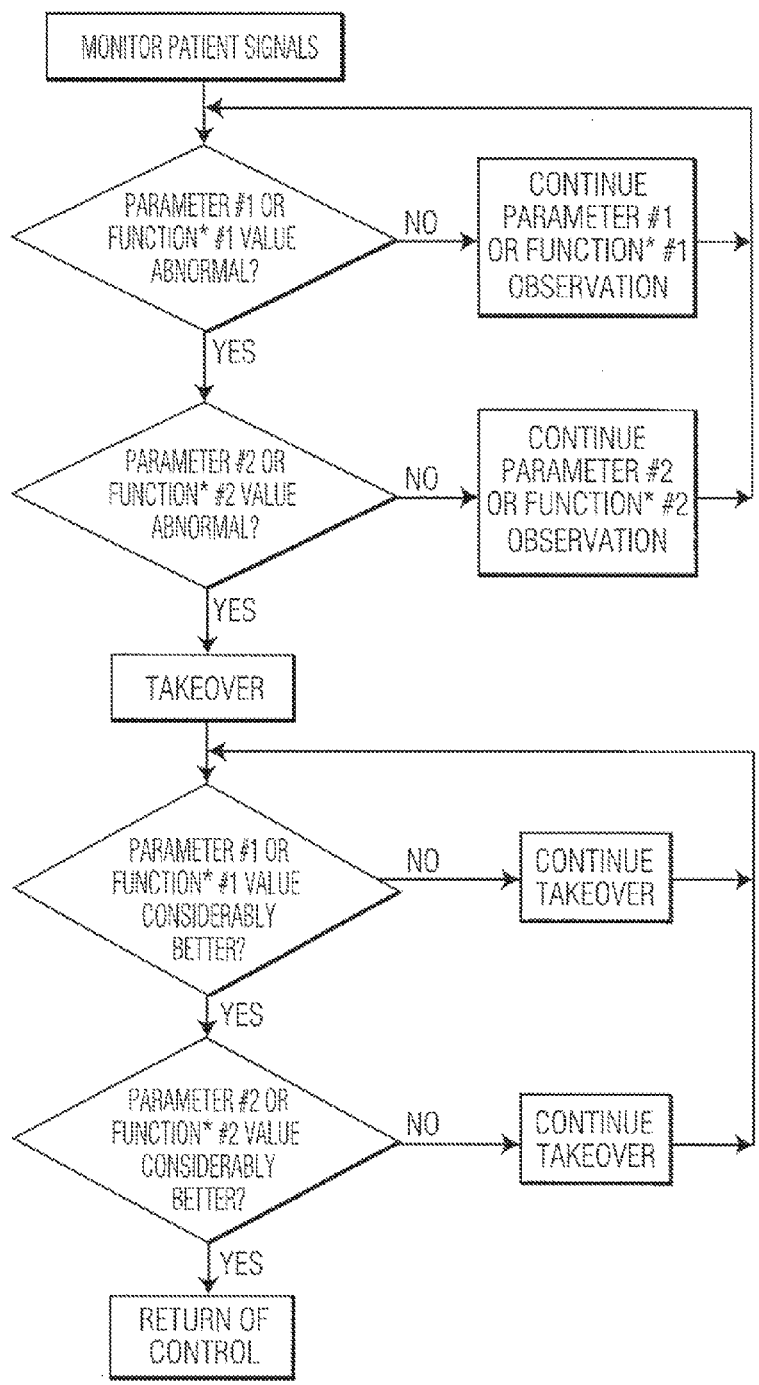
FIG. 62 is another flow diagram illustrating methods of shifting control of an IMD, in an IMD system.
Figure 63:
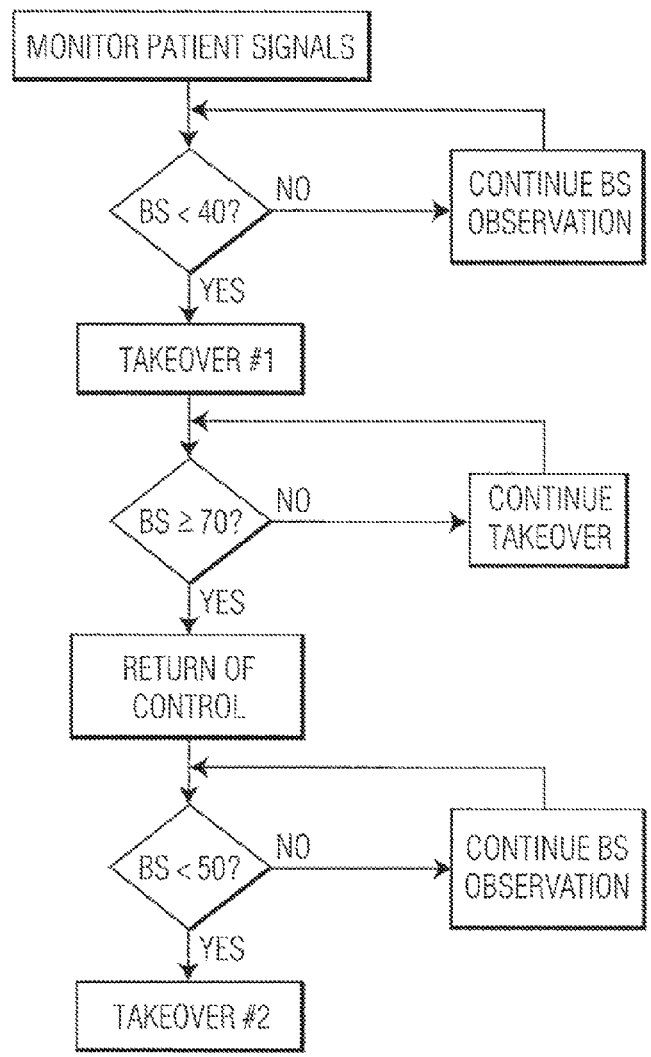
FIG. 63 is another flow diagram illustrating methods of shifting control of an IMD, in an IMD system.
Figure 64:
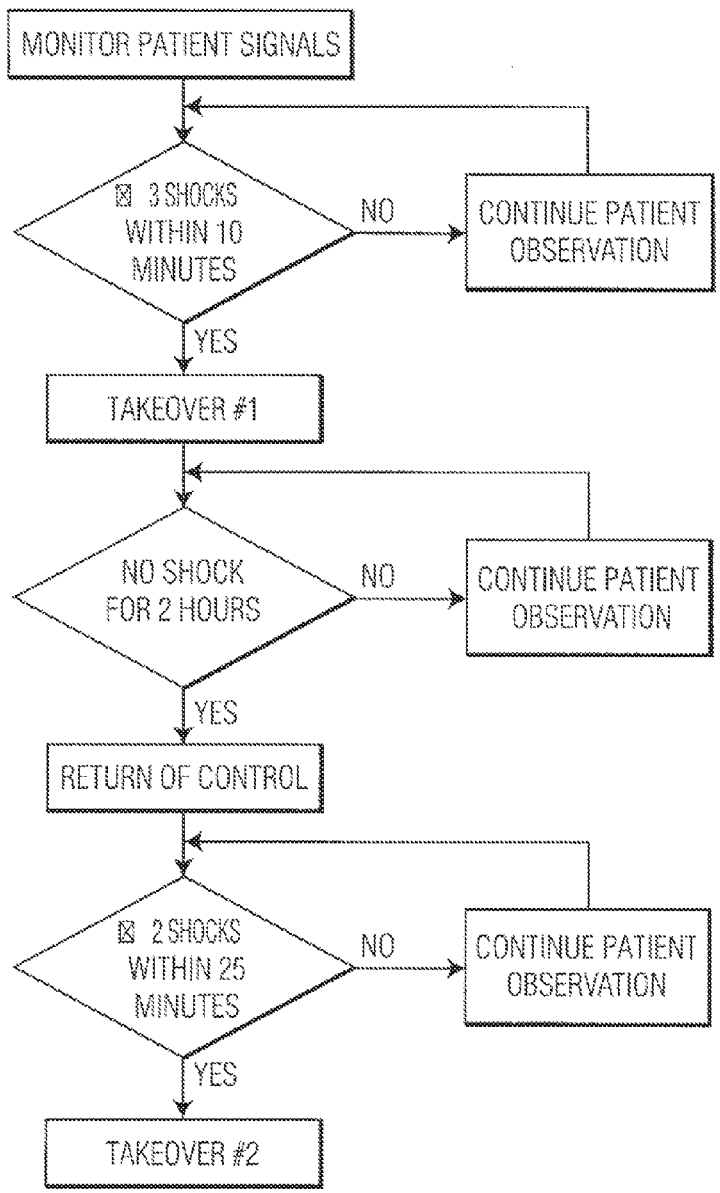
FIG. 64 is another flow diagram illustrating methods of shifting control of an IMD, in an IMD system.
Figure 65:
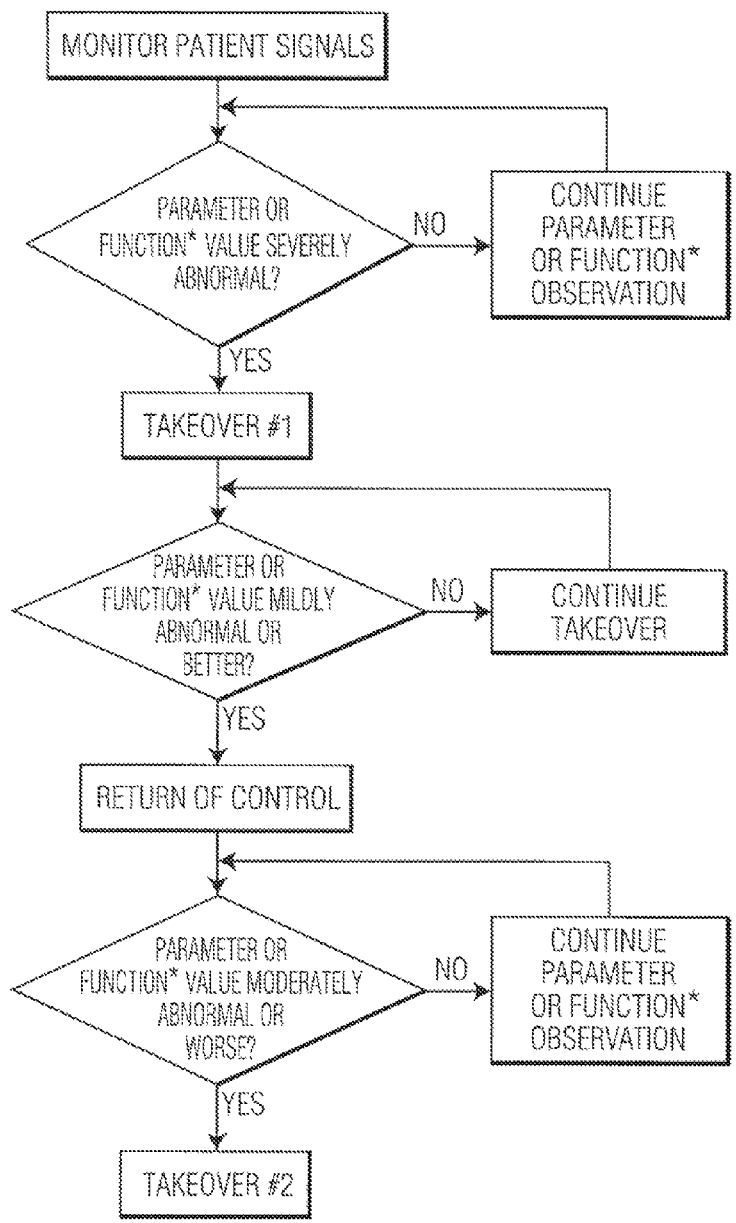
FIG. 65 is another flow diagram illustrating methods of shifting control of an IMD, in an IMD system.
Figure 66:
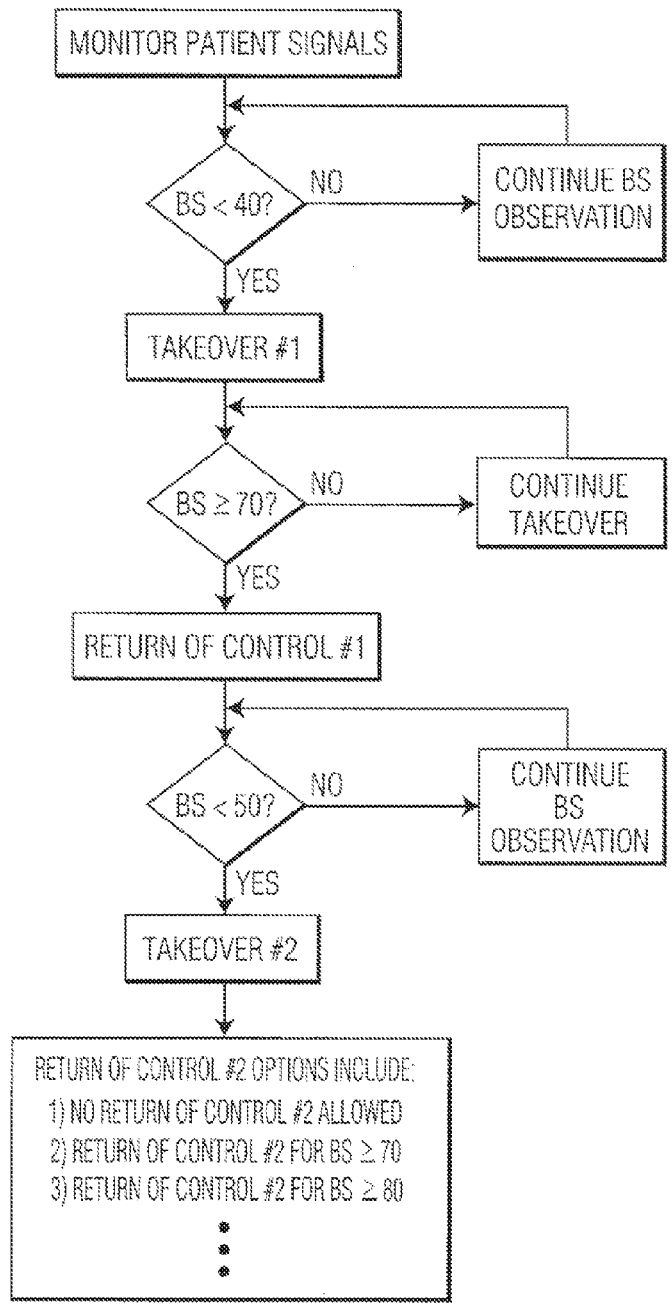
FIG. 66 is another flow diagram illustrating methods of shifting control of an IMD, in an IMD system.
Figure 67:
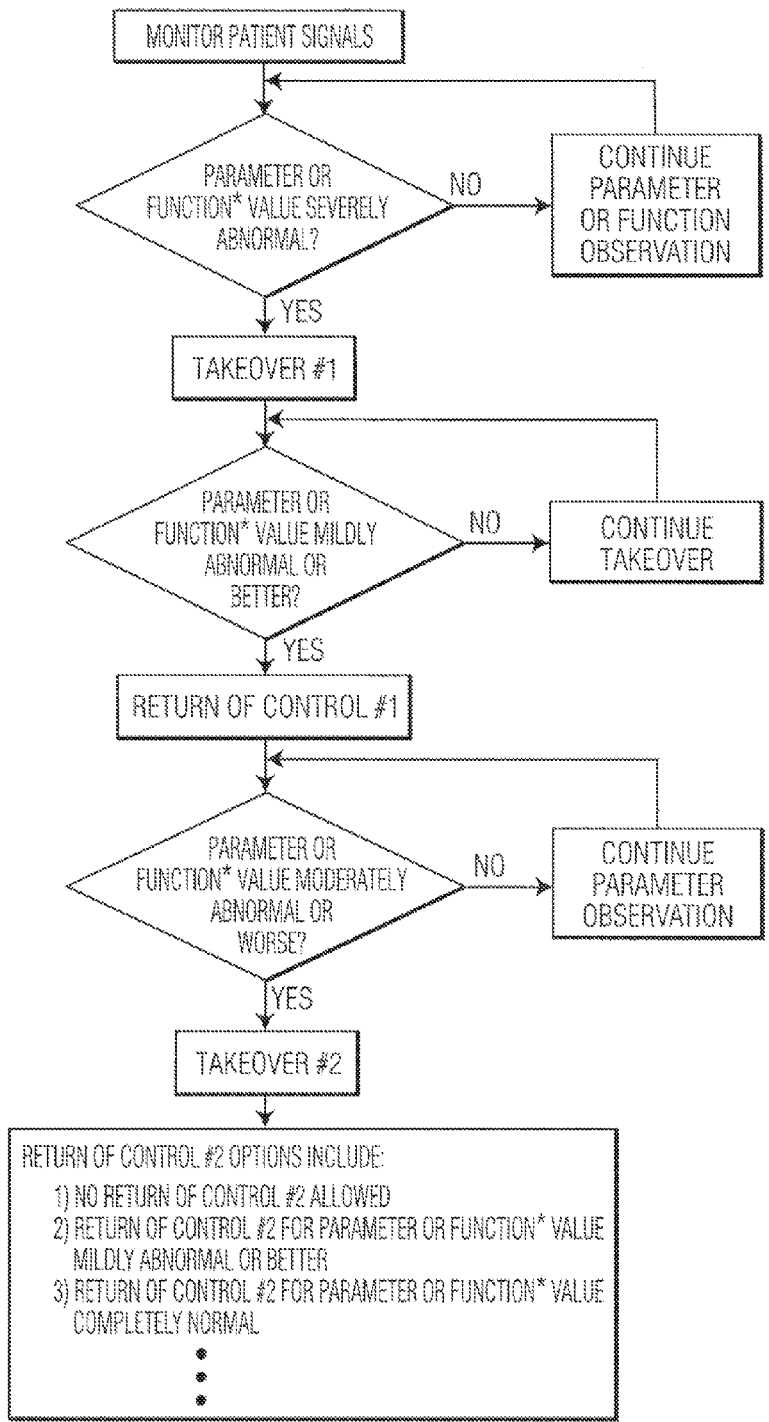
FIG. 67 is another flow diagram illustrating methods of shifting control of an IMD, in an IMD system.
Figure 68:
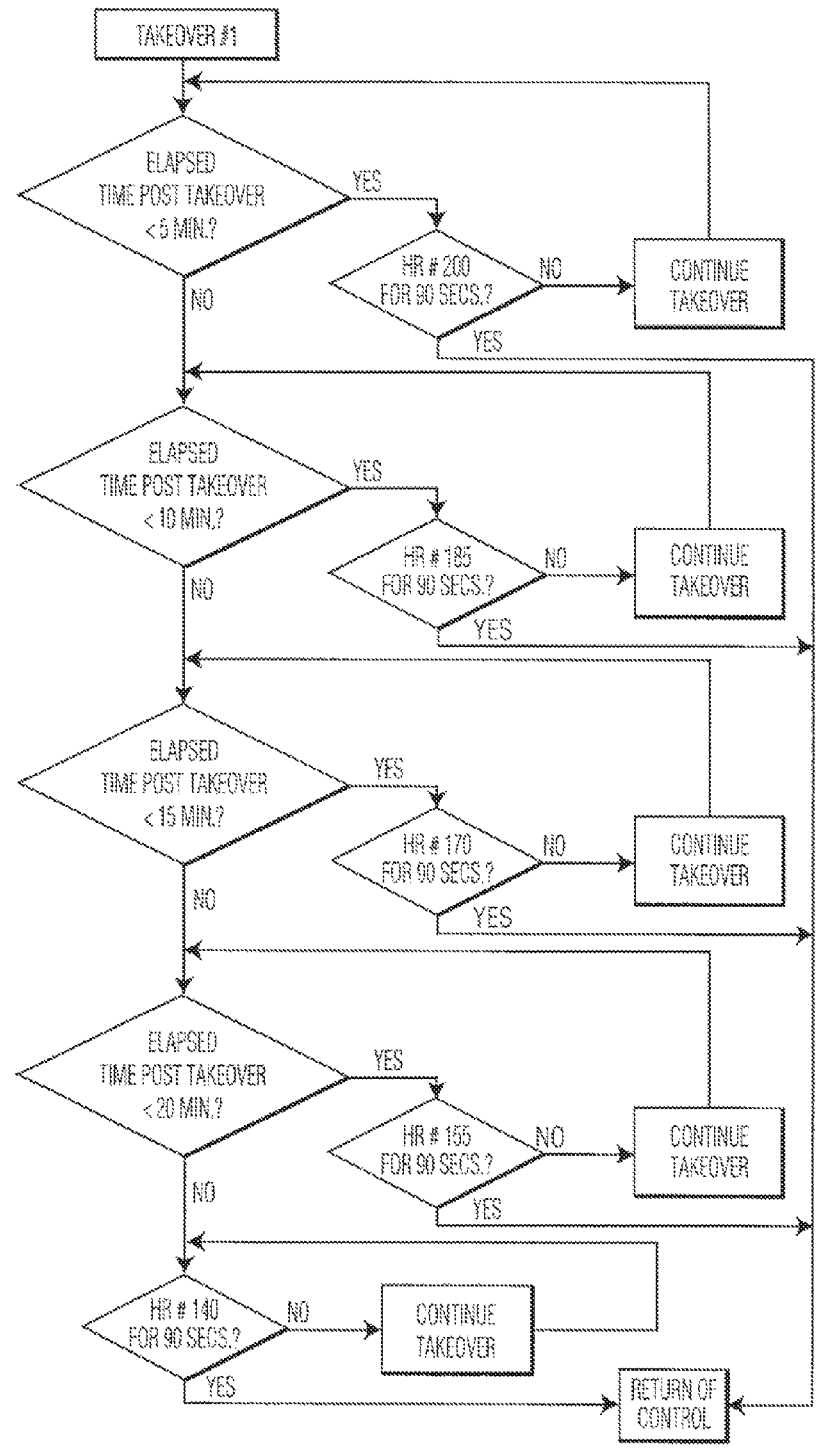
FIG. 68 is another flow diagram illustrating methods of shifting control of an IMD, in an IMD system.
Figure 69:
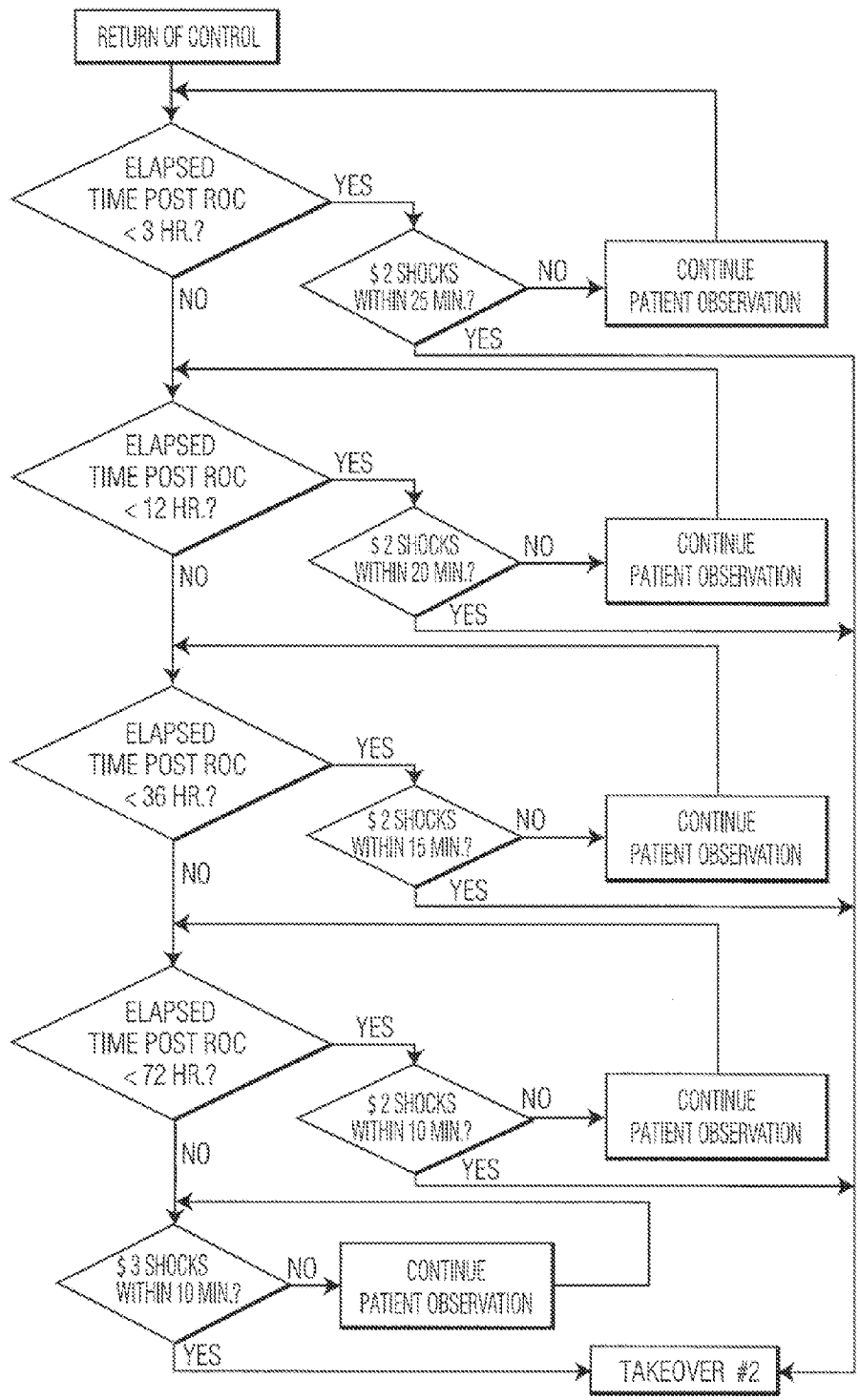
FIG. 69 is another flow diagram illustrating methods of shifting control of an IMD, in an IMD system.
Figure 70:
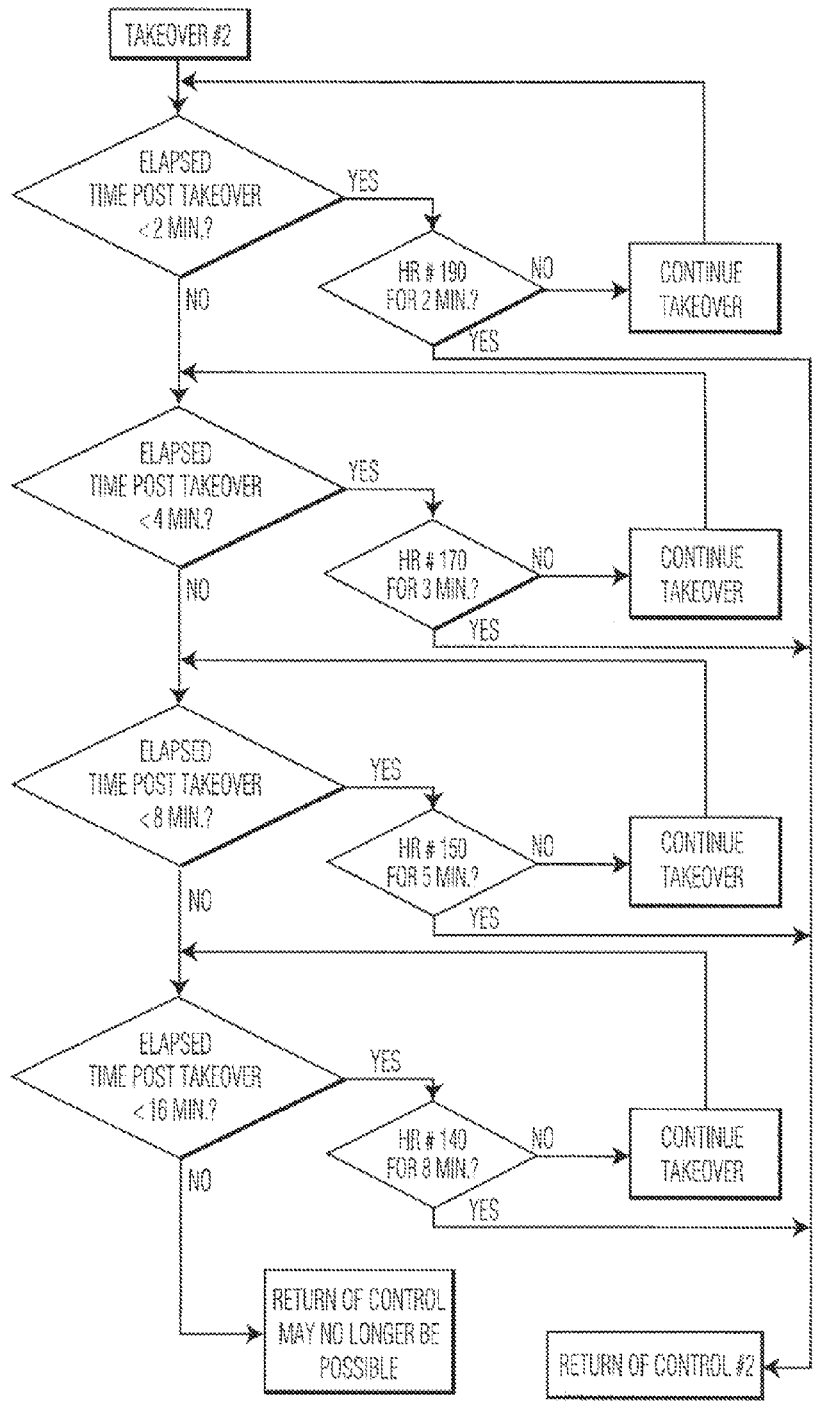
FIG. 70 is another flow diagram illustrating methods of shifting control of an IMD, in an IMD system.
Figure 78:
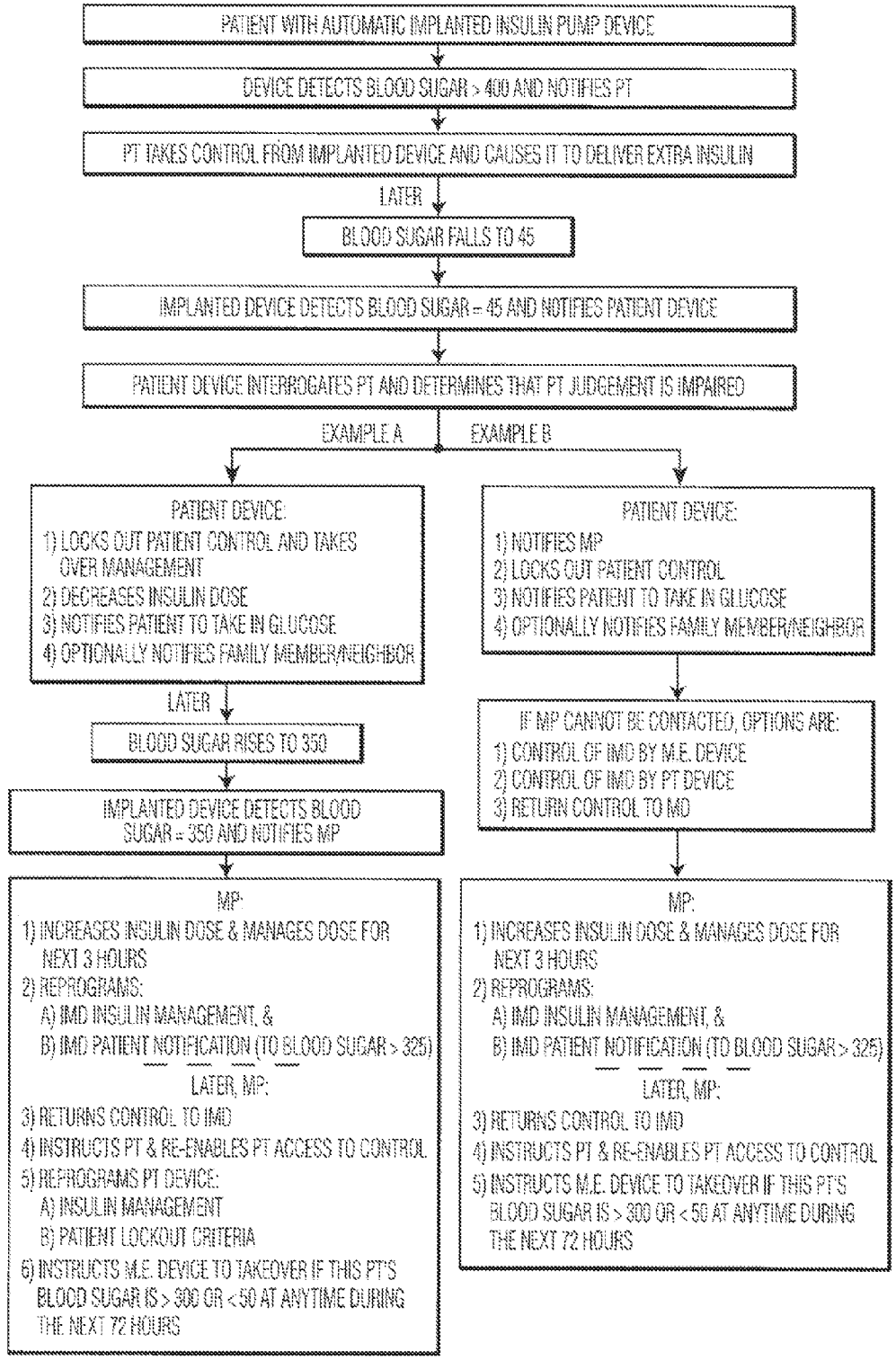
FIG. 78 is a block diagram illustrating examples of the transfer of control of an implantable glucose control system, among an IMD, a patient, a patient device and a medical professional.

| Contents and Associated FIGS.: | | |
|---|---|---|
| 1.0 | System Overview | FIGS. 1A-1F |
| 2.0 | Hardware | FIGS. 2-12 |
| 3.0 | Management Control Screens | FIGS. 13-21 |
| 4.0 | Triaging Using Function* | FIGS. 22A-24 |
| 5.0 | Patient Assessment Algorithms | FIGS. 25-26 |
| 6.0 | System Architecture Summary | FIGS. 27A-27C |
| 7.0 | System Management Algorithms, overview | FIG. 28 |
| 7.1 | 3-Entity Systems with IMD, Patient And Medical Professional or Medical Expert Device | FIGS. 29-37 |
| 7.2 | 3-Entity Systems with IMD, Patient and Patient Device | FIGS. 38-43 |
| 7.3 | Generalized 3-Entity Systems | FIGS. 44-45 |
| 7.4 | 2-Entity Systems with IMD and Patient | FIGS. 46-49 |
| 7.5 | 5-Entity Systems with IMD, Patient Device, Patient, Medical Expert Device And Medical Professional | FIGS. 50-52 |
| 7.6 | Alternate 3-Entity System with IMD, Patient and Medical Professional | FIG. 53 |
| 7.7 | Second Alternate 3-Entity System with IMD, Patient and Medical Professional | FIGS. 54-55 |
| 7.8 | Alternate > or = 5-Entity Systems with IMD, Patient Device, Patient, Medieal Expert Device and Medical Professional | FIGS. 56A-56D |
| 7.9 | Blending of Two or More Analysis or Control Algorithms | FIGS. 57-58 |
| 7.10 | Control Handoff Algorithms | |
| 7.10.1 | Takeover and Return of Control | FIGS. 59-62 |
| 7.10.2 | Takeover #2 | FIGS. 63-65 |
| 7.10.3 | Return of Control #2 | FIGS. 66-67 |
| 7.10.4 | Time Dependent Formats | FIGS. 68-70 |
| 8.0 | Use of Function* for Triage | |
| 8.1 | 2 Zone Formats | FIGS. 71-73 |
| 8.2 | 3 Zone Formats | FIGS. 74-76 |
| 9.0 | Clinical Examples, overview | FIG. 77 |
| 9.1 | Blood Sugar Management | FIG. 78 |
| 9.2 | Ventricular Tachycardia Management | FIGS. 79-82 |

1.0 System Overview

As used hereinafter, the term "personal medical device" (PMD) refers to a medical device capable of treating a patient which either: (a) is implanted inside the body; (b) is attachable to the body and outside of the body; (c) is partially implanted in the body, or (d) consists of subunits, at least one of which is inside the body, and at least one of which is outside the body.

Figure 1A:
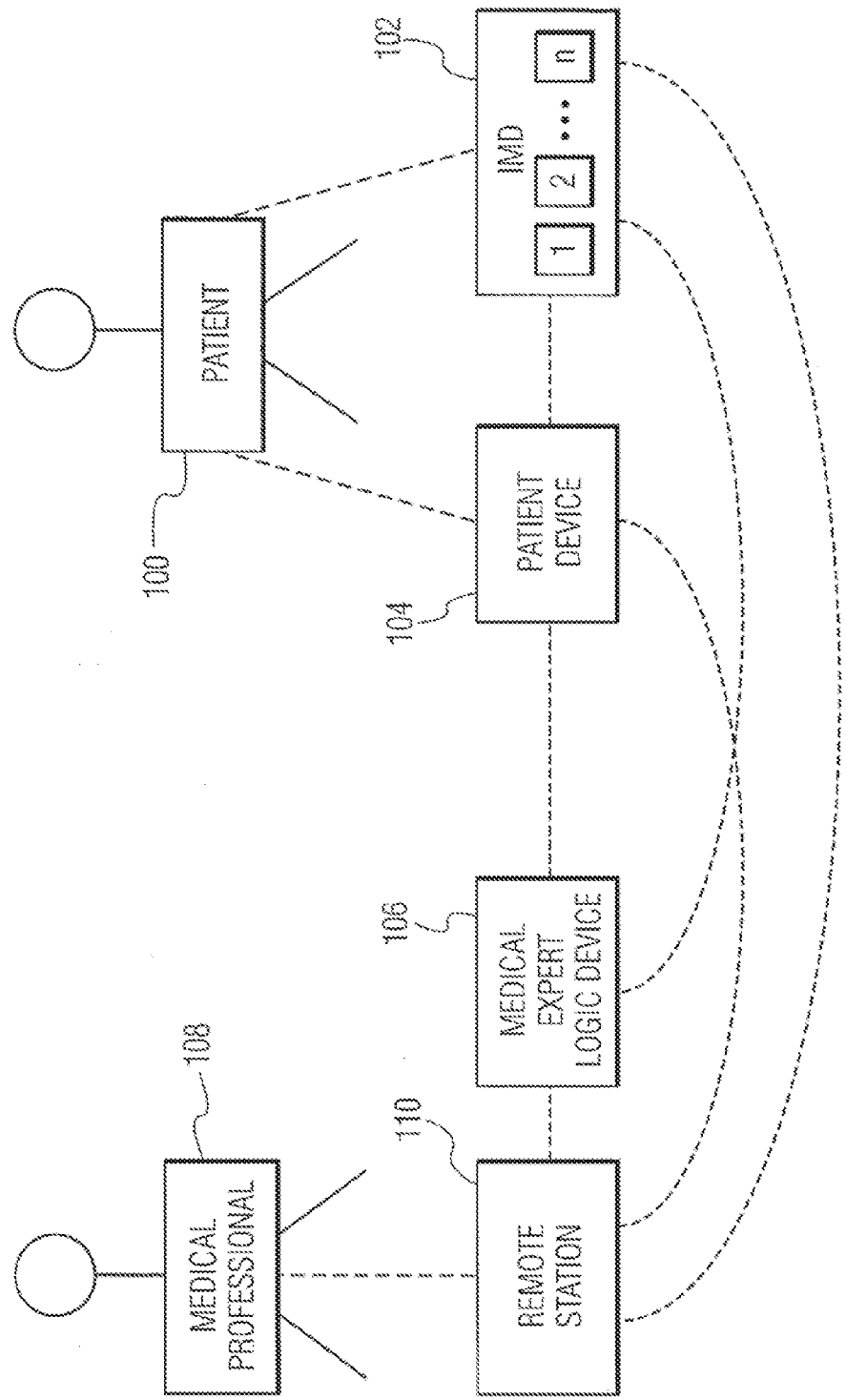
FIG. 1A is a block diagram showing system architectures for a system which links an IMD and one or more of a patient, a patient device, a medical expert device, and a central station staffed by a medical professional.

FIG. 1A shows a schematic representation of an IMD system which includes a patient 100 with an IMD 102, and additional potentially interacting system devices and persons. The broken lines in the figure indicate that (a) each of (i) the IMD, (ii) the patient device 104, (iii) a medical expert logic device 106, and (iv) a medical professional 108 in a remote station 110, may communicate with each other; and (b) the patient may communicate (i) directly, with the patient device, and (ii) via the patient device, with each of the IMD, the medical expert logic device and the medical professional. The broken line between the IMD and the patient indicates that the IMD is implanted in the patient, provides treatment to the patient, may receive physiologic information about the patient through sensors and may directly notify the patient of certain events by either emitting a tone, or producing a vibrating motion. The IMD may be an implantable defibrillator, a pacemaker, an insulin pump, an implantable drug infusion pump in general, a left ventricular assist device, an implantable heart, a brain or nerve stimulating device, a device for controlling blood pressure by stimulating carotid artery receptors, and in general, a device which is similar to that shown in FIG. 1 of U.S. Patent Application 20080300659 by Matos. The IMD in the figure contains boxes which indicate the possibility of running more than one simultaneous operating algorithm (discussed hereinbelow in conjunction with FIG. 7), but IMDs which run a single algorithm are applicable as well.

The IMD may function autonomously. Alternatively, it may be controlled by the patient device, the patient, the M.E. device or the medical professional. There may be circumstances where control by one of these agents is advantageous over autonomous control by the IMD or control by the other agents. Examples are given and discussed hereinbelow in conjunction with FIGS. 78-82. Control of the IMD may be real time (e.g. the MP causes an ICD to provide antitachycardia pacing ("ATP")), or may be via a command which affects the future performance of the IMD (e.g. reprogramming the IMD to allow patient control under certain circumstances).

The patient device (further described hereinbelow in conjunction with FIG. 6) allows:

(a) the patient, under certain circumstances, to control some or all functions of the IMD;

(b) the IMD to provide information to the patient, including information which may be useful for the patient to control the IMD;

(c) the patient to communicate with the M.E. device;

(d) the patient to communicate with the MP;

(e) any of the IMD, the patient device, the M.E. device or the MP to obtain information about the patient (either physiologic or cognitive), which facilitates the control of the IMD; and (f) control of the IMD by the patient device.

The M.E. device is an automated device for providing expert medical guidance. The advantage of the M.E. device over the logic circuits of the IMD and/or the patient device, is the ability to draw on a large database of information which may be useful for decision making. The M.E. device may have a collegial relationship with the MP, in which the device and the human MP compare evaluations and potential therapeutic plans. The M.E. device may also be used to evaluate experimental/investigational algorithms, and to evaluate and develop neural network-based approaches. It is further discussed hereinbelow in conjunction with FIG. 12, and in other sections.

The MP, a human medical professional with expertise in the management of the IMD and of the condition which it treats, may access the information provided by (a) the IMD, (b) the patient, (c) the patient device, and (d) the M.E. device; and, if he chooses to, may provide control signals to the IMD. Alternatively the MP may designate one of the other entities (i.e. the M.E. device, the patient device, or the patient) as the appropriate source of control, or may decide that the IMD should be the source of control. Some system architectures do not have an MP; Still other architectures include the MP on a selective basis, i.e. when certain medical states occur, the MP is notified and is thereby invited to participate. The MP may be (a) located in a central station which controls many IMDs, or (b) located in a peripheral station (as described in U.S. patent application 20070043585 by Matos), and referred. to by a centrally located MP, by a centrally located administrator, or by an automated call referral network. The MP may be the patient's physician, another physician, or anon-physician.

Figure 1B:
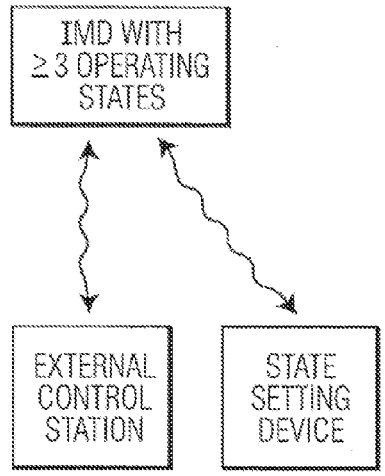
FIG. 1B is a block diagram showing a system architecture for a system with an IMD with 3 or more operating states, an external control station and a state setting device.
Figure 1C:
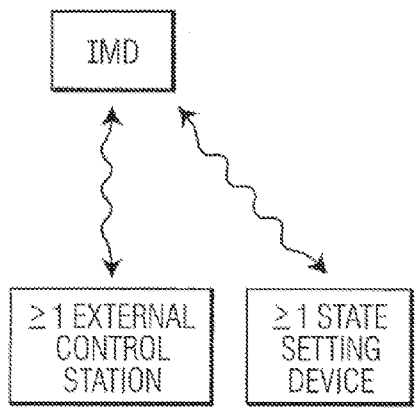
FIG. 1C is a block diagram showing a system architecture for a system with an IMD, at least one external control station and at least one state setting device.
Figure 1D:
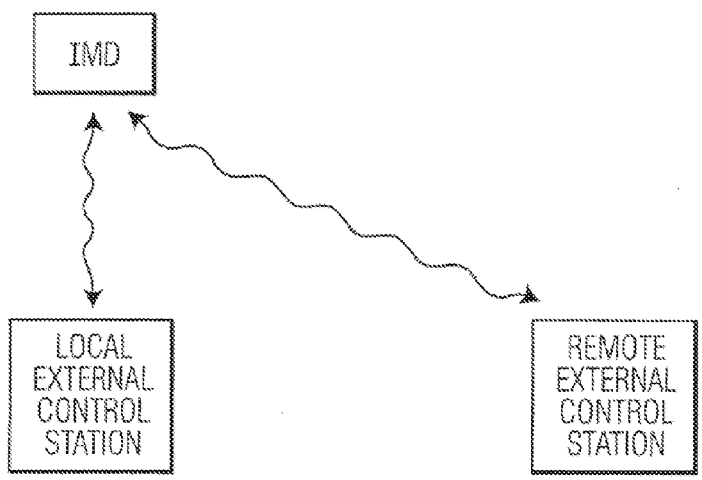
FIG. 1D is a block diagram showing a system architecture for a system with an IMD, a local external control station and a remote external control station.
Figure 1E:
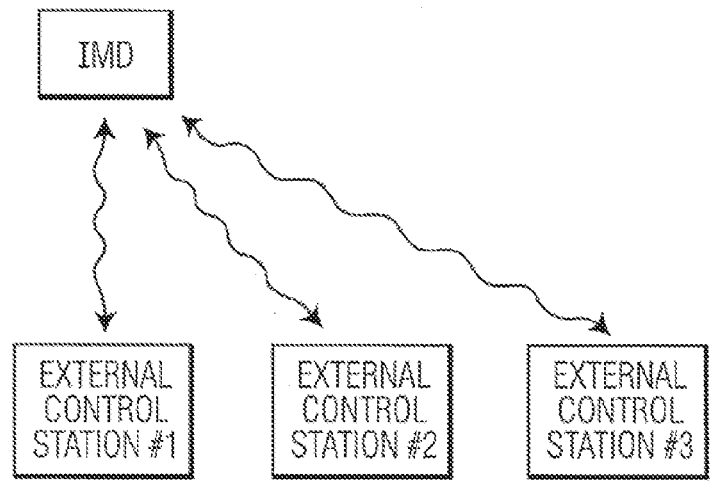
FIG. 1E is a block diagram showing a system architecture for a system with an IMD, and three external control stations.
Figure 1F:
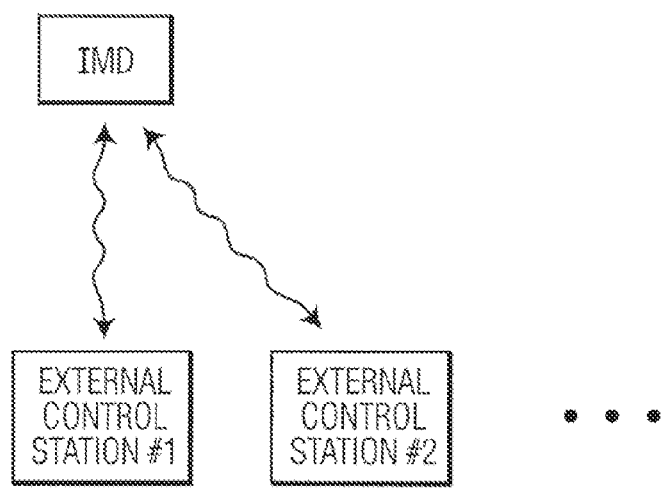
FIG. 1F is a block diagram showing a system architecture for a system with an IMD, and at least two external control stations.

FIGS. 1B to 1F show a variety of system and device architectures constructed from an IMD, and control stations and state setting devices. FIG. 1B shows an IMD with 3 or more operating states, and external control station and a state setting device for setting the operating state of the IMD. The wavy two-way arrows indicate communication between the devices linked by the arrows. FIG. 1C shows a system with an IMD, at least one external control station and at least one state setting device. FIG. 1D shows an IMD with a local external station, and a remote external station. FIG. 1E shows an IMD with three external control stations. FIG. 1F shows an IMD with at least two external control stations, with the three dots indicating the possibility of any number of additional stations.

2.0 Hardware

FIG. 2 shows a patient device 200 communicating (a) wirelessly with an IMD 202 and (b) either (i) wirelessly or (ii) by a connection (broken line) which may have both wired and wireless elements, with a remote station 204. Transmitting and receiving device #1 206 in the IMD communicates with transmitting and receiving device (hereinafter "T/R") #4 208 in the patient device, and T/R #3 210 in the patient device communicates with T/R #2 212 in the remote station. T/R #2 and T/R #3 may include apparatus to allow each of wired and wireless communications. T/R #3 and T/R #4 are linked, so that the patient device as configured in FIG. 2 may also serve as a relay unit for conveying information between the IMD and the remote station.

The input devices 214 and 216 allow for:

(a) the input of the unit by the patient with one or more of text, voice, and video; for purposes of inputting patient commands, patient requests for information and for patient communication with the MP and the M.E. device;

(b) determining patient availability, if patient management of the IMD is required;

(c) the patient to input the unit if a patient evaluation is necessary in order to properly proceed with IMD management; and (d) another person to input the unit, e.g. an arriving emergency medical person or any other on-scene assisting person. As shown in the figure, input device(s) A 214 is linked to T/R #3 for communication with the remote station and input device(s) B 216 is linked to T/R #4 for communication with the IMD; patient device configurations in which one set of input devices is linked to both T/R #3 and T/R #4 are possible as well. In addition, the input devices are linked to the processors, memory and control units 218 to allow for the aforementioned patient control and patient evaluation functions.

One or more sensors 220, for detection of and inputting patient-related physiologic information may be attached directly to the patient, or may be in proximity to the patient without direct attachment. They input the processor, memory and control unit, and are the subject of FIG. 5 and the associated specification.

The output device(s) 222 allow for the presentation of the patient with one or more of text, voice, and video; for purposes of:

(a) allowing the patient to obtain information from the IMD and or the patient device itself, for purposes of management decision making by the patient;

(b) patient communication with the MP;

(c) determining patient availability, if patient management of the IMD is required;

(d) the patient obtaining management information from the M.E. device;

(e) patient testing (cognitive or otherwise) during the process of patient evaluation; and (f) another on-scene person operating the unit.

Figure 6:
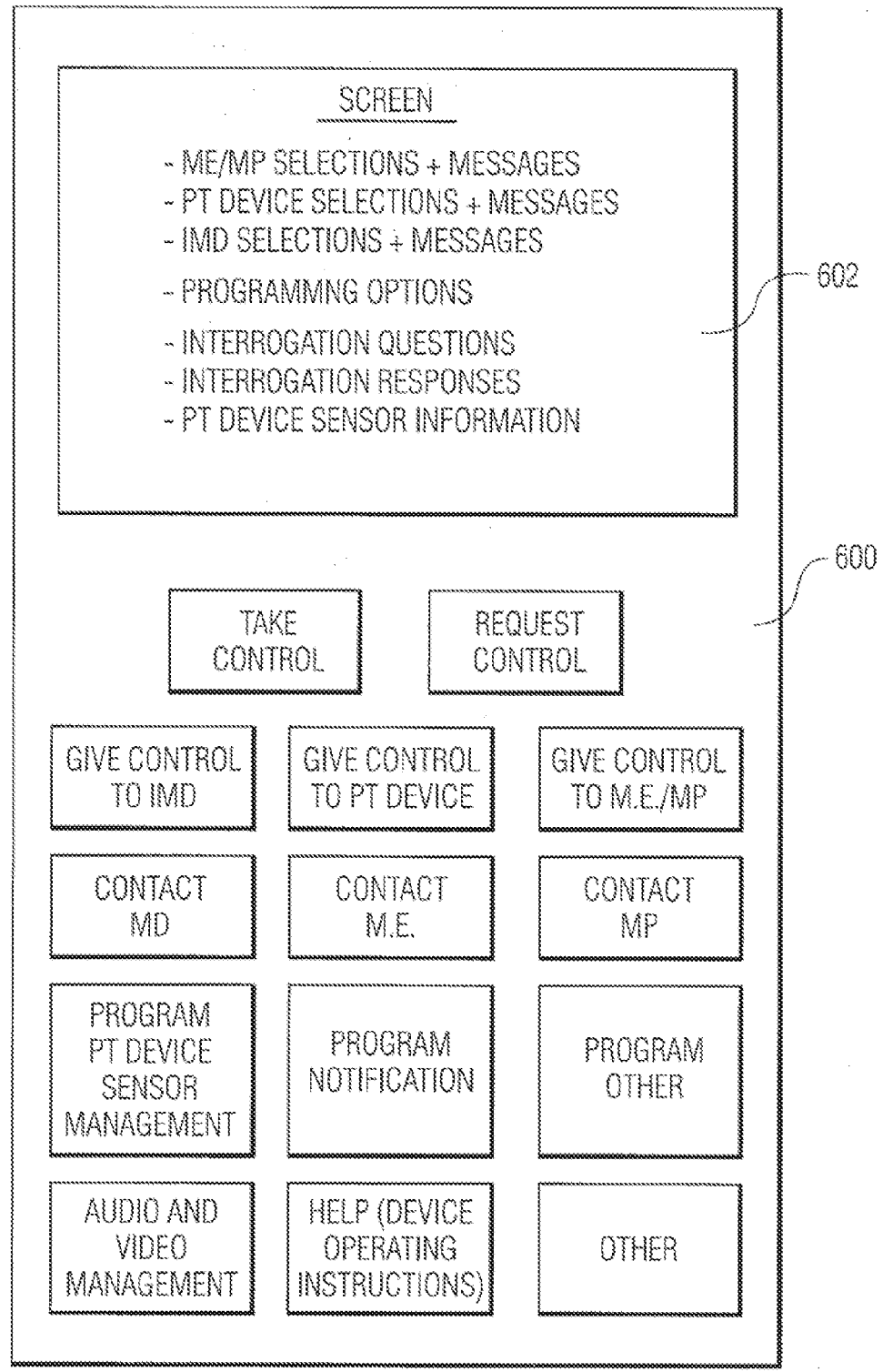
FIG. 6 is a representational diagram of a patient communications device.

The processor, memory and control unit:

(a) processes patient sensor information (see FIGS. 5, 17, and 19-21);

(b) performs and processes patient physiologic and cognitive evaluations (discussed hereinbelow in conjunction with FIG. 18);

(c) may notify the patient of patient device-detected physiologic conditions;

(d) may process information from the IMD concerning patient events and may blend this information with patient sensor information;

(e) processes patient commands (see FIG. 6);

(f) determines patient availability, if patient management of the IMD is required (discussed in conjunction with FIGS. 29-56D);

(g) may participates in the selection of a control entity, and may cause or process the enabling/disabling of patient access to control of the IMD system (also discussed in conjunction with FIGS. 29-56D);

(h) processes requests for patient sensor information;

(i) processes commands for sensor information processing

G) controls patient device output displays;

(k) may process IMD power reserve information and use the information for planning [i] communications with the IMD and [ii] system management in general;

(l) controls each of T/R #3, T/R #4 and the patient device-based output devices;

(m) stores software and firmware necessary to operate the patient device system and associated patient sensors, stores patient event related information, stores hierarchy/patient access information (see FIGS. 14, 15 and 56B-56D); stores passwords and/or access codes, stores encryption/decryption information; and (n) may perform other computational functions necessary to maintain the patient device system.

Figure 3A:
FIGS. 3A-3D are block diagrams showing possible system architectures in IMD systems with a patient device and one or more communication relay units.
Figure 3B:
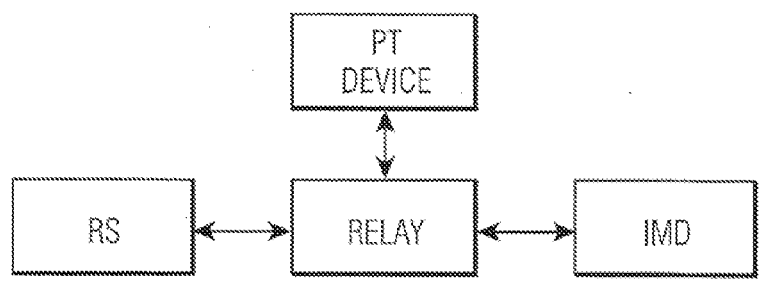
Figure 3C:
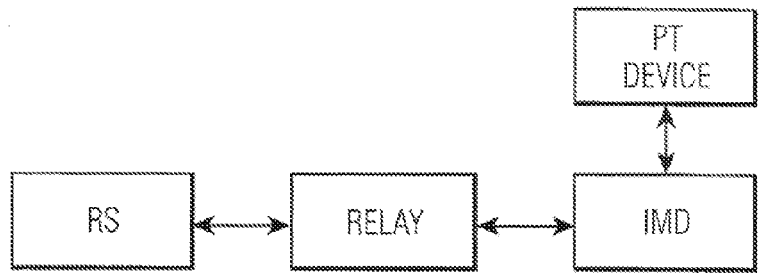
Figure 3D:
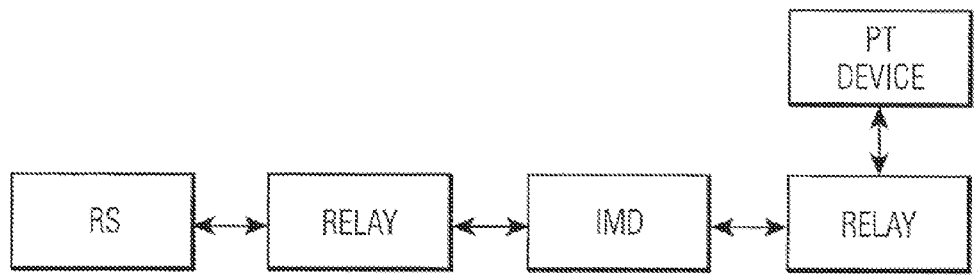

FIGS. 3A-3D show four ways in which the patient device may link to a system with an IMD, a remote station ("RS") and one or more relay units. In FIG. 3A, a single item performs both (a) the management functions listed hereinabove in conjunction with FIG. 2, and (b) the communication relay function, linking the IMD with the remote station. FIG. 3B shows a configuration in which a separate unit performs the relay function for communications among each of (a) the IMD, (b) the patient device, and (c) the remote station. FIG. 3C shows a system configuration in which the patient device communicates directly with the IMD, and in which the IMD communicates with the remote station via a separate relay device. In this configuration, the patient device may communicate with the remote station through the IMD. FIG. 3D shows a system architecture similar to that of FIG. 3C, except that the patient device communicates with the IMD through a separate communications relay device. Many other arrangements of relay devices are possible, including configurations in which (a) one or more of the entities communicate through a series of relay devices and in which (b) one or more of the entities communicate over a route that changes from time to time. Other system architectures which accomplish the same goals—that is, robust communication among the patient/patient device, the IMD and the remote station—will be obvious to those skilled in the art.

Figure 4A:
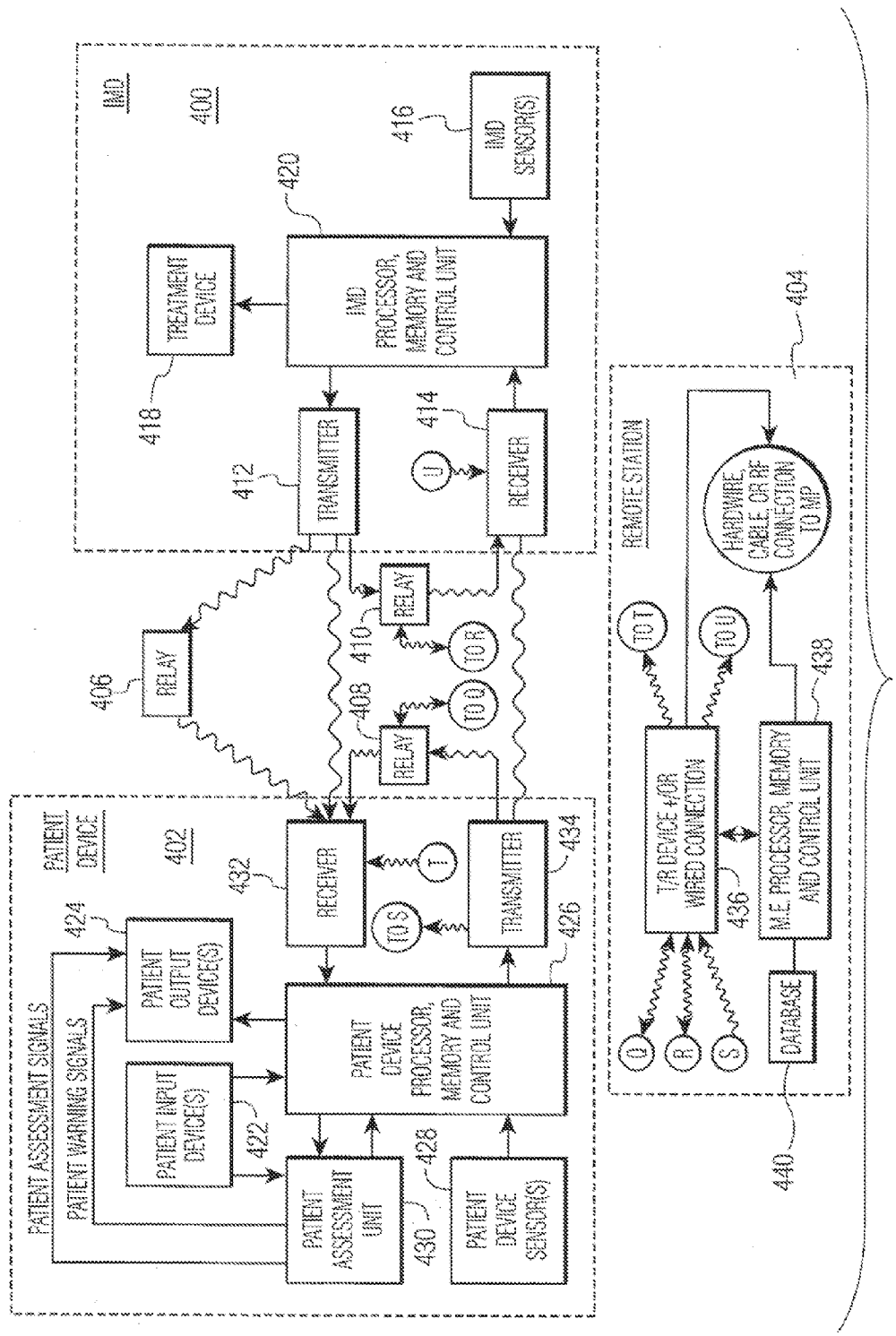
FIG. 4A is a block diagram showing module and system architecture for a system which includes an IMD, a patient device and a medical expert device.

FIG. 4A shows a detailed block diagram of one configuration of the invention, in which the (a) IMD 400, (b) the patient device 402 and (c) the remote station 404 are shown, as are relay units 406, 408, 410 which facilitate the communication among (a)-(c). The IMD device, showing a generalized IMD system (similar to that of FIG. 1 of U.S. Patent Application No. US/2008/0300659), includes a transmitter 412 and receiver 414 for communication with each other unit in the IMD-system, sensors 416 for inputting physiologic information, a treatment device 418, and processor, memory and control hardware 420.

The patient device in FIG. 4A shows a configuration with a single receiver 432 and transmitter 434. The patient device may communicate (a) directly with the IMD, (b) via one or more relay devices with the IMD, (c) directly with the remote station, (d) via one or more relay devices with the remote station. The IMD communicates with the remote station through one or more relay units. In one embodiment of the invention, it may also receive signals directly from the remote station.

Besides communications elements, the patient device also includes: the patient input device(s) 422, patient output device(s) 424, the processor, memory and control unit 426, and sensor(s) 428 (Patient device sensors are further discussed in conjunction with FIG. 5, hereinbelow), each as described hereinabove in conjunction with FIG. 2. FIG. 4A additionally shows apparatus in the patient device which allows for patient cognitive assessment. A patient assessment unit 430 causes one or more patient output devices 424 to present the patient with one or more of (a) questions or other prompts intended to assess patient cognitive function and (b) any system messages, warning signals, and notifications. The patient's response to each of these is inputted via one or more patient input devices 422 and the response is assessed by the assessment unit (see also FIGS. 9, 10, 18 and 19), and communicated to the processor, memory and control unit 426.

The remote station 404 includes (a) medical expert device components including [i] a database 440 for storing information useful for managing the IMD system, and [ii] a processor, memory and control unit 438 (see further discussion hereinbelow in conjunction with FIG. 12); (b) a T/R device and/or wired connection 436 for communicating with one or more of the other entities in the IMD system; and (c) a link to the medical professional which may involve a hard-wired connection, a cable connection, a wireless link or combinations of these.

FIG. 4B shows the exchange of signals within devices and among devices, comprising a system with an IMD 450, at least one external control station 470, and at least one external command station 476. Internal medical data 462 is sensed by first sensor circuit 454, which amplifies, digitizes and optimizes the internal medical data in a manner known to those skilled in the art. A sensor circuit output signal outputs via sensor circuit output 456, and goes to first processor 458. This processor generates internal control signal 460 in response to the sensor circuit output signal. The processor outputs a treatment device signal for controlling medical treatment device 452 in response to one of (a) the internal control signal and/or (b) one of the received external control signals. The external control signal(s) and the hierarchy-setting signal are both received by 464, transmitting/receiving (T/R) device #1. This T/R device also transmits patient information. Regarding element 464 and elsewhere hereinabove and hereinbelow, identical names may be utilized for an information carrying signal before it enters and after it exits an electronic circuit or device, it is to be understood that the amplitude, modulation, formatting, encoding and numerous other features of the signal may change during such transit. For reasons of clarity, an "X signal" is intended to mean a signal representing X information, and is not intended to specify the nature of the signal protocol, which will change as the signal is transmitted and/or conveyed from one device or structure to the next.

470 represents one or more external control stations, P in number. Each of the P external stations has a T/R device 474 for communication with T/R #1 of the IMD. The external station receives patient information (signal representing internal medical data), and provides, if appropriate, external control signals. A processor in each station 472, analyzes incoming information and generates, when appropriate, control signals.

476 represents one or more external command stations, Q in number. Each of the Q external stations has a transmitting or TiR device 478 for communication with T/R #1 of the IMD. The command station provides, if appropriate, hierarchy-setting signals for controlling the priority of each potential control signal for controlling the treatment device. A processor in each command station generates, when appropriate, command signals.

Figure 5:
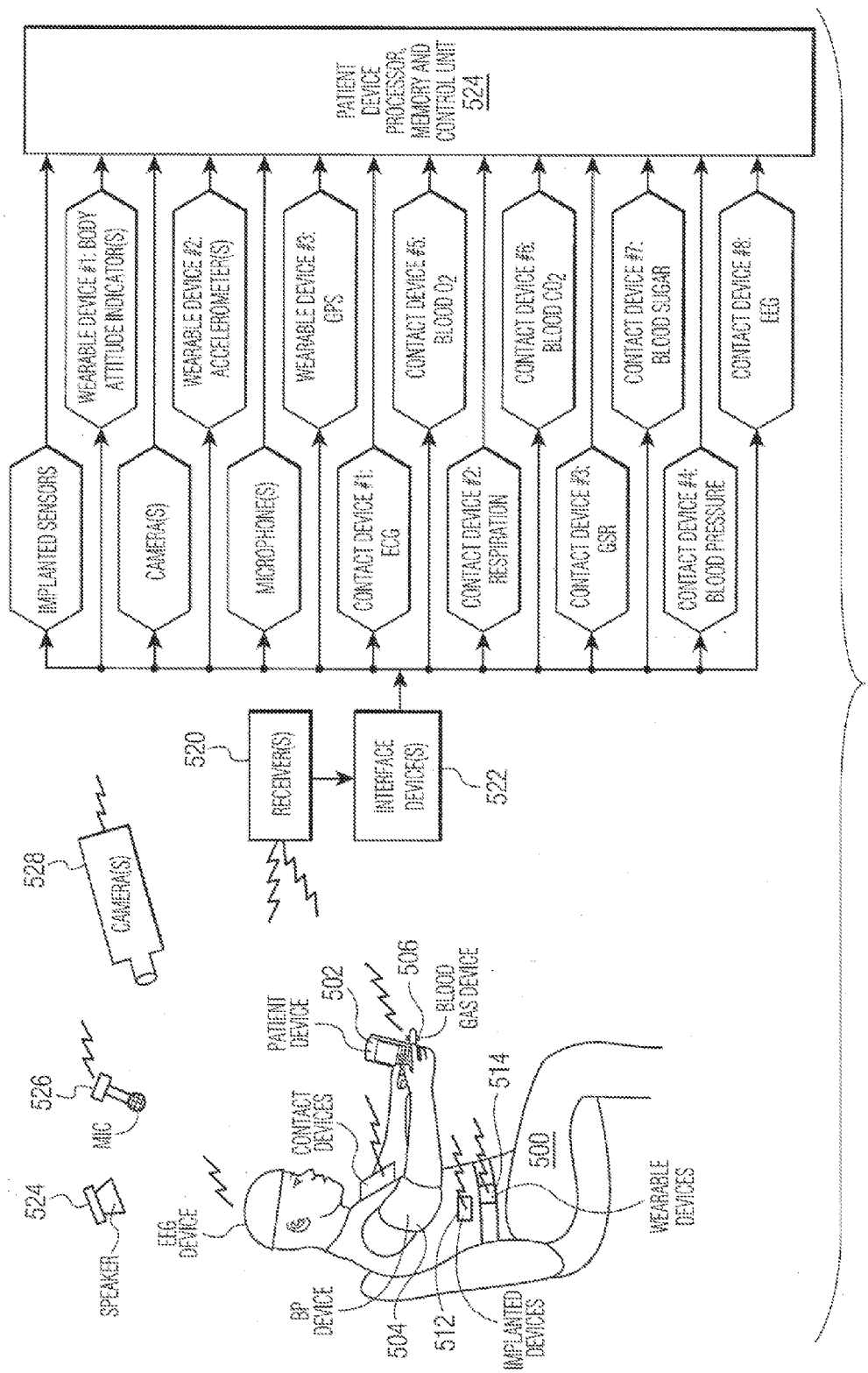
FIG. 5 is a representational diagram showing a patient with one or more IMDs and an array of sensors and a communication device for accessing the IMD system.

FIG. 5 shows the relationship between a patient 500, the patient device 502, sensors (which may be [a] implanted, [b] attached to the patient, and [c] in the vicinity of the patient) and other communication apparatus which is in the vicinity of the patient. The patient is holding the communication device (see FIG. 6). A speaker 524 and microphone 526 may facilitate communications when the patient is in a location that he/she frequents, e.g. the home or workplace; Alternatively these may be within the patient device or may be part of a wearable earphone/microphone. The camera(s) 528 may be used (a) for communications with the MP, (b) to assess patient availability (i.e. to assume a management role [discussed extensively in conjunction with FIGS. 29-56B]), (c) to assess whether the patient has had a syncopal episode (see FIGS. 10 and 21) and (d) to assist in the assessment of patient cognitive function.

The patient may continuously or intermittently be attached to one or more devices for obtaining physiologic information including (a) a blood pressure cuff 504 or other blood pressure sensing device, (b) a device for sensing one or more blood gases 506 (i.e. oxygen and/or carbon dioxide), (c) two or more contact devices for sensing the electrocardiogram, (d) a contact device for sensing respiratory motion (which may also be deduced from attached electrodes for sensing the electrocardiogram), (e) a contact device for sensing skin resistance, [All contact devices have been indicated by a single element 508 in the figure, without intending to imply that a single device performs all of the aforementioned sensing function.], (f) a contact device for sensing glucose (which may also be sensed by an implanted device) and (g) a device for sensing the electroencephalogram 510.

The patient has at least one implanted device 512, which is the IMD of the system discussed herein. The patient may have one or more other implanted devices which either (a) augment the functioning of the IMD system (e.g. [i] one or more implanted sensors which communicate with the system; [ii] one or more devices to facilitate communications with the IMD), or (b) serve other therapeutic needs of the same patient; For example, the patient may have an ICD and an implanted drug infusion pump. In such a circumstance: (a) both devices may be remotely controllable, each through a separate IMD control system, (b) both devices may be remotely controllable, each through the same IMD control system, (c) only one of the devices may be remotely controllable.

The patient's wearable device 514 may (a) serve as a communications relay unit as described in U.S. Provisional Patent Application 61/204,957, (b) be used for sensing either patient respiration and/or (c) be used for sensing patient attitude, motion or GPS coordinates. Acetone and other ketone compounds may be sensed by either a wearable or contact device.

Though any of the aforementioned sensor devices may input the patient device through a hardwired connection or an infrared connection, in a preferred embodiment of the invention, the inputs will be via a short range wireless connection, likely radiofrequency. Signals from the sensor devices input the patient device receiver(s) 520, and via an interface device 522 supply information to the patient device processor, memory and control unit 524. The 14 hexagonal shapes each indicate the movement of one type of sensor signal from the interface device to the patient device processor, memory and control unit, including:

(a) information from implanted sensors;
(b) video information;
(c) audio information;
(d) ECG information;
(e) (lung) ventilation information;
(f) skin resistance;
(g) blood pressure;
(h) blood oxygen content;
(i) blood carbon dioxide content;
(j) blood sugar (glucose);
(k) electroencephalogram information;
(l) body attitude information;
(m) information from one or more accelerometers; and
(n) GPS information.

The further processing of the aforementioned information is further discussed in conjunction with FIGS. 9, 10 and others hereinabove and below.

FIG. 6 shows a representational view of a patient device 600. Among the items which the patient may view on the screen 602 are:

(a) messages from any entity within the system including the IMD, the patient device, the M.E. device or the MP;
(b) requests to select an IMD-system controller (see FIGS. 31, 36, 40, 43, and 47);
(c) requests to take control of the IMD) system (see FIGS. 29-43 and 46-56B);
(d) programming choices and information which may be helpful in selecting among programming options;
(e) confirmation signals for commands sent by the patient;
(f) sensor information from the IMD;
(g) sensor information from the patient device (see FIGS. 8 and 9);
(h) patient interrogation questions and possible response choices;
(i) currently programmed hierarchical structure of the system (see FIGS. 14 and 56B);
(j) currently programmed patient notification criteria (see FIGS. 53-56B and 71A-76C);
(k) programming choices made by entities other than the patient;
(l) patient device and IMD battery reserve information; and
(m) help menus, informational and instructional screens.

Patient input to the device may be via a touch sensitive screen (which may have virtual "buttons"), actual "buttons" which are switches, or both.

Among possible patient controls (and shown in the figure) are:

(a) buttons which allow the patient (if given the option) to give control to the MP, the M.E. device (previous two shown as one button but either choice is possible), the patient device, the IMD or (if given the option) himself/herself;
(b) a button which allows the patient to request control (see FIG. 53);
(c) buttons which allow the patient to contact the MP, the M.E. device or the patient's MD(s);
(d) a button which allows the programming of patient device sensor management; Touching this button may lead to display of screens such as are shown in FIGS. 17-21 [which may be screens for the professional person setting up the patient environment, and which the patient may be locked out of];
(e) a button which allows the programming of patient notification; This may also be something that the patient is locked out of and is handled by the MP or the patient's MI) from a screen like that of FIG. 13; On the other hand, the patient may intermittently (or continuously) wish not to participate in IMD-system management, in which case he/she could indicate this choice when appropriate;
(f) audio and video management;
(g) access to help and instructional information; and
(h) access to a variety of other programming options, communication and informational options.

If the device in FIG. 6 is operative to also function as a conventional cellular telephone, then, in addition to the screen and touch button features discussed hereinabove, the device may also have screen and touch button features that allow cellular telephone functionality.

Figure 7A:
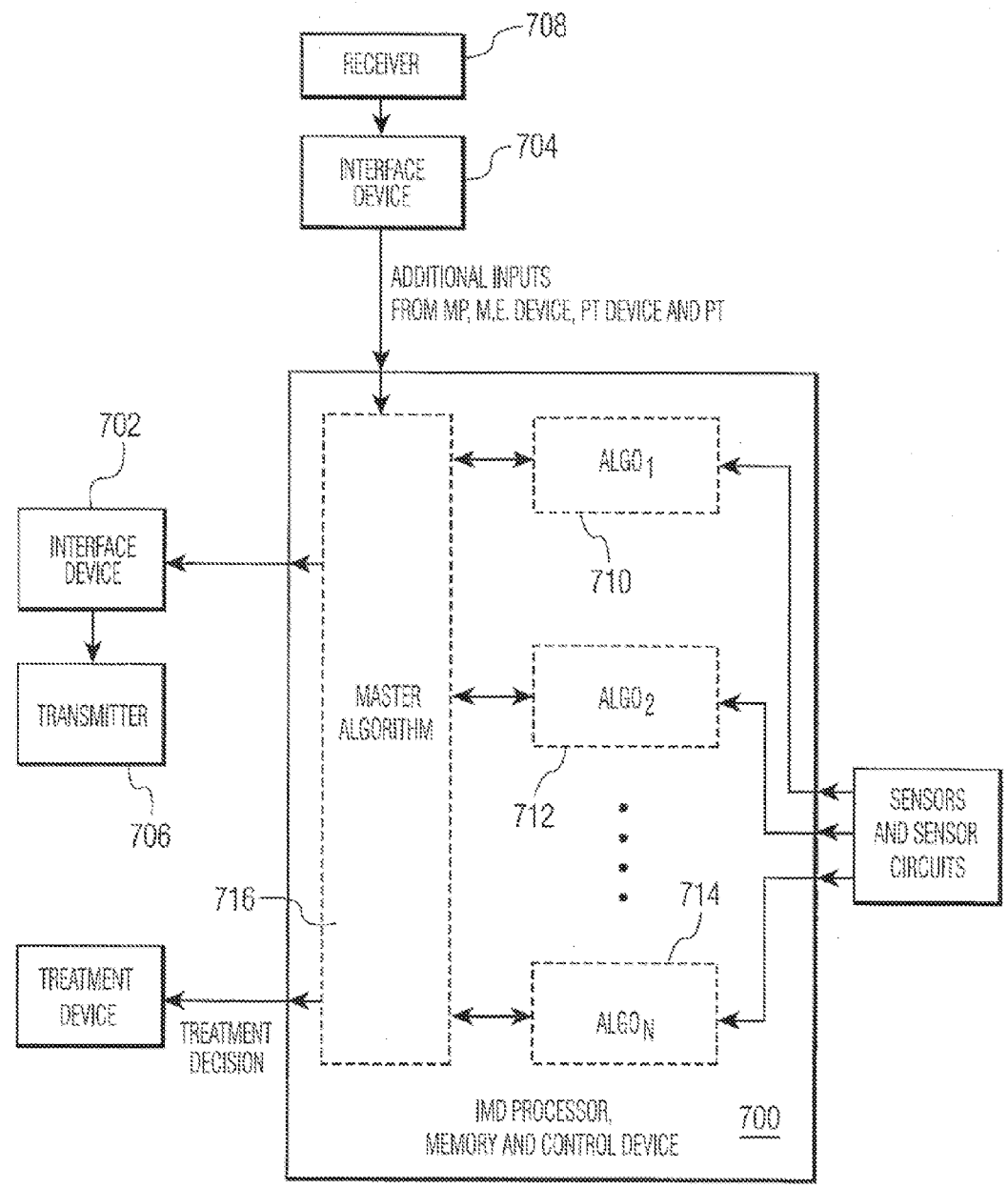
FIG. 7A is a block diagram of an iMD which can run multiple parallel algorithms to make a treatment determination.

FIG. 7A shows one feature of the invention, an IMD which may run more than one treatment determining algorithm. The IMD in the figure has a basic structure similar to that of the IMD shown in FIG. 4A. Interface devices 702 and 704 between (i) the processor, memory and control unit and (ii) each of the transmitter 706 and the receiver 708, are for purposes of encoding/decoding, encrypting/decrypting and any further signal processing needed to assure the compatibility of the units adjacent to the interface device. The receiver allows for the input of patient device sensor information, of patient cognitive information of M.E. device information and of MP recommendations.

The IMD processor, memory and control unit 700 shown in FIG. 7 includes three broken line rectangles labeled ALGO1 (element 7101), ALGO2 (element 712) and . . . ALGOn (element 714), intended to indicate the running of two or more different algorithms for the processing of patient data leading to a treatment-related decision by the IMD. The algorithms may:

(a) be similar to those known in the art, (e.g. an ICD algorithm which looks at rate, rate stability, electrogrammorphology, sudden onset, etc.);

(b) entail other transformations of IMD sensor information;

(c) blend the information from multiple IMD sensors;

(d) blend IMD sensor information with patient historical information;

(e) blend IMD sensor information with sensor information from the patient device (including blending/considering patient cognitive information);

(f) blend IMD sensor information with information from the M.E. device;

(g) blend an MP recommendation, if it is based on a not-total level of certainty about the diagnosis or optimum treatment;

(h) blend a patient recommendation with other information;

(i) entail neural network style learning features; and (j) use combinations of (a)-(i).

The recommendations of each of algorithms 1, 2 . . . n may be a yes/no decision, a numeric value indicating a treatment device setting, a numeric value indicating a level of certainty of a correct result, a list of options ranked according to preference, or a list of options with weighted rankings (e.g. an ICD algorithm which distributes 100 points among treatment options and, for a given event recommends:

shock=81 points anti-tachycardia pacing=17 points continue observation=2 points).

The algorithm outputs are inputted into a master algorithm 716 which processes the outputs of each of the individual treatment recommending algorithms 1, 2 . . . n (See details of such processing in FIGS. 57 and 58 and the associated specification). The value of a list of options (whether ranked or weighted), if available, is that it may facilitate the master algorithm's reaching a consensus among non-identical recommendations from the individual contributing algorithms 1, 2 . . . n.

With the availability of new management information at a later time, the MP or system administrator may choose to update/modify any one or more of algorithms 1, 2 . . . n, or the master algorithm, which may be done if/when access is permitted, via the IMD receiver.

The algorithms may run on the same processor or different processors. They may run serially or in parallel. Numerous variations in their format will be obvious to those skilled in the art.

IMDs which employ only a single treatment algorithm are possible, and are compatible with every other aspect of the inventions described herein.

Figure 7B:
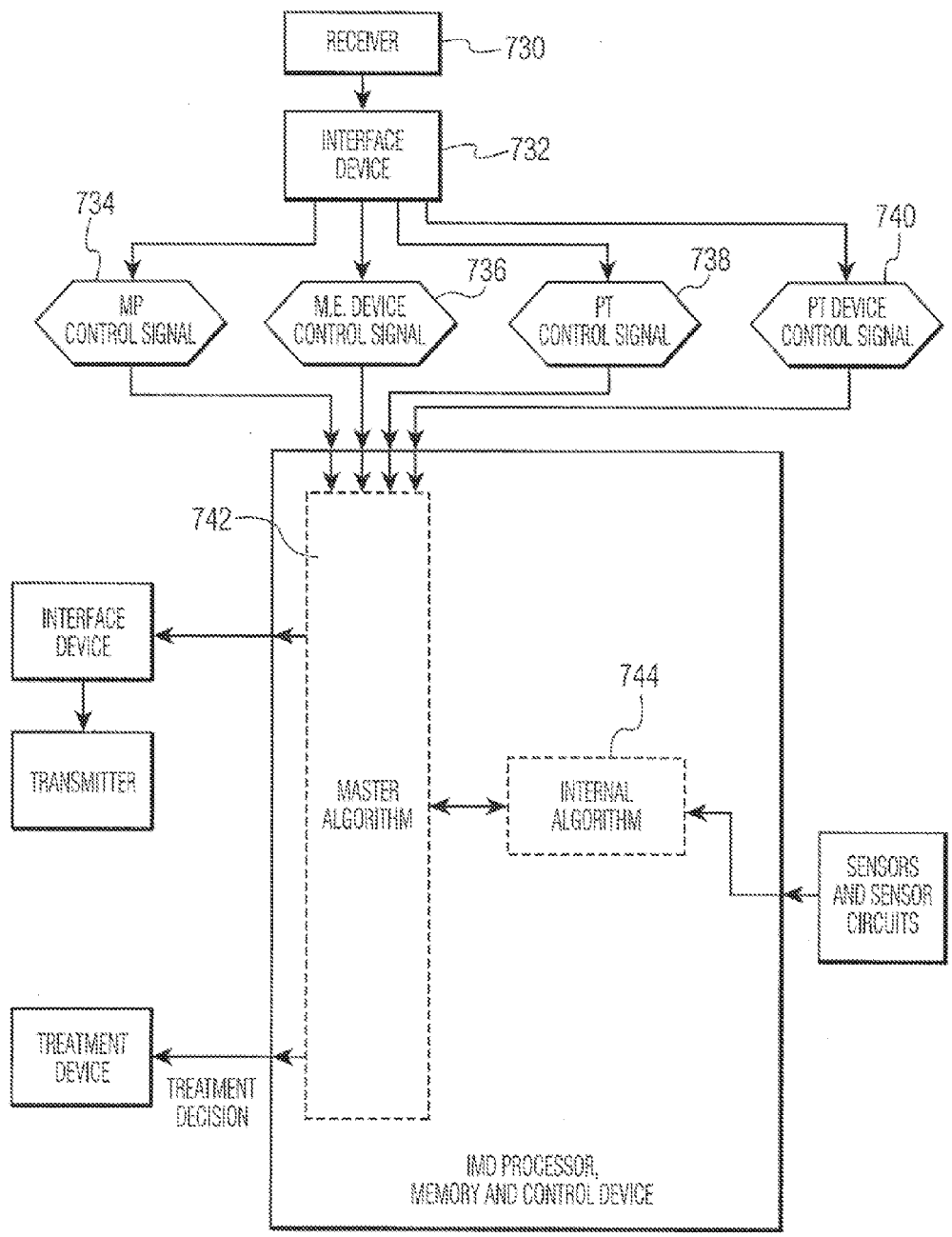
FIG. 7B is a block diagram of an iMD which can run an algorithm which is inputted by control signals from four different external sources and one internal source.

FIG. 7B shows an arrangement with multiple sources of control signals inputting into a master IMD algorithm 742. These include the treatment choice of the device internal algorithm 744 (this treatment choice reflected by the internal control signal 460 of FIG. 4B) based on information coming from device sensors among other things, a medical professional control signal 734, a patient control signal 738, and control signals from a medical expert device 736 and a patient device 740. These latter four signals are received by IMD receiver 730, and processed by interface device 732.

FIGS. 8-11 show block diagrams of each of the IMD and patient device transmitters and receivers, with a hexagonal box indicating each of the signal types that may be trafficked.

Figure 8:
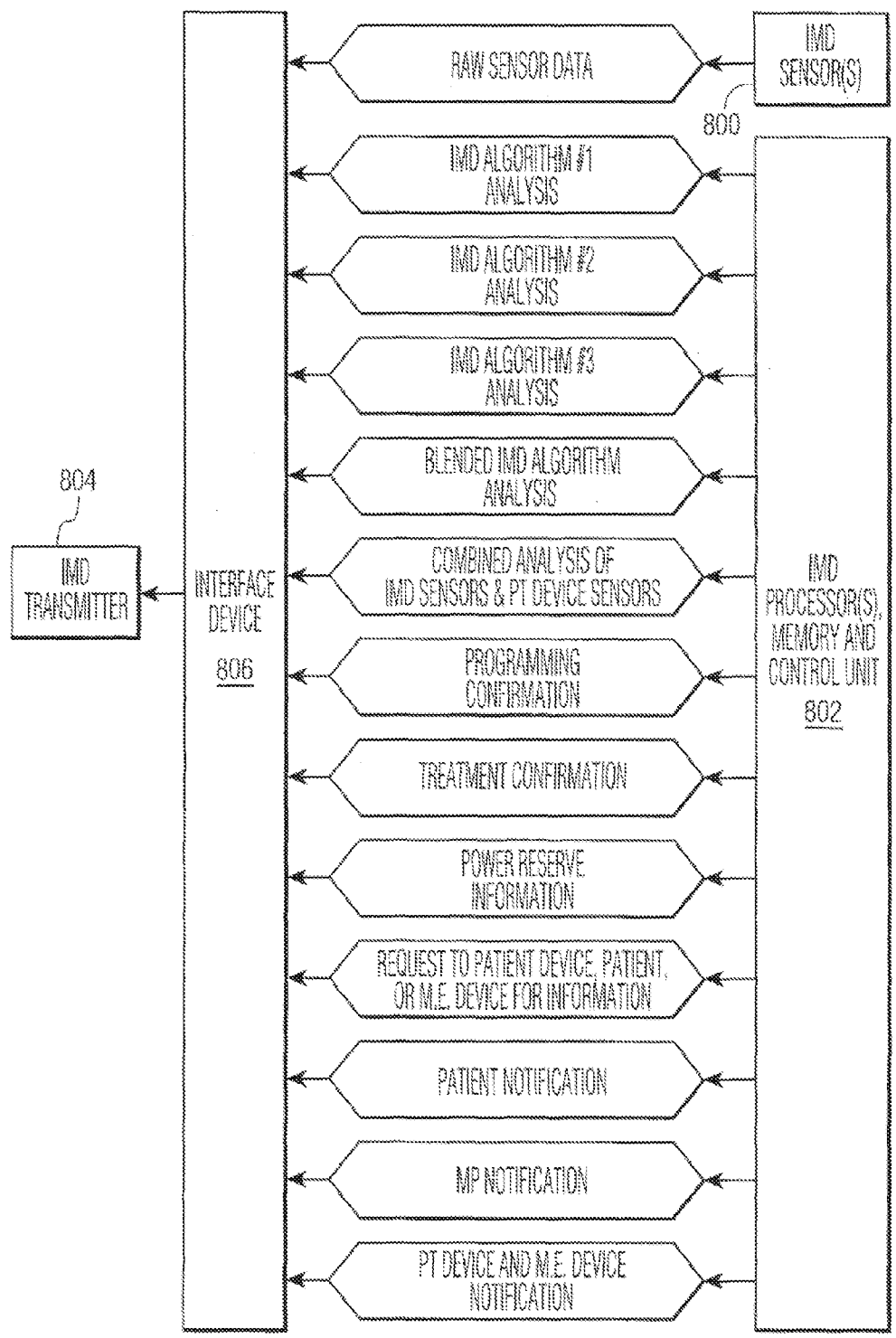
FIG. 8 is a block diagram showing information which may be transmitted by the IMD transmitter.

FIG. 8 shows signals transmitted by the IMD. Except for unprocessed sensor data coming from the IMD sensors 800, each other type of signal comes from the IMD processor(s), memory and control unit 802. The signals include:

(a) information indicating the results of the analysis of the IMD treatment algorithm, and if there is more than one such algorithm, information indicating the analysis of each such algorithm. This information may be useful to the MP for decision making. It may also be useful to the patient and/or the patient device, which may have access to additional information to blend with the IMD algorithm analysis. Alternatively, relevant patient and/or patient device information may be sent to the IMD (see FIG. 10) and blended, at the IMD, with the IMD algorithm outputs. The algorithm outputs may also be sent to the M.E. device for archiving, and future analysis, and for use in the formulation of M.E. device treatment instructions or recommendations;

(b) in the case of an IMD which runs multiple treatment algorithms as described in FIG. 7: information indicating the results of the blending of these multiple recommendations by the master algorithm (as discussed in conjunction with FIG. 7);

(c) in a case where the patient device has sent (to the IMD) sensor information with either physiologic information, cognitive information or both: the results of a combined analysis of that information with the IMD) sensor information;

(d) confirmation signals indicating:

(i) that a programming change has been properly executed;

(ii) that a treatment instruction has been properly executed;

(e) power reserve information related to one or more IMD batteries;

(f) requests to the patient, the patient device or the M.E. device for more information for decision making purposes; and (g) notification signals for one or more of:

(i) the patient, (ii) the MP, (iii) the patient device, and (iv) the M.E. device.

Each of the aforementioned signal types is passed to the IMD transmitter 804 via the interface device 806. The latter device has properties similar to those of the interface devices described in conjunction with FIG. 7, hereinabove.

Figure 9:
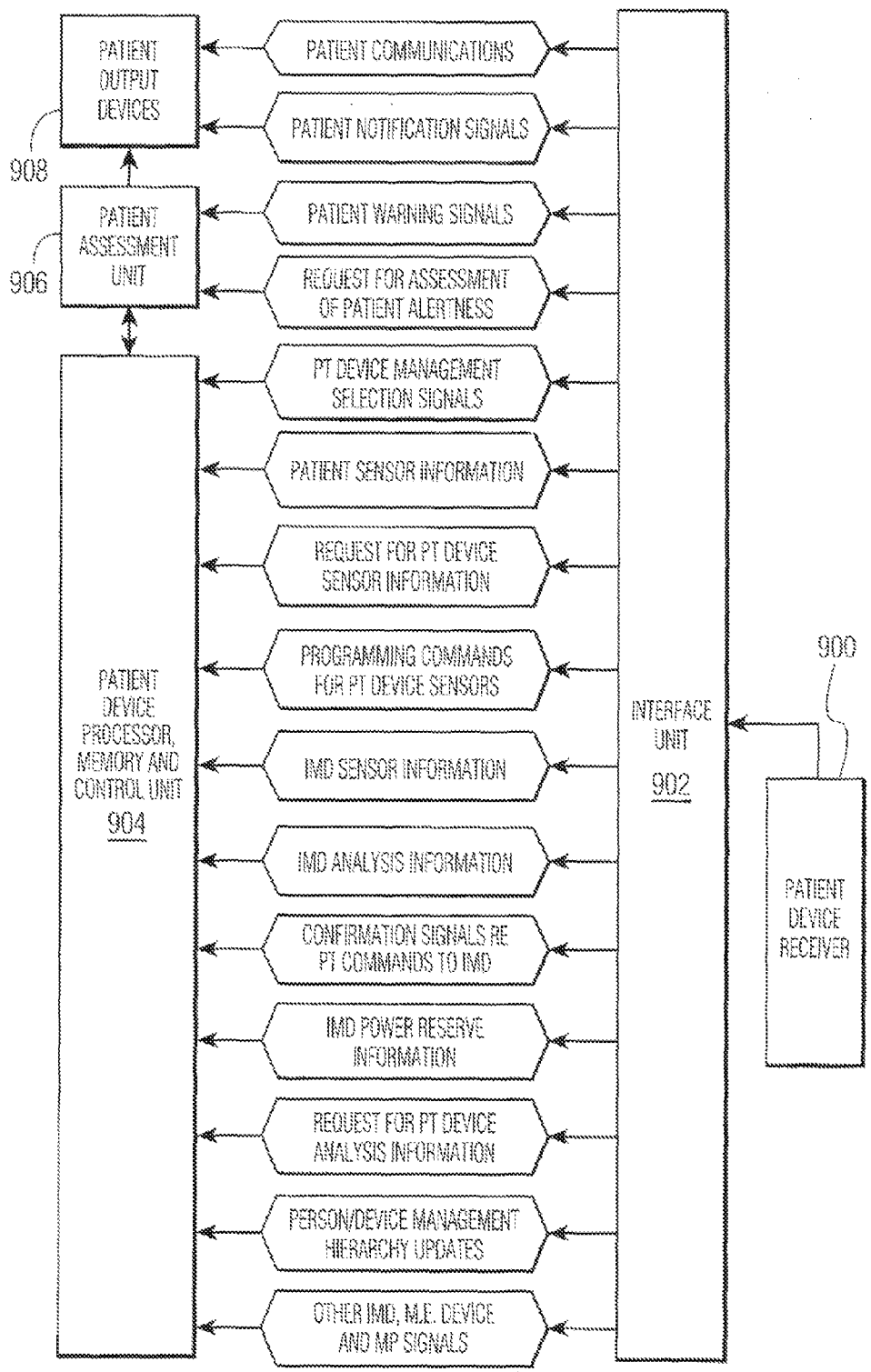
FIG. 9 is a block diagram showing information which may be received by the patient device receiver.

FIG. 9 shows the signal types coming into the patient device receiver 900. The interface unit 902 functions as described in FIGS. 7 and 8. The incoming signals include each of the types of signals discussed in conjunction with the signals outputted by the IMD transmitter (except for signals obviously targeted for other system entities [e.g. "MP Notification"]). In addition, the incoming signals include:

(a) patient sensor information (see FIG. 5);

(b) incoming communication signals during patient-MP exchanges;

(c) requests for assessment of patient alertness or other parameters of the patient cognitive state (as a reflection of [i] the patient's cardiac output, [ii] the patient's metabolic state, and/or [iii] the patient's neurologic condition);

(d) patient warning signals—e.g. of a system or device fault, a communications fault or weakness, or of a patient medical problem of which the patient may be unaware (and which does not require IMD therapy put is detectable by the system). As discussed in conjunction with FIG. 4A, the patient acknowledgment of and/or response to such warning signals may also serve as part of the patient cognitive evaluation;

(e) management selection signals, i.e. (i) signals which indicate that the patient or the patient device is requested to choose which of a number of IMD system entities will be the dominant/managing entity; (ii) signals which indicate that the patient or patient device has been selected to be the dominant/managing entity (see FIGS. 29-43 and 46-52), or (iii) signals requesting information about patient availability for either (i) or (ii) herein;

(f) programming commands for patient device sensors (see control screen FIGS. 17, 19-21);

(g) programming updates related to the status in the control hierarchy of either the patient, the patient device or both (see screen FIGS. 14 and 15, and algorithm flow diagram FIG. 56B); and (h) miscellaneous control or information request signals from any of the system entities.

Each of these incoming signals is conveyed to the appropriate one of (i) the patient device processor, memory and control unit 904, (ii) the patient assessment unit 906, or (iii) the patient output devices 908, as indicated in the figure.

Figure 10:
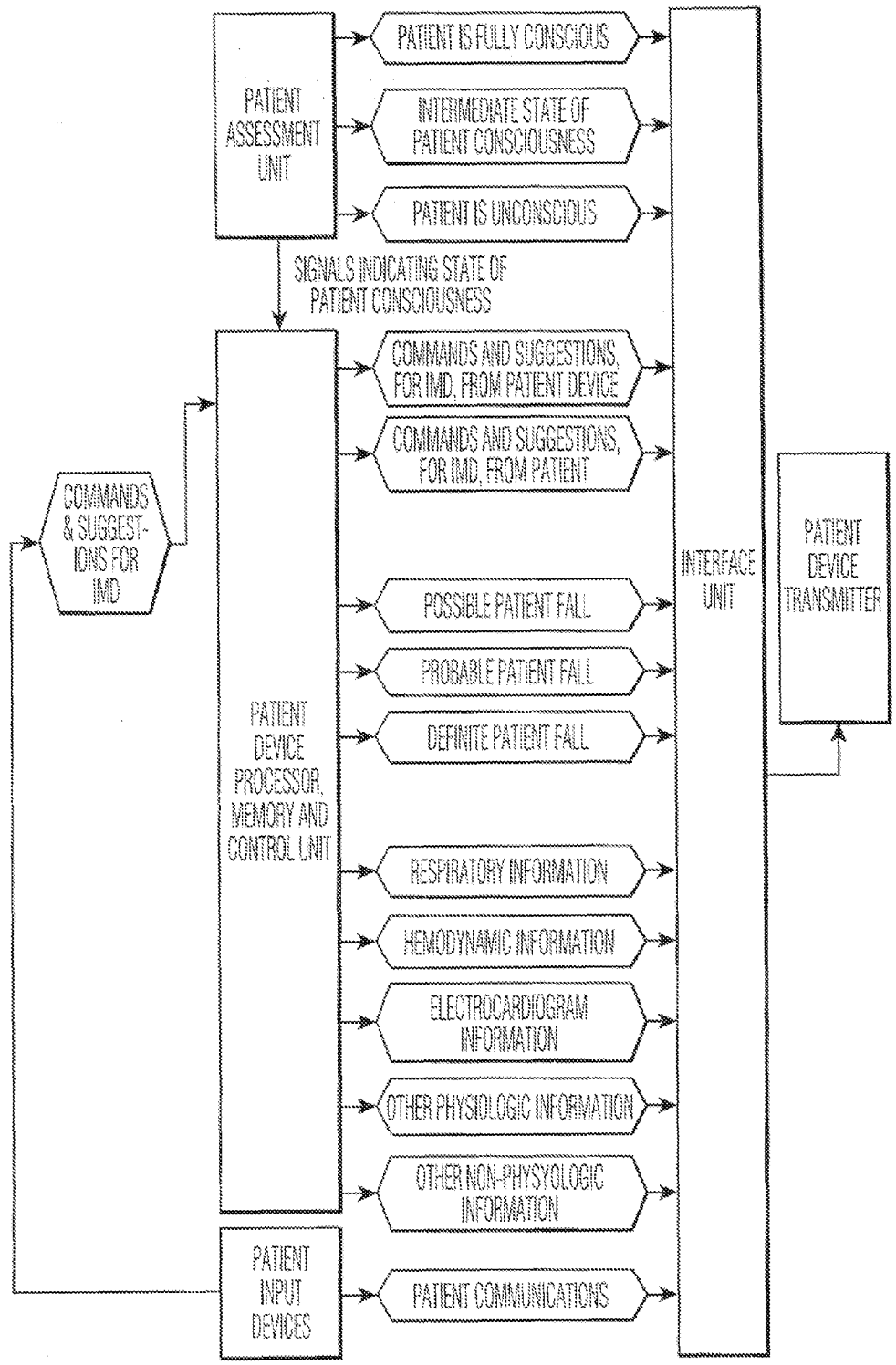
FIG. 10 is a block diagram showing information which may be transmitted by the patient device transmitter.

FIG. 10 shows signals which may be transmitted by the patient device:

(a) signals indicating a patient state of consciousness; Such signals may assign one of three classifications (fully conscious, unconscious or intermediate) as shown in the figure, may use a simpler system (conscious or unconscious), or a more complex system (e.g. indicating a numeric rating of the patient assessment unit);

(b) signals indicating the probability that a patient has fallen; Such signals may assign one of three classifications (possible, probable or definite) as shown in the figure; may use a simpler system (fall or no fall), or a more complex system (e.g. indicating a numeric rating of the probability of a fall); These signals may be derived from the analysis of information from sensing devices in the patient environment (see FIG. 5):

[i] information from one or more cameras;

[ii] information from one or more attitude indicators which may be worn by (or implanted in) the patient;

[iii] information from one or more devices which may sense a sudden deceleration which may be indicative of a fall, e.g. accelerometers; and/or

[iv] one or more microphones which may pick up the sounds associated with a patient fall;

(c) signals which provide patient physiologic information (see FIG. 5) such as;

[i] ECG information;

[ii] information about the patient's respiration;

[iii] information about the patient's hemodynamic function; and

[iv] other patient physiologic information;

(d) other information including:

[i] response to requests concerning patient availability to participate in clinical management decisions;

[ii] response to requests for the patient to select an entity in the IMD system for clinical management decisions;

(e) commands and suggestions for the IMD

[i] from the patient, if the patient has been granted such access;

[ii] from the patient device, if the patient device has been granted such access; and (f) outgoing communication signals during patient MP exchanges.

Figure 11:
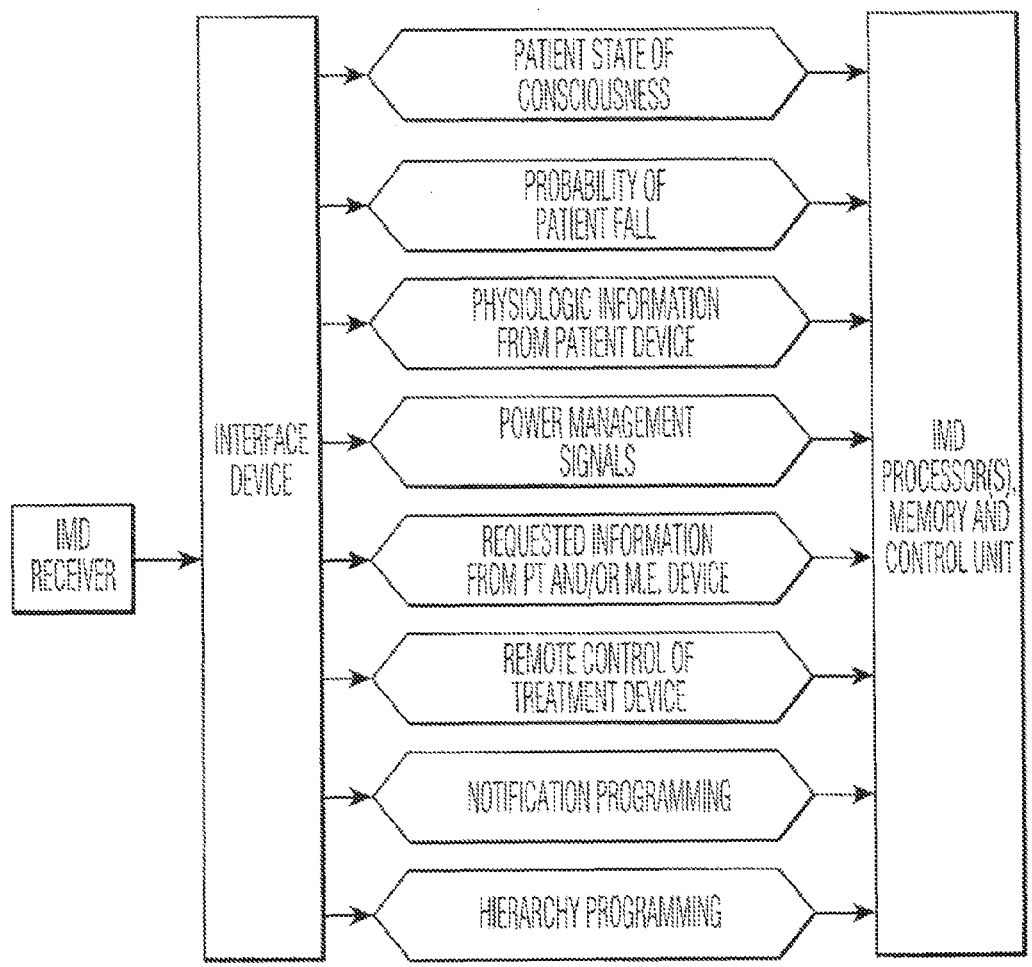
FIG. 11 is a block diagram showing information which may be received by the IMD receiver.

FIG. 11 shows signals which may be received by the IMD:

(a) signals transmitted by the patient device indicating the patient's state of consciousness;

(b) signals transmitted by the patient device indicating the probability that the patient has fallen;

(c) signals conveying physiologic information from the patient device;

(d) signals from any entity in the IMD system which either

[i] control the IMD treatment device (by either a control signal which results in real time treatment, or by a control signal which reprograms the IMD),

[ii] cause the IMD to control its own treatment device, or

Figure 14:
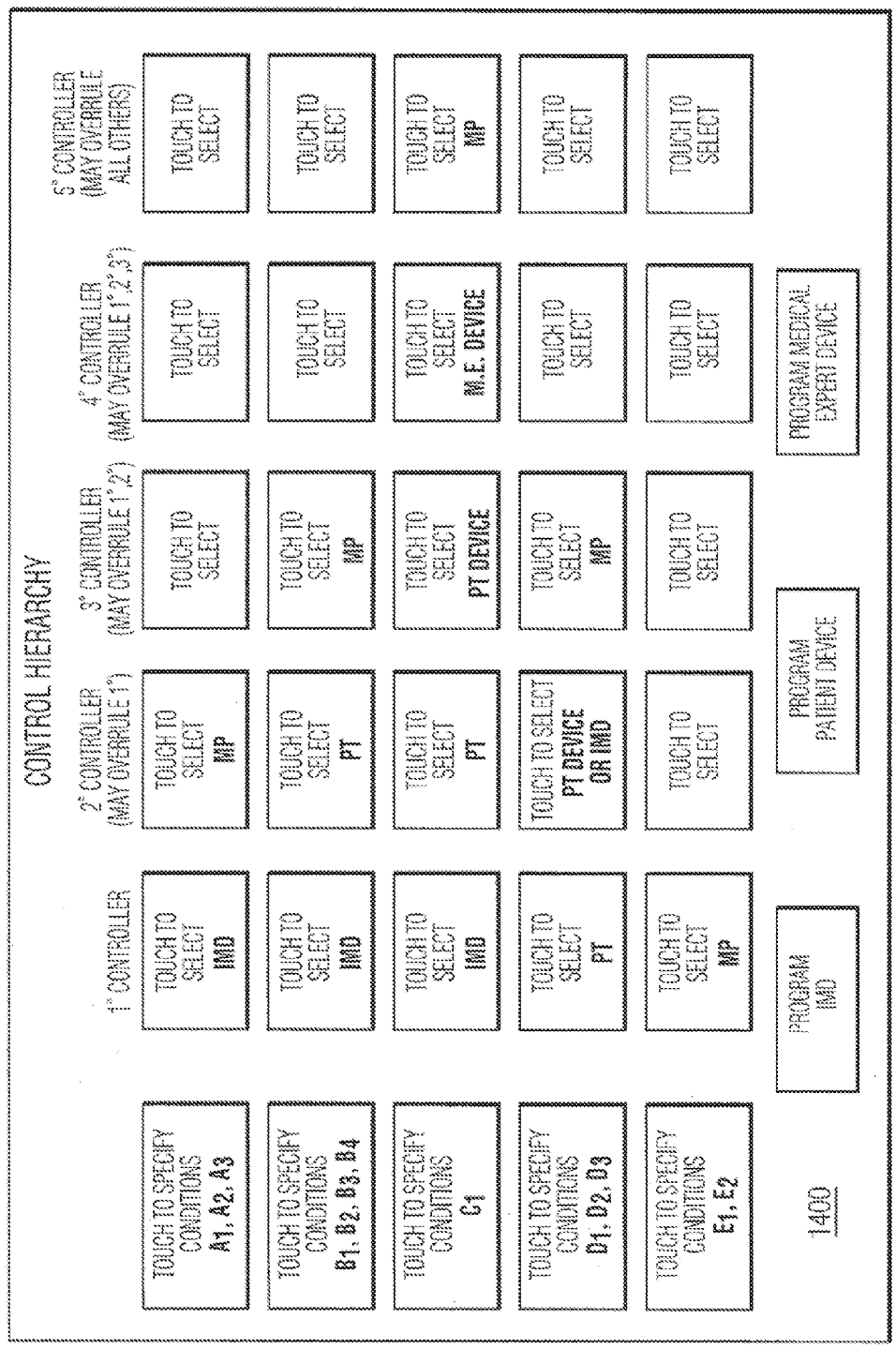
FIG. 14 illustrates a touch-sensitive programming and display screen for programming control hierarchy within the IMD system.

[iii] cause the IMD to select a control agent from among the allowed entities in the system;

(e) signals from the patient device or M.E. device (or the patient or the MP) which request the transmission of iMD information;

(f) signals which cause the programming or reprogramming of the criteria/conditions for which the IMD notifies one or more of the other IMD system entities; and (g) signals which result in the programming or reprogramming of the IMD status in the control hierarchy (see screen FIGS. 14 and 15, and algorithm flow diagram FIG. 56B).

Figure 12:
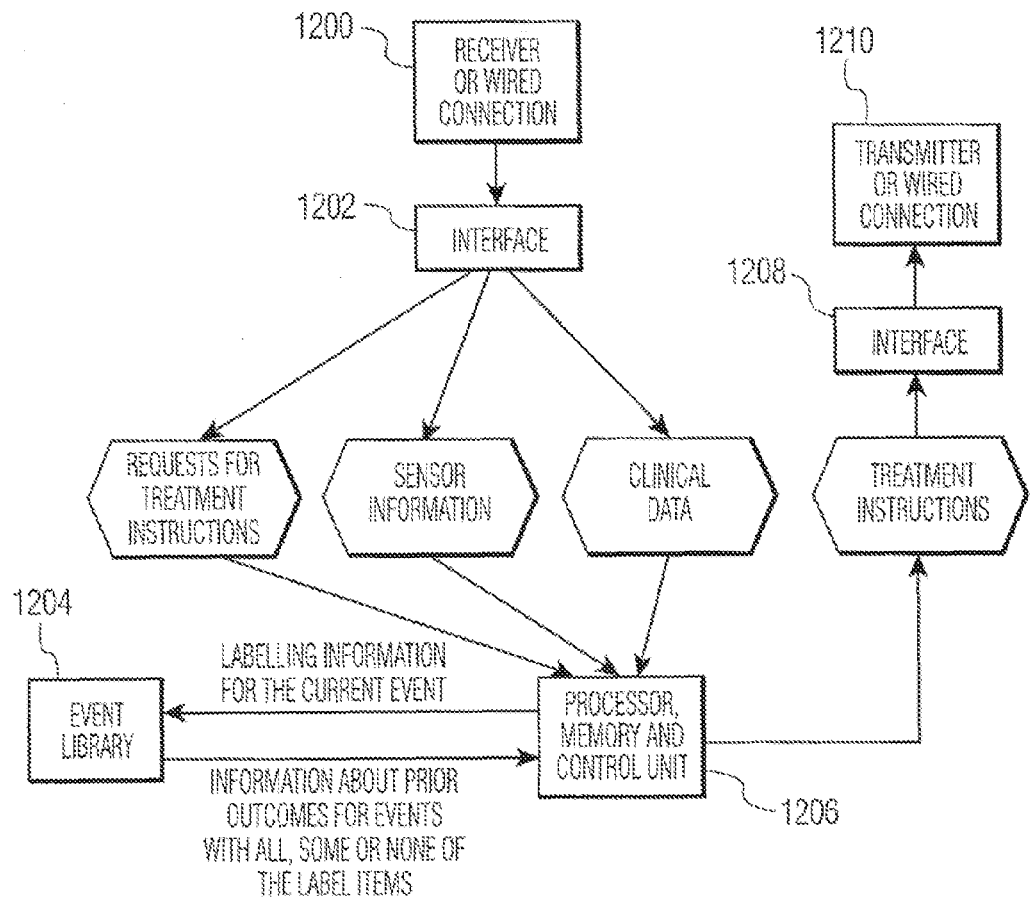
FIG. 12 is a block diagram illustrating the maintenance of a database of electrograms and/or data about patient-related events, and its use to generate treatment instructions.

FIG. 12 is a block diagram of one configuration of a medical expert device. The device stores information about patient events and provides automated expert advice. The M.E. device operates in three modes.

In the first mode, it categorizes and stores information about clinical events including both (a) descriptors of the event and associated clinical information; and (b) sensor information from [i] implanted device(s) and sensors, and [ii] external sensors, if any, thereby creating a library of such events.

In an optional second mode, the M.E. device analyzes the sensor information and the associated clinical information, searching for relationships among which associate sensor signals, clinical variables, treatment state and outcomes.

In a third operating mode, the device responds to requests for treatment advice or instructions; It provides this based on previously stored algorithms which may be supplemented by information in the event library, which is either (a) digested/processed, or (b) simply a match or near match for the current patient state.

As shown in the figure, information about a clinical event enters the M.E. device either via a wireless or wired connection 1200. The interface device 1202 for incoming signals functions as indicated hereinabove.

In the first operating mode, incoming sensor information (supplied by participating patients and/or MDs) may include minimally processed or unprocessed sensor signals (e.g. electrograms, signals from implanted brain electrodes) or processed signals (e.g. information about sequences of V-V intervals). Clinical data may include:

(a) patient identification information; (b) time and date of the event;

(c) the patient's implanted device model and serial number;

(d) information about associated implanted hardware (e.g. a lead model and serial number in the case of an ICD);

(e) information about the external patient device;

(f) the patient medications, and compliance with the regimen, if known, for the day or days preceding the event;

(g) additional information about the patient's medical history, both recent and remote;

(h) any unusual events that may have been going on at the time of the event, either medical or other;

(i) the identity of the patient's physician, and this physician's preferences, if known, about treatment of similar events;

G) information about any similar events which this patient may have experienced in the past; and (k) the results of treatment, if the data was collected at or around the time that the IMD was administering such treatment.

The set of sensor and clinical information is then assembled, labeled and stored in the event library 1204, so that it may be referenced by any one or more of search labels (a) through (k) and or by descriptors of the sensor signals.

In the second operating mode, the processor, memory and control unit 1206 may analyze information in the event library looking for patterns which either predict successful treatment outcomes, or patterns which predict serious or catastrophic events.

In the third operating mode, an incoming request for treatment information results in:

(a) standard treatment, if a previously developed algorithm has a high probability of a desirable outcome;

(b) a search of the medical library for comparable sensor signals, clinical data or some of each (from this patient and/or other patients), and uses this information to form the basis of a treatment recommendation; or (c) a combination of (a) and (b) herein, in which the medical library search results in the modification of an algorithm, or the selection of one of a number of optional branches of an algorithm, for treatment management.

The treatment instructions developed in this way are outputted (via the interface device 1208 with aforementioned function) from a wired or wireless connection 1210.

In the case of an ICD, sets consisting of both (a) electrograms or information about details of the heart rhythm and (b) clinical data, are labeled and stored in the M.E. device event library, as indicated hereinabove, for a variety of patient conditions, e.g. rest, exercise, tachycardia. Many such electrogram/clinical data sets, from many patients are stored in the event library, over a span of time. The trigger for storage of information in the event library may be (a) an event which required ICD therapy, (b) the retrieval of information about such treatment events at the time of a visit to the MD's office, (c) a voluntary patient transmission, and/or (d) a random sampling. Later, an entity in an ICD system (e.g. the LCD or the MP) may seek M.E. device guidance for the management of a particular episode of tachycardia. A request to the M.E. device for treatment instructions may triggers a search for:

(a) a similar electrogram, at a similar heart rate which was previously successfully treated, having occurred in the patient currently experiencing the tachycardia;

(b) a similar electrogram, at a similar heart rate which was successfully treated in another patient or group of patients; and/or (c) somewhat similar electrograms, in a plurality of previously successfully treated patients with very similar clinical data, compared to the current patient. If the search can be completed in an interval of time which would be acceptable, and if useful archival information is identified during that interval, then the referenced information about a prior successful treatment may be used to guide the current recommendation. If the search is not completed in an acceptable time, or if no match for the current condition and a successful treatment is found, then a stock treatment algorithm is employed by the M.E. device, or the M.E. device instructs the ICD to proceed with preprogrammed therapy.

The event library will be useful for any clinical situation where simple algorithmic management of highly complex sensor output information is inadequate or suboptimal for making complex treatment decisions. Such situations may occur with ICDs, with the analysis of brain signals to treat brain abnormalities including seizures and other neurologic disorders, with the management of blood sugar by an implantable insulin pump, and with other IMDs.

The M.E. device may be used in an IMD system with or without a patient device.

3.0 Management Screens

FIGS. 13-21 show nine computer screens each of which allows a person access to the various aspects of IMD system control. The person using these screens would likely be the MP, and might be a specially selected MP with skills to use these screens. Alternatively, one or more of the screens might be accessed by the patient's physician or by the physician who implants the IMD (e.g. FIG. 16). Still other screens might be accessed by a technical person setting up the patient device or the environment in which the patient device operates (e.g. FIGS. 20 and 21). The screens contain rectangular entities intended to indicate (a) touch-sensitive virtual "buttons" for indicating a user preference, and (b) display areas within a screen. Configurations of the system with actual buttons are possible; Configurations of the system with more than one simultaneously viewable screen are possible; Many such configurations will be evident to those skilled in the art.

Figure 13:
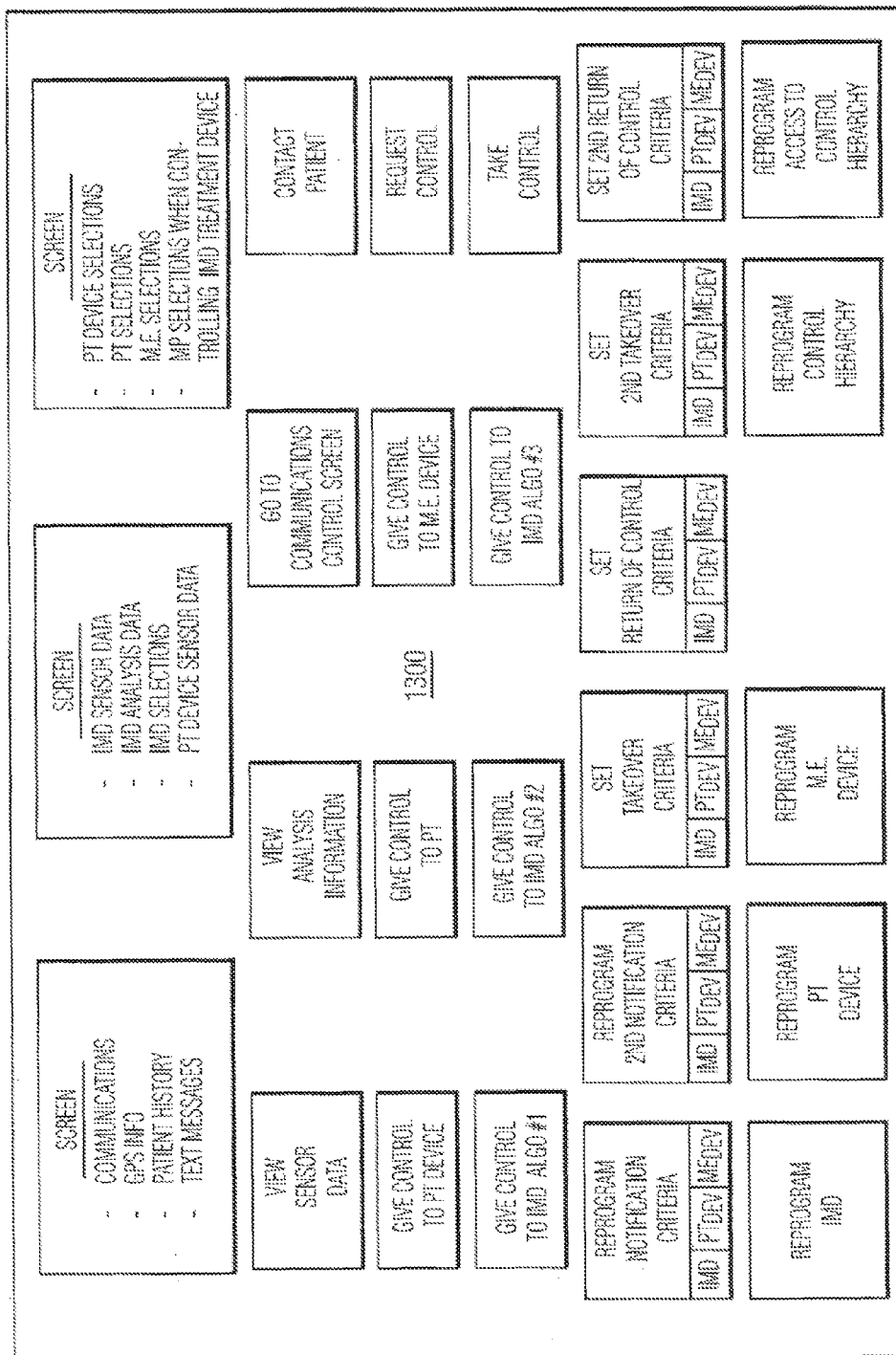
FIG. 13 illustrates a touch-sensitive programming and display screen for controlling the IMD system.

FIG. 13 shows a control screen 1300, which allows the MP a wide range of programming and control options including:

(a) giving the control of IMD function (e.g. for a fixed duration of time, or indefinitely, until reprogrammed again) to any of the possible control agents of the system (as shown in the algorithms, for example, of FIGS. 33, 38 and 52):

[i] himself/herself;
[ii] the M.E. device;
[iii] the patient;
[iv] the patient device; or
[v] the IMD.

In the screen configuration shown in the figure, the MP has the capability of giving control to any of three IMD algorithms. Embodiments of the invention with more or fewer IMD control algorithms are possible. In a preferred embodiment, would give control to the IMD in general, and if that IMD had multiple parallel internal IMD control algorithms, the MP would allow an IMD master algorithm (see FIG. 7) to automatically select therapy.

If the MP takes control of the IMD, then one or more of the three screens in the upper section of the figure will show one or more menus allowing the MP to exercise direct IMD control.

(b) request control of the IMD; This is a feature of the algorithm shown in FIG. 53, in which the MP and the patient may "negotiate" which if the two is to be the control agent;

(c) the programming or reprogramming of control hierarchy (see FIGS. 14, 15 and 56B), i.e. which of the IMD system entities has priority over which other entities; Touching this button will lead to the screen shown in FIG. 14;

(d) programming or reprogramming of access to control hierarchy i.e. the selection of which particular individuals are allowed to program control hierarchy; Touching this button will lead to the screen shown in FIG. 15;

(e) program or reprogram notification criteria (see, for example, FIGS. 71A-76C) or second notification criteria (see, for example, FIG. 23) at either the IMD, the patient device or the M.E. device;

(f) for each of the IMD, the patient device or the M.E. device, to program or reprogram one or more of criteria for:

[i] takeover,
[ii] return of control,
[iii] second takeover, and
[iv] second return of control, (see algorithms in FIGS. 59-70);

(g) program or reprogram other features of other devices in the IMD system, via the buttons labeled:

[i] IMD;
[ii] patient device; and
[iii] M.E. device; and (h) control IMD system communication features, by touching "GO TO COMMUNICATIONS CONTROL SCREEN", which leads to a menu driven tree of choices appearing within one or more of the screens shown at the top of the figure.

The IMD may choose to contact the patient for a variety of reasons (to discuss device programming, to discuss the management of an actual event, to directly evaluate the patient, to discuss a potential or actual malfunction, etc.), and can do so (via the patient device, or by other means) by touching "CONTACT PATIENT."

The MP is given access to a variety of information to facilitate his/her decision making;

(a) data from IMD and/or patient device sensors;

(b) IMD analysis of [i] IMD sensor information and/or [ii] patient device sensor information;

(c) the therapy selections of one or more other entities in the system;

(d) text messages from the patient, the patient device, the M.E. device or the IMD;

(e) archived information concerning the patient history (or additional information from the M.E. device library); and (f) GPS information, if a OPS device is part of either the IMD or the patient device.

FIG. 14 shows a control screen 1400, which allows the screen user to determine control hierarchy in an IMD system (to be used in conjunction with a control algorithm similar to that shown in FIG. 56B). The user may select a hierarchy which pertains to all medical conditions, or may select one such hierarchy for a first set of medical conditions (labeled A1, A2, A3), a different hierarchy for a second set of medical conditions (labeled B1, B2, B3, B4), etc. The specific medical conditions are specified by touching the button(s) labeled "TOUCH TO SPECIFY CONDITIONS . . . " after which specific conditions (e.g. for an ICD, a range of heart rates) are entered. The hierarchy is programmed by:

(a) for each set of conditions, touching the button in the primary controller column which will lead to a menu showing each of the entities in the IMD system; One of these is selected;

(b) then, if there is to be a secondary controller, touching the button in the secondary controller column which will lead to a menu showing each of the remaining entities (i.e. other than the already selected primary controller) in the IMD system; One of these is selected;

(c) then, if there is to be tertiary and higher order controllers, touching the buttons in the corresponding controller columns, which will each lead to a menu showing each of the remaining entities (other than the already selected ones) in the IMD system; These are selected as required.

In the figure, an example is shown in which:

(a) for conditions A1-A3, the IMD is the primary controller, and the MP—as the secondary controller—may overrule the IMD;

(b) for conditions B1-B4, the IMD is the primary controller, the patient—as the secondary controller—may overrule the IMD, and the MP—as the teritary controller—may overrule each of the patient and the IMD;

(c) for conditions C1, the IMD is the primary controller, the patient is the secondary controller, the patient device is the tertiary or third level controller, the M.E. device is the fourth level controller, and the MP is the highest level controller; In the nomenclature selected, each entity may overrule each other lower level entity;

(d) for conditions D1-D3, the patient is the primary controller, the patient device or the IMD is the secondary controller [intended to indicate that either example is possible], and the MP is the tertiary controller, and (e) for conditions E1 and E2, only the MP may control the IMD.

FIG. 54 hereinbelow shows an algorithm which would be affected if the selections in the second row of FIG. 14 were made. The specification in conjunction with FIG. 54 includes two examples of IMD systems that might function accordingly. One of the control scenarios addressed by U.S. Pat. No. 7,277,752 (Section 8.6 and FIG. 60) parallels that which would be affected if the selections in the first row of FIG. 14 were made. An algorithm similar to that shown in FIG. 56A herein would be affected if the selections in the third row of FIG. 14 were made (though that in FIG. 56A has the patient as the tertiary controller and the patient device as the secondary controller).

The specification in conjunction with FIG. 56B discusses having a single IMD programmed so that it operates with different control hierarchies for different medical conditions. For example, an ICD could be programmed:

for relatively slow tachycardias (e.g. rate 140 to 160 b.p.m.), to operate with the hierarchy indicated in row 2 of FIG. 14, in which the IMD is the primary controller, the patient may overrule the IMD and the MP may overrule either the patient or the IMD;

for most other tachycardias (e.g. rate 160 to 460 b.p.m), to operate with the hierarchy indicated in row 1 of the figure, in which the IMD is primary, the MP may overrule, and the patient does not have control access; and for a specific set of conditions in which there is a very high likelihood that sensor signals are being generated by a malfunctioning lead (e.g. repetitive short bursts of very high rate signals [with or without additional evidence from the patient device that these signals do not correspond to true cardiac rhythm abnormalities]), to operate with the hierarchy indicated in row 5 of the figure, in which only the MP has access to control.

The MP or other person using the control screen shown in FIG. 14 may program any of the devices in the IMD system by making his/her hierarchy selections and then touching the corresponding button from among those three in the bottom row of the screen.

FIG. 15 shows a control screen 1500, for programming the access to the control screen for control hierarchy shown in FIG. 14. Since control hierarchy is at the core of system functioning, and since its proper programming may depend on the ability of one individual (e.g. the MP) to assess the competence of other individuals (e.g. the patient, or the patient's physician), in a preferred embodiment of the inventions, a mechanism should be in place to establish and maintain the control of control hierarchy. An example of such an approach is the touch sensitive screen shown in FIG. 15.

The user is instructed to select one choice in each of the first three rows. Row 1 is setup at the time of initial system setup, and is used to determine whether, in the future, an MP may access the system autonomously, or whether the MP will requires additional permission, i.e. from the patient's physician, or from a specifically designated physician. MP access could be further restricted to only certain MPs, and the passwords of those MPs who are allowed system access may be entered by touching the "ENTER MP PASSWORD" button, and entering the appropriate passwords using either an actual keyboard or a touch sensitive screen.

By touching one of the buttons in row 2, the individual performing the setup determines which physician(s), if any will have access to the programming of control hierarchy. The setup individual may restrict access to specific MDs (and enter their passwords by touching the "ENTER MD PASSWORD BUTTON"), or restrict access to MDs who have MP permission at the time. Alternatively, the setup individual may decide to deny MD access in general. (Such a decision would not be irreversible, since, at a future time, a MP with access to the control screen shown in FIG. 15 could alter the decision.)

Whether the patient may have access to control hierarchy programming is determined when one of the buttons in row 3 is touched. The choices, in the embodiment of the invention shown in the figure, are (a) the patient who has the patient device (without restriction except for the need for password entry), (b) the patient, with MP permission at the time of programming, (c) the patient, with physician permission at the time of programming, and (d) no patient access allowed. If the patient is allowed access, the setup person enters their password by touching the "ENTER PT PASSWORD" button.

Figure 16:
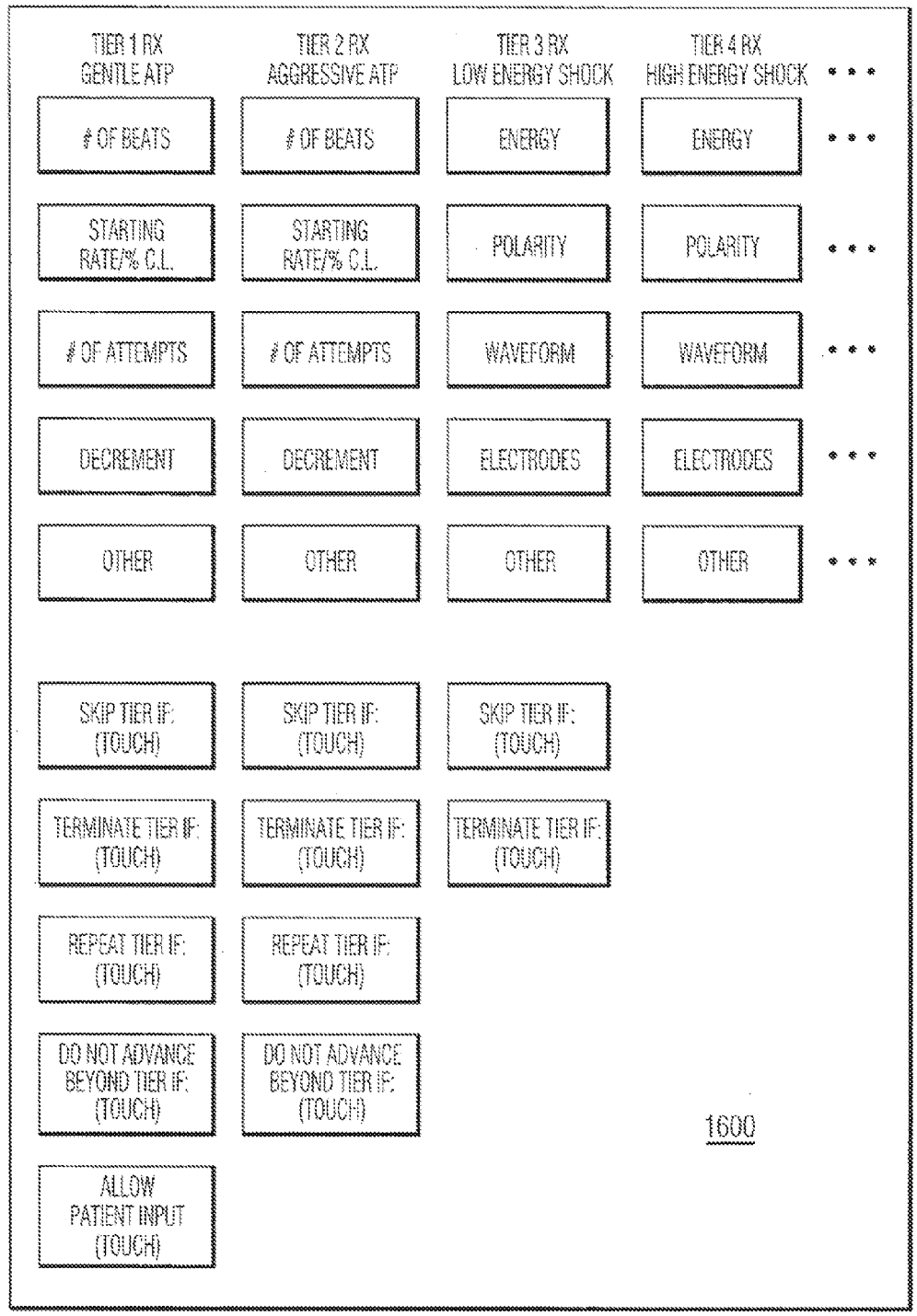
FIG. 16 illustrates a touch-sensitive programming and display screen for programming an IMD whose function may be influenced by information obtained by a patient device.
Figure 17:
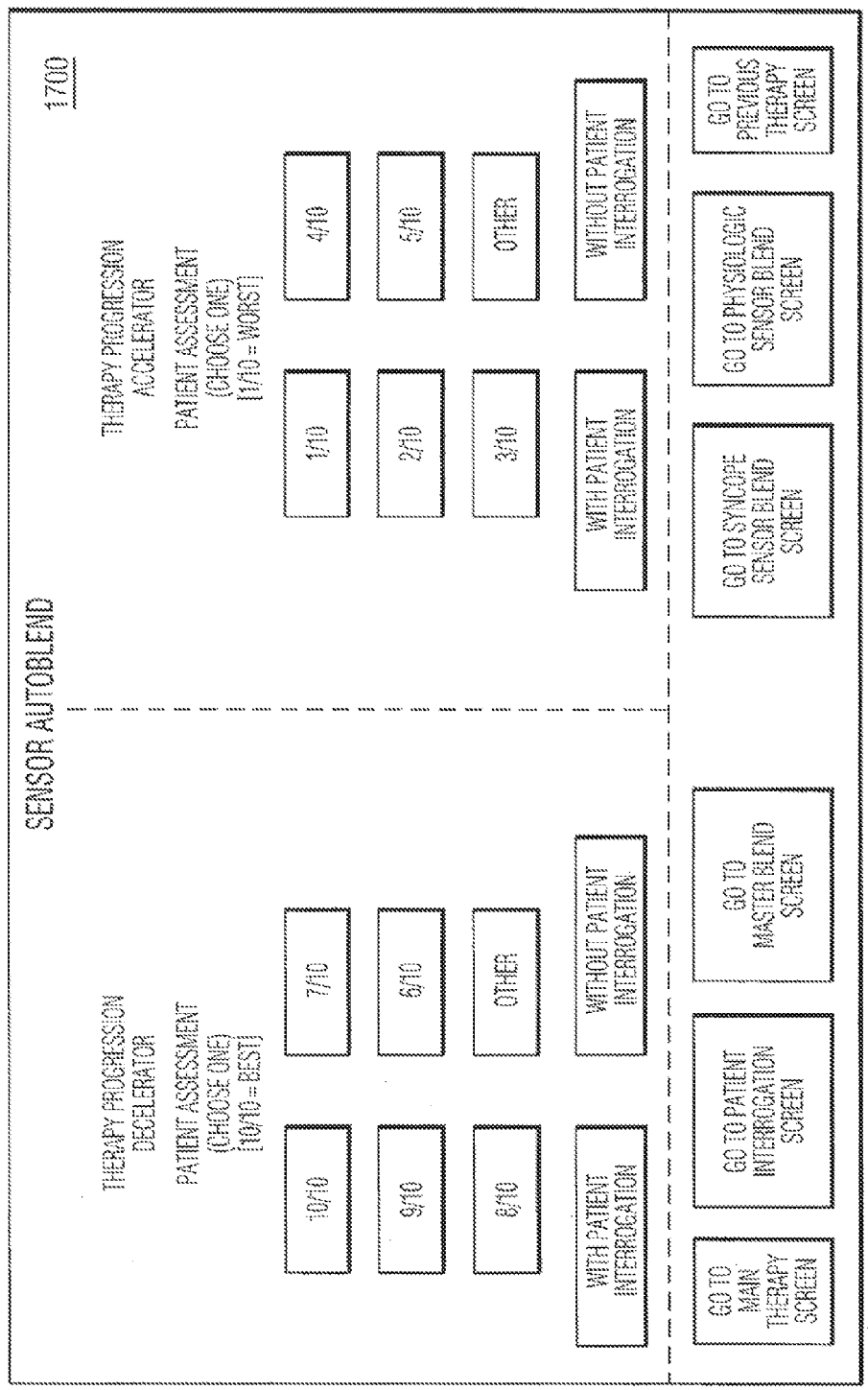
FIG. 17 illustrates a touch-sensitive programming and display screen for programming the mixing of information coming from a patient device.

FIGS. 16 and 17 show an example of control screens for programming an ICD which allow for the use of information about the patient obtained at the patient device to either accelerate or decelerate the typically escalating aggression of ICD therapy for an episode of tachycardia.

Referring to FIG. 16, within control screen 1600, each of the four columns of rectangular buttons program one "tier" of ICD therapy, with increasing aggressiveness of therapy from the left-most to the right most column, as is known in the art. Shown in the figure are:

(a) a least aggressive tier of therapy which consists of gentle antitachycardia pacing ("ATP");

(b) a more aggressive tier of therapy which consists of more aggressive ATP (e.g. shorter pacing cycle lengths, more rapidly escalating pacing rate from one pacing attempt to the next, etc.);

(c) a still more aggressive tier of therapy which consists of a low energy shock;

(d) an even more aggressive tier of therapy which consists of high energy shock. Typically, additional high energy shocks would be programmed to occur following the fourth tier, In the ATP tiers, categories of choices are shown which allow for the selection of details of the ATP such as the pacing rate, the number of paced beats and the number of pacing attempts, etc.—typical of present day ATP programming. Each touch button leads to a menu of options (e.g. number of beats could be selected from 3, 4, 5, 6 . . . ). Similarly, submenus may be accessed for the selection of shock-related parameters such as shock energy, polarity, waveform, electrode choice, etc., each leading to a menu of choices. Numerous variations of therapy, of formatting ICD therapy menus, and of selecting from among the choices on the menus are known and used on an everyday basis.

The lower five rows of buttons in the figure show how information about the patient's condition obtained at the patient device may be used to modulate the aforementioned escalating therapy.

If the patient device indicates that the patient condition is poor, then the ICD may be programmed to skip a tier of therapy. Furthermore, if the patient's condition, as assessed by the patient device, worsens while a tier is in progress, the ICD may be programmed to terminate that therapy tier and move to the next one upon such detection.

If the patient device indicates that the patient condition is good, then the ICD may be programmed (1) to repeat a tier of therapy one or more times, or (ii) to not advance beyond a particular tier of therapy. Furthermore, if the patient indicates that their condition is good, then such an indication may be allowed to cause a repeat or a non-advancement of therapy.

There are numerous ways in which patient condition may be assessed, and the control screen 1700 shown in FIG. 17 illustrates one approach: Overall patient condition is semi-quantitatively assessed by assigning it an integer value between the number 1 and the number 10, where 10 indicates the best condition, and 1 indicates the worst condition. The definition of each of the ten states so delineated may be either (a) explicitly programmed by using the screens in FIGS. 18-20, or (b) selected by an "autoblend" feature, in which a predetermined method of weighting of one or more sensor input values, and of blending the values if there are two or more, is used to determine the integer corresponding to the patient state, on the 10 integer scale.

For example, using a single sensor, one possible set of default values for a respiratory assessment would be:

TABLE A

| Patient Assessment | Respiratory Rate (per min.) |
|---|---|
| 10 | 12-18 |
| 9 | 11 or 19 |
| 8 | 10 or 20 |
| 7 | 9 or 21-22 |
| 6 | 8 or 23-24 |
| 5 | 7 or 25-26 |
| 4 | 6 or 27-28 |
| 3 | 5.5 or 29-30 |
| 2 | 5 or 31-32 |
| 1 | less than 5, or more than 32 |

Other tables of values or curves representative of such tables could be entered via the screen shown in FIG. 20 (see below).

A possible set of default values for blood pressure assessment would be:

TABLE B

| Patient Assessment | Systolic Blood Pressure (mm. Hg) |
|---|---|
| 10 | >100 |
| 9 | 95-100 |
| 8 | 90-95 |
| 7 | 85-90 |
| 6 | 80-85 |
| 5 | 75-80 |
| 4 | 70-75 |
| 3 | 65-70 |
| 2 | 60-65 |
| 1 | <60 |

In an example using two sensors, one for respiratory rate and one for blood pressure, a possible set of default values for a respiratory assessment would be:

TABLE C

| Blended Assessment of BP Score and Respiratory Score | RESPIRATORY SCORE: | | | |
|---|---|---|---|---|
| | 8-10 BP Score | 6-7 BP Score | 4-5 BP Score | 1-3 BP Score |
| 10 | 10 | | | |
| 9 | 9 | | | |
| 8 | 8 | 10 | | |
| 7 | 7 | 9 | | |
| 6 | 6 | 8 | 10 | |
| 5 | 5 | 7 | 9 | |
| 4 | 4 | 6 | 8 | 10 |
| 3 | 3 | 5 | 7 | 9 |
| 2 | 2 | 3-4 | 5-6 | 6-8 |
| 1 | 1 | 1-2 | 1-4 | 1-5 |

Patient assessment, besides the use of standard physiologic parameters may also involve a brief neurophysiologic assessment. The assessment may be quick, involving the patient response to one or a few questions (via the patient device), and may be valuable for assessing hemodynamic consequences that are not fully reflected by blood pressure, or for assessing metabolic or neurologic states. An example of a setup screen for such an assessment is shown in FIG. 18, and is discussed below. In the example shown, the output of the assessment is a cognitive rating of either "good", "fair", or poor. Many other rating scales will be apparent to those skilled in the art.

Below is a table in which one physiologic parameter and the results of a cognitive evaluation are combined to generate a single integer valued 1 through 10, reflecting the patient overall state:

TABLE D

| Blended Assessment of Respiratory Score and Patient Interrogation | COGNITIVE SCORE: | | |
| --- | --- | --- | --- |
| | GOOD Resp. Score | FAIR Resp. Score | POOR Resp. Score |
| 10 | 10 | | |
| 9 | 9 | | |
| 8 | 8 | | |
| 7 | 7 | 10 | |
| 6 | 5-6 | 9 | |
| 5 | 3-4 | 8 | |
| 4 | 2 | 6-7 | |
| 3 | 1 | 4-5 | 8-10 |
| 2 | | 2-3 | 6-7 |
| 1 | | 1 | 1-5 |

Referring again to Table 16, the person programming the screen in FIG. 16 may elect to skip Tier 1 therapy if the semi-quantitative assessment of patient condition, based on the patient's respiratory status only, is less than or equal to 5 on the aforementioned scale of 10. (See Table A, above.) This would be programmed by:

(i) touching the "SKIP TIER IF" box in column 1 of the screen in FIG. 16, which would lead to the screen in FIG. 17;

(ii) then touching "5/10" in the "THERAPY PROGRESSION ACCELERATOR" section of the screen shown in FIG. 17, and (iii) then touching "WITHOUT PATIENT INTERROGATION."

If there are additional physiologic sensors besides respiratory rate, then the screen shown in FIG. 19 would be used to specifically select respiratory rate (see below).

If desired, the programming person could then return to the screen in FIG. 16 by touching either "GO TO MAIN THERAPY SCREEN" or "GO TO PREVIOUS THERAPY SCREEN," to perform additional programming. Referring again to column 1 of the figure, the "TERMINATE TIER IF" would be set up in a manner similar to the "SKIP TIER IF," procedure discussed hereinabove.

The programming person may wish to program "therapy progression decelerators," i.e. physiologic standards which, if met, result in additional time spent with the delivery of non-aggressive therapy, resulting in the deferral, or possibly the prevention of more aggressive therapy. For example, the person programming the screen in FIG. 16 may elect to repeat Tier I therapy if the semi-quantitative assessment of patient condition, based on the patient's respiratory and cognitive status, is greater than or equal to 8 on the aforementioned scale of 10. (See Table D, above.) This would be programmed by:

(i) touching the "REPEAT TIER IF" box in column I of the screen in FIG. 16, which would lead to the screen in FIG. 17;

(ii) then touching "8/10" in the "THERAPY PROGRESSION DECELERATOR" section of the screen shown in FIG. 17, and (iii) then touching "WITH PATIENT INTERROGATION."

Figure 19:
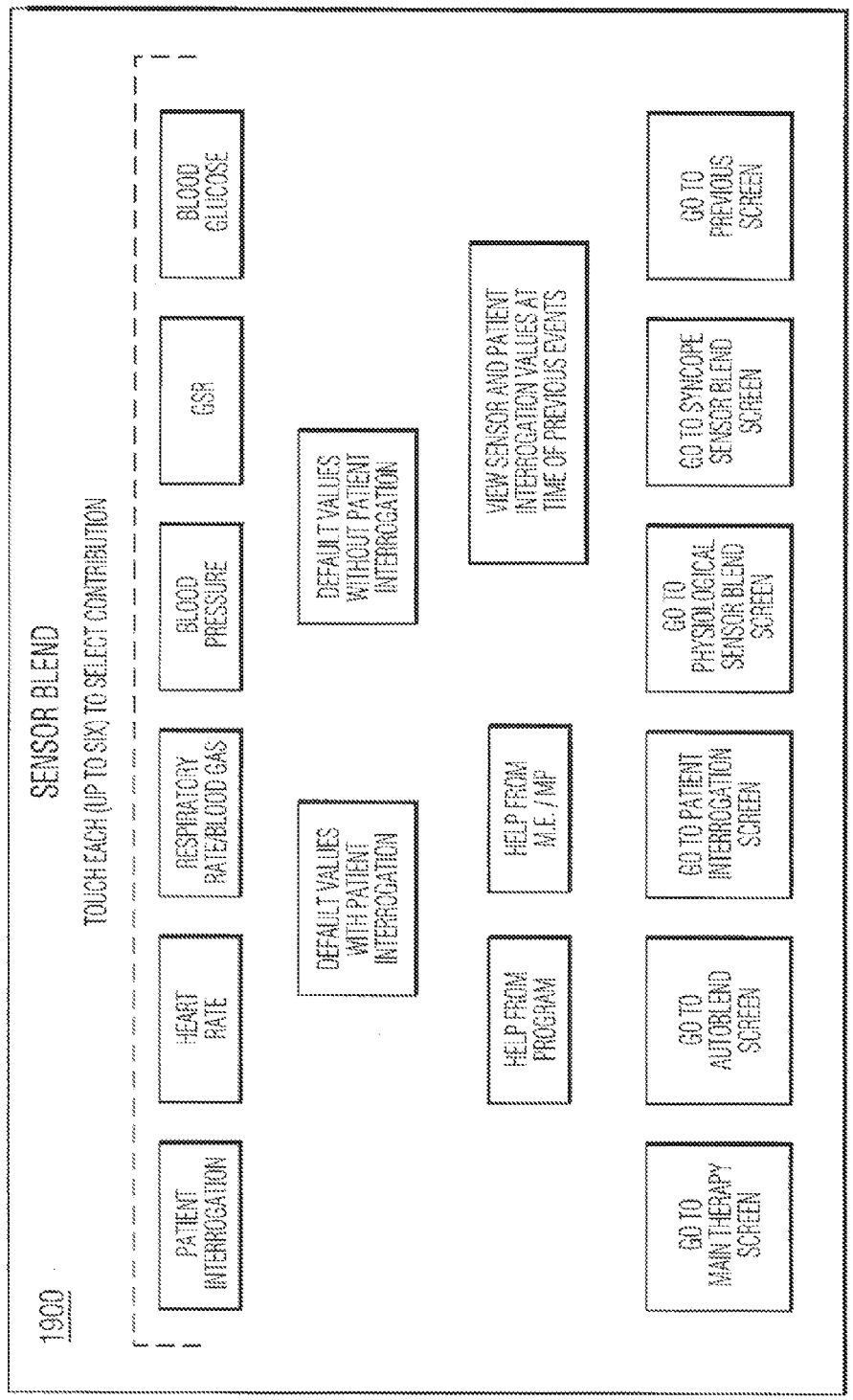
FIG. 19 illustrates a touch-sensitive programming and display screen for programming the blending of two or more patient-related inputs.

As indicated above, the screen in FIG. 19 may need to be additionally accessed.

If desired, the programming person could then return to the screen in FIG. 16 (as described above) to perform additional programming. Referring again to column 1 of the figure, the "DO NOT ADVANCE BEYOND TIER IF" could be set up in a manner similar to the "REPEAT TIER IF," procedure discussed hereinabove, except that a value of "9/10" might be selected for this therapeutic approach.

The programming person may find it advantageous to allow for direct patient input at the time of a rhythm abnormality. The input could be a therapy decelerator or accelerator, and the specific amount of latitude that the patient could have would be pre-specified. For example, it may be desirable to prevent the advancement beyond Tier 1 if both (a) the patient overall assessment is "10/10" and (b) the patient, based on his/her own sense that he/she is tolerating the tachycardia well, would like to defer higher tiers of therapy. To program this condition (with patient interrogation), the programming person;

(i) touches the "ALLOW PATIENT INPUT IF" box in column I of the screen in FIG. 16, which would lead to screen 1700;

(ii) then touches "10/10" in the "THERAPY PROGRESSION DECELERATOR" section of screen 1700, and (iii) then touching "WITH PATIENT INTERROGATION."

Examples with therapy acceleration will be possible, using the "THERAPY PROGRESSION ACCELERATOR" portion of the screen shown in FIG. 17, in conjunction with the "ALLOW PATIENT INPUT IF" button.

Referring again to the screen 1600, the programming of therapy accelerators and decelerators for Tier 2 (column two of the figure), proceeds along the same conceptual and methodologic lines as for the Tier 1 programming described hereinabove. "ALLOW PATIENT INPUT" has been omitted, based on the lesser degree of appropriateness for patient input to a more aggressive therapy. For example, the person programming the screen in FIG. 16 may elect to repeat Tier 2 therapy if the semi-quantitative assessment of patient condition, based on the patient's blood pressure and respiratory, is greater than or equal to 8 on the aforementioned scale of 10. (See Table C, above. It would include: [i] states with both of (1) respiratory score 8-10 and (2) blood pressure score 8-10; and [ii] states with both (1) respiratory score 6-7 and (2) blood pressure score 10.) This would be programmed by:

(i) touching the "REPEAT TIER IF" box in column 2 of screen 1600, which would lead to screen 1700;

(ii) then touching "8/10" in the "THERAPY PROGRESSION DECELERATOR" section of the screen 1700, and (iii) then touching "WITH PATIENT INTERROGATION."

If there are additional physiologic sensors besides respiratory rate and blood pressure, then the screen shown in FIG. 19 would be used to specifically select these two choices (see below).

Referring again to screen 1600, the programming of therapy accelerators for Tier 3 (column three of the figure), proceeds along the same conceptual and methodologic lines as for Tier 1 and 2 programming described hereinabove. Therapy decelerators have been omitted.

Embodiments of the invention with numerous variations in the above-discussed programming features are possible (e.g. allowing more patient access, allowing no patient access, allowing greater or fewer opportunities for therapy acceleration or deceleration based on pre-programmed algorithms which use patient assessment, etc.).

Figure 18:
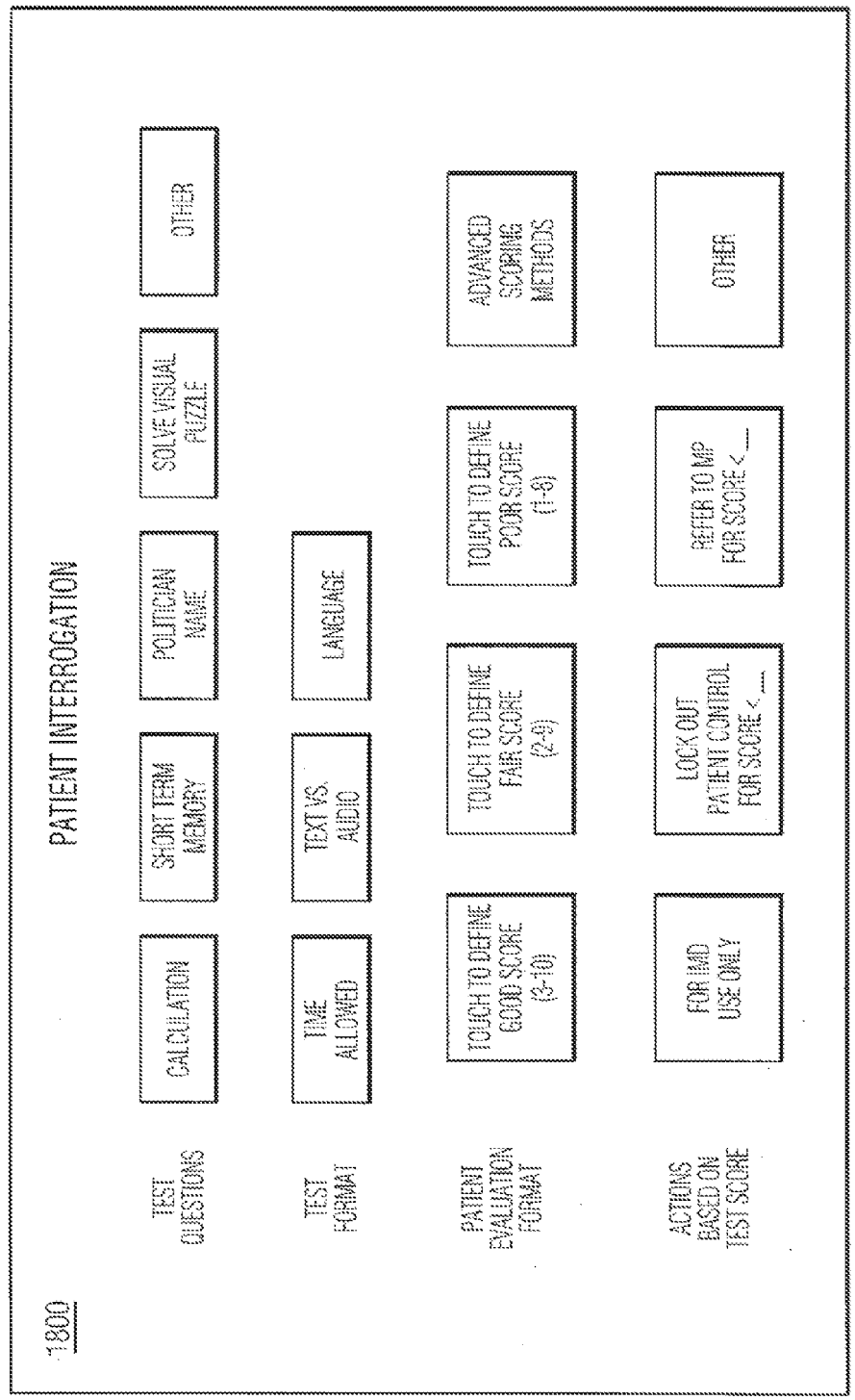
FIG. 18 illustrates a touch-sensitive programming and display screen for programming cognitive evaluation of a patient with a patient device.
Figure 21:
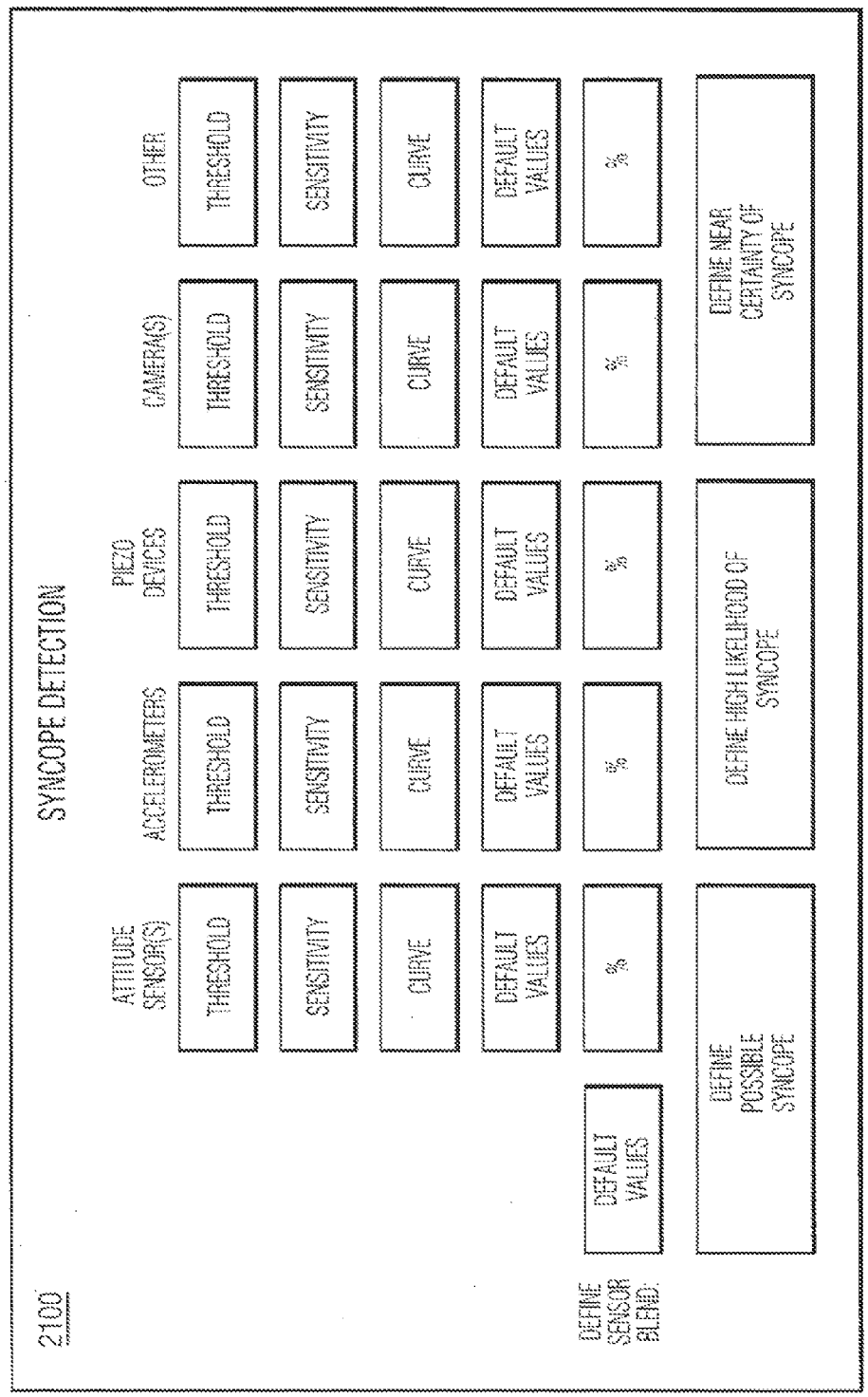
FIG. 21 illustrates a touch-sensitive programming and display screen for the detection of a syncopal event by a patient device.

There are four additional navigation buttons at the bottom of screen 1700:

(a) "GO TO PATIENT INTERROGATION SCREEN" leads to the screen shown in FIG. 18, allowing detailed programming of patient cognitive assessment;

(b) "GO TO MASTER BLEND SCREEN" leads to the screen 1900 in FIG. 19, allowing the programming of the details of sensor blending;

(c) "GO TO SYNCOPE SENSOR BLEND SCREEN" leads to screen 2100 shown in FIG. 21, allowing the blending and individual adjustment of sensors which allow the assessment of whether the patient has fallen and/or had a syncopal episode; and (d) "GO TO PHYSIOLOGIC SENSOR BLEND SCREEN" leads to screen 2000 shown in FIG. 20, allowing the blending and individual adjustment of physiologic sensors associated with the patient device.

Patient interrogation allows for a performance assessment of the functioning of the patient's brain, which generates additional information on which to base therapy decisions. The interrogation information may supplement the assessment of cardiac performance, of metabolic state, and of neurologic state. The setup screen shown in FIG. 18 is one of many possible screens that perform this function.

As indicated in the discussion of FIG. 4A, the patient evaluation process may consist of at least one of (a) assessing whether the patient response to system prompts and warning signals is timely and/or appropriate, and (b) assessing the response and timing of the response to test questions posed to the patient. Although such responses can not be instantaneous, important information can become available in a fraction of a minute, which in some circumstances may be available for decision making. The patient (a) may be presented with an audio format, (b) may be shown a text version of the questions on the screen for the patient device shown in FIG. 6, or (c) may be presented with a text version following an alerting audio announcement or tone. The patient answers may be via a touch sensitive screen on the patient device, or spoken words.

Using the buttons shown for the top/first line of 1800, the control screen shown in FIG. 18, the programming person may choose one or more types of test questions, to be posed to the patient when necessary. The categories shown on the screen are (a) calculations (e.g. simple mental arithmetic), (b) short term memory (remember the names of three objects after a given time interval, e.g. 20 or 30 seconds), (c) politician names ("Who is the Governor?") and (d) solving a visual puzzle (e.g. a maze or an exercise that requires inverting a rotating a visual image). Touching each of the virtual buttons corresponding to these categories: (a) may lead to the inclusion of this category of question, without further input by the programming person, or (b) may lead to additional choices which allow the programming person to specify [i] the number of questions to be asked, [ii] the difficulty of the question(s), and/or [iii] the actual question(s). The programming person may select more than one category of questions. By touching "OTHER", the programming person may select other question categories (e.g. a request for time and date, a logic puzzle, etc.), either (a) from either a menu, or (b) by directly entering question material through a keyboard or other input port.

The second line of buttons allow the programming person to determine test format issues including the time allowed (either for each question. or for the total set of questions, or both); whether the presentation format is text, audio or both; and the language to be used for the test.

The third line of buttons allows the programming person to determine the scoring method. For example, the three left buttons in the row allow the setup person to define a three level score (good/fair/poor), based on the number of correct answers, which may be weighted in a manner that produces a score between 1 and 10. Thus "good" could be defined as a score of 9 or 10, fair as a score of 6, 7 or 8, and poor as a score of 5 or below; These values may be entered by access to a menu which lists them (upon touching one of the three leftmost boxes of row three), or by a keyboard entry. Touching the "ADVANCED SCORING METHODS" button allows access to more complex scoring techniques, including:

(a) scoring with a greater or lesser number of result possibilities than three;

(b) having the score depend on one or more prior patient evaluations;

(c) truncating the evaluation when it is only partially completed, if it is clear that the patient is doing either exceptionally poorly, or exceptionally well;

(d) extending the evaluation, if an indeterminate result is obtained;

(e) truncating the evaluation if either [i] the patent condition is tenuous (demanding a quick evaluation) from the start of the evaluation, or [ii] the patient condition deteriorates during the evaluation; and (f) extending the evaluation if either [i] the patent condition is good (therefore allowing for a more detailed evaluation) from the start of the evaluation, or [ii] the patient condition improves during the evaluation.

The fourth row of buttons allows the programming person to determine how such evaluation information is to be utilized. The possibilities shown (accessed by touching the respective virtual buttons, for example) include:

(a) using the information for IMD therapy selection (e.g. therapy acceleration or deceleration, in the ICD example discussed hereinabove);

(b) locking out patient access to IMD control for a score which is less than a certain value (value to be entered);

(c) contacting the MP for a score which is less than a certain value (value to be entered);

(d) other uses (e.g. the performance of patient evaluations during non-critical times, to establish a patient performance baseline/standard).

As shown in FIG. 10, the results of a patient assessment are transmitted from the patient device. Although the format in the figure shows three possible transmitted results ([i] fully conscious, [ii] intermediate state of consciousness and [iii] unconscious), many other formats are possible (e.g. [i] transmitting the actual score, [ii] transmitting the actual patient responses, etc.). As shown in FIG. 11, information about the patient state of consciousness is received by the IMD, in embodiments of the invention in which patient interrogation is a feature.

FIG. 19 shows a control screen 1900 which illustrates one approach to determining the contribution of each of a plurality of patient device sensors to an overall patient assessment. In the approach shown in FIG. 19, the desired relative weighting of the contribution of each of a plurality of sensors is inputted by the programming person. The FIG. 19 illustration shows a linear weighting process among sensors. Non-linear weighting among sensors is also possible, e.g. blood pressure weighted at 50% of the sum of all sensor contributions (to the overall patient assessment), unless the blood pressure falls below a certain value, in which case blood pressure is weighted at a larger percentage than 50. (See discussion below about linear versus non-linear weighting within a sensor parameterization format.)

To use the screen 1900, the programming person touches any button in the first row corresponding to a sensor in use in the patient device. Touching the any of the six buttons would lead to a menu with choices of a fractional or percentage value (e.g. 5%, 10%, 15%, etc.). For example, the programming person could enter 75% for blood pressure and 25% for respiratory rate. If the BP score was 6 and the respiratory rate score was 10, this would lead to an overall score of 7.

Other modalities shown in FIG. 19 for possible inclusion in the overall patient assessment include:

(a) a semi-quantitative assessment of the patient state of consciousness or cognitive function, as discussed hereinabove;

(b) the heart rate, which may be assessed at the patient device by either two or more electrodes attached to the patient, by conductive elements which the patient touches, or by a mechanical or acoustic transducer in the vicinity of one of the large arteries;

(c) a measurement of blood oxygen saturation, content or partial pressure and/or a measure of either blood or end tidal carbon dioxide content—each as a measure of the adequacy of patient ventilatory function—which may serve as a supplement to, or instead of a direct measure of the respiratory rate;

(d) the monitoring of galvanic skin resistance, which could supplement the functioning of any IMD, when an assessment of sympathetic tone would be useful; and (e) the monitoring of blood glucose (or tissue glucose) which could be intermittently sampled externally (i.e. by the patient device) for systems with an automatic (or semi-automatic) implantable insulin delivery apparatus.

If the programming person wishes to use the "autoblend" feature, in which the system selects a preset blend for a given sensor mix, he/she can select either "DEFAULT VALUES WITH PATIENT INTERROGATION" or "DEFAULT VALUES WITHOUT PATIENT INTERROGATION", depending on whether patient interrogation is to be included in the patient assessment.

The screen is configured to allow for a number of help options for the programming person including:

(a) help from a help program including definitions and, possibly, suggestions;

(b) help from the medical expert device (which may be more sophisticated than that available on the device which directly supports screen setup); and (c) live help from a medical professional (if an MD is doing the programming).

In addition, the programming person may be given the opportunity to view (i) sensor data and (ii) patient interrogation data, from previously managed events, as a basis for setting up new management parameters. This information may be stored in one or more of the IMD, the patient device, the M.E. device or the remote station.

The bottom row of virtual buttons allows the system user to navigate between the screen 1900 and each of:

(a) the main therapy screen 1600 shown in FIG. 16;
(b) the autoblend screen 1700 shown in FIG. 17;
(c) the patient interrogation screen 1800 shown in FIG. 18;
(d) the physiologic sensor blend screen 2000 shown in FIG. 20;

(e) the syncope sensor blend screen 2100 shown in FIG. 21; and (f) the screen that was in previous use by the programming person.

Embodiments of the invention are possible in which a change in one or more sensor values (or a change in the weighted sum of all of the sensor values) that takes place during a treatment event results in a change in:

(a) the sensor parameterization scheme (e.g. the mathematical relationship between blood pressure and the score);

(b) the sensor blending scheme (i.e. the relative weight of each sensor);

(c) the actual treatment algorithm (e.g. exclusion of one or more tiers of therapy).

For example, if the patient interrogation parameter indicated that, during treatment, an ICD patient made a transition from conscious to unconscious, then regardless of the values of other sensors, each of the low level tiers of therapy (e.g. tier #1, tier#2 and tier#3 in the screen configuration shown in FIG. 16) would be skipped, and a high energy shock would be administered.

FIG. 20 shows an example of a setup screen 2000 for 6 types of sensors, in which the programming person may input information which determines the mathematical relationship between a physiologic parameter and the score which represents that parameter. If the relationship is a linear one, i.e. where the equation:

$$Y=AX+B,$$

where
Y is the value of the parameter score,
X is the value of the parameter
A is the sensitivity; and
B is the threshold value, then entering the desired values of threshold and sensitivity will specify the relationship between the parameter and the parameter score. For example, the equation:

$$\text{blood pressure score}=0.2\times(\text{systolic blood pressure})-10$$

generates a relationship between blood pressure score and systolic blood pressure which is similar to that shown in Table B. To enter such a relationship, the programming person, using the screen shown in FIG. 20 would:

(a) touch the "THRESHOLD" button under "BP", see a sub-menu (not shown in the figures) and select the value "−10"; and (b) touch the "SENSITIVITY" button under "BP", see a sub-menu (not shown in the figures) and select the value "0.2".

The "CURVE" button in each column leads to other options including:

(a) access to the programming of a non linear relationship between parameter values and parameter scores. The programming of a non-linear relationship could be accomplished by selecting an equation of second degree or higher [e.g. $Y=CX^3+DX^2+EX+F$] and specifying each of its defining elements [i.e. C, D, E and F, in the example];

(b) selecting from a menu of curves (which may be illustrated in a screen-in-screen configuration). The menu would include curves with exponential segments, logarithmic segments, parabolic shapes and other shapes, (c) allowing the programming person to draw, using the touch sensitive screen, a suitable curve, refine the drawing if necessary, and enter this shape along with the value of two or more points on the curve;

(d) allowing the programming person to enter two or more pairs of values of parameter value and parameter score, after which the programming person is presented with a menu of curves which fit these points. The programming person may select one such curve, and/or specify one or more additional pairs of values to refine the curve;

(e) access to the programming of segments of a curve or line, which, when such segments are assembled, delineates the full relationship between the parameter value and the parameter score;

(f) entering cutoff values (e.g. in Table B hereinabove, any systolic blood pressure value less than 60 mm. Hg. generates a blood pressure parameter value of "1");

(g) combinations of (a)-(f).

Alternatively, the programming person may decide to use a default relationship between parameter value and parameter score, which can be selected for any of the sensors by touching "DEFAULT" in the column of buttons corresponding to that sensor.

The programming person may define the sensor blend from the screen 2000, using the buttons in the fifth row, in the same manner as was the case for the first row of buttons for the screen 1900.

For each sensor, the programming person may select an "alert value", i.e. a parameter score (or parameter value) that results in the alerting of one or more of the IMD system entities. For example, the patient may be alerted for a glucose value below 70 mg./dl. By touching the button in row 6, in the GLUCOSE column, the programming person may enter (a) the value above or below which the alert is triggered, and (b) the entity to be alerted.

Similarly, for each sensor, the programming person may select an "alarm value", i.e. a parameter score (or parameter value) that results in the triggering of an alarm for one or more of the IMD system entities. For example, the patient may be presented with an alarm tone for a glucose value below 60 mg./dl. By touching the button in row 7, in the GLUCOSE column, the programming person may enter (a) the value above or below which the alarm is triggered, and (b) the entity to be alarmed. In the same hypothetical event with blood sugar of 60 mg./dl., the MP may be alerted (programmed as indicated hereinabove) when the patient is presented with the alarm tone.

The blood gas sensor may determine oxygen, carbon dioxide or another gas. Screens with fewer, more and with other sensors are possible, FIG. 21 shows a control screen 2100 for the management of a number of devices which may, either individually or in combination, allow fir the determination or the making of a conditional statement, about whether the patient has fallen or has suffered a syncopal episode. Such an arrangement is the subject of FIGS. 19A, 19B, 19F, 19G, 19I and 37 of U.S. Patent Publication No. US/2007/0043585A1. The devices, are indicated by the headings of columns 2 through 5 of FIG. 21 herein, i.e.

(a) one or more attitude sensors; These indicate the orientation of the patient's body in space;

(b) one or more accelerometers, which, by the detection of a sudden deceleration, may give evidence of a fall;

(c) one or more piezoelectric devices, which, by the detection of a discrete impulse, may indicate a fall;

(d) one or more cameras in the environment of the IMD patient, which, with image processing software known in the art, may allow for the detection of a fall; and (e) other devices which may make use of one or more of [i] sound, [ii] polarized light, and [iii] the detection of alternating current carrying conductors in a floor, (in FIGS. 19E, 19J and 19H of U.S. Patent Publication No. US/2007/0043585A1.

The values to be entered in each column: "threshold", "sensitivity", and "curve", are conceptually the similar to the methods for such entry described in the specification for FIG. 20. However, since some of the sensors which are the subject of FIG. 21 do not process one dimensional data (e.g. systolic blood pressure), but instead process more complex information (e.g. camera images), one or more additional steps for converting the complex information to a score (e.g. a scale of 10) reflecting the probability that a camera image or a sequence of such images represents a patient fall) will be necessary. The control of these steps may be outside the expertise of the MP, MD or other programming person who sets up the IMD system; Alternatively, the programming person may be allowed such access, which in turn may be through menus obtained by touching the "CURVES" button, or by adding other buttons which allow for such access.

As an alternative to entering threshold, sensitivity and curve information, the programming person may decide to use a default relationship between parameter value and parameter score, which can be selected for any of the sensors by touching "DEFAULT" in the column of buttons corresponding to that sensor; and which can be selected simultaneously for all of the sensors by touching the left most button in row five labeled "DEFAULT VALUES".

The programming person may define the sensor blend from the screen in FIG. 21, using the buttons in the fifth row, in the same manner as was the case for the first row of buttons for the screen shown in FIG. 19. Alternatively the programming person may choose to select a default blend of the available fall/syncope sensors.

The final step in the setup of fall/syncope detection is the programming of one or more definitions of one or more levels of certainty that a fall/syncopal episode has occurred. For example, if two sensing devices are operative (e.g. (a) a group of cameras and (b) a group of accelerometers), and each group generates a group value indicating, on a scale of ten, the probability that that group of sensors detected a syncopal event, then the programming person might program:

(a) "near certainty of syncope" as a sum of the two sensor group values (with each of the two group values ranging between 1 and 10) totaling 18 to 20;

(b) "high likelihood of syncope" as a sum of the two sensor group values (with each of the two group values ranging between 1 and 10) totaling 14 to 17; and (c) "possible syncope" as a sum of the two sensor group values (with each of the two group values between 1 and 10) totaling 10 to 13.

Many other formats for fall and/or syncope detection will be obvious to those skilled in the art.

Although most of the FIGS. 16-21 use the ICD and its management as examples, the concepts embodied could apply to other IMDs and the patient devices and sensors associated with them.

4.0 Triaging Using Function*

In an IMD system with multiple possible control entities, where each entity does not review all incoming IMD and/or patient data, methods and means of classifying the data in terms of urgency or potential urgency are necessary, in order to decide when data sharing among system entities is necessary. The classification system allows for data reflecting clinical events that exceed a predetermined level of urgency to be transmitted to potential control entities for review, in a process referred to as "notification". The IMD system described herein makes extensive reference to such notification, e.g. in the communicated signals in FIGS. 8-11, in screen FIG. 13, in the examples shown in FIGS. 22-24 and 77-82, and among the algorithms shown in FIGS. 29-58 (especially FIGS. 53-56B), and in the specification associated with each of these figures.

The level of urgency of a clinical event may be ascertained in a straightforward manner if the value of a single, easily measurable, physiologic parameter contains enough information for such determination. However, not infrequently, a single parameter-based evaluation is not as telling as an evaluation based on multiple parameters. For example, the combination of both heart rate and blood pressure are often more useful for clinical decision making in the management of a tachycardia, than is either heart rate or blood pressure alone.

It is therefore useful to have a logical process by which the value of two or more physiologic parameters—the "input variables"—are processed to produce one or more "output parameters", each such output parameter indicating (a) a "notify/do-not-notify" decision or (b) a "treat/do not-treat" decision. Three ways of performing this task are:
  (a) a flow diagram-based approach;
  (b) setting up a 2×2 matrix for the case of two input variables (and, in general, an N-dimensional, matrix for the case of N input variables), where each cell is defined by a range of values of each of the N input variables, and where each cell is assigned one or more output parameters, each of which indicates either a treat/no-treat decision, or a notify-entity-X/do-not-notify-entity-X decision. Table C and Table D hereinabove could be easily converted into 2×2 tables with row labels indicating one input variable (i.e. blood pressure, in the case of Table C) and column labels indicating another input variable (i.e. respiratory rate in the case of Table C); and with each cell in the 2×2 matrix containing a digit ranging from 1 to 10 (each of which digits may be used more than once), each digit indicating the output variable (referred to hereinabove as the "blended assessment"); or
  (c) arithmetically manipulating the input variables, so that they generate a single value, which reflects the severity of a clinical situation. That value is then utilized for notification and treatment decisions.

Each of the three approaches will lead to the same results; i.e. using any of approaches (a)-(c) hereinabove, the values of each of a plurality of sets of input variables may be matched to values of one or more output parameters. Any particular set of values of input variables is associated with a single set of treat/no-treat and notify/do-not notify decisions. The third approach is utilized frequently hereinbelow, and the arithmetic entity which amalgamates the information about the input variables into a single number is referred to as "Function*". The assembly of multidimensional clinical information into a single parameter reflecting the need for and the urgency of treatment mirrors how physicians deal with urgent clinical situations. The use of Function* for decision making may be viewed as an arithmetic method of carrying out the triaging process.

FIGS. 22A-24 illustrate the use of Function* in making treatment and notification decisions. Function* is further examined in FIGS. 71A-76C and the associated specification (and is also a consideration in FIGS. 60, 62, 65 and 67 and the associated specification). In the examples of Function* shown in FIGS. 22A and 22B, Function* is simply a restatement of a clinical parameter value; In the examples shown in FIGS. 23 and 24, Function* is a more detailed entity.

The example shown in FIG. 22A considers treatment and notification decisions in an ICD. Function* is identical to the heart rate. The multi-tier treatment/notification format is similar to that used in FIGS. 5A and 5B of U.S. Patent Publication No. US/2008/0300659. FIG. 22A herein indicates:

(a) ICD therapy (viz. bradycardia pacing) for heart rate of less than 60 b.p.m.;
  (b) no treatment for heart rates between 60 and 125 b.p.m.;
  (c) patient notification, but no treatment, for heart rates between 125 and 150 b.p.m.;
  (d) ICD treatment, without notification, for heart rates between 150 and 240 b.p.m.; and
  (e) both ICD treatment and MP notification, for heart rates above 240 b.p.m.

In the case of FIG. 22A and each similarly formatted figure, neither the figure nor the discussion dwell on the subtlety of whether heart rates which are exactly at the border between zones (e.g. 60, 125, 150 and 240 b.p.m in the case of FIG. 22A) are to be associated with the management zone above or the management zone below the border; a decision which does not affect the conceptual basis of the approach.

FIG. 22B shows an example of an implantable blood sugar management device in which:
  (a) the patient and the MP are notified for a blood sugar of less than 40 mg./dl.;
  (b) the patient (but not the MP) is notified for a blood sugar between 40 and 65 mg./dl.;
  (c) there is no treatment or notification for blood sugar values between 65 and 120;
  (d) the implanted device manages the blood sugar without notification, for blood sugar values between 120 and 160 mg./dl.;
  (e) the implanted device manages the blood sugar and notifies the patient, for blood sugar values between 160 and 350 mg./dl.; and
  (f) the implanted device manages the blood sugar and notifies both the patient and the MP, for blood sugar values greater than 350 mg./dl.;

FIG. 23 shows each of:
  (a) an example of a more complex Function*;
  (b) a two dimensional contingency table which contains the same relationships between the input variables (heart rate and ICD shock frequency), and the output (variables treatment and MP notification);
  (c) a text summary of ICD operation based on either (a) or (b).

The rationale for the treatment and notification format is:
  (a) MP notification may be desirable for a very severe tachycardia;
  (b) MP notification may be desirable for a less severe tachycardia if it is recurring; and
  (c) MP notification may be desirable for an even less severe tachycardia if it is recurring on a frequent basis.

In the algorithm used in the example, a tachycardia which occurs within 24 hours of a previous ICD shock is considered to be of greater concern, and a tachycardia which occurs within 20 minutes of a previous ICD shock is considered to be of even greater concern. These heightened levels of concern are used to lower the threshold for MP notification from a base value of notification at 250 b.p.m., to gradually lower notification thresholds values until, with multiple shocks as described hereinbelow, MP notification occurs with a tachycardia at 180 b.p.m.

As indicated in the figure:

$$\text{FUNCTION*}=A\cdot(10+2B+C)$$

where:
  A=Heart Rate for rates ≥180 b.p.m., and
  A=0 for rates <180 b.p.m.
  B=# of ICD shocks in past 24 hours, and
  C=# of ICD shocks in part 20 minutes The box on the left side of the figure shows an operating format which is defined by the selection of which actions are to be associated with which values of Function*. In the case shown:

(a) There is no treatment for values of Function* less than 1800;

(b) The ICD functions autonomously for values of Function* between 1800 and 2500; and (c) The ICD treats the tachycardia and notifies the MP for values of Function* above 2500.

A text statement of the operation of the algorithm, appearing at the bottom of the figure states:

(a) MP notification occurs for:
  (i) heart rate >250 b.p.m., without a shock within the last 24 hr.;
  (ii) heart rate ≥228 b.p.m., with 1 shock delivered between 20 min. and 24 hr. in the past;
  (iii) heart rate ≥209 b.p.m., with either [a] 2 shocks, each delivered between 20 min. and 24 hr. in the past, or [b] 1 shock delivered within the last 20 min.;
  (iv) heart rate ≥193 b.p.m., with either [a] 3 shocks, each delivered between 20 min. and 24 hr. in the past, or [b] 1 shock delivered between 20 min. and 24 hr. in the past and 1 shock delivered within the last 20 min.; and
  (v) heart rate >180 b.p.m. with either [a]4 or more shocks delivered between 20 min. and 24 hr. in the past, or [b]3 or more shocks delivered between 20 min. and 24 hr. in the past and I shock delivered within the last 20 min. or [c]2 or more shocks delivered within the last 20 min.; and (b) ICD therapy is triggered by a heart rate >180 b.p.m.

The 6 row by 5 column contingency table on the right side of the figure shows an operating format whose performance is identical to that of the Function* discussed herein.

Although the contingency table format readily illustrates system performance when the number of parameters is limited, it becomes unwieldy as soon as another parameter is added, and virtually impossible to display if yet another parameter is added. For example, one may consider the case where treatment and notification depend on (a) heart rate, (b) shock number, and (c) respiratory rate: A three dimensional table would be needed to show the contingencies. Alternatively they could be shown in a set of two dimensional tables, one for each value of the respiratory rate parameter. By way of further example, if the prior shock history were in a more complex algebraic format (than 2B+C in FIG. 23) and depended on a not-easily-lumped B and C parameter, then the inclusion of respiratory rate would require a table with a highly repetitive two dimensional structure, because of (a) the impossibility of visualizing a four or more dimensional table, and (b) the difficulty of dealing with multiple three dimensional tables.

FIG. 24 shows an example in which Function* is used to blend (a) heart rate and (b) a parameter with four possible values which indicates the likelihood of a syncopal episode (e.g. based on sensors which might be used in conjunction with the screen shown in FIG. 21). The possibility of syncope causes the operating format to be more reactive to a given rate of tachycardia, where more reactivity refers to a lowering of each of (a) the threshold for interrogating a patient, (b) the threshold for treatment, and (c) the threshold for MP notification. In the example shown, the greater the degree of certainty that a syncopal episode has occurred, the greater the lowering of the threshold for each of patient interrogation, treatment and MP notification.

The figure layout parallels that of FIG. 23, i.e. the upper left illustrates Function*, the upper right illustrates a contingency table which illustrates the same operating format as the Function* to its right, and the lower part of the figure summarizes the operation of the system in text/tabular format.

As indicated in the figure:

$$FUNCTION^* = D + E$$

where $$D = \text{Heart Rate (b.p.m.)} - 70$$

$$E = 80 \cdot (-1 + [\text{Sensor Value}]^{0.2}),$$

and

Sensor Value=1 indicates nil chance of patient fall
Sensor Value=2 indicates possible patient fall
Sensor Value=3 indicates high likelihood of patient fall
Sensor Value=4 indicates near certainty of patient fall The box on the left side of the figure shows an operating format which is defined by the selection of which actions are to be associated with which values of Function*. In the case shown:

(a) There is no treatment for values of Function* less than 76;

(b) For values of Function* between 76 and 96, the ICD interrogates the patient, and, based on the interrogation, makes a decision about whether or not to treat the tachycardia (and/or whether to apply a particularly gentle form of treatment);

(c) The ICD functions autonomously for values of Function* between 96 and 156; and (d) The ICD treats the tachycardia and notifies the MP for values of Function* above 156.

Examples of tachycardias which might be appropriate for such patient assisted analysis are:

(a) a tachycardia which may or may not be sinus tachycardia, and where a patient explanation of circumstances or indication of very good toleration would argue for non-aggressive management; and (b) a tachycardia which may be treated with either an aggressive (e.g. shock) or gentle (e.g. ATP) approach, where the selection is based on patient toleration.

The text/tabular summary at the bottom of the figure shows that for this example, the effect of increasing likelihood of syncope results in a decrease in the triggering heart rate of 12, 20 or 26 beats per minute (depending on the likelihood of syncope) for each of patient interrogation, ICD treatment and MP notification.

The table on the right side of the figure illustrates all possible contingencies for this example of Function* and the 4-level response to the Function* values.

Numerous other examples of the use of Function* will be obvious to those skilled in the art. Some are shown in FIGS. 71A-76C. Some examples of complex IMD management scenarios are shown in FIGS. 77-82.

5.0 Patient Assessment Algorithms

FIGS. 25 and 26 show algorithms for the use of cognitive information by either the IMD (FIG. 25) or the MP (FIG. 26). The hardware for obtaining the information is shown in FIGS. 4 and 6. Signal traffic carrying such information is shown in FIGS. 8-11. Whereas FIG. 18 (and 17 and 19) discuss the use (for treatment decision making) of an already completed patient interrogation, FIG. 25 shows the processing of information obtained from patient interrogation in real time.

Referring to FIG. 25, if the IMD is programmed for a mode of therapy in which a knowledge of the patient cognitive state is useful for determination of the aggressiveness of therapy, the IMD sends a prompt to the patient requesting a response. If the IMD does not receive a response within a given time interval t1, the assumption is made that the patient is not capable of a response, e.g. because of a dire medical state (though the non-response could be for other reasons [e.g. patient not in proximity to patient device]), and the IMD selects an aggressive therapy (e.g. a high energy shock, in the case of an ICD detecting a tachycardia). If the IMD receives a response to the prompt, options include:

(a) accept the response as evidence that the patient condition is good enough for the selection of a non-aggressive therapy (e.g. burst pacing, in the case of an ICD detecting a tachycardia); and (b) ask the patient a test question, and utilize the quality of the response to the test question for further decision making.

The programming and use of such questions to assess the patient cognitive state is discussed hereinabove in conjunction with FIG. 18. The physical source of the question and the evaluation of the response may be the IMD, the patient device or both (with the two units operating in a complementary fashion).

The response to the aforementioned question may be classified as good, fair or poor (or classified in a format with two or with more than three categories of response). If good, then non-aggressive IMD treatment is the result; If poor, then aggressive treatment is the result; If fair, then either:

(a) the IMD) may then select either aggressive or non-aggressive treatment, especially if there is time-pressure to make such a decision; or (b) the patient may be asked an additional question.

In similar manner to the algorithm response to the first question, the response to the second question may be classified as good, fair or poor (or classified in a format with a different number of categories of response). If good, then non-aggressive IMD treatment is the result; If poor, then aggressive treatment is the result; If fair, then either:

(a) the IMD may then select either aggressive or non-aggressive treatment;

(b) the patient may be asked an additional question, after which the algorithm proceeds as indicated herein for the response to the second question;

(c) the IMD may contact the MP for further guidance (who may then review the results of the interrogation as well as the medical situation in progress which necessitated the interrogation); or (d) the IMD may request the evaluation of either [i] the patient device (as indicated by the specification in conjunction with FIG. 18 [concerning cognitive issues] and FIGS. 17 and 19-21 [concerning non-cognitive patient assessment issues]), or [ii] the M.E. device (e.g. concerning one or more prior experiences [of this patient or others] with similar circumstances).

The algorithm shown in FIG. 25 could, with essentially nothing more than labeling changes (in which "patient device" and "IMD" are switched) would illustrate a patient interrogation algorithm performed by the patient device itself (rather than the interrogation conducted by the IMD described hereinabove, in which the patient device acts as an interface between the IMD and the patient). In such a figure conversion, the boxes in the figure original FIG. 25 which indicate the IMD selecting therapy, would indicate either (a) that the patient device selects therapy, or that the patient device provides its information to the IMD, so that the IMD may make the therapy selection.

FIG. 26 shows an algorithm in which an MP, in the process of managing a clinical situation determines that he/she would make a better decision with more knowledge of the patient's mental state. The MP sends a prompt to the patient requesting a response, if the MP does not receive a response within a given time interval t2, the assumption is made that the patient is not capable of a response, and the MP selects an aggressive therapy. If the MP receives a response to the prompt, options include:

(a) accept the response as evidence that the patient condition is good enough for the selection of a non-aggressive therapy;

(b) the MP utilizes the pre-programmed test question feature of the patient device (see FIGS. 18 and 25) to further assess the patient, and utilizes the quality of the response to the test question(s) for further decision making; and (c) the MP converses with the patient (preferably by audio, if not, then by text messaging), and utilizes the quality of the patient responses for further decision making.

If option (b) is selected, the response to the aforementioned question(s) may be classified as good, fair or poor (or classified in a format with two or with more than three categories of response). If good, then non-aggressive IMD treatment is the result; If poor, then aggressive treatment is the result; If fair, then either:

(i) the MP may then select either aggressive or non-aggressive treatment, especially if there is time-pressure to make such a decision;

(ii) the patient may be asked an additional question;

(iii) the MP may elect to give control of the IMD to either of the IMD, the patient device, or the M.E. device;

(iv) the MP may check the therapy recommendation of one or more of the IMD, the patient device, or the M.E. device;

(v) in unusual circumstances, the MP may elect to give control of the IMD to the patient; or (vi) the MP may choose to further evaluate the patient by conversing with him/her. The result of the conversation may then be classified as good, fair or poor (or in a truncated or expanded format with greater or fewer response categories, respectively). If good, then non-aggressive IMD treatment is the result; If poor, then aggressive treatment is the result; If fair, then any of options (i) (v) hereinabove may be selected.

If option (c) is selected, the response to the aforementioned conversation may be classified as good, fair or poor. If good, then non-aggressive IMD treatment is the result; If poor, then aggressive treatment is the result; If fair, then (1) the MP may select any of options (i), (iii), (iv) or (v), (2) the MP may utilizes the pre-programmed test question feature of the patient device to further assess the patient, and utilize the quality of the response to the test question(s) for further decision making. The result of the pre-programmed question evaluation may then be classified as good, fair or poor. If good, then non-aggressive IMD treatment is the result; If poor, then aggressive treatment is the result; If fair, then any of options (i), (iii), (iv) or (v) hereinabove may be selected.

Many other formats for patient evaluation are possible and will be obvious to those skilled in the art. They will be substantially dependent on the amount of time available for such evaluation; At times the evaluation may need to be truncated if the IMD or one or more sensors indicate a deteriorating patient condition, 6.0 System Architecture Summary FIG. 27A and FIG. 27B, Tables 1A and 1B respectively, show a partial list of the source of control in two, three, four and five entity IMD systems. The entities are selected from the list:

(1) the MP, (2) the medical expert device, (3) the patient, (4) the patient device, and (5) the IMD (which, if it runs parallel treatment decision algorithms, may be considered as multiple entities, one for each such algorithm).

The simplest systems are the two entity systems, where control is by either the IMD or by one of (a) the MP, (b) the M.E. device, (c) the patient, or (d) the patient device. The final two entity entry in the table refers to an IMD in which more than one algorithm may run, and where each of two algorithms may be the source of a treatment decision. Two entity systems include:

systems involving the IMD and the patient, the subject of FIGS. 46-69 herein;

systems involving the IMD and the MP, the subject of U.S. Patent Publication Nos. US/2007/0043585A1, US/2007/0299473, US/2008/0058884, US/2008/0300659, and Provisional Patent Application 61/204,957; and systems involving the IMD and an M.E. device, the subject of U.S. Patent Publication No. US/2008/0300659.

Three entity systems are the subject of 19 of the 29 algorithms discussed in conjunction with FIGS. 29 to 56B. They include:

an important system configuration: the IMD/patient/MP system [FIGS. 29-37 and 53-55 herein], also discussed in U.S. Patent Publication No. US/2008/0300659;

the IMD/patient/patient device system [FIGS. 38-43 herein]; and the IMD/M.E. device/MP system discussed in U.S. Patent Publication No. US/2008/0300659, and (c) a number of system architectures with multiple IMD algorithms, Four entity systems include the important system configuration which is a variation of IMD/patient/MP: IMD/patient device/patient/MP system. As seen in the table, the number of system configurations with multiple IMD algorithms running in parallel increases geometrically as the number of total entities increases, Five entity systems are shown in Table 1B/FIG. 27B. The important entry IMD/patient device/patient/M.E. device/MP is the subject of the algorithms shown in FIGS. 50-52, 56A and 56B, and is extensively discussed in conjunction with specification concerning system hardware, screens and examples. A partial list of the large number of configurations with multiple IMD algorithms is shown in the five entry section of the table.

FIG. 27C shows a 2×2 table for the control of an IMD which may be either internally controlled or externally controlled, with 4 possible operating states. The states are defined by each of two parameters: (i) the source of moment-to-moment control, which may be internal or external, and (ii) the highest priority source of control, which may be internal or external and need not be the same as the source of moment-to-moment control. Specifically:

(a) in the state in which the internal processor is both moment-to-moment controller and the highest priority controller, we have the function of a classic IMD such as a pacemaker. (The actual figure does describe such a classic IMD, since these devices are not programmable to be in each of the four states delineated by the figure;

(b) in the state in which the internal processor is the moment-to-moment controller but the external control station has the highest priority, we have an IMD whose operation can be overruled by an external control source;

(c) in the state in which the external processor is both moment-to-moment controller and the highest priority controller, we have the function of a classic EMD (external medical device). As indicated in the case of (a) above, the figure does not describe a classic EMD, which is not programmable to each of the other three states indicated herein;

(d) in the state in which the external processor is the moment-to-moment controller but the internal control station has the highest priority, we have an externally controlled medical device whose operation can be overruled by an internal control source. An example of such a situation would be one in which the device is primarily patient controlled, but in which the device may, under certain circumstances overrule the patient (e.g. if patient use of the device is deemed to be inappropriate). More complex examples are described in conjunction with FIGS. 77 to 82, 7.0 System Management Algorithms, Overview FIG. 28 shows Table 2: Classification of Some Possible System Algorithms. These algorithms are examples—some specific and some general—of flow diagrams showing where patient abnormalities are detected and analyzed, and the process by which an entity is selected to control the management of the abnormality. The flow diagrams are presented in FIGS. 29 to 56B.

7.1 3-Entity Systems with IMD, Patient and Medical Professional

FIGS. 29-33 involve primary monitoring at the IMD, and selection of one of three control entities (the IMD, the patient or the MP) by each of five possible agents. FIGS. 34-37 parallel FIGS. 29 to 33, but involve primary monitoring at the patient device, and selection of one of three aforementioned control entities by each of four possible agents.

Figure 38:
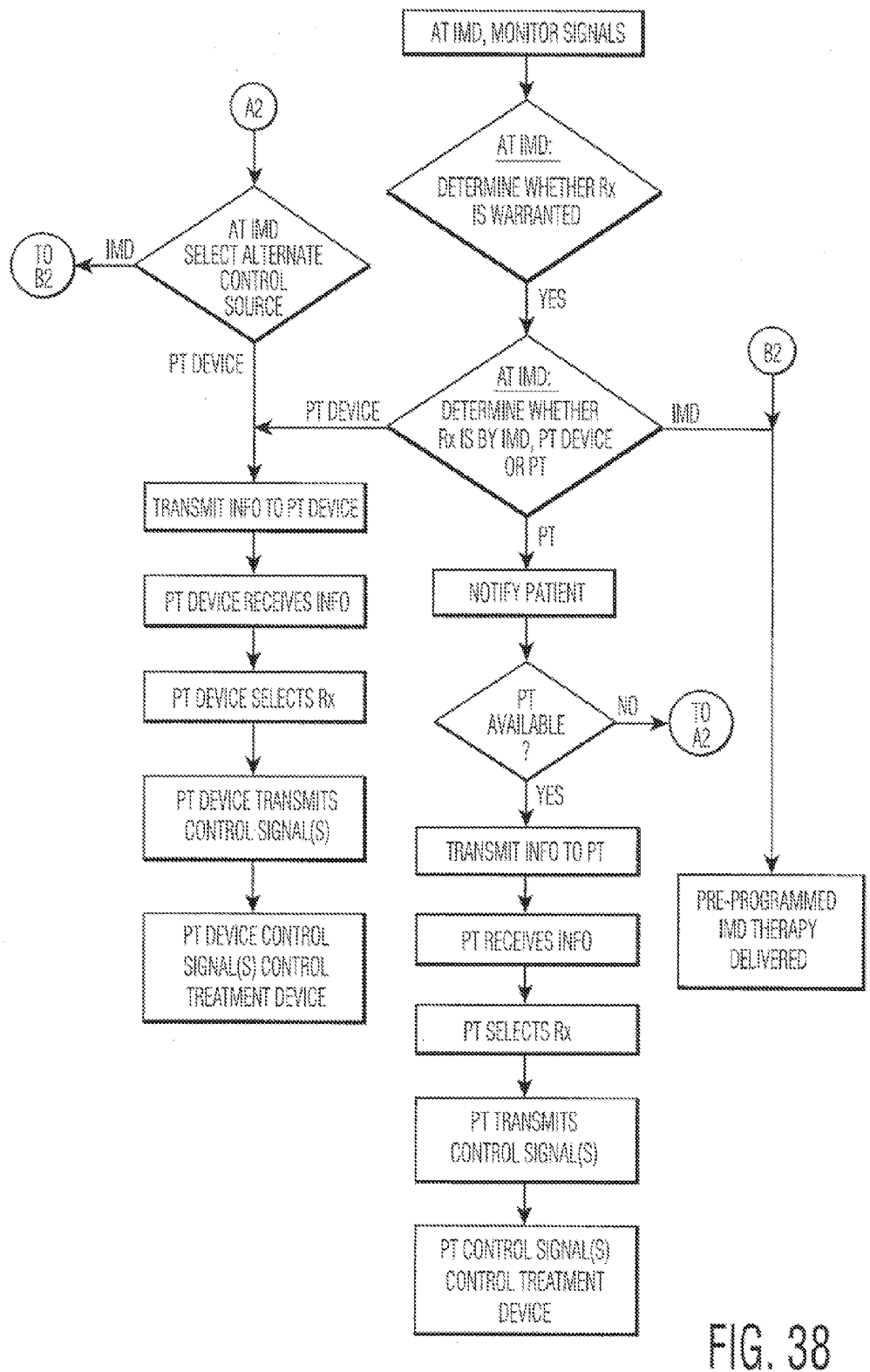
FIG. 38 is a flow diagram illustrating the control of a 3 entity IMD system, which may be controlled by each of an IMD, a patient device and a patient.
Figure 39:
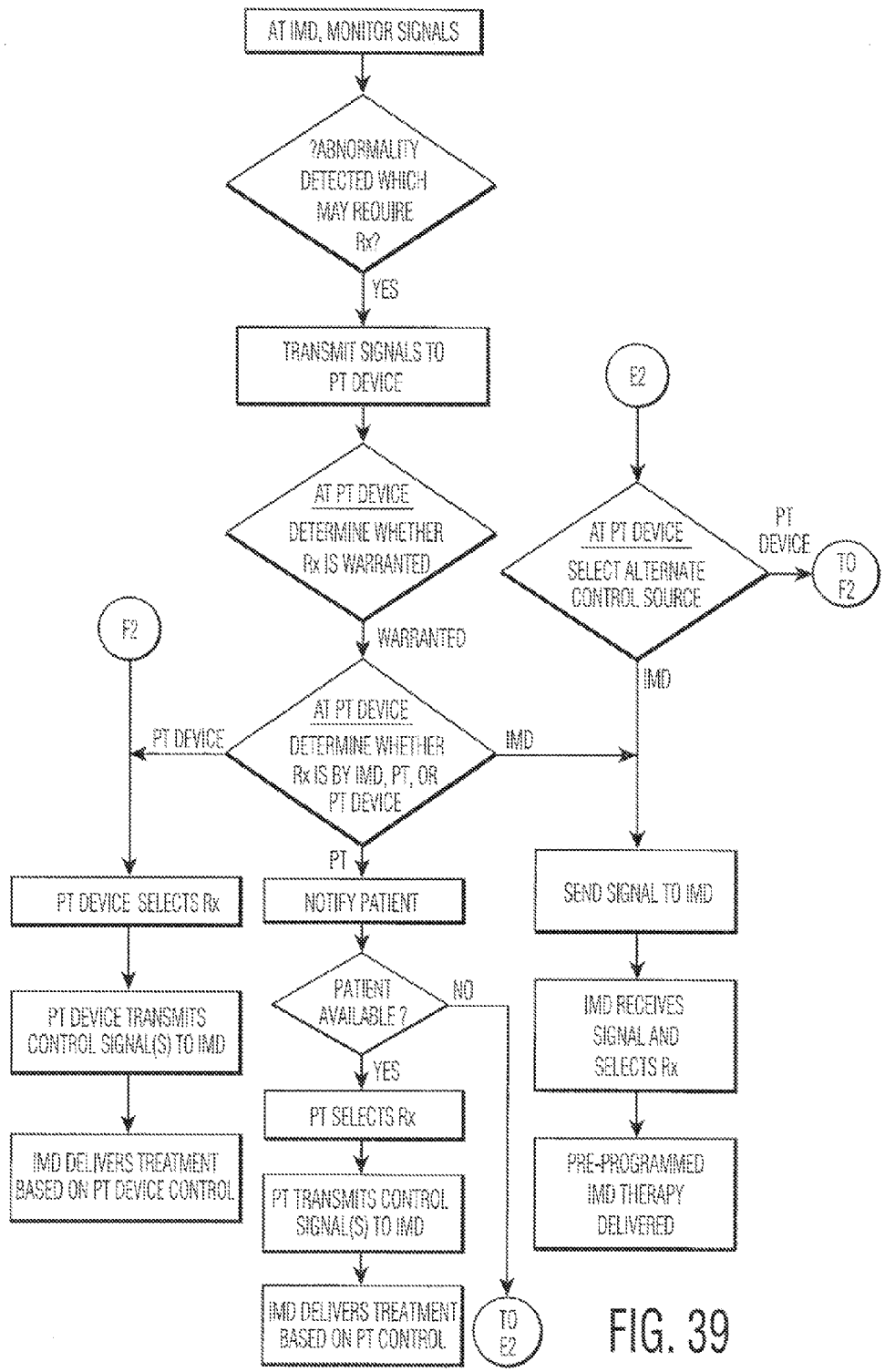
FIG. 39 is another flow diagram illustrating the control of a 3 entity IMD system, which may be controlled by each of an IMD, a patient device and a patient.
Figure 40:
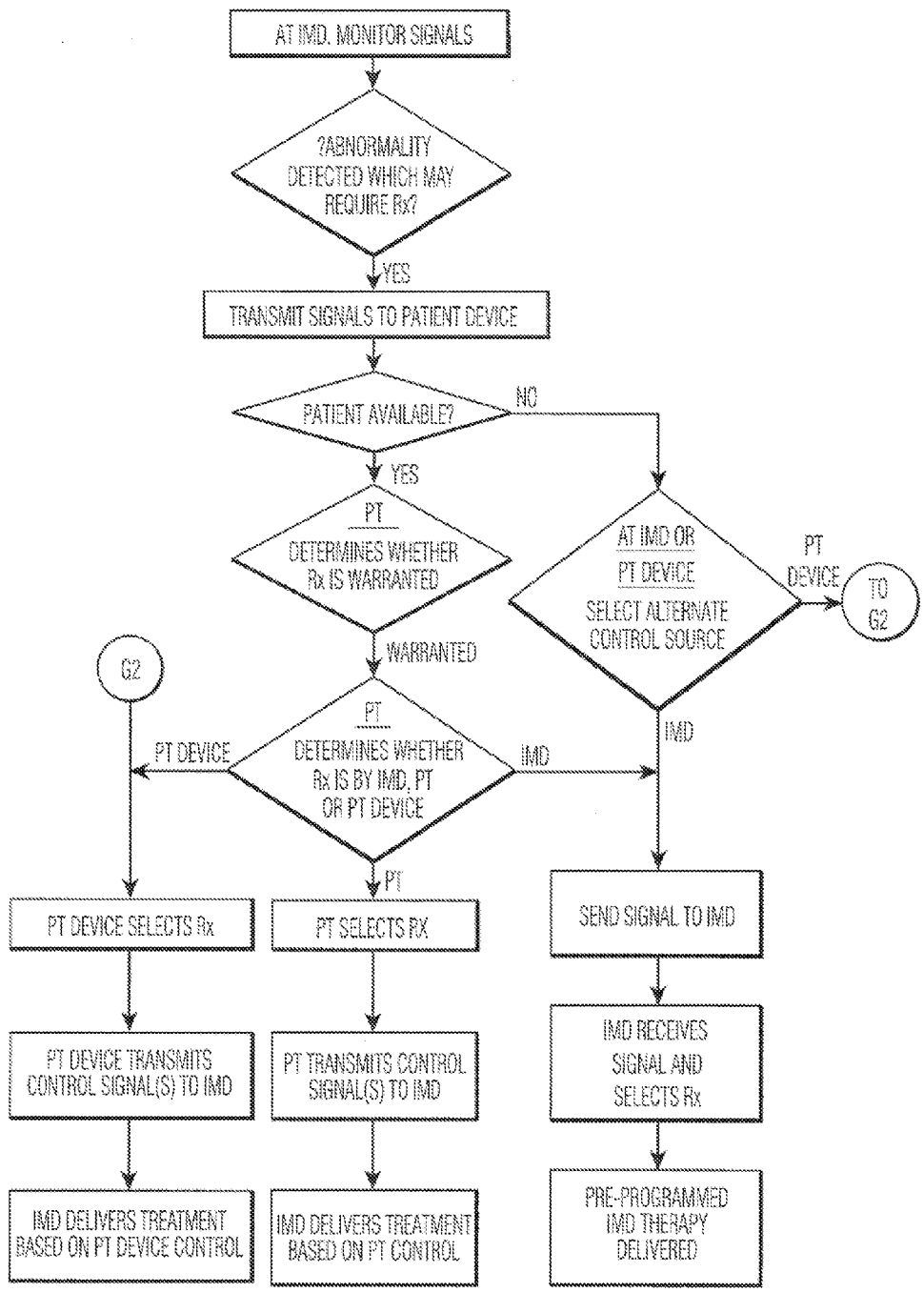
FIG. 40 is another flow diagram illustrating the control of a 3 entity IMD system, which may be controlled by each of an IMD, a patient device and a patient.
Figure 41:
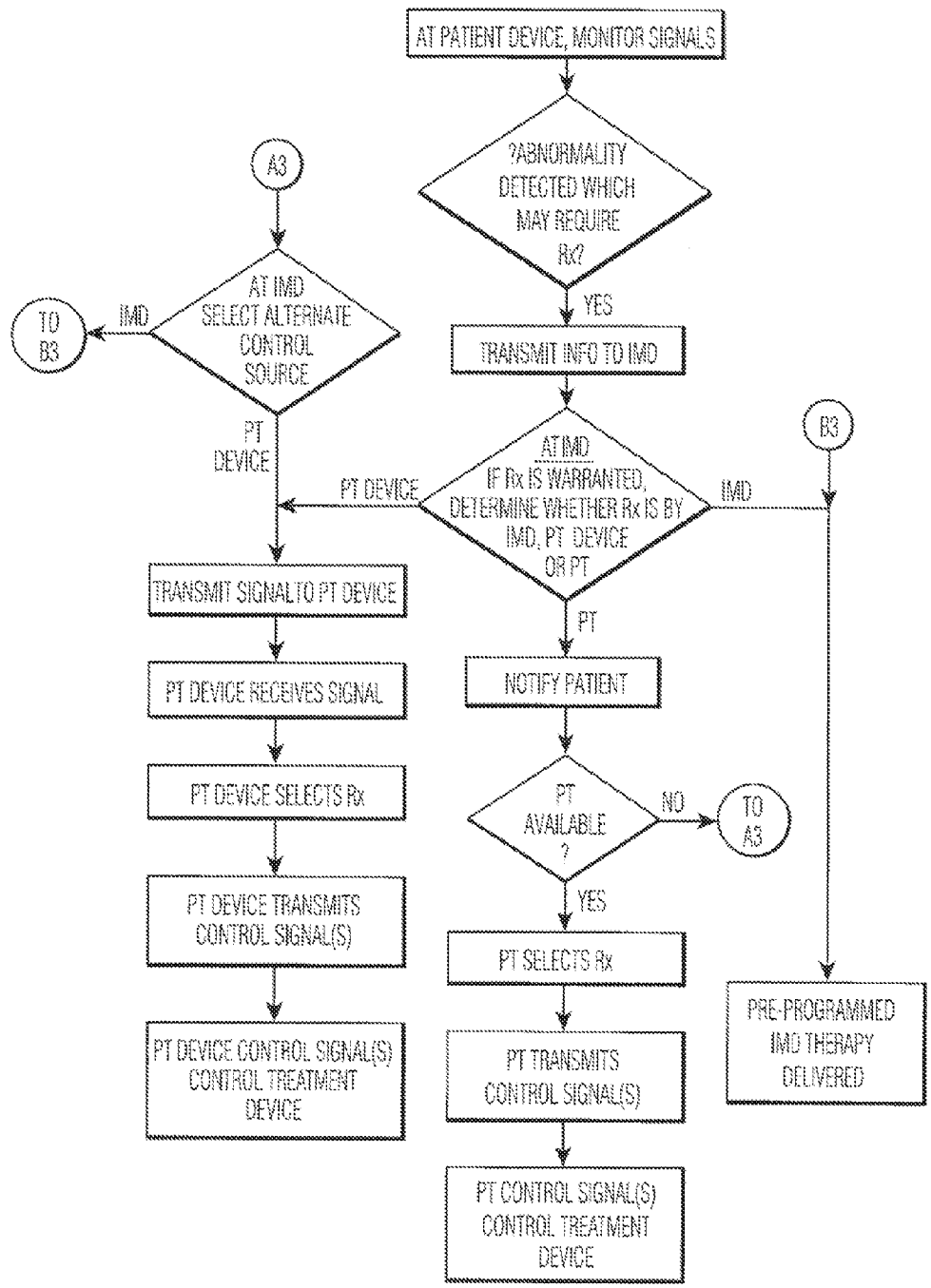
FIG. 41 is another flow diagram illustrating the control of a 3 entity IMD system, which may be controlled by each of an IMD, a patient device and a patient.

FIGS. 38-40 involve primary monitoring at the IMD, and selection of one of three control entities (the IMD, the patient device or the patient) by each of three possible agents. FIGS. 41-43 parallel FIGS. 38 to 40, but involve primary monitoring at the patient device, and selection of one of three aforementioned control entities by each of three possible agents.

FIGS. 44 and 45 are generalized algorithms for IMD systems with three entity control. In FIG. 44, the entity which does the primary monitoring also determines the choice of control entity. In FIG. 45, the entity which does the primary monitoring is not the first choice for determining the choice of control entity.

FIGS. 46-49 show algorithms for IMD systems with two possible control entities; while FIGS. 50-52 show systems with five possible control entities. Each of FIGS. 46-52 is structurally similar to the three entity flow diagrams of FIGS. 29-45. FIGS. 53-56B show flow diagrams with a substantially different format than those of FIGS. 29-52.

FIG. 53 shows a flow diagram in which the IMD is the default control source, and in which either of the patient or the MP may overrule the IMD.

FIGS. 54 and 55 show another approach in which the hierarchy among the MP, the patient and the IMD are predetermined, i.e. determined in advance by system programming, although the choice of entity which actually controls a particular situation will also depend on which notification criteria are met, and may depend on whether the MP or the patient chooses to exercise control.

FIGS. 56A and 56B show five entity versions of the algorithms shown in FIGS. 54 and 55. FIG. 56B illustrates a flow diagram which shows how the control screen in FIG. 14 may control a five-entity IMD system.

Figure 29:
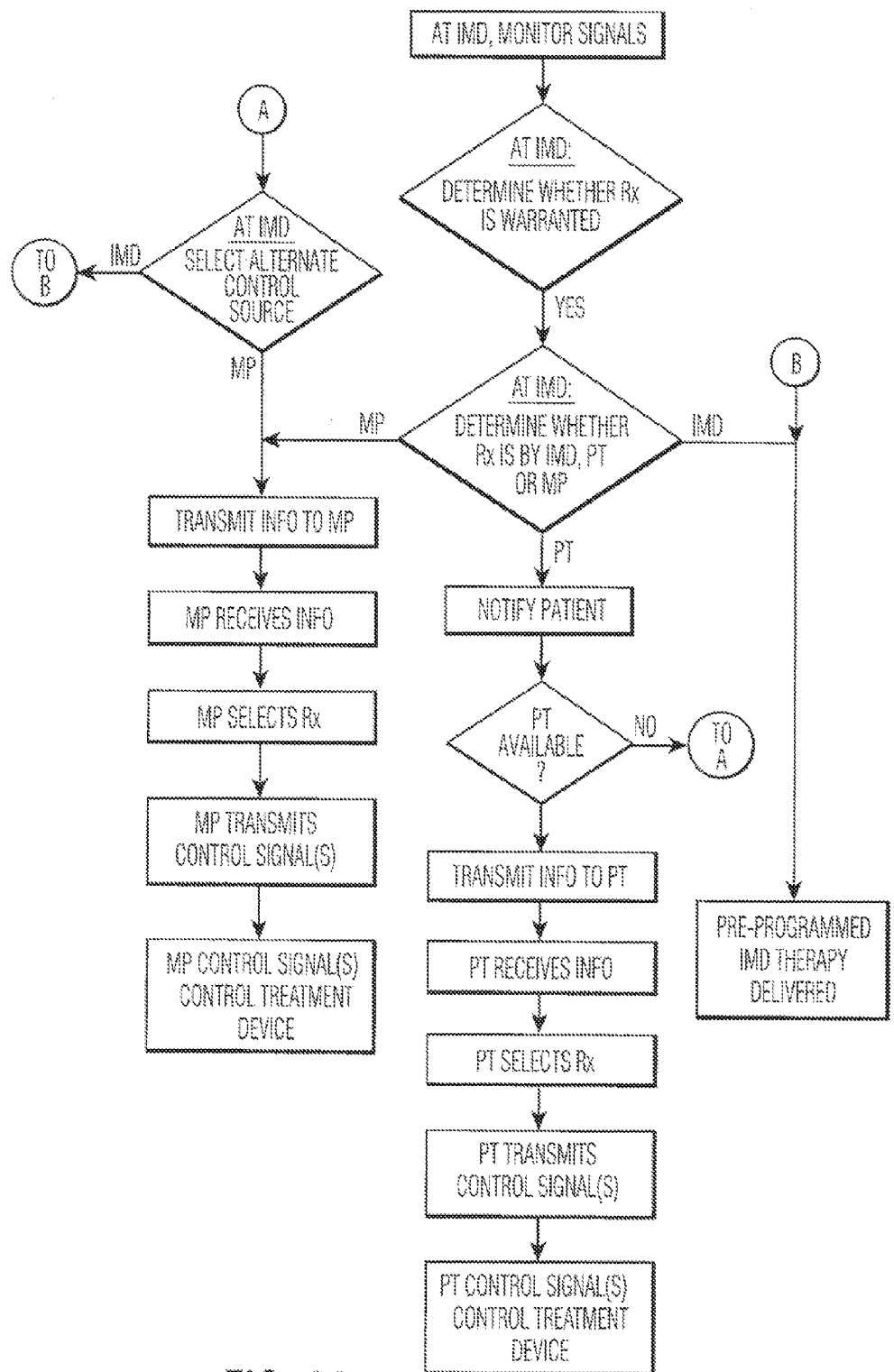
FIG. 29 is a flow diagram illustrating the control of a 3 entity IMD system, which may be controlled by each of an IMD, a patient and a medical professional.

FIG. 29 shows an algorithm for management of a system with an IMD, a patient with patient device and an MP. Signals are monitored primarily at the IMD. If an abnormality is detected which requires therapy, a decision is made by the IMD as to which of the IMD, the patient or the MP will be the source of control. The decision may be based on a pre-selected format, e.g. the IMD ideally manages the abnormality for straightforward situations, and in non-straightforward situations, it selects the patient, unless the patient is unavailable, in which case it selects the MP; Many other divisions of management responsibility are possible, and are discussed hereinabove and hereinbelow in sections related to notification of the other entities which may serve as a source of control (see the specification which discusses FIGS. 71A to 76C). Alternatively, rather than basing the selection of control agent a pre-selected format, the IMD may make a selection based on "secondary information," i.e. information which comes from a source other than the primary source; In such an instance the primary (IMD sensor) information would be augmented by the secondary (patient device) information, concerning the current condition (either physiologic, cognitive or both) of the patient.

In the algorithm shown in FIG. 29, if the IMD determines that therapy is warranted and the IMD selects IMD management, it proceeds with its own pre-programmed management algorithm. If it determines that therapy is warranted and selects patient management, then before therapy can proceed, it must be determined if the patient is available. Availability can refer to:
 (a) the adequacy of communications between the IMD and the patient device;
 (b) the patient being in proximity to the patient device;
 (c) whether the patient has the ability, as the result of his/her current medical state, to perform the required decision making function; and
 (d) whether the patient is willing to perform the management function.

The IMD, through the patient device, queries the patient to determine availability. It could also directly indicate to the patient that a patient input is requested by notifying the patient directly from the IMD, by either the emission of a tone, or a vibration. If the patient is available, the information is presented to the patient. If appropriate, the patient receives the information, selects a treatment via the patient device, which transmits control signals indicative of the choice to the IMD. The IMD then executes the treatment ordered by the patient. If the patient is unavailable, the IMD then selects either the MP or the IMD as the source of control.

If the IMD determines that therapy is warranted and the MP is selected as the source of control (either because this was the IMD first choice, or because the IMD chose the patient, but the patient was unavailable, and the IMD then chose the MP), the IMD transmits information to the MP sufficient to allow the MP to make a management decision. The MP receives the information, and selects the therapy (including the possibility of selecting no therapy). The MP then transmits the appropriate control signals to the IMD, allowing for execution of the MP choice. Not shown in this algorithm, but the subject of the patent and applications incorporated herein by reference (and also discussed in conjunction with FIGS. 44 and 78 hereinbelow), in the event that communication with the MP is impaired or is not possible, the IMD may seek other remedies including (a) managing the situation according to its preprogrammed algorithm, (b) contacting the patient (if this was not already tried), and (c) continuing to try to contact the MP.

Figure 30:
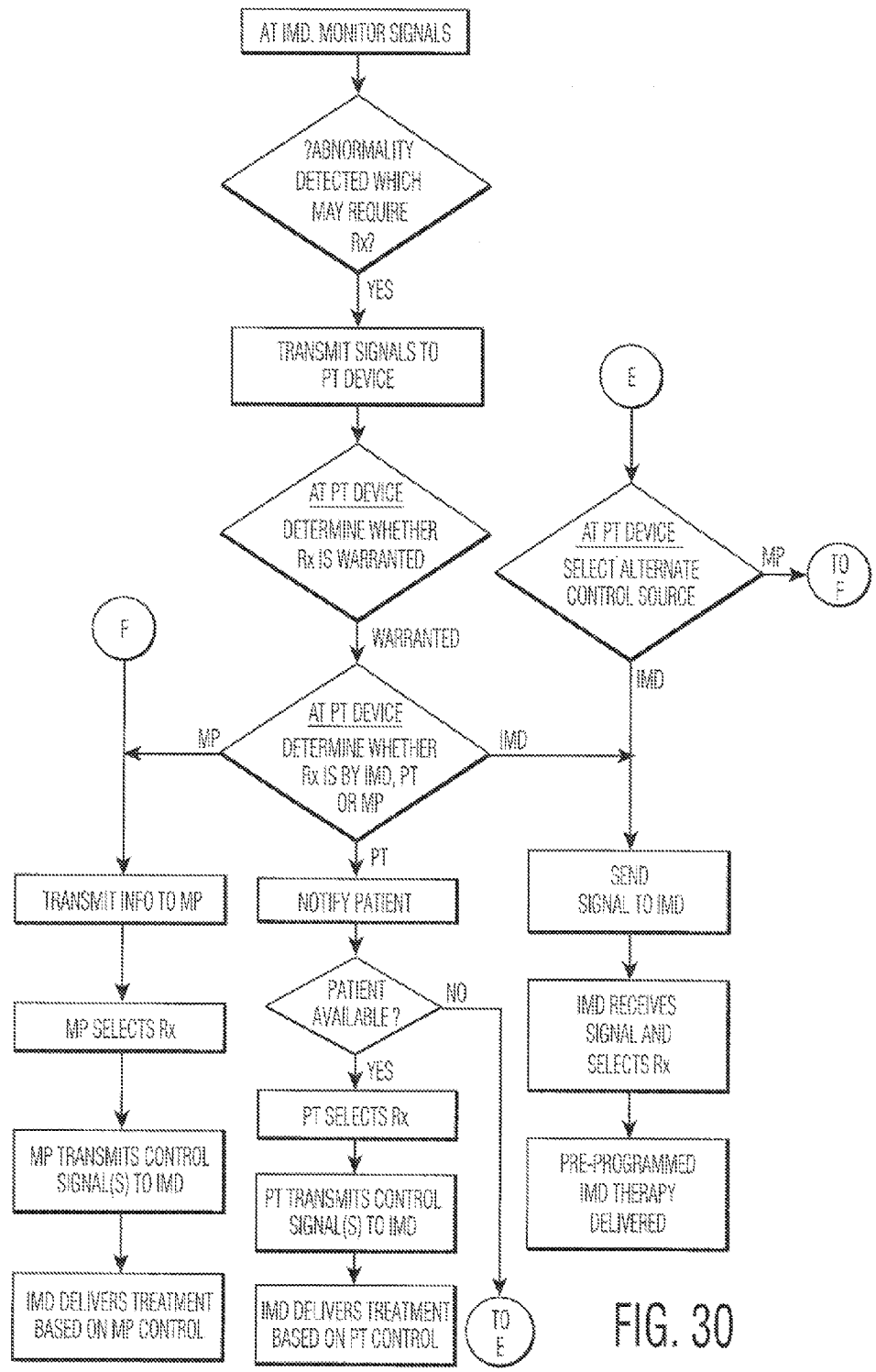
FIG. 30 is another flow diagram illustrating the control of a 3 entity IMD system, which may be controlled by each of an IMD, a patient and a medical professional.

FIG. 30 shows an algorithm for management of a system with an IMD, a patient with patient device, and an MP, in which the choice of controlling agent occurs at the patient device. Signals are monitored at the IMD. If an abnormality is detected which may require therapy, signals are transmitted to the patient device, where a decision is made by the patient device as to whether therapy is warranted, and if it is, as to which of the IMD, the patient or the MP will be the source of control. The transmitted signals will preferably carry information obtained by the sensors in the IMD (including one or more of (a) raw sensor data, (b) processed sensor data, and (c) data indicative of the therapy selection/recommendation by the IMD algorithm[s]), and may carry additional information, such as the latest programming of the IMD. The patient device decision may be based on a pre-selected format, or it may make a selection based on recently obtained information which the patient device has access to, concerning the current condition (either physiologic, cognitive or both) of the patient.

In the algorithm shown in FIG. 30, if therapy is warranted and the patient device selects IMD management, it signals the IMD to proceed with the IMD pre-programmed management algorithm. If therapy is warranted and the patient device selects patient management, then before therapy can proceed, it must be determined if the patient is available. The patient device queries the patient to determine availability. If the patient is available, the information is presented to the patient. The patient receives the information, selects a treatment via the patient device, which transmits control signals indicative of the choice of therapy to the IMD. The IMD then executes the treatment ordered by the patient. If the patient is unavailable, the patient device then selects either the MP or the IMD as the source of control.

If therapy is warranted and the MP is selected as the source of control, the patient device and/or the IMD transmits information to the MP sufficient to allow the MP to make a management decision. The MP receives the information, and selects the therapy. The MP then transmits the appropriate control signals to the IMD, allowing for execution of the MP choice. The aforementioned reference to possible remedies for inadequate communication with the MP apply.

Figure 31:
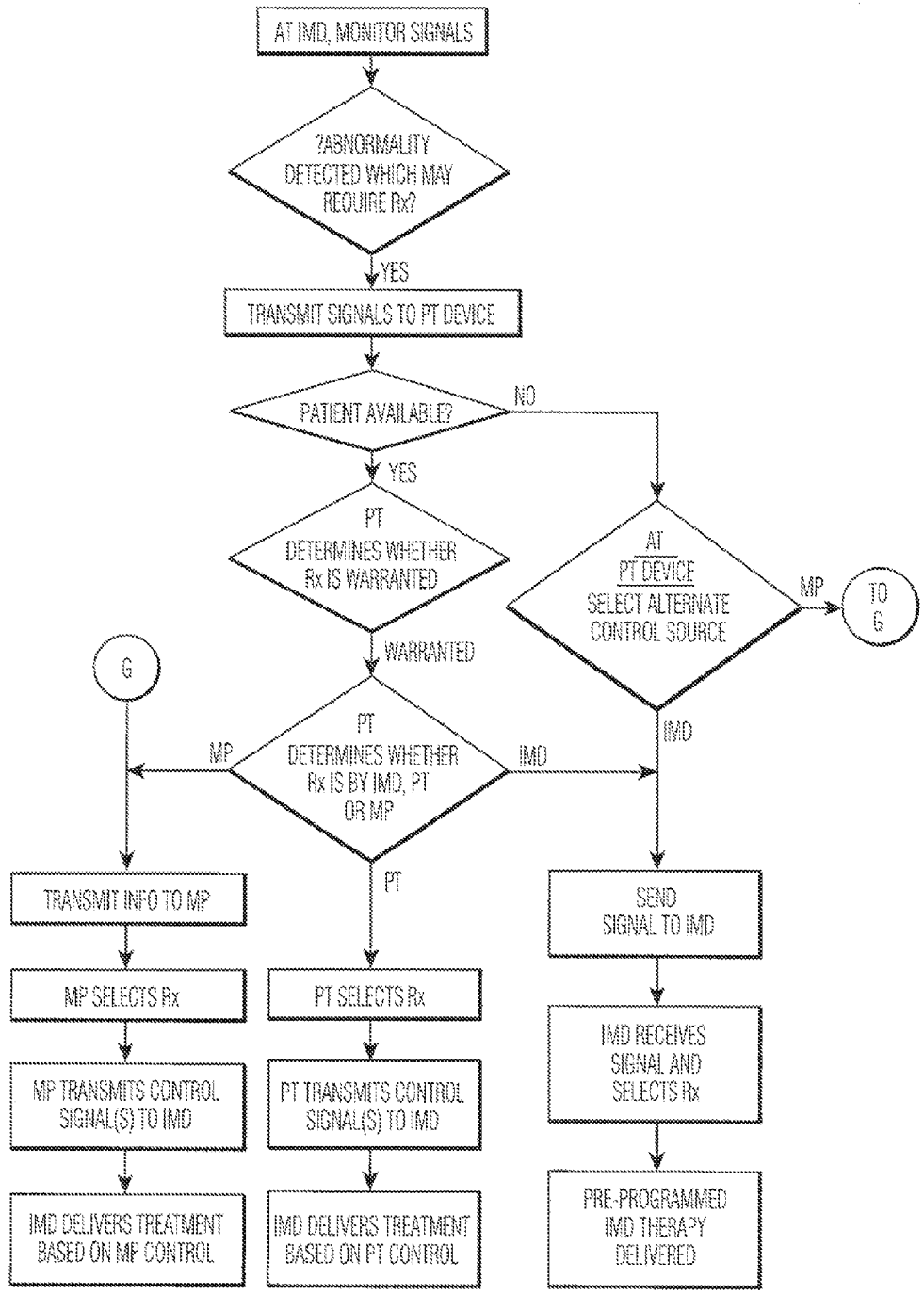
FIG. 31 is another flow diagram illustrating the control of a 3 entity IMD system, which may be controlled by each of an IMD, a patient and a medical professional.

FIG. 31 shows an algorithm for management of a system with an IMD, a patient with patient device, and an MP, in which the patient is given the option of making the choice of which entity is in control. Signals are monitored at the IMD. If an abnormality is detected which may require therapy, signals are transmitted to the patient via the patient device, and then patient availability is determined. If the patient is available, a decision is made by the patient as to whether therapy is warranted, and if it is, as to which of the IMD, the patient or the MP will be the source of control. Information available to the patient includes the aforementioned IMD-based sensor and programming information, patient device-based sensor information, and the patient's knowledge of how he/she is feeling, and his/her attitude about the various available therapeutic options. The patient reviews the information, and makes the aforementioned decision(s). If the patient determines that treatment is warranted and selects himself/herself as the treatment agent, the patient selects their choice of therapy and indicates it via that patient device, which transmits control signals indicative of the choice to the IMD. The IMD then executes the treatment ordered by the patient. If the patient is not available, the patient device (or, not indicated in the figure, the IMD) makes a selection of either the IMD or the MP, the selection being based on either a pre-programmed format, on information obtained by the patient device (or the IMD) at the time that the decision is made, or both.

In the algorithm shown in FIG. 31, if the patient determines that treatment is warranted and selects IMD management, the patient device signals the IMD to proceed with the IMD pre-programmed management algorithm. If the patient determines that treatment is warranted and selects the MP, the patient device and/or the IMD transmits information to the MP sufficient to allow the MP to make a management decision. The MP receives the information, and selects the therapy. The MP then transmits the appropriate control signals to the IMD, allowing for execution of the MP choice.

Figure 32:
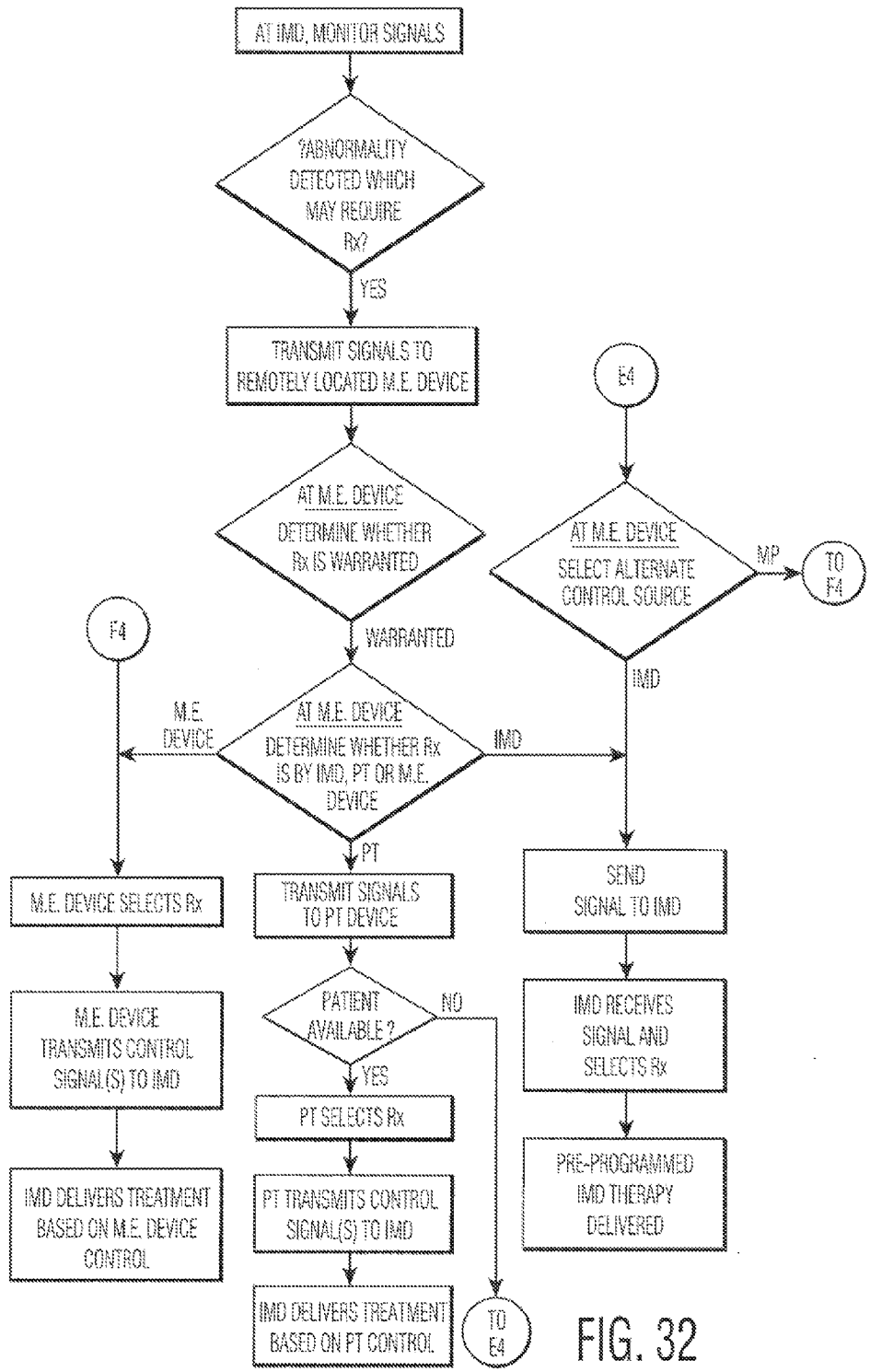
FIG. 32 is another flow diagram illustrating the control of a 3 entity IMD system, which may be controlled by each of an IMD, a patient and a medical expert device professional.

FIG. 32 shows an algorithm for management of a system, with an IMD, a patient with a patient device, and a medical expert device, in which the M.E. device is given the option of choosing which entity is in control. Signals are monitored at the IMD. If an abnormality is detected which may require therapy, signals are transmitted to the medical expert device, where a decision is made by the M.E. device as to whether therapy is warranted, and, if it is, as to which of the IMD, the patient or the M.E. device will be the source of control. The transmitted signals will preferably carry information obtained by or processed from the sensors in the IMD, and may carry additional information, such as the latest programming of the IMD, and information from the patient device (either transmitted via the IMD, or directly from the patient device to the M.E. device). The M.E. device decision will be based on one or more of:

(a) information obtained from the IMD (b) information obtained from the patient device [including one or more of physiologic and cognitive information], and (c) information obtained from the M.E. device database, including one or more of:

(i) information about the past performance of the actual IMD which is implanted in the patient
  (ii) information about the past performance of the same model of IMD in other patients
  (iii) information about the past performance of any actual associated hardware (e.g. a defibrillator lead wire) which is implanted in the patient
  (iv) information about the past performance of the same model of associated hardware in other patients
  (v) information from a library of electrograms from this patient and/or other patients
  (vi) information about this patient's last known medication list and dosages, vis-à-vis their effect on current management
  (vii) information about this patient's past medical history
  (viii) information about the preferences of this patient's physician.

The M.E. device may also consult with the MP.

In the algorithm shown in FIG. 32, if the M.E. device determines that treatment is warranted and selects IMD management, it signals the IMD to proceed with the IMD pre-programmed management algorithm. If the M.E. device determines that treatment is warranted and selects patient management, then before therapy can proceed, it must be determined if the patient is available. The patient is queried by the patient device to determine availability. If the patient is available, the information is presented to the patient. The patient receives the information, selects a treatment via the patient device, which transmits control signals indicative of the choice of therapy to the IMD. The IMD then executes the treatment ordered by the patient. If the patient is unavailable, the M.E. device then selects either the M.E. device or the IMD as the source of control.

If the M.E. device determines that treatment is warranted and selects itself as the source of treatment management, it selects the therapy and then transmits the appropriate control signals to the IMD. In the event of inadequate communication with the M.E. device, the remedies are analogous to the aforementioned remedies for inadequate communication with the MP.

Not shown as a separate figure, but analogous to FIG. 32, is an algorithm in which the M.E. device selects a control agent from the group: (a) IMD, (b) patient, and (c) MP. In such an algorithm, if the M.E. device selected the MP as the control agent, the MP would need to be supplied with sufficient information to make a therapeutic decision. A four agent algorithm is also possible, in which the M.E. device selects a control agent from the group: (a) IMD, (b) patient, (c) M.E. device and (d) MP (See the first listing under "4 entity systems" in Table 1a/FIG. 27A). Five entity systems are the subject of FIGS. 50-52, 56A and 56B, and the associated specification.

Figure 33:
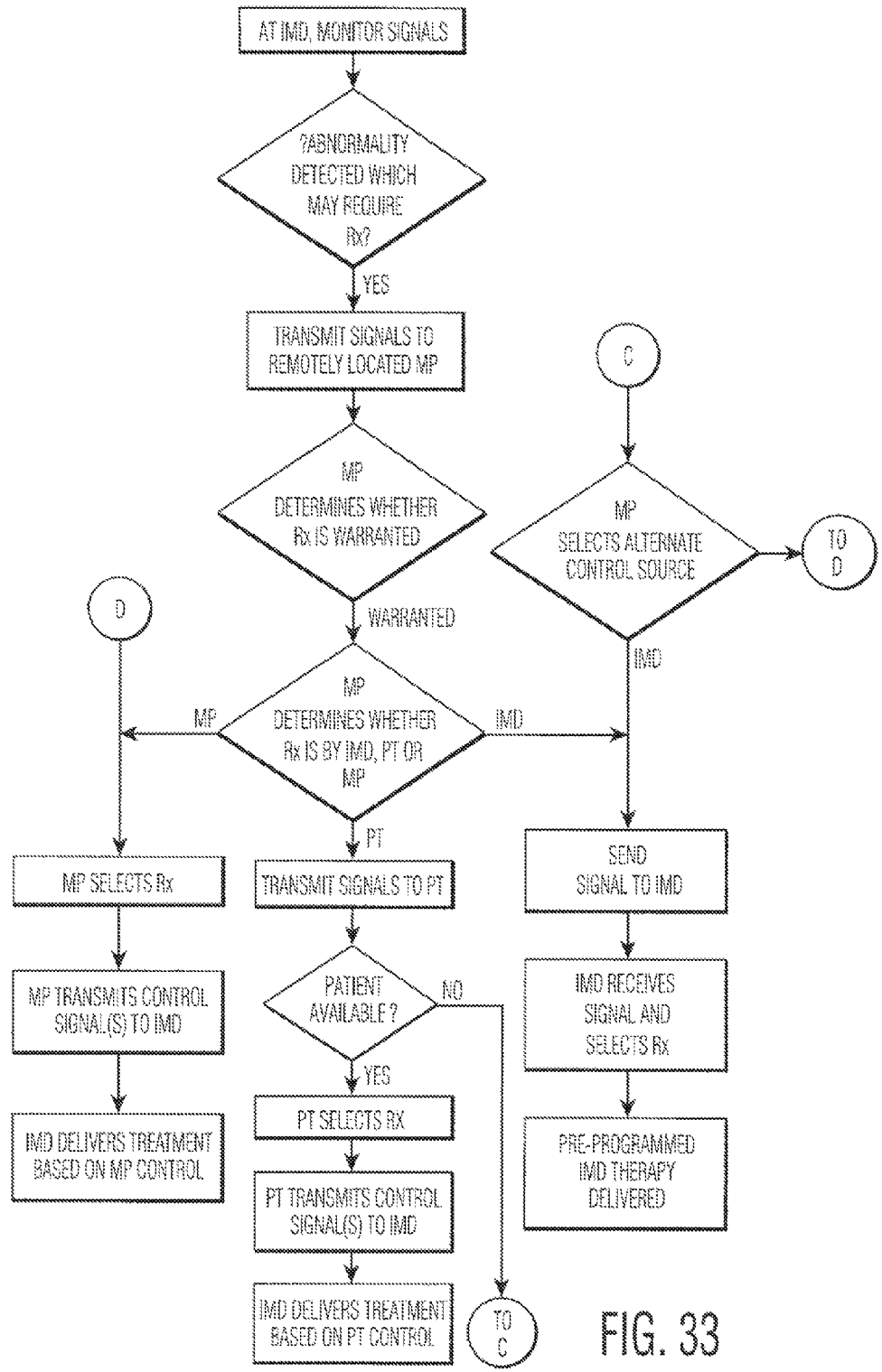
FIG. 33 is another flow diagram illustrating the control of a 3 entity IMD system, which may be controlled by each of an IMD, a patient and a medical professional.

FIG. 33 shows an algorithm for management of a system with an IMD), a patient with a patient device, and an MP, in which the MP is given the option of choosing which entity is in control. Signals are monitored at the IMD. If an abnormality is detected which may require therapy, signals are transmitted to the MP, who determines if therapy is warranted, and if it is, makes a decision as to which of the IMD, the patient or the MP will be the source of control. (The case of an unreachable MP has already been discussed hereinabove, and is also addressed in conjunction with FIGS. 44 and 78 hereinbelow.) The transmitted signals will carry the aforementioned information from the IMD, and may carry additional information from the patient device. The MP decisions may be based on a pre-selected format, or he/she may make a selection based on information which the patient device provides concerning the current condition (either physiologic, cognitive or both) of the patient; or the MP decision may be based on the MP (a) experience with this particular patient, (b) experience with the device that the patient has, (c) experience with the current abnormality that the patient has, (d) experience with the current medications taken by the patient, (e) awareness of current medical literature and developments, or (f) a combination of two or more of (a)-(e). The MP may also make his/her decision after consulting the M.E. device database.

In the algorithm shown in FIG. 33, if the MP determines that treatment is warranted and selects IMD management, he/she signals the IMD to proceed with the IMD pre-programmed management algorithm. If the MP determines that treatment is warranted and selects patient management, then the patient is queried by the patient device to determine availability. If the patient is available, the appropriate information is presented to the patient. The patient receives and reviews the information, selects a treatment via the patient device, which transmits control signals indicative of the choice of therapy to the IMD. The IMD then executes the treatment ordered by the patient. If the patient is unavailable, the MP then selects either the MP or the IMD as the source of control.

If the MP determines that treatment is warranted and self selects, then he/she goes on to select the appropriate treatment, and then transmits the corresponding control signals to the IMD, allowing for execution of the MP choice, Whereas FIGS. 29-33 show algorithms in which the monitoring of information at the IMD may initiate a therapeutic action, FIGS. 34-37 show four algorithms in which monitoring of information at the patient device may initiate such an action.

Figure 34:
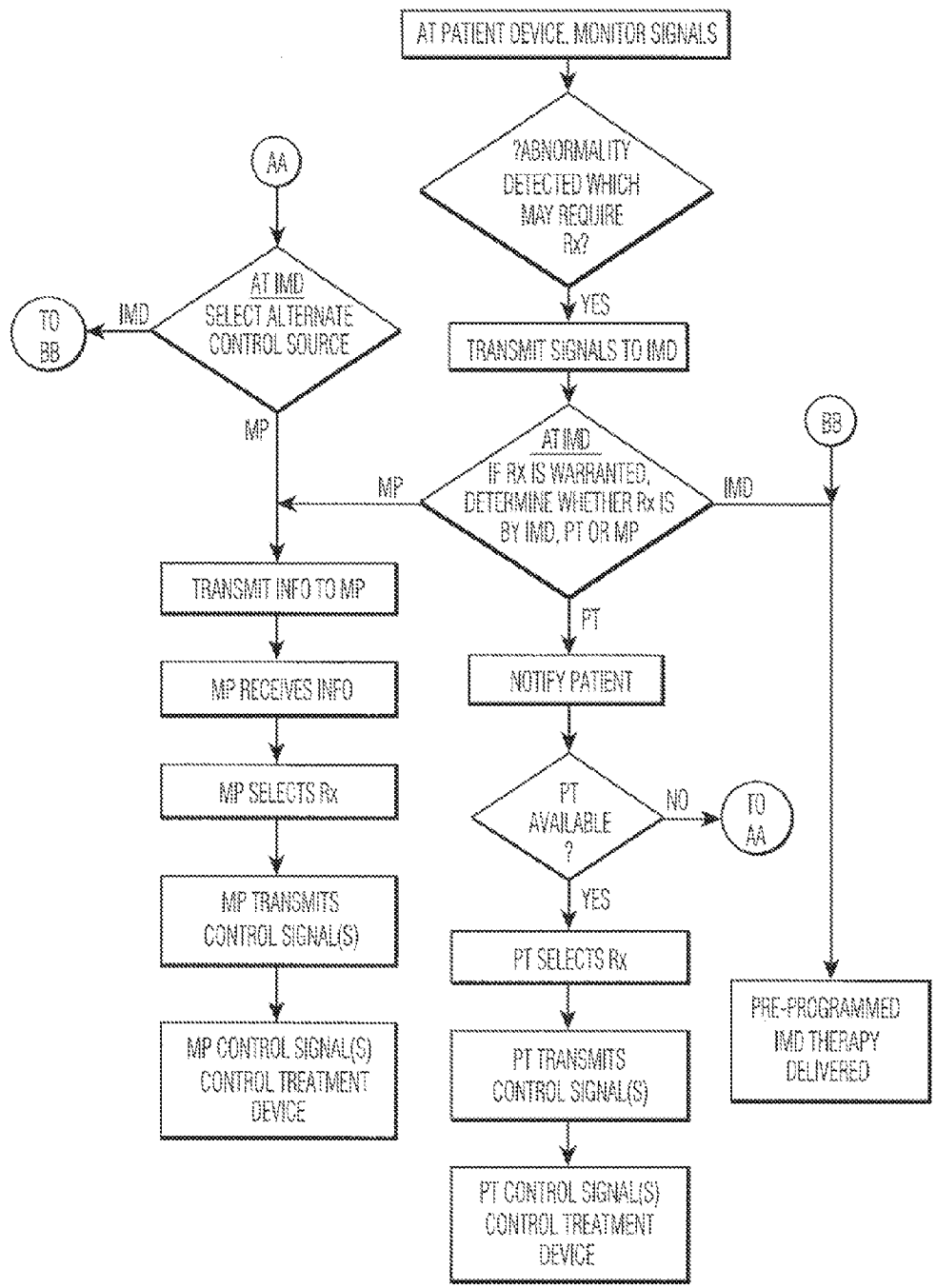
FIG. 34 is another flow diagram illustrating the control of a 3 entity IMD system, which may be controlled by each of an IMD, a patient and a medical professional.

FIG. 34 shows an algorithm for management of a system with an IMD, a patient with patient device and an MP, in which the decision to consider treating an abnormality takes place at the patient device. This algorithm is analogous to the one shown in FIG. 29, since in both algorithms and figures, the choice of which of three entities does the treating takes place at the IMD, but in the FIG. 29 algorithm, the decision to consider treatment takes place at the IMD. A decision to consider treatment may occur at the patient device (FIG. 34) rather than at the IMD (FIG. 29) in a case where sensors inputting the patient device indicate a dire patient state, which may be undetected by the IMD.

If an abnormality is detected at the patient device which may require therapy, information about the patient device observation is transmitted to the IMD. At the IMD, a decision is made as to whether treatment is warranted. The decision may be based on (a) the information transmitted by the patient device, (b) information derived from the IMD sensor(s), or (c) both (a) and (b). If the decision is to treat, the IMD makes a decision as to which of the IMD, the patient or the MP will be the source of control. The decision may be based on a pre-selected format (e.g. the IMD ideally manages the abnormality for straightforward situations, and in non-straightforward situations, it selects the patient, unless the patient is unavailable, in which case it selects the MP), or it may make a selection based on information which the patient device has provided, concerning the current condition (either physiologic, cognitive or both) of the patient.

In the algorithm shown in FIG. 34, if the IMD determines that treatment is warranted and selects IMD management, it proceeds with its own pre-programmed management algorithm. If it determines that treatment is warranted and selects patient management, then it queries the patient to determine patient availability for management of the current event. If the patient is available, the information is presented to the patient. The patient receives the information, selects a treatment via the patient device, which transmits control signals indicative of the choice to the IMD. The IMD then executes the treatment ordered by the patient. If the patient is unavailable, the IMD then selects either the MP or the IMD as the source of control.

If the IMD determines that treatment is warranted and the MP is selected, the IMD transmits information to the MP sufficient to allow the MP to make a management decision. The MP receives the information, and selects the therapy (including the possibility of selecting no therapy). The MP then transmits the appropriate control signals to the IMD, allowing for execution of the MP choice.

Figure 35:
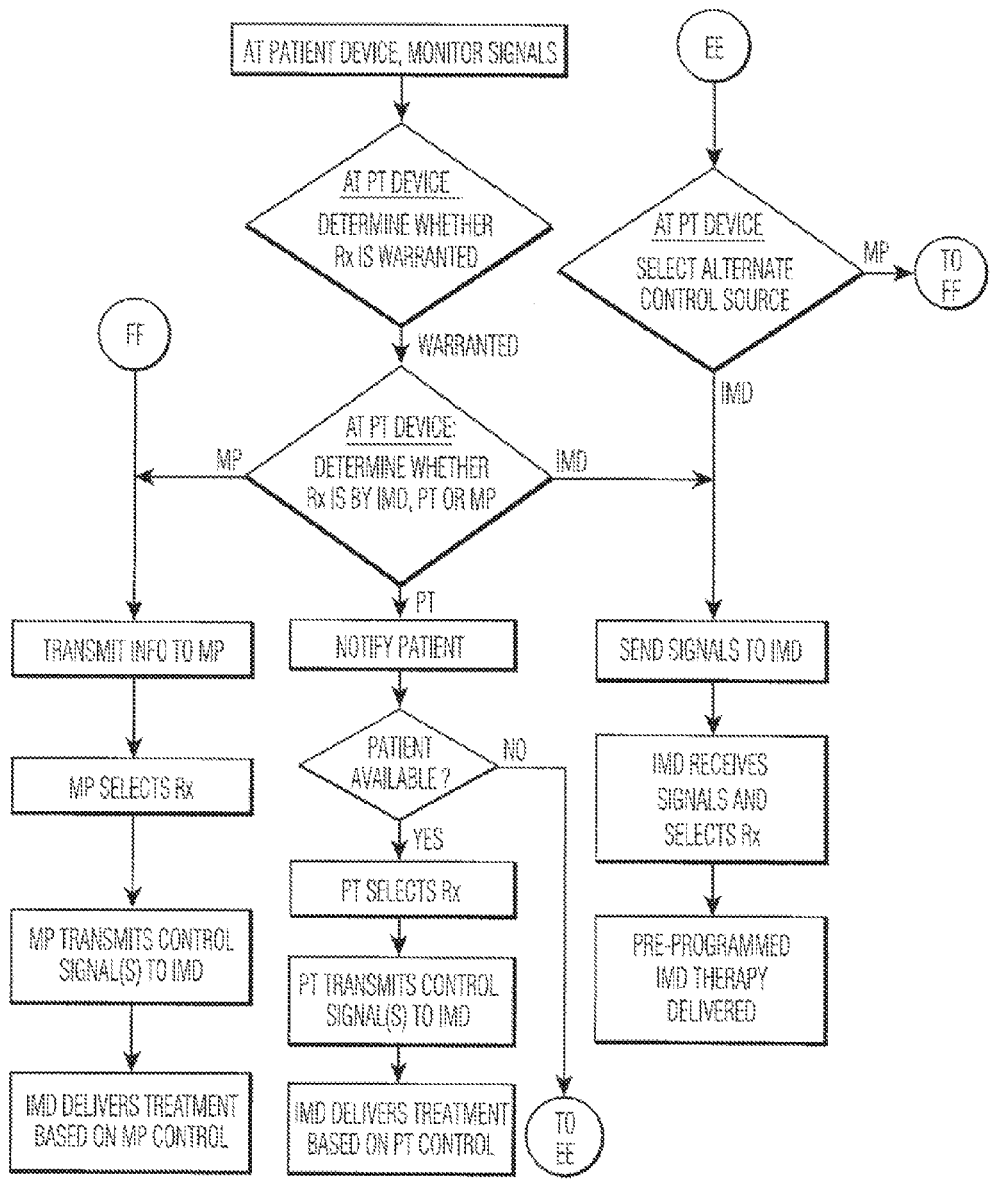
FIG. 35 is another flow diagram illustrating the control of a 3 entity IMD system, which may be controlled by each of an IMD, a patient and a medical professional.

FIG. 35 shows an algorithm for management of a system with an IMD, a patient with patient device, and an MP. Signals are monitored at the patient device. If an abnormality is detected which requires therapy, a decision is made by the patient device as to which of the IMD, the patient or the MP will be the source of control. Additional information may be requested from the IMD (as shown in FIG. 10).

In the algorithm shown in FIG. 35, if the patient device selects IMD management, it sends signals to the IMD which allow the IMD to make a therapeutic decision. An example of this, VT associated with syncope, where (a) the VT rate is less than programmed the detect rate of an ICD, (b) the patient device detects the untreated but symptomatic tachycardia and selects the ICD to treat; and (c) the ICD treats the tachycardia, is discussed hereinbelow, in conjunction with FIG. 79.

If the patient device selects patient management, then the patient device queries the patient to determine availability. If the patient is available, the information is presented to the patient. The patient receives the information, selects a treatment via the patient device, which transmits control signals indicative of the choice of therapy to the IMD. The IMD then executes the treatment ordered by the patient. If the patient is unavailable, the patient device then selects either the MP or the IMD as the source of control.

If the MP is selected, the patient device transmits information to the MP to allow the MP to make a management decision. The patient device information may be augmented by information transmitted from the IMD to the MP, at the request of either the MP or the patient device. The MP receives the information, and selects the therapy. The MP then transmits the appropriate control signals to the IMD, allowing for execution of the MP choice. The aforementioned remedies for inadequate communication with the MP apply. An example of this, VT associated with syncope, where (a) the VT rate is less than programmed the detect rate of an ICD, (b) the patient device detects the untreated but symptomatic tachycardia and selects the MP to treat; and (c) the MP treats the tachycardia, is discussed hereinbelow, in conjunction with FIG. 80.

Figure 36:
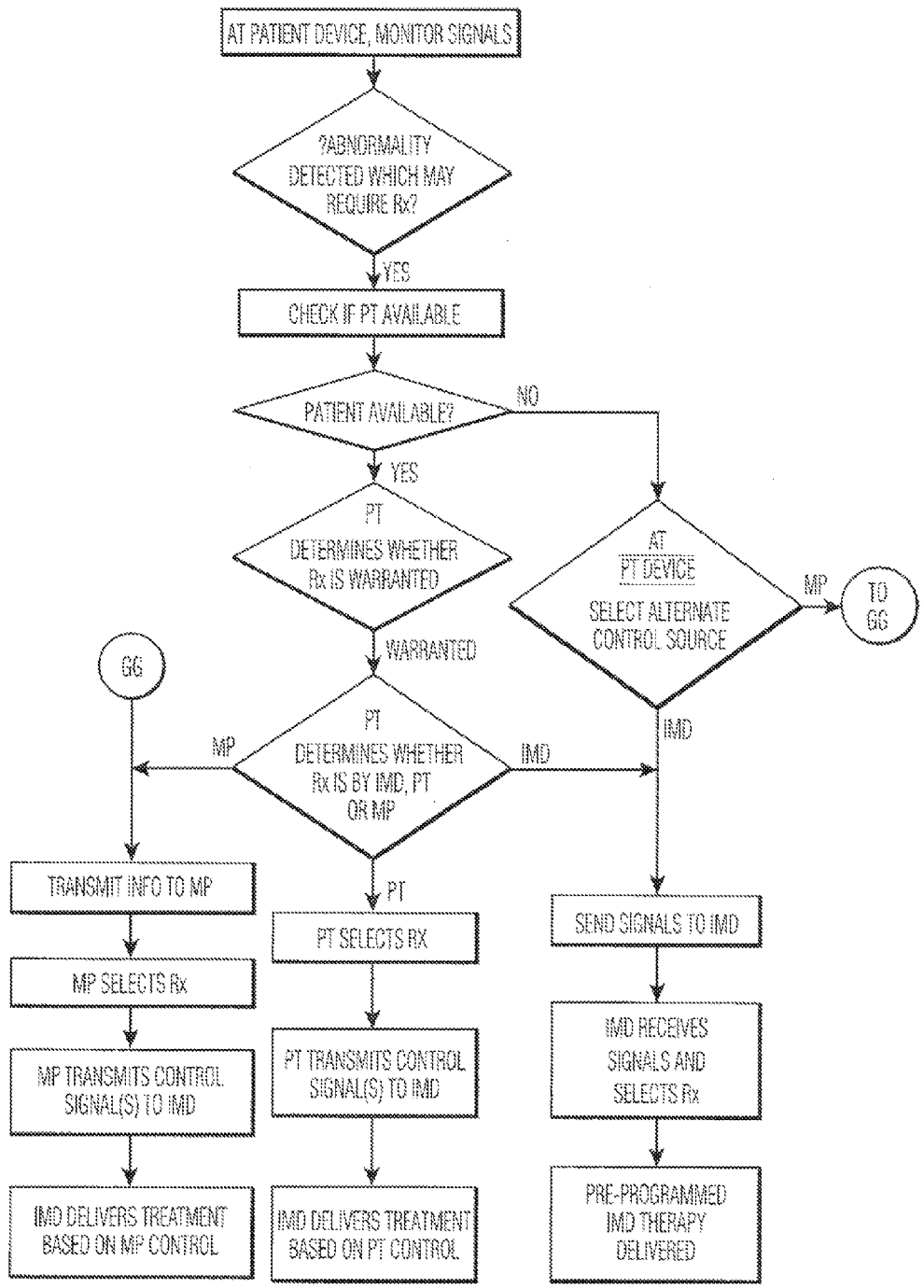
FIG. 36 is another flow diagram illustrating the control of a 3 entity IMD system, which may be controlled by each of an IMD, a patient and a medical professional.

FIG. 36 shows an algorithm for management of a system with an IMD, a patient with patient device, and an MP, in which the patient is given the options of deciding whether therapy is warranted, and if it is, of making the choice of which entity is in control. The algorithm is analogous to that of FIG. 31, but differs in that FIG. 31 entails primarily monitoring at the IMD, while FIG. 36 entails primarily monitoring at the patient device. If an abnormality is detected which may require therapy, signals are transmitted to the patient via the patient device, and then patient availability is determined. If the patient is available, a decision is made by the patient as to whether treatment is warranted, and if warranted, as to which of the IMD, the patient or the MP will be the source of control.

Information available to the patient includes patient device-based sensor information, and the patient's knowledge of how he/she is feeling, and his/her attitude about the various available therapeutic options; It may also include information sent by the IMD. Options for providing IMD information include:

(a) only providing information when requested by outside agent/entity (e.g. the patient or the patient device); and/or (b) provide information to outside agent if pre-programmed notification criteria are met for that agent.

The patient reviews the information, determines if treatment is warranted, and if it is, selects a treatment agent via the patient device. If the patient determines that treatment is warranted and selects himself/herself as the treatment agent, the patient selects their choice of therapy and indicates it via that patient device, which transmits control signals indicative of the choice to the IMD. The IMD then executes the treatment ordered by the patient. If the patient is not available, the patient device makes a selection of either the IMD or the MP as the source of control, the selection being based on either a pre-programmed format, on information obtained by the patient device at the time that the decision is made, or both.

Figure 37:
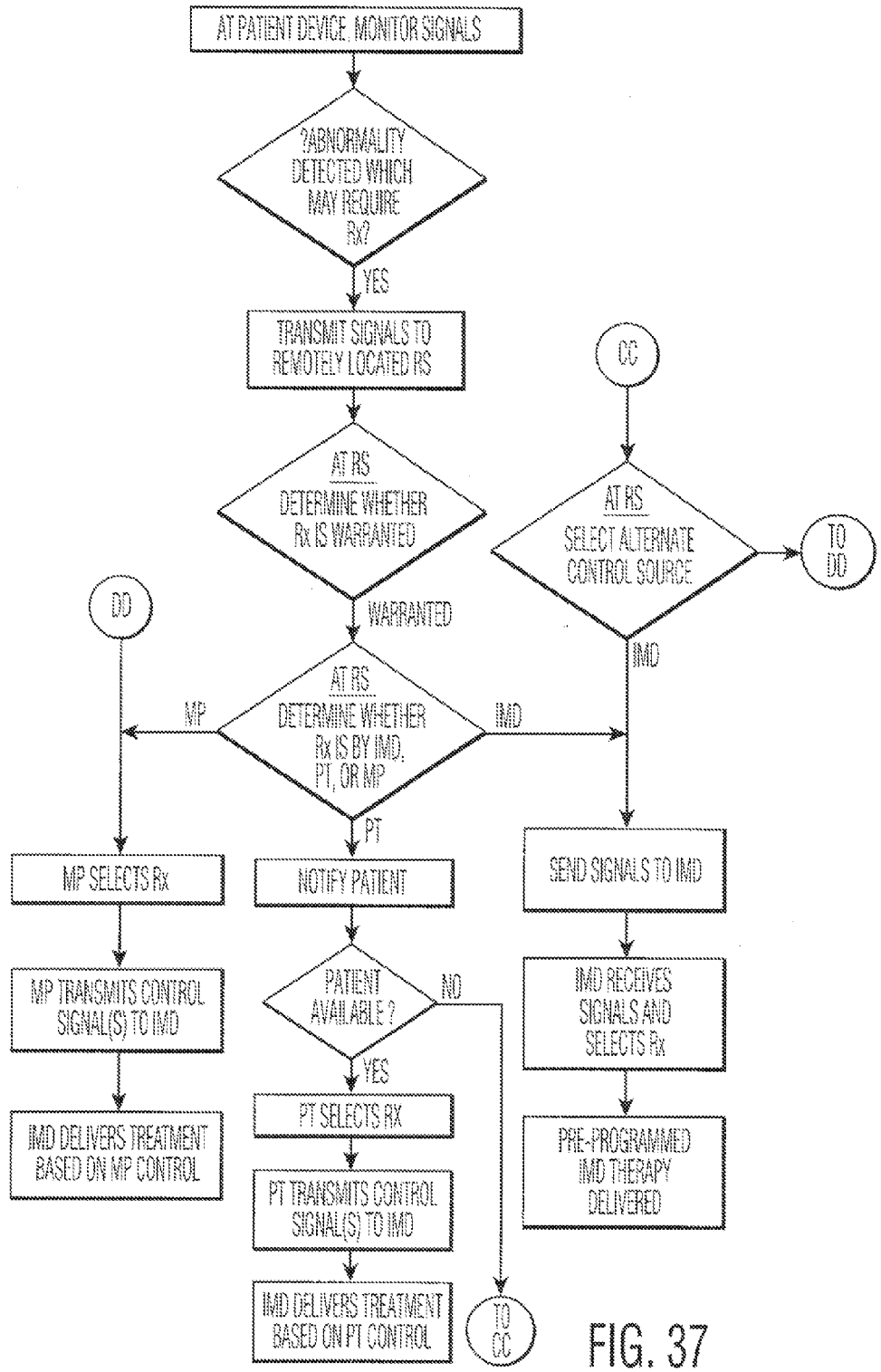
FIG. 37 is another flow diagram illustrating the control of a 3 entity IMD system, which may be controlled by each of an IMD, a patient and a medical professional.

In the algorithm shown in FIG. 36, if the patient determines that treatment is warranted and selects IMD management, the patient device signals the IMD to proceed with the IMD pre-programmed management algorithm. If the patient determines that treatment is warranted and selects the MP, the patient device and/or the IMD transmits information to the MP sufficient to allow the MP to make a management decision. The MP receives the information, and selects the therapy. The MP then transmits the appropriate control signals to the IMD, allowing for execution of the MP choice, FIG. 37 shows an algorithm for management of a system with an IMD, a patient with a patient device, and an MP, in which the MP is given the option of choosing which entity is in control, and in which signals are primarily monitored at the patient device. If an abnormality is detected which may require therapy, signals are transmitted to the MP at the remotely located remote station ("RS"), who makes a decision as to whether therapy is warranted, and if it is, as to which of the IMD, the patient or the MP will be the source of control. The transmitted signals will carry the aforementioned information from the patient device, and may carry additional information from the IMD. The MP decision may be based on a pre-selected format, or the medical professional in the remote station may make a selection based on information which the patient device provides concerning the current condition (either physiologic, cognitive or both) of the patient; or the MP decision may be based on the MP experience and knowledge, as indicated in conjunction with the specification for FIG. 33. The MP may also make his/her decision after consulting the M.E. device database.

In the algorithm shown in FIG. 37, if the MP determines that treatment is warranted and selects IMD management, he/she signals the IMD to proceed with the IMD pre-programmed management algorithm. Supplementary information obtained at the patient device may be provided to the IMD. If the MP determines that treatment is warranted and selects patient management, then the patient is queried by the patient device to determine availability. If the patient is available, the appropriate information is presented to the patient. The patient receives and reviews the information, selects a treatment via the patient device, which transmits control signals indicative of the choice of therapy to the IMD. The IMD then executes the treatment ordered by the patient. If the patient is unavailable, the MP then selects either the MP or the IMD as the source of control.

If the MP determines that treatment is warranted and self selects, then he/she goes on to select the appropriate treatment, and then transmits the corresponding control signals to the IMD, allowing for execution of the MP choice.

In an algorithm analogous to that shown in FIG. 37 but not illustrated in a figure, the patient device could notify the medical expert device, instead of notifying the MP for decisions about whether treatment is warranted and which entity is the treatment agent. The figure showing such an algorithm would be similar to that of FIG. 37, except that references to the MP would be replaced by references to the M.E. device. In still other variations:

(a) The M.E. device could select a control agent from among the group: (i) IMD, (ii) patient, and (iii) MP (rather than M.E. device);

(b) The MP or M.E. device could select a control agent from among the group: (i) IMD, (ii) patient, (iii) M.E. device and (iv) MP; and (c) Five (or more) agent control sharing arrangements are possible.

IMD system architectures are possible in which there is neither an MP nor a medical expert device, in which the only human source of control is the patient, and in which the other sources of control are the patient device, and the IMD itself. Management algorithm examples of such three entity systems in which signal monitoring is primarily at the IMD are shown in FIGS. 38-40; and management algorithms in which signal monitoring is primarily at the patient device are shown in FIGS. 41-43.

7.2 3-Entity Systems with IMD, Patient, and Patient Device

FIG. 38 shows an algorithm for management of a system with an IMD, a patient and patient device, in which the decision to consider treating an abnormality takes place at the IMD. This algorithm is analogous to the one shown in FIG. 29, since in both algorithms and figures, the choice of whether treatment is warranted, and if it is, which of three entities does the treating takes place at the IMD.

If an abnormality is detected at the IMD which requires therapy, the IMD and if the IMD selects IMD management, it proceeds with its own pre-programmed management algorithm. If it determines that treatment is warranted and selects patient management, then it queries the patient to determine patient availability for management of the current event. If the patient is available, the information is presented to the patient. The patient receives the information, selects a treatment via the patient device, which transmits control signals indicative of the choice to the IMD. The IMD then executes the treatment ordered by the patient. If the patient is unavailable, the IMD then selects either the patient device or the IMD as the source of control.

If the IMD determines that treatment is warranted and the patient device is selected, the IMD transmits information to the patient device sufficient to allow the patient device to make a management decision. The patient device receives the information, and selects the therapy (including the possibility of selecting no therapy). The patient device then transmits the appropriate control signals to the IMD, allowing for execution of the patient device choice.

FIG. 39 shows an algorithm for management of a system with an IMD, and a patient with patient device, in which the choice of controlling agent occurs at the patient device. Signals are monitored primarily at the IMD. If an abnormality is detected which may require therapy, signals are transmitted to the patient device, where a decision is made by the patient device as to whether therapy is warranted, and if it is, as to which of the IMD, the patient or the patient device will be the source of control.

In the algorithm shown in FIG. 39, if the patient device determines that therapy is warranted and the patient device selects IMD management, it signals the IMD to proceed with the IMD pre-programmed management algorithm. If the patient device determines that therapy is warranted and the patient device selects patient management, then before therapy can proceed, it must be determined if the patient is available. The patient device queries the patient to determine availability. If the patient is available, the information is presented to the patient. The patient receives the information, selects a treatment via the patient device, which transmits control signals indicative of the choice of therapy to the IMD. The IMD then executes the treatment ordered by the patient. If the patient is unavailable, the patient device then selects either itself or the IMD as the source of control.

If therapy is warranted and the patient device is selected as the source of control, the patient device selects the therapy. It then transmits the appropriate control signals to the IMD, allowing for execution of the patient device choice.

FIG. 40 shows an algorithm for management of a system with an IMD, and a patient with patient device, in which the patient, if available, is given the options of deciding if therapy is warranted, and, if it is, of making the choice of which entity is in control. Signals are monitored primarily at the IMD. If an abnormality is detected which may require therapy, signals are transmitted to the patient via the patient device, and then patient availability is determined. If the patient is available, a decision is made by the patient as to whether therapy is warranted, and if it is, as to which of the IMD, the patient or the patient device will be the source of control. Information available to the patient includes the aforementioned IMD-based sensor and programming information, patient device-based sensor information, and the patient's knowledge of how he/she is feeling, and his/her attitude about the various available therapeutic options. The patient reviews the information, and makes the aforementioned decision(s). If the patient determines that treatment is warranted and selects himself/herself as the treatment agent, the patient selects their choice of therapy and indicates it via that patient device, which transmits control signals indicative of the choice to the IMD. The IMD then executes the treatment ordered by the patient. If the patient is not available, the patient device or the IMD makes a selection of an alternate source of control, the selection being based on either a pre-programmed format, on information available at the time that the decision is made, or both.

In the algorithm shown in FIG. 40, if the patient determines that treatment is warranted and selects IMD management, the patient device signals the IMD to proceed with the IMD pre-programmed management algorithm. If the patient determines that treatment is warranted and selects the patient device, the patient device analyzes the IMD information and selects the therapy. The patient device then transmits the appropriate control signals to the IMD, allowing for execution of the patient device choice.

FIG. 41 shows an algorithm for management of a system with an IMD, and a patient with patient device, in which the decision to consider treating an abnormality takes place at the patient device. This algorithm is analogous to the one shown in FIG. 34, since in both algorithms and figures, monitoring takes place primarily at the patient device, but the choice of which of three entities does the treating takes place at the IMD. A decision to consider treatment may occur at the patient device rather than the IMD in a case where sensors inputting the patient device indicate a dire patient state, which may be undetected by the IMD.

If an abnormality is detected at the patient device which may require therapy, information about the patient device observation is transmitted to the IMD. At the IMD, a decision is made as to whether treatment is warranted. The decision may be based on (a) the information transmitted by the patient device, (b) information derived from the IMD sensor(s), or (c) both (a) and (b). If the decision is to treat, the IMD makes a decision as to which of the IMD, the patient or the patient device will be the source of control.

In the algorithm shown in FIG. 41, if the IMD determines that treatment is warranted and selects IMD management, it proceeds with its own pre-programmed management algorithm. If it determines that treatment is warranted and selects patient management, then it queries the patient to determine patient availability for management of the current event. If the patient is available, the information is presented to the patient. The patient receives the information, selects a treatment via the patient device, which transmits control signals indicative of the choice to the IMD. The IMD then executes the treatment ordered by the patient. If the patient is unavailable, the IMD then selects either the patient device or the IMD as the source of control.

If the IMD determines that treatment is warranted and the patient device is selected, the IMD transmits information to the patient device sufficient to allow the patient device to make a management decision. The patient device receives the information, and selects the therapy (including the possibility of selecting no therapy). The patient device then transmits the appropriate control signals to the IMD, allowing for execution of the patient device choice.

FIG. 42 shows an algorithm for management of a system with an IMD, and a patient with patient device. Signals are monitored at the patient device. If an abnormality is detected which requires therapy, a decision is made by the patient device as to which of the IMD, the patient or the patient device will be the source of control. Additional information may be requested from the IMD (as shown in FIG. 10).

In the algorithm shown in FIG. 42, if the patient device selects IMD management, it sends signals to the IMD which allow the IMD to make a therapeutic decision. If the patient device selects patient management, then the patient device queries the patient to determine availability. If the patient is available, the information is presented to the patient. The patient receives the information, selects a treatment via the patient device, which transmits control signals indicative of the choice of therapy to the IMD. The IMD then executes the treatment ordered by the patient. If the patient is unavailable, the patient device then selects either itself or the IMD as the source of control. If the patient device is selected it selects the therapy. It then transmits the appropriate control signals to the IMD, allowing for execution of the patient device choice.

FIG. 43 shows an algorithm for management of a system with an IMD, and a patient with patient device, in which the patient is given the option of making the choices as to whether therapy is warranted, and, if it is, as to of which entity is in control. If an abnormality is detected which may require therapy, signals are transmitted to the patient via the patient device, and then patient availability is determined. If the patient is available, a decision is made by the patient as to whether treatment is warranted, and if warranted, as to which of the IMD, the patient or the patient device will be the source of control.

Information available to the patient and options for providing IMD information are similar to those indicated in the specification of FIG. 36 hereinabove. The patient reviews the information, determines if treatment is warranted, and if it is, selects a treatment agent via the patient device. If the patient determines that treatment is warranted and selects himself/herself as the treatment agent, the patient selects their choice of therapy and indicates it via that patient device, which transmits control signals indicative of the choice to the IMD. The IMD then executes the treatment ordered by the patient. If the patient is not available, the patient device or the IMD makes a selection of either the IMD or the patient device as the source of control, the selection being based on either a pre-programmed format, on information obtained by the patient device and/or the IMD at the time that the decision is made, or both.

In the algorithm shown in FIG. 43, if the patient determines that treatment is warranted and selects IMD management, the patient device signals the IMD to proceed with the IMD pre-programmed management algorithm. If the patient determines that treatment is warranted and selects the patient device, the patient device selects the therapy. It then transmits the appropriate control signals to the IMD, allowing for execution of the patient device choice.

7.3 Generalized 3-Entity Systems

In FIGS. 44 and 45, the term "entity" refers to any of the possible choices of monitoring or control agent, i.e. the IMD, the patient device, the patient, the medical expert device, or the MP. FIG. 44 shows a generalization of three entity control formats in which both primary monitoring and the decision as to whether therapy is warranted take place at the same entity (which is arbitrarily designated as Entity #1). Furthermore, if therapy is warranted, the choice of which of the three entities is the control agent takes place at the entity which does the primary monitoring. The algorithm is structurally parallel to those shown in FIGS. 29, 35, 38 and 42, except that, besides the provisions being made for the possibility that one of the entities is unavailable (which in the aforementioned specification was generally the patient), additional provisions are made for another of the entities being unavailable (which may be, for example, the MP, if communications with the MP are inadequate).

In the algorithm, Entity #1 determines if treatment is warranted, and, if it is, selects from among itself, Entity #2 and Entity #3 as the choice of treatment agent. If either Entity #2 (or Entity #3) is selected and is unavailable, then Entity #1 selects between itself and Entity #3 (or Entity #2) as the control agent. If both Entity #2 and Entity #3 is unavailable, Entity #1 provides the control.

FIG. 45 shows a generalization of three entity control formats in which primary monitoring and the decision as to whether therapy is warranted take place at different entities, designated as Entity #1 and Entity #2, respectively. If Entity #2 is available, it determines if therapy is warranted, and if it is, it selects from among itself, Entity #1 and Entity #3 as the choice of control agent. It is assumed that Entity #1 is available, since the algorithm was initiated with a monitoring and a transmission event by Entity #1. If Entity #3 is selected by Entity #2 but is unavailable, Entity #2 selects from among itself and Entity #1.

If Entity #2 is unavailable, system programming (e.g. by the Control Hierarchy programming screen shown in FIG. 14) will have predetermined whether Entity #1 or Entity #3 is dominant (a) If Entity #1 is dominant, it determines if treatment is warranted, and if warranted selects between itself and Entity #3 as the control agent. If Entity #3 is selected by Entity #1 but is unavailable, then Entity #1—assumed to be available as indicated hereinabove—becomes the control agent. The selected and available entity from among Entities #1 and #3 then controls management.

(b) If Entity #3 is dominant, its availability is then determined. If available, it determines whether treatment is warranted, and then selects from among itself and Entity #1 as the control agent. The selected entity from among Entities #1 and #3 then controls management.

7.4 2-Entity Systems with IMD and Patient

Figure 46:
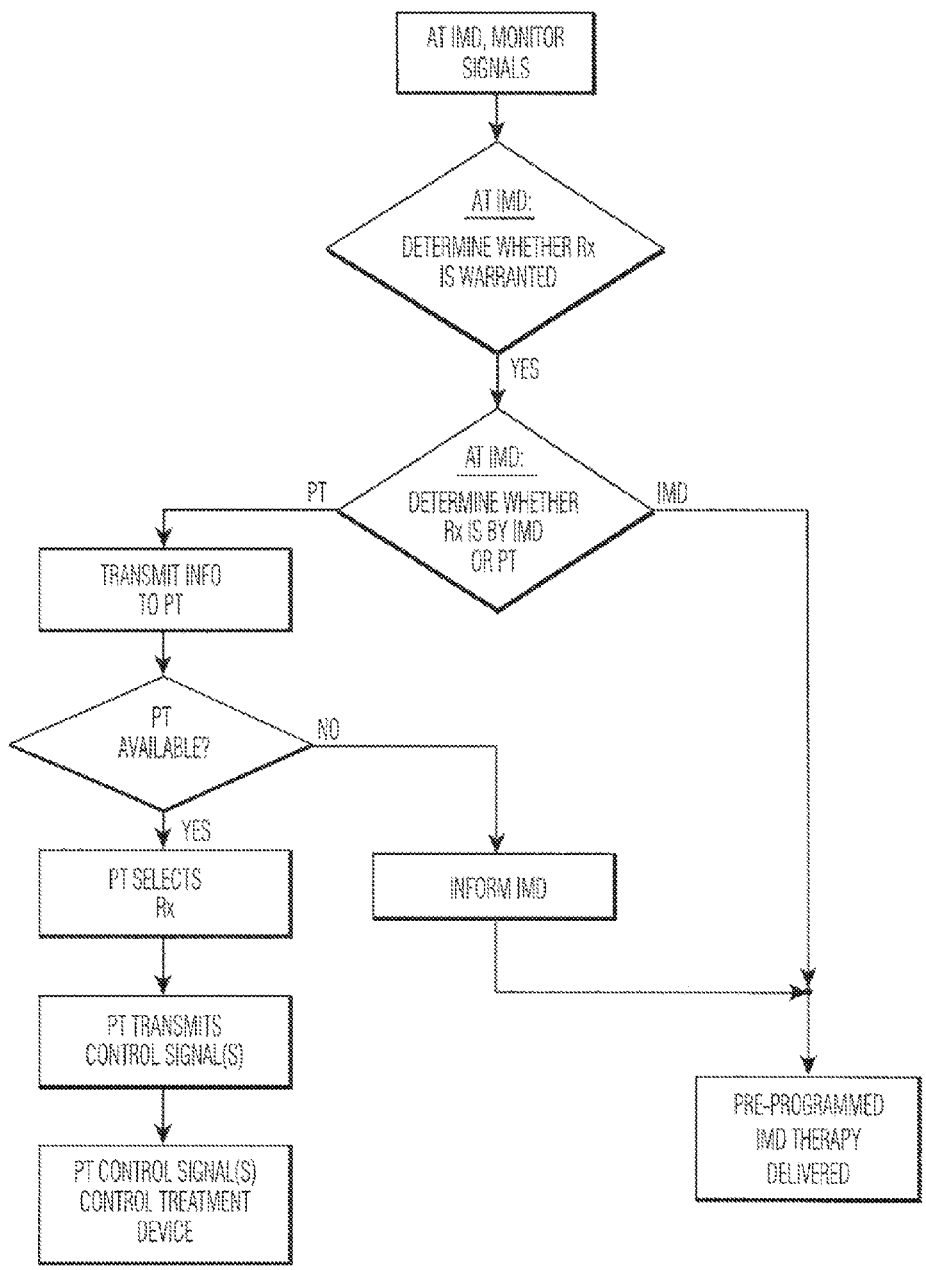
FIG. 46 is a flow diagram illustrating the control of a 2 entity IMD system, which may be controlled by each of an IMD and a patient.
Figure 47:
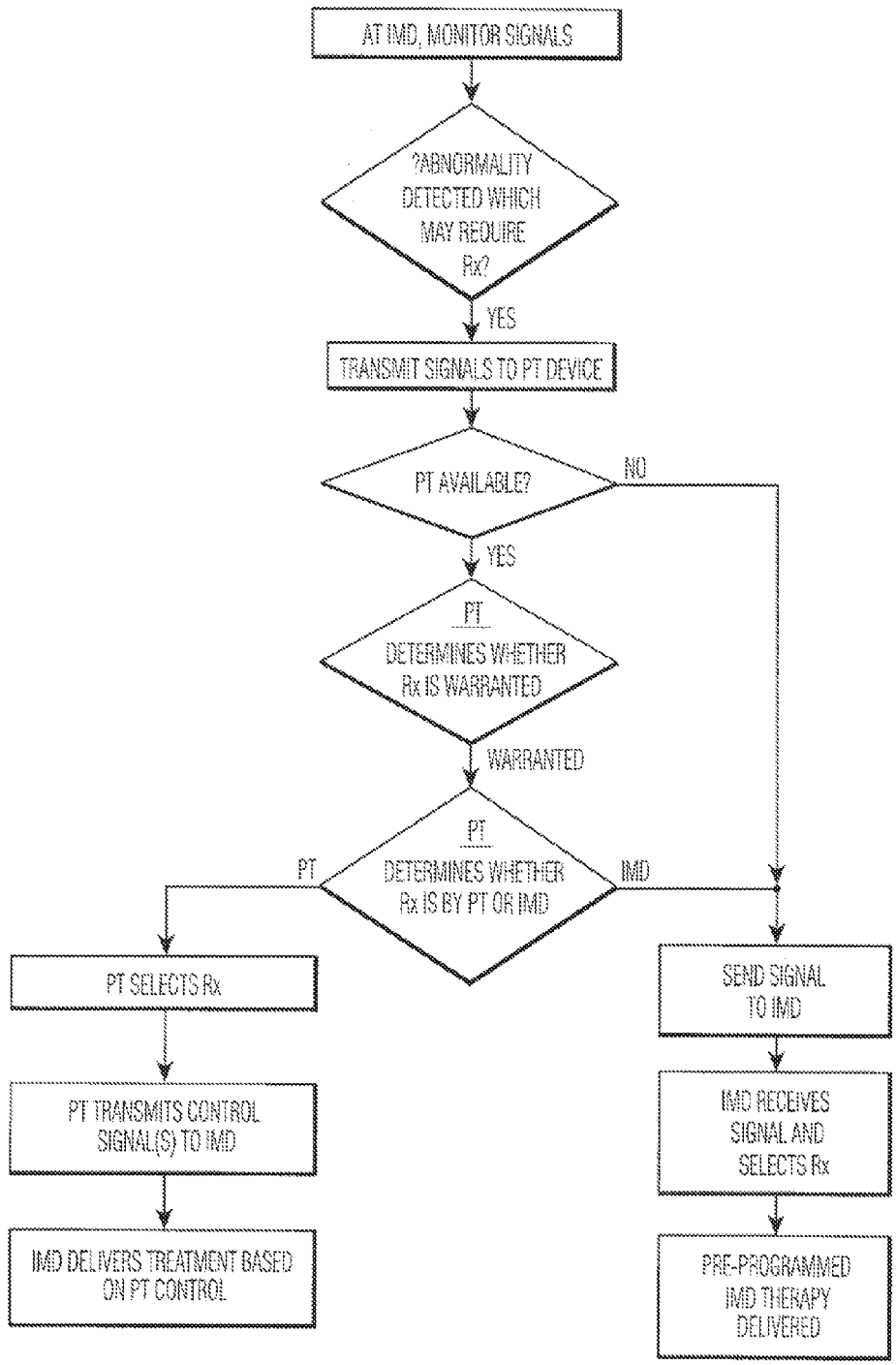
FIG. 47 is another flow diagram illustrating the control of a 2 entity IMD system, which may be controlled by each of an IMD and a patient.

FIGS. 46-49 illustrate algorithms for two-entity IMD systems in which either (a) the IMD decision making circuits or (b) the patient in whom the IMD is implanted, control treatment administration by the IMD. In order for the patient to be able to interact with the IMD, there would be a patient device, but—as is the case with the algorithms of FIGS. 29, 31 and 33—the patient device is not one of the possible control entities. In FIGS. 46 and 47, primary monitoring occurs at the IMD, while in FIGS. 48 and 49, primary monitoring is at the patient device.

In the algorithm shown in FIG. 46, if the IMD determines, based on its monitoring, that therapy is warranted, it next determines if the optimum approach is management by the IMD treatment algorithm or by the patient. Certain ranges of treatment abnormality may best be suited to patient management, and others to IMD management. These may be determined by preprogrammed notification criteria (see FIGS. 71A-76C). If the IMD is selected, it functions as pre-programmed. If the patient is selected, patient availability is checked. If the patient is available, he/she selects a treatment option and transmits the appropriate control signal to the IMD; If the patient is not available, the IMD is so informed, and it selects therapy.

In the algorithm shown in FIG. 47, if the IMD determines, based on its monitoring, that therapy may be warranted, it attempts to notify the patient via the patient device. If the patient is available, the patient is presented with adequate information from the IMD to determine if treatment is warranted and to make a choice between choice therapy selection by the IMD or by the patient. The patient may base the decision on known general guidelines, on additional testing that the patient may then perform, or on how the patient is then feeling. If the patient self selects, he/she selects the therapy and signals the choice to the IMD via the patient device. If the IMD is selected, the patient so notifies the IMD and it functions as pre-programmed. If the patient was unavailable, the IMD is notifies and it selects the therapy.

In the algorithm shown in FIG. 48, if the patient device determines, based on its monitoring, that therapy may be warranted, it next transmit signals to the IMD to inform it of the patient device data. Such data may also include a request from the patient to initiate or consider the initiation of therapy. At the IMD, a decision about whether therapy is warranted is then made. Next a decision about the choice of control entity—patient or IMD—is made. if the patient is selected, patient availability is determined. If the patient is available, the patient selects therapy and cause the patient device to transmit the appropriate signals informing the IMD of the selection. The IMD controls therapy selection if either (a) the patient is not available after being selected or (b) IMD management was the choice of the IMD agent selection process.

In the algorithm shown in FIG. 49, if the patient device determines, based on its monitoring, that therapy is warranted, it next attempts to alert the patient and assess patient availability. It the patient is available, the patient determines whether therapy is warranted, and if it is, selects the control agent from among itself and the IMD. If the patient selects the IMD, the patient device informs the IMD, after which pre-programmed IMD management occurs. The pre-programmed management may include one approach when the IMD is not signaled by the patient in this way, and an alternate approach when it is signaled by the patient. If the patient selects self-management, the patient makes a therapeutic choice and signals the IMD of the choice via the patient device, after which the IMD delivers the selected therapy.

7.5 5-Entity Systems with IMD, Patient Device, Patient, Medical Expert Device and Medical Professional FIGS. 50-52 show algorithms for the management of a 5-entity IMD system including: an IMD, a patient device, a patient, a medical expert device (as discussed hereinabove) and a medical professional. The three figures are distinguished by the location at which (a) monitoring occurs and (b) the choice of agent to select therapy is made. In FIG. 50, the location is the IMD. In FIG. 51, the location is the patient device. In FIG. 52 the location is the remote station. In principle, 25 such figures may be generated, i.e. $5\sup(2)$, since there are five possible monitoring locations and five possible locations at which to choose the agent which selects therapy. When a monitoring location is not the location where signals carrying patient information originate, such signals (either un-analyzed or already analyzed) may be forwarded to the monitoring location as can be seen from FIG. 4. Furthermore, algorithms are possible in which any of the 5 possible entities may be selected for each of (a) the monitoring location, (b) the location for the determination of whether therapy is warranted, and (c) the location for the determination of which entity selects therapy; Thus as many as 125 algorithms, i.e. $5\sup(3)$ are possible.

FIG. 50 shows primary monitoring at the IMD. If the IMD determines that therapy is warranted, the IMD selects one of the five possible entities to become the control agent. If the patient is selected, a determination is made as to whether the patient is available; If not, the IMD selects an alternate source of control. If the IMD self-selects, it administers a pre-programmed therapy choice. If the IMD selects another agent, then that other agent receives the necessary information to make a choice of therapy, that agent makes the choice, and transmits information indicating the choice to the IMD. The situation in which one or more of the possible choices for control agent is not able to be communicated with is discussed hereinabove, and would result in an alternate selection for choice of controlling agent. If no other agents are available, the IMD would act autonomously.

FIG. 51 shows primary monitoring at the patient device. If the patient device determines that therapy is warranted, the patient device selects one of the five possible entities to become the control agent. If the patient is selected, a determination is made as to whether the patient is available; If not, the patient device selects an alternate source of control. If the patient device self-selects, it determines the appropriate control signal(s), and transmits them to the IMD. if the patient device chooses the IMD as the control agent, the patient devices so notifies the IMD, which then selects the appropriate therapy. If the patient device selects a control agent other than itself or the IMD, then that other agent receives the necessary information to make a choice of therapy, that agent makes the choice, and transmits information indicating the choice to the IMD. The situation in which one or more of the possible choices for control agent is not able to be communicated with has been discussed hereinabove.

FIG. 52 shows primary monitoring at the remote station. This would entail the transmission of at least one of (a) IMD information, and (b) patient device information, to the remote station. In the case of both (a) and (b), the remote station may amalgamate the information transmitted from each of the IMD and the patient device. Alternatively, such amalgamation may take place at either the IMD (by transmission of patient device information from the patient device to the IMD, as shown in FIGS. 10 and 11), or at the patient device (by transmission of IMD information from the MDI) device to the patient device, as shown in FIGS. 8 and 9), and be followed by transmission of the amalgamated information to the remote station.

At the remote station, a determination is then made, as to whether therapy is warranted. If therapy is warranted, the remote station selects one of the five possible entities to become the control agent. If the patient is selected, a determination is made as to whether the patient is available; if not, the remote station selects an alternate source of control. If the IMD is selected, it administers a pre-programmed therapy choice. If the remote station selects another agent, then that other agent receives the necessary information to make a choice of therapy, that agent makes the choice, and transmits information indicating the choice to the IMD. The situation in which one or more of the possible choices for control agent is not able to be communicated with is discussed hereinabove, and would result in an alternate selection for choice of controlling agent. If no other agents are available, the IMD would act autonomously.

A single remote station may house both the MP and the medical expert device, or the MP and the M.E. device may each be situated in separate remote stations. In either case, the MP and M.E. device may be in communication, as indicated by FIG. 4 herein and by FIG. 2C of U.S. patent application Ser. No. 12/154,079.

7.6 Alternate 3-Entity System with IMD, Patient and Medical Professional

FIG. 53 shows an IMD system control algorithm which differs in format from those algorithms shown in FIGS. 29-52. Whereas the algorithms in FIGS. 29-52 are analogous to those in FIGS. 6C and 6D of U.S. patent application Ser. No. 12/154,079, the algorithm shown in FIG. 53 is analogous to that shown in FIG. 6A of Ser. No. 12/154,079, in which the IMD functions autonomously unless it is inhibited and/or induced to apply therapy by a remotely originating signal.

Rather than remotely transmit all IMD data—which would impose a major IMD battery drain—a notification signal is transmitted to a medical professional if notification criteria for the MP are met, and to the patient, if notification criteria for the patient are met. The notification criteria for the MP and for the patient may not be the same, and each of the two notification criteria may differ from the treatment criteria for the IMD (as discussed in conjunction with FIGS. 71A-76C).

If either one of the MP or the patient is notified, they have the option, after reviewing data pertaining to the event which triggered such notification, of causing or changing treatment by the IMD. If either of them decides to do so, they select and transmit appropriate commands, whether inhibitory, or causative of treatment. The commands are decrypted, decoded and enacted by the IMD, after which it sends a confirmation signal to the person who was the source of the command(s). If both the MP and the patient are notified, they may (a) work out a treatment plan together, after which one of them sends the appropriate control signal(s) to the IMD; (b) negotiate which of the two is to be the controlling entity, after which the controlling entity selects and transmits IMD instructions; (c) agree that IMD control is the best option.

Versions of FIG. 53 in which other non-IMD entities other than the MP and the patient have the opportunity to alter IMD treatment after they are notified are possible. If there are two or more such entities, then there must be a negotiation or transaction in which the possible controlling entities agree on treatment or agree on the selection of treating entity.

7.7 Second Alternate 3-Entity System with IMD, Patient and Medical Professional

FIGS. 54 through 56B show four algorithms in which there is neither (a) the negotiation or transaction discussed in conjunction with FIG. 53, nor (b) an overarching selection by one entity at the time of a patient event, as to choice of control agent, as in FIGS. 29-52. Instead, as shown in FIGS. 54-56B, a preprogrammed, control hierarchy is established, in which:

(a) each possible control entity is ranked;

(b) the highest ranked control entity may control the IMD if (i) it is notified, and (ii) it chooses to exert such control;

(c) another entity may control the IMD, if all possible control entities which are more highly ranked do not exert such control; and (d) the lowest ranked entity controls the IMD, if none of the other possible control entities exert such control, These figures are analogous to FIG. 6B of U.S. patent application Ser. No. 12/154,079, which shows a conceptually similar algorithm for a two entity system consisting of the IMD and the MP.

In one embodiment of the invention, such a control hierarchy is established only once, (a) at the time that the IMD is implanted, (b) before it is implanted, or (c) at a time later than the implant. In another embodiment of the invention, the hierarchy may be altered on one or more occasions. FIG. 14 shows a programming screen which sets up or alters such a hierarchy, and FIGS. 13 and 15 show programming screens which allow (or do not allow) access to such programming.

FIG. 54 shows an algorithm in which control of the IMD may be shared among three entities: (1) the IMD therapy decision-making elements, (2) the patient (via a patient device) and (3) the medical professional (via a remote station). The control hierarchy (for the example shown in the figure) is such that the MP is placed most highly, the patient next and the IMD lowest. Thus the patient, if notified, may overrule the IMD, and the MP, if notified, may overrule either the patient or the IMD. Since notification criteria are programmable, and since even the hierarchy is programmable (though such programming would result in a different algorithm than that shown in FIG. 54), there is a very large amount of potential flexibility in the control of the IMD.

Analysis of sensor signals at the IMD may lead to one or more of: (a) IMD treatment criteria met (b) patient notification [and receipt of IMD data] if patient notification criteria are met, and (c) MP notification [and receipt of IMD data] if MP notification criteria are met. A particular patient condition may trigger none, any one, any two or all three of (a), (b) and (c). Notification of either the MP or the patient is considered to be an invitation to control treatment, which may or may not be accepted by the receiving entity. Thus if the MP is notified and the MP decides to control treatment, then he/she analyzes the received data, decides on appropriate therapy, transmits it to the IMD; The IMD decrypts and decodes the information, enacts the transmitted commands, and sends a confirmation signal to the MP. The MP may optionally reprogram the IMD after such notification.

If the MP was either not notified, or chose not to react to the notification, then the patient—if notified—has the opportunity to initiate therapy in a sequence similar to that of the MP: The patient analyzes the received data, decides if therapy is warranted and, if so, decides on appropriate therapy. Using a patient device which converts the patient selected choices into IMD command signals, the patient then controls the IMD; The IMD decrypts and decodes patient command signals and delivers therapy and sends a confirmation signal to the patient. The patient may optionally reprogram the IMD after such notification.

If neither the MP nor the patient intervenes with a command signal, then, as shown in the figure, the IMD therapy which is programmed for the particular conditions that currently obtain is applied, and an optional confirmation signal may be sent to either the patient, the MP or both.

In a simple example, if the notification criteria for each of the MP and the patient are the same as the treatment criteria of the device, then when those criteria are met both the MP and the patient will be notified and have the opportunity to intervene. The MP gets the highest priority. If the MP declines, the patient has the opportunity to control the IMD. If both the MP and the patient decline, the IMD performs based on its pre-programmed treatment algorithm.

The flow diagram includes the possibility that MP or patient notification was programmed for a medical state for which no IMD therapy is programmed. An example is the case of a the management of relatively slow tachycardia:

IMD is an ICD
Treatment Criteria: Rate greater than 120 b.p.m.
Patient Notification Criteria: Rate greater than 120 b.p.m.
MP Notification Criteria: Rate greater than 135 b.p.m.
ICD Programming: Automatically treat tachycardia with rate >150 b.p.m.
In the case of a tachycardia with rate 130 b.p.m.:
(a) The MP is not notified because the rate is less than 135 b.p.m.
(b) The patient is notified, feels no symptoms, is exercising, and reasonably concludes that the tachycardia requires no treatment.
(c) The ICD does not treat because its rate cutoff (for automatic treatment) is 150 b.p.m.
A more complex example involving an ICD:
Treatment Criteria: Tachycardia with rate > or =140 b.p.m. for 10 seconds
Patient Notification Criteria: Tachycardia with rate between 140 and 160 b.p.m. for 10 seconds
MP Notification Criteria: Tachycardia with rate greater than 340 b.p.m. for 1.5 seconds.
ICD Programming: Tachycardia detection for rate >160 b.p.m.
This particular algorithm would operate as follows:

For tachycardia with rate between 140 and 160 beats per minute for 10 or more seconds, the patient is offered the opportunity to dictate treatment. The patient could choose to inhibit therapy (e.g. if he/she felt perfectly fine and had good reason to believe that the heart rate elevation was due to sinus tachycardia). The patient could also choose a non-aggressive therapy, rather than a more aggressive treatment which might be programmed for the ICD response. If the patient does not intervene, the ICD delivers pre-programmed therapy.

For tachycardia with rate greater than 160 b.p.m. and up to 340 b.p.m., neither the patient nor the MP is notified, and the ICD operates autonomously.

For tachycardia with a rate greater than 340 b.p.m. and lasting 1.5 or more seconds, the MP is notified. The MP has priority over the ICD. The MP may issue a command to inhibit therapy if the MP believes that the high rate signals are due to the malfunction of either the defibrillator lead, the defibrillator, the interface between the lead and the defibrillator, or that the high rate signals are due to electromagnetic interference. Such a command serves the purposes of (a) potentially avoiding the delivery of an inappropriate ICD shock, and (b) potentially avoiding a series of capacitor charges and dumps, if the period of observed high rate is not long enough to trigger shock delivery but is long enough to trigger the start of capacitor charging. If the MP believes that there is a significant chance that the observed high rate signal represents a very fast tachycardia, the MP may allow the ICD to proceed with treatment, or the MP may initiate treatment himself/herself.

Many other complex patterns of programming are possible and will be obvious to those skilled in the art. Such patterns are further discussed in conjunction with FIGS. 71A to 76C and 78 to 82.

FIG. 55 shows an algorithm that is morphologically similar to that of FIG. 54. However, in the FIG. 55 algorithm, the hierarchical positions of the MP and the patient are switched with respect to that shown in FIG. 54; In FIG. 55, the patient occupies the highest position in the control hierarchy, the MP occupies the intermediate position and the IMD occupies the lowest position. Thus, in the FIG. 55 algorithm, the MP may overrule the IMD, and the patient may overrule both the IMD and the MP.

7.8 Alternate 5-Entity System with IMD, Patient Device, Patient, Medical Expert Device and Medical Professional FIG. 56A shows a five-entity version of the algorithms shown in FIGS. 54 and 55. The hierarchical sequence, from highest to lowest is: MP, medical expert device ("M.E.D." in the figure, and "M.E. device" in other figures), patient, patient device ("PT.D." in the figure, and "PT device" and "PTdev" in other figures) and the IMD. Thus, for example, the IMD may overrule no other entity, and the MP may overrule all other entities.

The algorithm shown in FIG. 56B is similar to that of FIG. 56A except that the FIG. 56B algorithm also shows the operational aspects of the programming of control hierarchy. In order for any entity to participate, their response must be enabled. Such enabling would be the result of programming of control hierarchy, and such programming is illustrated by the control screen shown in FIG. 14.

Referring again to FIG. 56B, in order for the MP to have the option to intervene in therapy, the MP response must have been enabled. The same is true for each of the M.E. device, the patient and the patient device. In an exemplary circumstance in which neither the M.E. device nor the patient device are enabled, the algorithm shown by FIG. 56B will function in a manner similar to that of FIG. 54. In FIG. 14, the programming of such an algorithm would be accomplished as is seen in the second row of items, beginning with "conditions B1, B2, B3 and B4" [which could be, in the case of an ICD, related to one or more of (a) heart rate, (b) sudden onset, (c) interval stability and (d) morphology], and including a control hierarchy in which the IMD is at the lowest level, the patient at an intermediate level and the MP at the highest level.

In a further exemplary circumstance in which none of (a) the M.E. device, (b) the patient response, and (c) the patient device control are enabled, the algorithm shown by FIG. 56B will function in a manner similar to that of FIG. 6B of U.S. patent application Ser. No. 12/154,079. In FIG. 14, the programming of this algorithm would be accomplished as is seen in the first row of items, beginning with "conditions A1, A2, and A3", and including a control hierarchy in which the IMD is at the lower level, and the MP at the higher level.

One IMD may be programmed to have different control hierarchies for different medical states. For example, a single ICD, at one time, with an operating algorithm consistent with that shown in FIG. 56B, could be programmed:

(a) to have the control hierarchy indicated by row 1 of FIG. 14 (with MP dominant over IMD) for conditions labeled A1, A2 and A3;

(b) to have the control hierarchy indicated by row 2 of FIG. 14 (with MP dominant over patient, and patient dominant over IMD) for conditions labeled B1, B2 B3, and B4; and (c) to have the control hierarchy indicated by row 5 of FIG. 14 (with MP the only source of control) for conditions labeled E1, and E2.

Just as FIG. 55 is a variation of FIG. 54, in the sense that it shows an alteration in the sequence of control hierarchy (The MP dominates over patient in FIG. 54 and the patient dominates over the MP in FIG. 55), many such alterations are possible with a five-entity format. There are 5 factorial, or 120 possible algorithms. Thus the programming of the algorithm for line 3 of the screen shown in FIG. 14 would result in a flow diagram similar to that shown in FIG. 56B; To construct such a figure, one starts with the diagram shown FIG. 56B and switches the labels for "PT" (patient) with the labels for "PT.D." (patient device). The result is a flow diagram in which:

(a) the IMD is the default control entity;
(b) the patient may overrule or preempt the IMD;
(c) the patient device may overrule or preempt each of (i) the patient and (ii) the IMD;
(d) the medical expert device may overrule or preempt each of the (i) the patient device, (ii) the patient and (iii) the IMD;
(e) the medical professional may overrule or preempt each of the (i) the medical expert device, (ii) the patient device, (iii) the patient and (iv) the IMD.

FIG. 56C shows a generalized version of FIG. 56B. This figure accommodates any possible relationship between an MP, a patient, a patient device, a medical expert device and an IMD. It could apply to a different list of control sources (e.g. multiple different caregivers). It could also apply to any kind of PMD, i.e. a purely internal device, a purely external device or a hybrid device. "Other Options A" refers to a situation in which none of the entity responses is enabled. This might be the case for a device which is at end of service, or a device which is incompatible with a particular patient. Such options include no action, and include notification of an appropriate person. "Other Options B" refers to a situation in which none of the authorized device controllers responds. Such non-response may be clinically appropriate, in which case no action may be appropriate. Alternatively, re-notification of any of the entities, or a more aggressive form of notification are options.

FIG. 56D carries the generalization of FIG. 56C one step further, by indicating that any number of control sources is possible.

7.9 Blending of Two or More Analysis/Control Algorithms

As indicated hereinabove in FIG. 7A, and also in FIGS. 1, 7B, 8, 13, 27A, 27B, and hereinbelow in FIGS. 77 and 82, and in the specification associated with each of the aforementioned, there are embodiments of the invention in which the IMD has a plurality of algorithms, each of which independently analyzes and/or assesses the need for treatment and/or selects the appropriate treatment. In such embodiments, a need exists to determine a choice, if the algorithms do not agree with each other, in terms of analysis or treatment recommendation. Hereinbelow, with respect to the specification of FIGS. 57 and 58, the output of each of the three algorithms (and of the master algorithm) is generally referred to as a treatment recommendation, but the process shown in the figures is equally applicable to dealing with non-identical event analyses by the three algorithms (see, for example, FIG. 82). FIG. 57 shows a master algorithm to be used for selecting the treatment to be implemented from among the outputs of three algorithms which operate in parallel. FIG. 58 shows a master algorithm for dealing with IMDs with two parallel algorithms; the FIG. 58 algorithm may also operate with a three algorithm device, when combined with the FIG. 57 algorithm.

Referring to FIG. 57, each of the three IMD algorithms analyzes sensor data and produces a management decision (or an analysis). If the three decisions (or analyses) are identical, then this uniform decision is implemented. It the three are not identical, then options include contacting the MP, contacting the patient, or further analysis prior to final assessment.

With respect to FIGS. 57 and 58, the choice of which option is selected from a multiplicity of options, will generally be preprogrammed; This pre-programming may be simple (e.g. if two out of three of the algorithms agree, select their choice; and if not, refer to the patient), or it may be more complex, and depend on the urgency of the situation, details of the situation, the availability of the patient and other factors). The same is true of each of the multi-option branches in the algorithms in FIGS. 57 and 58.

If contacting the patient or MP is selected, the IMD proceeds as indicated hereinabove. As shown in FIG. 8, the IMD may transmit:

(a) the analysis of one or more of algorithms #1, #2 and #3;
(b) "raw," i.e. unprocessed or minimally processed sensor data;
(c) the results of a blending or an averaging process (see hereinbelow) in which the master algorithm attempts to combine two or more non-identical recommendations; and/or
(d) the final decision of the master algorithm.

If proceeding with the algorithm is selected, it queries whether two of the three IMD algorithm decisions are identical. If yes, the options are (a) to select that majority decision, or (b) to notify the patient or MP). Alternatively, if the disagreement among the algorithms does not involve a yes/no decision or a choice among different therapies, but does involve a numerical choice (e.g. the dose of a drug to be administered, or the selection of a rate of stimulation or an intensity of stimulation), an "averaging" process may be used (see hereinbelow), in which all three recommendations contribute. If two of three IMD algorithm decisions are not identical, then the options include (a) further analysis, or (b) contacting the patient or MP. If further analysis is chosen, then the algorithm queries whether any two of the three decisions are nearly identical. If they are not, the options include (a) contacting the patient or MP, and (b) an "averaging" process.

The averaging process may be a strict average; For example, if antitachycardia pacing at 180 b.p.m. is the recommendation of algorithm #1, and ATP at 195 b.p.m. is the recommendation of algorithm #2, and ATP at 225 b.p.m, is the recommendation of algorithm #3, then the numerical average of the three, 200 b.p.m. might be selected. Alternatively, (a)

the middle value may be selected, or (b) there may be a process by which each of the three recommendations is assigned a weight, and a weighted average is performed. The weight may, for example, depend on the past performance of each algorithm. In yet another approach, the average of the two closest values (in the aforementioned example: 180 and 195 b.p.m.) may be selected (discussed hereinbelow). Hereinabove and hereinbelow, the term "average", when used with quotation marks, is intended to indicate all of the above averaging options.

If two of the algorithm decisions are nearly identical, the master algorithm queries whether all three are nearly identical. If not then the options include:

(a) selecting one of the two closest decisions (if a determination of "closeness" is applicable [i.e. if the decisions are qualitatively the same, but quantitatively different); The method of selection will be preprogrammed (e.g. [i] always select the most aggressive decision, [ii] always select the least aggressive decision, [iii] make the decision based on prevailing conditions, etc.);

(b) selecting an "average" of the two closest (as defined hereinabove) decisions; and (c) contacting either the MP or the patient.

If all three of the IMD algorithm decisions are nearly identical, then the options include each of the three choices (a)-(c) immediately hereinabove, and (d) performing and selecting the "average" of all three IMD algorithm recommendations.

FIG. 58 shows a master algorithm for the management of IMDs which run two parallel analysis and/or treatment selecting algorithms; The algorithm shown in FIG. 58 may also be used for a three-algorithm device. If the analysis and/or management recommendation of each of the two algorithms is identical, then that recommendation is implemented (referred to in the figure as that of algorithm #1, which in this case is identical to algorithm #2). If the decisions are not identical, then the master algorithm queries whether the decision involves a yes/no decision (or other decision with choices not amenable to an "averaging" process). If the format is yes/no, then options include (a) notifying the patient or MP, and thereby requesting their input; and (b) if the IMD has a third algorithm, checking for the recommendation of that third algorithm, and then proceeding from the denoted entry point to the master algorithm shown in FIG. 57. Alternatively (not shown in the figure for this branch of the algorithm), a decision to select one of the choices of algorithm #1 or algorithm #2 may be made (based on preprogrammed decision criteria, as indicated hereinabove).

If the decision format is not a yes/no issue, but rather involves similar aspects which differ by a numeric parameter, then the algorithm queries whether the two IMD recommendations are nearly identical. If they are not, then the options are identical to those immediately hereinabove for the situation in which there is a yes/no format. However, if the two recommendations are nearly identical, then the option list, besides including each of the options immediately hereinabove for the yes/no format (including selecting one of algorithm #1 or algorithm #2), the additional option of implementing the "average" of algorithm analysis/recommendation #1 and of algorithm analysis/recommendation #2 is available.

The analysis/management concepts discussed hereinabove with regard to FIGS. 57 and 58 may be generalized to IMD systems with four or more algorithms. With larger numbers of algorithms, there will be more latitude in terms of using statistical measures and means known in the art, when the analyses and/or recommendations do not agree.

The step in the algorithm shown in FIG. 58 which calls for the inclusion of a third algorithm, after two algorithms produce non-identical results may use an algorithm that is outside of the IMD, i.e. an algorithm which runs in either;

(a) the patient device,
(b) the M.E. device, or
(c) another IMD.

Alternatively, the opinion of the patient (or even the MP) may be utilized as the third algorithm output.

The most general statement about the inputs to each of FIGS. 57 and 58, is that any of the algorithm inputs may represent either a device or a person. For example, the three algorithm inputs to the master algorithm of FIG. 57 could be:

(a) the IMD,
(b) an algorithm which runs on the patient device, and
(c) the opinion of the patient.

7.10 Control Handoff Algorithms

Hysteresis in a treatment algorithm allows for the conditions which trigger the transition from a first to a second treatment state to differ from the conditions which trigger the transition back to the first treatment state from the second treatment state. For example, if:

the first treatment state is the absence of ventricular demand pacing at 60 b.p.m., the second treatment state is the presence of ventricular demand pacing at 60 b.p.m., the conditions which trigger the transition from the first treatment state to the second treatment state are the heart rate falling below 50 b.p.m., and the conditions which trigger the transition from the second treatment state to the first treatment state are the heart rate rising above 60 b.p.m.;

Then a patient with a pacemaker so programmed will begin pacing (at 60 b.p.m.) when his/her heart rate falls below 50 b.p.m., and continue to pace until the heart rate rises above 60 b.p.m.

The term hysteresis, in the case of the IMD system, refers to asymmetric conditions for (i) on the one hand, the transition from one of the entities (e.g. the IMD) being in control, to another entity (e.g. the patient device) being in control, and (ii) on the other hand, the reverse transition.

7.10.1 Takeover and Return of Control

Figure 59:
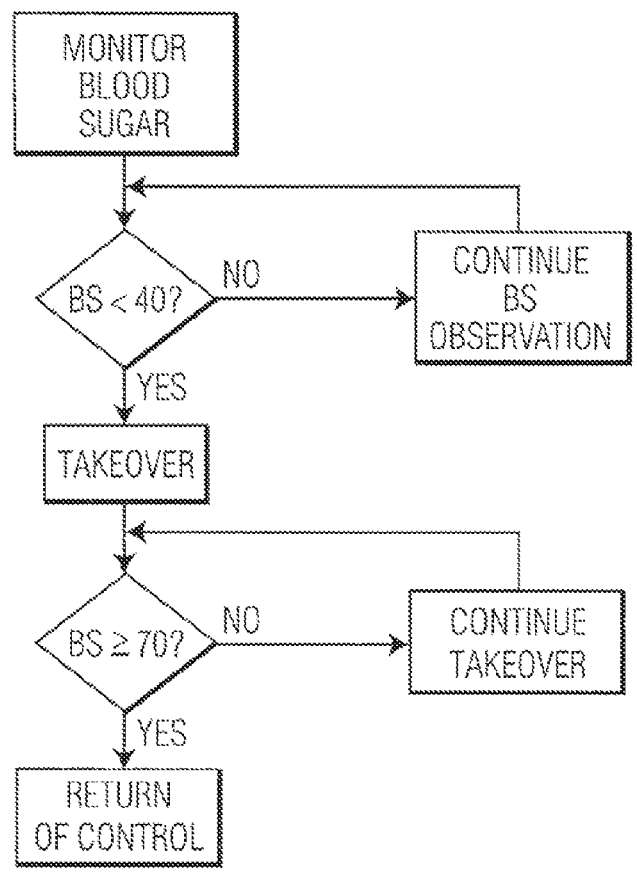
FIG. 59 is a flow diagram illustrating methods of shifting control of an IMD, in an IMD system.

For example: FIG. 59 shows a flow diagram for the sharing of control of an implanted blood sugar control device between (i) the implanted device logic circuits; and (ii) a patient-carried device logic circuits, which may additionally have input from the patient. The implanted device initially monitors the blood sugar, and continues to do so, unless the blood sugar concentration fall below 40 mg./dl.; in which case a takeover of control by the patient device occurs. The patient device may at that point do a better job of controlling the blood sugar (i) because of a better algorithm, (ii) because of access to external patient sensors, and/or (iii) because the patient may be allowed access to insulin does decision making. In the algorithm shown in the figure, the patient device remains in control until the blood sugar rises to a value considerably better than the one at which the transition took place from implanted device-based control to patient device-based control.

This type of hysteresis format may apply to:

(a) other types of device systems, e.g. an ICD; and
(b) the act of taking and returning control by other devices within an IMD system, e.g. the M.E. device.

Furthermore, it can also apply to taking (and returning) control from (and to) a human (e.g. the patient), as well as from (and to) another device. It can also apply to transitions caused by humans (i.e. the patient or the MP), though human decision making will not generally by absolutely locked in to simple algorithmic formats.

Figure 60:
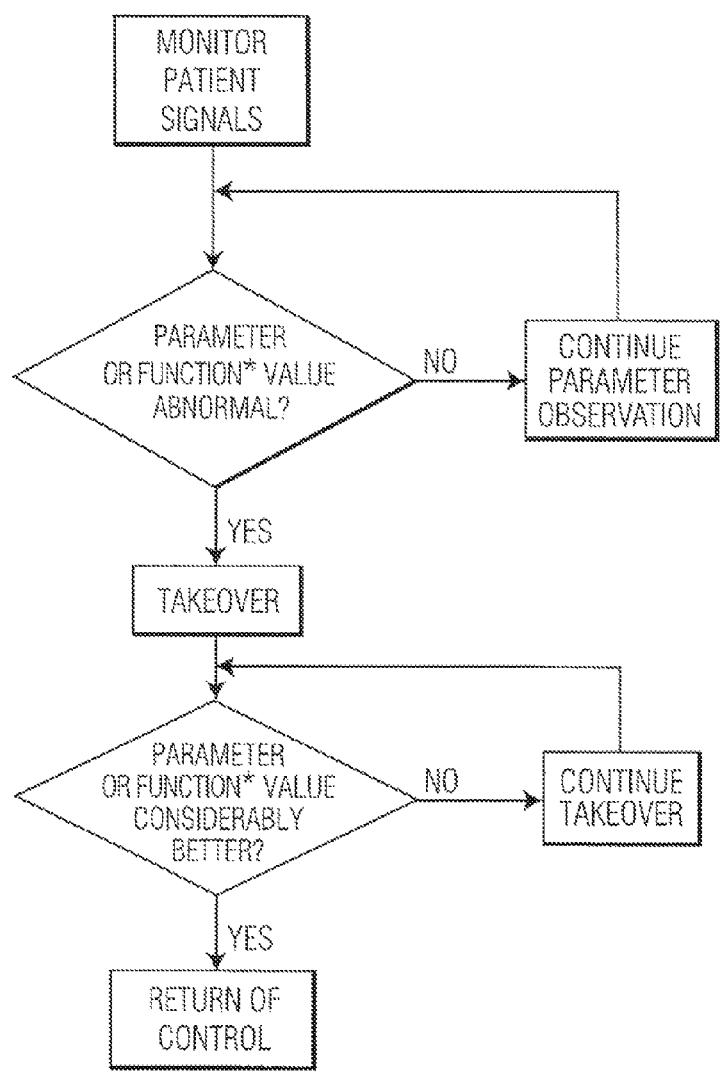
FIG. 60 is another flow diagram illustrating methods of shifting control of an IMD, in an IMD system.

FIG. 60 illustrates a generalized algorithm for enacting control similar to that shown in FIG. 59. Takeover of control ("takeover") occurs when the value of a parameter or of Function* (as defined and discussed in conjunction with FIG. 22A-24) becomes sufficiently abnormal, but return of control to the entity from which it was taken does not occur until the value of the parameter or of Function* becomes incrementally more normal ("considerable better", as stated in the figure) than was the case at the time of the initial takeover, (Herein, "incrementally more normal" and "considerably better" mean that the value returns not just to the cutoff point for the takeover transition, but to a more normal value than the takeover point—as was exemplified in the description of FIG. 59.)

FIG. 61 illustrates a hysteresis scenario in which the criterion which distinguishes takeover from return of control is the duration of an abnormality—in this case, the duration of an abnormal heart rate. In the figure, takeover occurs for a heart rate above 200 b.p.m. for a duration of 25 consecutive seconds. Return of control (e.g. from the M.E. device to the IMD) occurs if heart rate falls below 200 for 90 consecutive seconds.

It may be desirable to have a format in which the conditions which trigger a takeover depend on two different parameter or Function* values; This situation is shown in FIG. 62. In order for takeover to occur, both (i) the value of parameter #1 or Function* #1 and (ii) the value of parameter #2 or Function* #2 must be abnormal. Once takeover occurs, in order to restore the initial source of control, there must be a normalization of the values of both parameters or Function*s to a degree such that they both are incrementally more normal than was their value at the time of the initial takeover.

If, after the sequence of takeover of control followed by return of control, the patient condition again becomes such that control by the primary device may be considered to be suboptimal, a second takeover may be desirable. Furthermore, if the timing of the second deterioration in patient condition is such that it is in close temporal proximity to the first deterioration, it may be desirable to make the conditions for a second takeover less extreme than those which precipitated the first takeover, i.e. to institute a method of heightened patient surveillance after the first takeover. Hereinbelow, the term "first takeover" is used to refer to the first such takeover, and "second takeover" to refer to the second such takeover.

7.10.2 Takeover #2

FIG. 63 shows an example of second takeover criterion differing from first takeover criterion. In the example, first takeover (from the IMD, for example) occurs when the patient's blood sugar falls below 40 mg./dl. Return of control occurs when the blood sugar rises to 70 mg./dl. Second takeover occurs if the blood sugar falls to 50 mg./dl. (rather than 40 mg./dl., as was the cutoff for first takeover).

FIG. 64 shows an example in which the criteria for first and second takeover differ in two ways: (a) number of ICD shocks, and (b) width of moving window in time in which the cutoff number of shocks must occur. In the algorithm shown in the figure, the occurrence of three ICD shocks within 10 minutes triggers a takeover of the IMD by an external device (either the patient device [with or without input from the patient], or the medical expert device). Return of control to the ICD occurs if a two hour period elapses without a shock having been delivered to the patient. However, as shown in the figure, following such a sequence, the criteria for takeover are changed to two shocks within a 25 minute period. The altered takeover criteria (i.e those for the second takeover) may (i) persist indefinitely, (ii) persist until the MP or other system entity resets the initial (or other) criteria, or (iii) transition gradually back to the first takeover criteria in a pre-programmed manner over time, as shown hereinbelow in conjunction with FIG. 69.

FIG. 65 shows an algorithm which is a generalization of the process of second takeover. First takeover is triggered by a specific abnormality of a parameter or of Function*. Return of control is triggered by an improvement to a value of the parameter of Function* which is incrementally better than that which triggered the first takeover. Second takeover is triggered by a later occurring value of the parameter or Function* which is not as abnormal as that which triggered the first takeover.

Alternative second takeover formats are possible. The value of the parameter or Function* which triggers second takeover need not be more abnormal than the value which triggered return of control. For example, with the blood sugar management system considered in FIG. 63, second takeover could occur when the blood sugar falls below 70 mg./dl. In still other formats, the parameter of Function* value which triggers second takeover may be:

(a) the same as the one which triggers first takeover (a trivial case); and (b) more abnormal than the one which triggers first takeover (e.g. blood sugar less than 35 mg./dl in FIG. 63 example); This would constituted the opposite of heightened surveillance, i.e. it would constitute diminished surveillance (perhaps an acknowledgement of a "brittle" management situation in a diabetic patient).

7.10.3 Return of Control #2

Just as the conditions for second takeover may differ from those of first takeover, the criteria for return of control after a second takeover (i.e. the "second return of control") may differ from those which trigger return of control after the first takeover (i.e. the "first return of control"). FIG. 66 shows an example of an algorithm which illustrates this approach. In a patient with an implantable blood sugar stabilization device, first takeover by an external device (e.g. the patient device) occurs when the blood sugar falls below 40 mg./dl. First return of control occurs when conditions improve to the extent that the blood sugar rises to 70 mg./dl. Second takeover occurs when the blood sugar falls below 50 mg./dl. As indicated in the figure, there are a variety of second return of control options including:

(a) second return of control not allowed;

(b) second return of control for blood sugar 70 mg./dl. or above (i.e. the same criteria as for first return of control); or (c) second return of control for blood sugar 80 mg./dl. or above (i.e. more restrictive [i.e. more normal] criteria than for first return of control).

Many other second return of control criteria for a blood sugar management system are possible and will be obvious to those skilled in the art.

FIG. 67 shows an algorithm which illustrates a generalization of second return of control. First takeover is triggered by a severe abnormality. (The words of "severe" or "severely abnormal" herein, hereinabove and hereinbelow may be considered to be a relative terms, chosen so that they might easily, semi-quantitatively be compared with other descriptors such as "non-severe", "moderately abnormal", "mildly abnormal", etc.) First return of control is triggered when the value of the parameter or Function* which refers to the abnormality improves to a mildly abnormal value, i.e. a value which is incrementally better than that which triggered first takeover. Second takeover then may occur when the value of the parameter or Function* becomes moderately abnormal, i.e. more abnormal than the value which triggered first return of control, and less abnormal than the value which triggered first takeover. Second return of control:

(a) may not be allowed;
(b) may be triggered by an improvement in the parameter value or Function* value to:
   (i) a mildly abnormal value (i.e. the same value as the one which triggered first return of control, or it may be triggered by an even better value);
   (ii) a normal value;
   (iii) a value which is minimally better than the one which triggered second takeover; or
   (iv) other values.

Other second return of control scenarios are associated with each of the alternate second takeover formats hereinabove. For example:

(a) second takeover and first takeover criteria may be identical (e.g. blood sugar of 40 mg./dl.), but second return of control may be more demanding than first return of control (e.g. blood sugar of 80 mg./dl. And 70 mg./dl., respectively); and (b) first takeover and first return of control are triggered by identical parameter or Function* values (e.g. blood sugar values of 40 mg./dl.), i.e. no hysteresis for first cycle; but second return of control requires a parameter or Function* value which is incrementally less abnormal than the value which triggered second takeover (e.g. blood sugar values of 50 mg./dl, for second takeover and 60 mg./dl. for second return of control), i.e. hysteresis in effect for second cycle.

Still other second return of control criteria for IMD systems are possible (for the general and for the specific cases) and will be obvious to those skilled in the art. In addition, systems are possible in which third (and higher order) takeover criteria, and third (and higher order) return of control criteria are programmable, using the same principles as have been detailed herein.

A control screen for the programming of each of (a) takeover criteria, (b) return of control criteria, (c) second takeover criteria, and (d) second return of control criteria is shown in FIG. 13. The screen shows that each of the IMD, the patient device and the medical expert device may be programmed accordingly. Each would be programmed with criteria which were not identical to another device in the IMD system.

7.10.4 Time Dependent Formats

Each of the control shifts after a takeover [(a) first return of control, (b) second takeover, and (c) second return of control, etc.] may be programmed in a time-dependent manner. That is, if an unstable or undesirable patient situation resulted or may have resulted from inadequate or suboptimal control by one of the devices in the IMD) system leading to a first or second takeover, then the duration of time that it takes to rectify that unstable or undesirable state may influence the criteria which determine the whether a reversal of the takeover is permitted. Similarly, following a return of control, the duration of the period of stability may influence the criteria for a second takeover.

An example is shown by the algorithm in FIG. 68. The conceptual starting point for the figure is FIG. 61, in which takeover occurs after a heart rate of greater than 200 b.p.m for 25 consecutive seconds and return of control occurs after a heart rate of less than or equal to 200 b.p.m. for 90 seconds. The FIG. 68 algorithm indicates that if the heart rate of greater than 200 b.p.m. persists for 5 or more minutes, then a more strict criterion, i.e. a heart rate of less than or equal to 185 b.p.m. for 90 consecutive seconds is required for return of control. The underlying concept is that greater patient stability (the rate less than 185 b.p.m., as opposed to 200 b.p.m.) is required before return of control to the entity whose management resulted in or allowed the current persistent tachycardia. Furthermore, as shown in the figure:

(a) If return of control has not occurred within 10 minutes after the start of takeover, then a further degree of improvement (in this case, the rate falling to less than or equal to 170 b.p.m. for 90 consecutive seconds) is required to trigger return of control; and (b) If return of control has not occurred within 15 minutes after the start of takeover, then a still further degree of improvement (in this case, the rate falling to less than or equal to 155 b.p.m. for 90 consecutive seconds) is required to trigger return of control.

If return of control has not occurred within 20 minutes after the start of takeover, then a still further degree of improvement (in this case, the rate falling to less than or equal to 140 b.p.m. for 90 consecutive seconds) is required to trigger return of control, FIG. 69 shows an example of time-dependent takeover #2. The conceptual starting point for this figure is FIG. 64, in which first takeover is triggered by 3 shocks within 10 minutes and, after return of control (triggered by no shock for a two hour period), second takeover is triggered by 2 shocks within a 25 minute moving window of time. This creates a state of heightened surveillance after the multiple shock situation.

In the time-dependent algorithm of FIG. 69, the 2 shock per 25 minute criterion gradually (in four steps over 72 hours) returns to 3 shocks per 10 minutes. The approach is based on the concept that as time elapses after the storm of shocks, a gradual return to the baseline takeover criteria is desirable. As shown in FIG. 69:

(a) during the period up to 3 hours after return of control, takeover #2 is triggered by 2 shocks in 25 minutes;

(b) during the period from 3 hours and up to 12 hours after return of control, takeover #2 is triggered by 2 shocks in 20 minutes;

(c) during the period from 12 hours up to 36 hours after return of control, takeover #2 is triggered by 2 shocks in 15 minutes; and (d) during the period from 36 hours up to 72 hours after return of control, takeover #2 is triggered by 2 shocks in 10 minutes;

Thereafter the takeover criteria return to those that were in effect before any shocks were delivered; i.e. at that point the second takeover criteria equal the first takeover criteria.

FIG. 70 shows an example of time dependent second return of control. In the example, with the passing time after second takeover, a progressively greater degree of normalization of the heart rate is required in order to allow second return of control. The algorithm shown might follow that shown in FIG. 68 (showing time dependent first return of control for a tachycardia managed by an ICD, which in turn follows from the algorithm shown in FIG. 61 showing an example of takeover and return of control for heart rate of 200 b.p.m.). Compared to the FIG. 68 algorithm, that shown in FIG. 70 entails (i) a more rapidly evolving return of control criterion, as well as (ii) a more demanding one ([1] Heart rate decrements in each step are by larger amounts in FIG. 70, and [2] Each progressive step requires a greater duration of more favorable heart rate before return of control is allowed). The FIG. 70 algorithm specifically calls for:

(a) Within the first 2 minutes after second takeover, second return of control occurs if the heart rate falls to 190 b.p.m. or below for 2 minutes;

(b) From 2 minutes up to 4 minutes after second takeover, second return of control occurs if the heart rate falls to 170 b.p.m. or below for 3 minutes;
(c) From 4 minutes up to 8 minutes after second takeover, second return of control occurs if the heart rate falls to 150 b.p.m. or below for 5 minutes;
(d) From 8 minutes up to 16 minutes after second takeover, second return of control occurs if the heart rate falls to 140 b.p.m. or below for 8 minutes; and
(e) After 16 minutes, return of control may no longer be possible.

In a preferred embodiment of the invention—if an algorithm called for lockout of the automated return of control—the MP would, if he/she deemed appropriate, be able to reset the system to allow return of control to the entity from which it was taken.

Generalized versions of the aforementioned time dependent takeovers and returns of control will be apparent to those skilled in the art.

The aforementioned discussion of FIGS. 59-70 may involve the transfer of control between two entities, has been presented in terms of the transfer of control back and forth between two entities: In general terms, the takeovers involve the transfer of control from Entity #1 to Entity #2 and the returns of control are from Entity #2 to Entity #1. However, more complex scenarios are possible in which:

(a) The first round of takeover and return of control is between Entity #1 (e.g. an IMD) and Entity #2 (e.g. a patient device), and a second round of takeover and return of control is between Entity #1 and Entity #3 (e.g. a medical expert device), v.i.z.:
  (i) first takeover transfers control from Entity #1 to Entity #2;
  (ii) first return of control transfers control from Entity #2 to Entity #1;
  (iii) second takeover transfers control from Entity #1 to Entity #3; and
  (iv) second return of control transfers control from Entity #3 to Entity #1.
(b) A cyclic process occurs in which:
  (i) first takeover transfers control from Entity #1 to Entity #2;
  (ii) second takeover transfers control from Entity #2 to Entity #3; and
  (iii) return of control transfers control from Entity #3 back to Entity #1; and
(c) A more complex series of handoffs occurs in which:
  (i) first takeover transfers control from Entity #1 to Entity #2;
  (ii) second takeover transfers control from Entity #2 to Entity #3;
  (iii) first return of control transfers control from Entity #3 to Entity #2; and
  (iv) second return of control transfers control from Entity #2 to Entity #1.

In the scenarios listed above as (b) and (c), a change in the sequence of transfer types is presented: i.e. a second takeover occurs before the first return of control. Specific examples will be apparent to those skilled in the art, as will be examples of complex scenarios involving third (and higher order) takeovers and returns of control, and scenarios involving more than three entities.

8.0 Use of Function* for Triage

As indicated hereinabove, notification, the process of sending information from a monitoring device (i.e. the IMD, or the patient device), the "notifying party", to any other entity of the IMD system (i.e. the patient device, the patient the M.E. device or the MP), the "notified party", may be viewed as an invitation to take over control. Because different entities may have different notification criteria, there is the opportunity to set up a control structures with all degrees of complexity. FIGS. 71A to 76C illustrate a number of examples of such structures.

Notification is a feature of all of the algorithms of FIGS. 29 to 56B and is discussed explicitly in conjunction with FIGS. 53-56B. The programming of notification in an IMD system has been discussed in conjunction with FIG. 6 (by the patient) and 13 (by the MP). The transmission of notification signals by the IMD is shown in FIG. 8, and the receipt of notification signals by the patient device is shown in FIG. 9. The receipt of notification programming signals by the IMD is shown in FIG. 11. The arithmetic blending of patient information to produce Function* is presented in FIGS. 22A-24. Notification examples are shown in the examples in FIGS. 78-82. Second notification—i.e. notification concerning an event temporally related to that which triggered first notification—is illustrated by the control screen shown in FIG. 13 and the example in FIG. 82; The latter also illustrates time dependent second notification criteria.

The simplest notification structure would be one in which the notification occurs for all detected abnormalities, or for all treatments—for example an ICD which notifies an MP for each time it treats a tachycardia. Advantages related to more refined notification formats—in which notification occurs only for some but not all events are (a) a decrease in batter power consumption of the notifying device—. especially important if that device is the IMD, (b) a decrease in attention time and effort required of a human if the automatic functioning of a device suffices, and (c) decreasing the frequency of complex device-device and device-human interactions.

8.1 2-Zone Formats

It thus becomes desirable to consider notification formats in which notification occurs for some but not all events, and in which the IMD functions autonomously (including the possibility of monitoring but not treating) for the remainder of events. FIGS. 71A and 71B show simple formats in which the IMD functions autonomously for events considered to be normal (in which case it provides no therapy), and for events which constitute non-severe abnormalities (for which it treats the condition but provides no outside notification). However, in the event of a severe abnormality: (a) notification of both the patient and the MP and IMD treatment is shown in FIG. 71A, and (b) notification of both the patient and the MP without IMD treatment is shown in FIG. 71B. In the FIG. 71A format, the purpose of notifying them and instituting IMD treatment would be to allow them to override the treatment if they so desired, but to get the treatment started while they are briefed about and considering their own views about treatment; This might be the case for a very high blood sugar, where at least some insulin administration is desirable, but where the exact amount may be best determined by a human. In the FIG. 71B format, no treatment occurs without the patient or MP authorizing it; This might be the case for high frequency electrogram signals which might be due to a defibrillator lead malfunction.

FIGS. 71A-F illustrate notification structures in which the severity of the abnormality is denoted by an increasing value of the arithmetic entity Function*. Function* is discussed hereinabove in conjunction with FIGS. 22A-24; It may be as simple as heart rate, or a more complex summation of a number of parameters, each appropriately weighted. The horizontal lines in each figure are intended to indicate boundaries for Function* values, as shown in FIGS. 22A and 22B. Thus FIG. 71B could illustrate (a) a normal heart rate range up to 160 beats per minute, (b) an ICD treatment only range of 160 to 400 beats per minute, and (c) a notify patient and MP range for greater than 400 beats per minute.

FIGS. 71, 72, 74 and 75 illustrate "half formats," i.e. formats in which the zone with the lowest value of Function* is the normal range; FIGS. 73 and 76 illustrate full formats. Half formats are appropriate when the IMD only treats and notifies for elevated values of Function*. Though half formats are useful for simplifying the illustrative process, many actual devices will require at least one of treatment or notification for values os Function* which are above or below the normal range. An example of the latter is an ICD which performs bradycardia pacing for low heart rates and defibrillation for high heart rates (in which case Function* may simply be the heart rate).

The formats in FIGS. 71-76 involve three entities, i.e. the IMD, the patient and the MP. Formats involving four or more entities (e.g. the IMD, the patient, the M.E. device and the MP) are possible and are generally more complex. Two-entity formats are also possible.

Simple formats—those in FIG. 71—are considered to be those in which notification, when it occurs, always involves both the MP and the PT. The complex formats of FIGS. 72-76 illustrate some zones in which only one of the MP and PT is notified.

FIGS. 71C and 71D illustrate notification formats in which:
 (a) for non-severe abnormalities, the patient and MP are notified, without IMD treatment; and
 (b) for severe abnormalities, there is IMD treatment either with (71D) or without (71C) notification of the patient and MP.

FIGS. 71E and 71F illustrate notification formats in which:
 (a) for non-severe abnormalities, the patient and MP are notified, with IMD treatment; and
 (b) for severe abnormalities, there is either notification of the patient and MP (71E) or IMD treatment (71F).

FIG. 71 show all six possible two zone half-formats in which neither or both the MP and the patient are simultaneously notified. Formats in which one (or neither or both) the MP and the patient are simultaneously notified are more numerous; There are 42 possible two zone formats of this type. The six such formats in which a non-severe abnormality (as evaluated by Function*) results in IMD treatment without any notification, after shown in FIGS. 72A-72F:

Formats in which a severe abnormality results in patient notification are shown with (FIG. 72A) and without (FIG. 72D) IMD treatment in the severe zone;

Formats in which a severe abnormality results in MP notification are shown with (FIG. 72B) and without (FIG. 72E) IMD treatment in the severe zone; and Formats in which a severe abnormality results in both patient and MP notification are shown with (FIG. 72C) and without (FIG. 72F) IMD treatment in the severe zone.

There are numerous (1764) possible two-zone full formats in which, within any zone there is at least one of (a) IMD treatment, (b) patient notification, and (c) MP notification. Three such formats are illustrated in FIGS. 73A-73C.

FIG. 73A is symmetrical, in the sense that upward and downward deviations from normal have identical notification formats. For non-severe deviations from normal (both upward and downward), the IMD operates autonomously, and for more severe deviations, there is both IMD treatment and patient notification. As indicated hereinabove, patient notification is considered an invitation to patient action. Possible patient actions include (a) the patient overriding the decision of the IMD to treat, (b) the patient causing the IMD to provide less aggressive treatment, (c) the patient causing the IMD to provide more aggressive treatment, and (d) the patient consulting with either an M.E. device or the MP.

FIG. 73B illustrates a non-symmetrical notification format. it is identical to that of FIG. 73A except that for severe deviations of the value of Function* from normal in the downward direction, the MP (rather than the patient—as is the case in FIG. 73A) is notified. An example would be a severely decreased value of blood sugar, in which circumstance patient functioning may be so impaired that MP (rather than patient) notification is advisable.

FIG. 73C illustrates a greater degree of asymmetry, in that the number of notification zones for downward deviation from normal (one) differs from the number for upward deviation (two). An ICD-pacemaker which (a) paces for slow heart rates, (b) defibrillates for high heart rates and (c) defibrillates and notifies the patient for extremely high heart rates is one possible scenario. (The aforementioned scenario might involve patient notification for short bursts of very high rates, and ICD treatment for very high rates last more than six consecutive seconds.) Alternatively, the zone with the highest values of Function* could involve IMD treatment and MP notification, or could involve MP notification only.

8.2 3-Zone Formats

FIGS. 71-73 illustrate two zone formats: FIGS. 74-76 illustrate three zone formats. FIG. 74 illustrate simple three zone formats, i.e. those in which, if patient notification occurs, MP notification also occurs. There are 12 possible three zone half formats, six of which are shown in FIGS. 74A-74F.

In FIG. 74A, (a) for mild abnormalities of Function*, IMD treatment only occurs; (b) for moderate abnormalities of Function*, IMD treatment and patient and MP notification occur; and (c) for severe abnormalities of Function*, only patient and MP notification occur. Such a notification format is another one that could be utilized for a potentially malfunctioning ICD lead system.

FIGS. 74B and 74C both illustrate formats in which:
 (a) for mild abnormalities of Function*, IMD treatment and notification of both patient and MP occur;
 (b) for moderate abnormalities of Function*, IMD treatment only occurs; and
 (c) for severe abnormalities of Function*, patient and MP notification with (74C) and without (74B) IMD treatment occur.

A scenario in which such formats might be programmed is situations in which there is both (i) concern about ICD lead function [leading to the programming for severe values of Function* abnormality] and (ii) concern about whether the programming of a treatment for a mild tachycardia actually constitutes overtreatment.

FIGS. 74D and 74E both illustrate formats are similar to FIGS. 74C and 74B respectively, differing only in the approach to mild abnormalities of Function*. In FIGS. 74D and 74E:
 (a) for mild abnormalities of Function*, notification of both patient and MP occur;
 (b) for moderate abnormalities of Function*, IMD treatment only occurs; and
 (c) for severe abnormalities of Function*, patient and MP notification with (74D) and without (74E) IMD treatment occur.

A scenario in which such formats might be programmed is situations similar to the scenario discussed in conjunction with FIGS. 74B and 74C, now differing in that for mild tachycardias, notification without treatment is programmed.

In the situation for which notification is programmed as per FIG. 74F, the patient and MP are notified for any degree of abnormality of Function*, but IMD treatment occurs only for intermediate ranges of Function* elevation.

In FIG. 75 complex three-entity half formats, in which notification criteria for the MP and for the patient are not necessarily identical, are presented. FIGS. 75A-75C show three formats in which (1) there is IMD therapy in all zones, and (2) the zone for mild abnormalities of Function* results in autonomous IMD therapy, and (3) notification occurs in each of the zones for moderate and severe abnormalities of Function*, as follows:
- in the FIG. 75A format: (i) notification of patient only, for moderate abnormalities and (ii) notification of patient and MP for severe abnormalities;
- in the FIG. 75B format: (i) notification of patient and MP for moderate abnormalities and (ii) notification of MP only, for severe abnormalities;
- in the FIG. 75C format: (i) notification of patient only, for moderate abnormalities and (ii) notification of MP only, for severe abnormalities.

In FIGS. 75D and 75E the IMD operates autonomously in the event of a moderate abnormality of Function*, while notification without IMD therapy occurs in both the mild and the severe zones, as follows:
- in the FIG. 75D format: (i) notification of patient only, for mild abnormalities and (ii) notification of MP only, for severe abnormalities; and
- in the FIG. 75E format: (i) notification of MP only, for mild abnormalities and (ii) notification of MP and patient for severe abnormalities.

The format for FIG. 75F is identical to that of 75E, except that MP notification is added to the zone for moderate abnormalities of Function*.

FIG. 76 shows three full formats involving three zones. FIG. 76A, shows a symmetrical format in which IMD treatment occurs in all zones, and in which:
- (a) the IMD functions autonomously for mild abnormalities of Function*;
- (b) patient notification occurs for moderate abnormalities (i.e. either above or below the normal range); and
- (c) patient and MP notification occur for severe abnormalities.

The format illustrated in FIG. 76B is an example of an asymmetric notification. It is identical to 76A except that for the lowest values of Function* (i.e. the lowest zone in the diagram, constituting a severe abnormality with values of Function* in the lowest range below normal), only MP notification occurs (as opposed to both patient and MP notification shown in FIG. 76A).

The format illustrated in FIG. 76C shows an example of a greater extent of asymmetry in that there is only one zone below the normal range (in which the IMD operates autonomously, i.e. without notifying either the patient or the MP); and there are three zones above the normal range in which:
- (a) for mild abnormalities, the IMD operates autonomously;
- (b) for moderate abnormalities, the IMD applies treatment and notifies the patient; and
- (c) for severe abnormalities, the IMD applies treatment and notifies both the patient and the MP.

Such a notification format could also be used to institute corrective action in the case of a defective ICD lead.

9.0 Clinical Examples, Overview

FIGS. 78-82 show a selected set of examples of clinical situations in which the IMD-system functions advantageously. FIG. 77 shows a table which summarizes the examples in shown FIGS. 78-82.

Referring to FIG. 77, summarizes five exemplary figures related to four clinical scenarios. The IMD system which is the subject of FIG. 78 is a blood sugar control system, and the IMD which is the subject of the remaining figures is an ICD. The system and component descriptions described hereinabove are not limited to these two types of IMDs, as indicated hereinabove. In columns four through seven, the table classifies the one or more transfer(s) of control from one system entity (e.g. the IMD) to another (e.g. the patient), during the example. The ">" signs in the headings and subheadings of each column are intended to be read as the words "takes control from". Thus the heading of column four, "DEVICE>DEVICE" is read as "device takes control from device", and the subheading below and to the left, "PT.sub.DEV>IMD" is read as "patient device takes control from IMD". Examples of each of:
- (a) device taking control from device;
- (b) device taking control from a human;
- (c) human taking control from a device; and
- (d) human taking control from a human are presented. When horizontal lines divide the information about one of the figures into two or three sections, the figure indicates more than one scenario. The numerals in columns 4-7 and the associated sub-columns indicate the sequence of control transfers. For example, the "A" example shown in FIG. 78 involves, sequentially, the transfer of control from:
(1) the IMD to the patient;
(2) then, from the patient to the patient device;
(3) and then, from the patient device to the medical professional.

9.1 Blood Sugar Management

FIG. 78 illustrates an example of a patient with an implanted insulin pump. In the system that is the subject of the example, the pump may function autonomously or may be controlled externally. In the example, the device detects a high blood sugar and notifies the patient, having been programmed to have patient notification criteria that trigger this notification. The patient, not satisfied with device management, takes control from the implanted device and causes it to deliver additional insulin. Following the additional insulin, the blood sugar falls to a low value (45 mg./dl.); The implanted device detects the low value, has been programmed to notify the patient device of the low value, and does so (the choice of patient device over patient as the notification target is based on the concept that with a blood sugar as low as 45 mg./dl., the patient's judgment may be impaired.

The patient device then interrogates the patient to check his/her judgment. Hardware FIGS. 4, 5 and 6 are relevant to such an interrogation; the control screen shown in FIG. 18 shows the programming of such an interrogation (though it is not the screen that would be used for patient responses [if a screen is used]). A very similar algorithm to the one shown in FIG. 25 for patient interrogation by an IMD, could be utilized for patient device interrogation (This is discussed in the specification for FIG. 25 hereinabove). The flow diagram in FIG. 78 then bifurcates into an "ExampleA", and "Example B".

Referring to the Example A, the patient device, upon determining that both the patient and the IMD have not managed the insulin dosage with satisfactory result, locks out patient control. FIG. 10 shows a control signal "COMMANDS AND SUGGESTIONS FOR IMD FROM PATIENT DEVICE" which accomplishes such a task. Algorithm figures which illustrate such a patient device include FIG. 51 (for a 5-entity system), FIG. 39 (for a 3-entity system). In addition, the programming of the control hierarchy shown in line 3 of FIG. 14 (C1 conditions), in association with a variant of the FIG.

56B algorithm (discussed hereinabove in conjunction with FIG. 561) could allow the patient device to have this level of control.

Referring again to FIG. 78, in addition to patient control lockout, the patient device:
(a) causes the IMD to interrupt or decrease the rate of insulin infusion (if it is still being administered);
(b) notifies the patient to take in more glucose immediately, if possible; and
(c) optionally notifies a family member, neighbor, or the patients physician.

In the example, the blood sugar then rises to 350 mg./dl. This is detected by the IMD which is programmed to notify the MP under such circumstances. (In other possible examples, the IMD, the patient device, or any other entity could be programmed to deal with this glucose elevation.)

The MP: causes the IMD to increase the insulin dose, and, because of the recent instability of the clinical situation, manages it himself/herself for a period of three hours (Numerous other variations are possible). Before returning control to the IMD, the MP reprograms:
(a) insulin management by the IMD; and
(b) the criteria for the IMD to notify the patient of hyperglycemia, to a lower notification value.

When the MP is convinced that the situation has stabilized, the MP returns control to the IMD and, in the example:
(a) instructs the patient in better management techniques and, if satisfied with the patient's comprehension of them and the newly re-established clinical stability, re-enables the patient's access to IMD control;
(b) reprograms the patient device's insulin management and may reprogram the patient lockout criteria; and
(c) activates a "watchdog" function of the medical expert device, which the MP instructs to takeover control if, at any time during the upcoming 72 hours the blood sugar excessively rises (e.g. to >300 mg./dl.) or falls (e.g. to <50 mg./dl.).

In Example B of FIG. 78, at the time when significant hypoglycemia associated with impaired patient judgment is detected, the patient device, instead of itself taking control, seeks to notify the MP so that he/she may take control. If the MP can not be contacted because of a communications problem, any of the device entities (M.E. device, patient device or the implanted device) may be chosen; The choice would have been pre-programmed by the hierarchy control screen of FIG. 14. As is the case with Example A, the patient device also (a) locks out patient control, (b) notifies the patient to take in more glucose, and (c) may notify a family member or neighbor.

The MP, when contacted performs all of the steps performed by the MP in Example A, except for reprogramming the patient device, since in Example B, management by the patient device has not led to a clinical problem (as was the case in Example A).

A very large number of possible variations of this example, in terms of system entities involved, their respective actions, and in terms of the clinical scenario itself are possible, and will be obvious to those skilled in the art.

9.2 Ventricular Tachycardia Management

Figure 79:
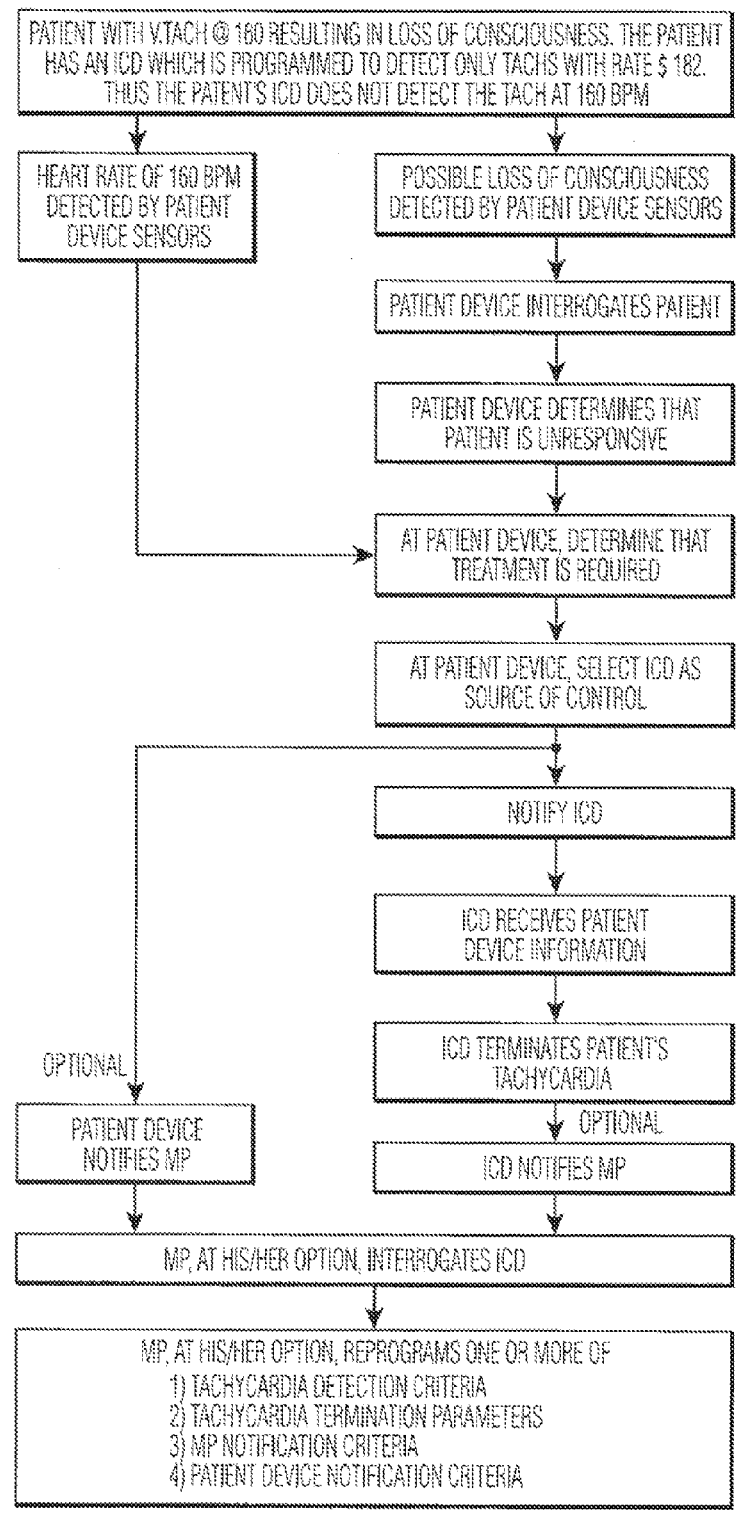
FIG. 79 is a block diagram illustrating an example of the interaction of an implantable cardioverter defibrillator, a patient device, and a medical professional.
Figure 80:
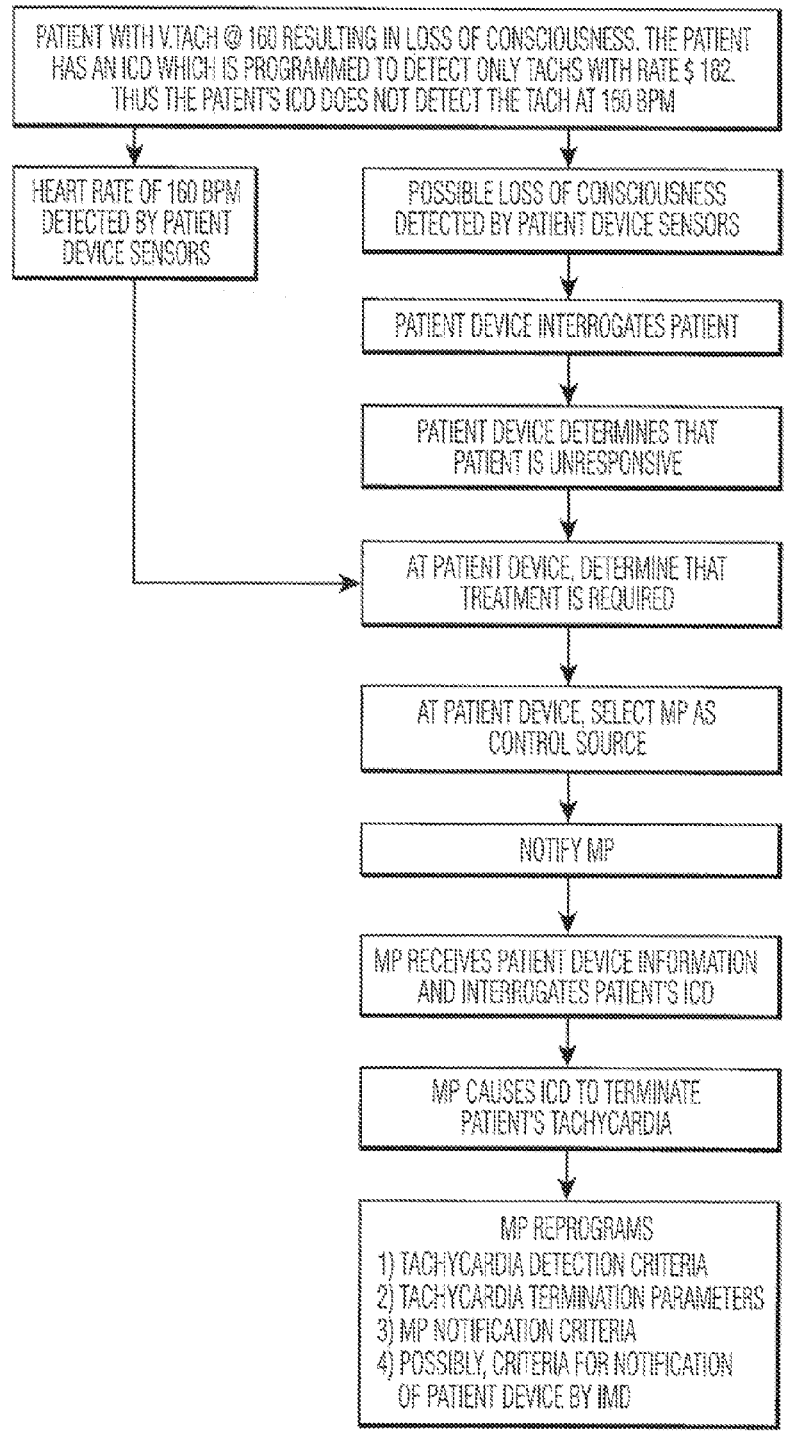
FIG. 80 is another block diagram illustrating an example of the interaction of an implantable cardioverter defibrillator, a patient device, and a medical professional.

FIGS. 79 and 80 show examples in which the IMD is an ICD and fails to detect an episode of ventricular tachycardia, because the VT rate is less than the programmed VT detect rate of the ICD. In both examples, the problem is detected by the patient device. In the version shown in FIG. 79 (referred to as the "A" example in FIG. 77), the ICD is notified by the patient device and resolves the problem. In the version shown in FIG. 80 (referred to as the "B" example in FIG. 77), the MP is notified by the patient device and resolves the problem.

Referring to FIG. 79: VT at 160 b.p.m is not detected by the ICD which is programmed react to tachycardias with a rate greater than 182 b.p.m. The patient device may detect the tachycardia in a variety of ways:
(a) a heart rate sensor, either attached to the patient, or worn by the patient or implanted in the patient may detect the tachycardia. In the latter case (implanted device detects tachycardia), the implanted device may be either (i) a device other than the ICD which detects the tachycardia, or (ii) the ICD) itself, which may be programmed to report heart rates which are rapid (but less rapid than the programmed treatment rate cutoff) to the patient device;
(b) via any of the apparatus (discussed in conjunction with FIG. 5 and control screen FIG. 21 [See also the Function* example of FIG. 24.]) for the detection of a patient fall or loss of consciousness. In this case, the patient device may confirm that treatment us warranted by interrogating the patient and determining that the patient is unresponsive;
(c) via abnormalities which may be detected by one or more other sensors, e.g. respiration, GSR, pulse oximeter or other pulse monitoring device, etc.

Up to this point in the example, FIGS. 79 and 80 are identical; after this point, they diverge. The determination by the patient device that the patient is tachycardic and unresponsive leads, in the example shown in FIG. 79, to the patient device selecting the IMD as the source of management. An algorithm illustrating such a process is shown in FIG. 35. The ICD is informed of the problem, and of its selection as the entity to terminate the tachycardia. It may use a preprogrammed algorithm for management in such circumstances, or alternatively, may be instructed by the patient device. The tachycardia is thus terminated by the ICD.

The MP may be informed of these events (a) following the tachycardia termination, or (b) earlier, at the time that the ICD is informed (or neither (a) nor (b)).

The MP may then interrogate the ICD and reprogram one or more of:
(a) tachycardia detection criteria;
(b) tachycardia termination parameters;
(c) MP notification criteria; and
(d) criteria for notification of the patient device by the IMD (e.g to notify the patient device of tachycardia in the range of 160 b.p.m., if this has not already been done).

In the algorithm shown in FIG. 80, at its point of divergence from the FIG. 79 algorithm, the patient device selects the MP for management and notifies it (e.g. in a FIG. 35-like algorithm). The MP receives the notification, and information pertinent to managing the current event. The MP may bypass interrogation and go directly to a control point in the ICD algorithms, e.g. for performing a non-invasive electrophysiologic test, or may formally interrogate the patient's ICD first. The MP then causes the ICD to terminated the tachycardia, either by directly selecting the therapy and causing its administration, or by programming the ICD to sense a tachycardia at a rate of 160 b.p.m. or a slower rate. The MP may then do one or more of:
(a) formally interrogate the ICD if he/she has not already done so;
(b) reprogram the tachycardia detection rate and other detection enhancement criteria (if not already performed);
(c) reprogram the MP notification criteria; and
(d) reprogram the criteria for notification of the patient device by the IMD.

Figure 81:
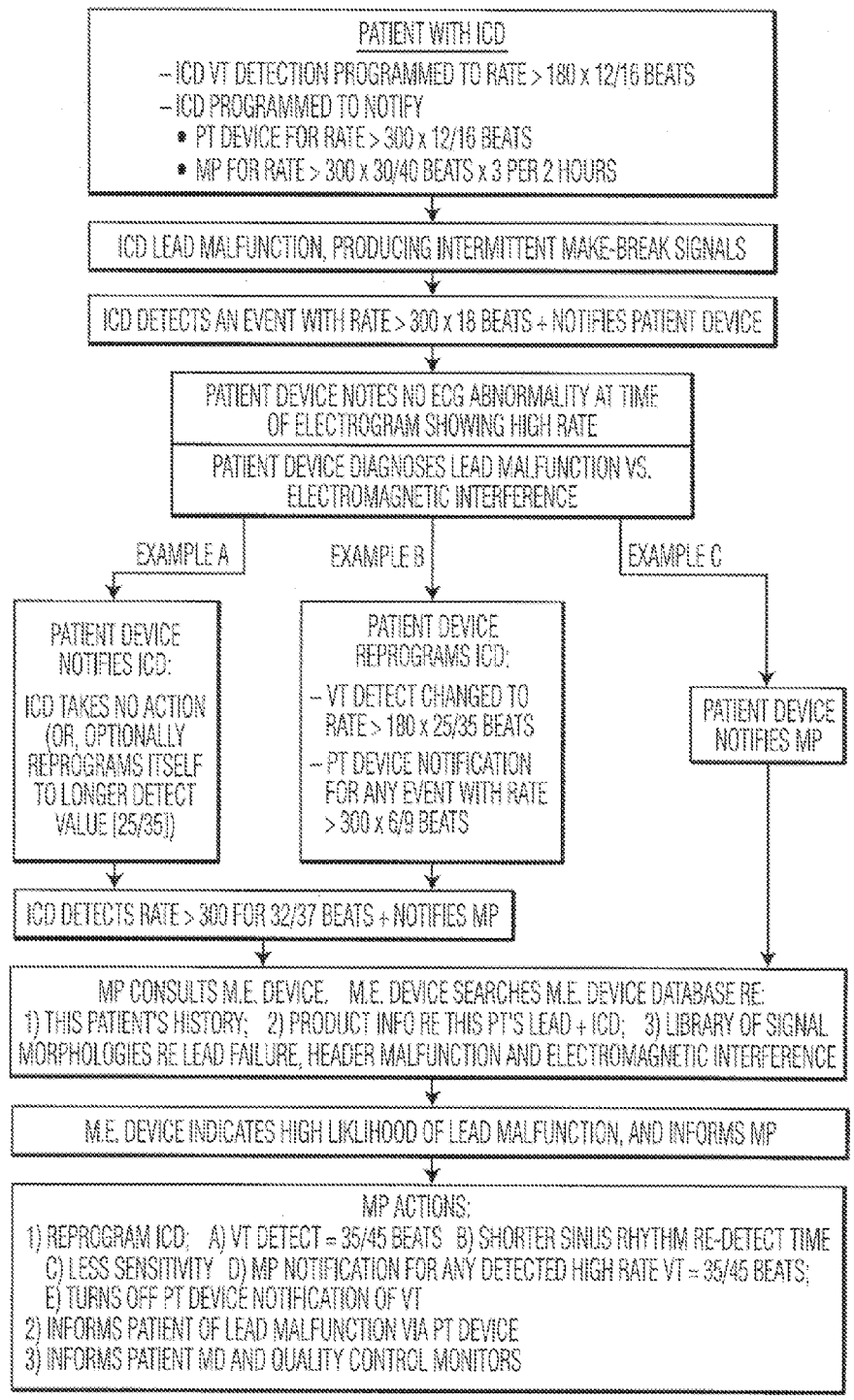
FIG. 81 is a block diagram illustrating examples of the interaction of an implantable cardioverter defibrillator, a patient device, and a medical professional.

FIG. 81 shows an example in which the patient device is able to determine that signals detected by an ICD and labeled as VT are actually make-break signals from a failing ICD lead (or header). The example branches in Examples A, B and C.

In the common initial portion of the example, the following features are shown to be programmed into the ICD:

(a) VT detection at 180 b.p.m. for 12 out of 16 beats;

(b) Notify the patient device for rate >300 b.p.m. for 12 out of 16 beats; and (c) Notify the MP for rate >300 for 30 out of 40 beats, occurring three times within a two hour moving window of time.

Because of the ICD lead malfunction, make-break signals are produced intermittently. At one point, 18 such events (with rate corresponding to over 300 b.p.m.) occur in close enough proximity to satisfy the ICD's patient device notification criterion, and patient device is informed. The patient device may have ECG capability if either (a) there is an attached, worn or implanted ECG sensing device already in place (see discussion in conjunction with FIG. 79), or (b) if the patient device, upon receipt of the information indicating the detection of extremely rapid VT, requests that the patient attach such an ECG monitoring device. (The patient could also be queried by the patient device, as to whether any symptom (e.g. dizziness) occurred in temporal relation to the high rate electrograms, with a negative answer being suggestive that the high rate electrograms do not correspond to a clinical rhythm abnormality.) The patient device may also, as indicated in conjunction with FIG. 79, be able to determine the non-concordance of the high rate electrogram signal with a clinical rhythm abnormality via one or more other external sensors.

Once the patient device has the opportunity to demonstrate that the high rate electrograms do not have a clinical correlate, it concludes that the signal represents either make-break events, or electromagnetic interference. At this point, the example shown in the figure has three branches.

In the branch corresponding to Example A. the patient device notifies the ICD. The ICD may then ignore the corresponding event, and the process (of ICD detection of high rate electrograms, followed by notification of the patient device, followed by notification of the IMD to ignore the event) may continue to repeat. Alternatively, the ICD may be pre-programmed to allow self programming to a longer detect window (e.g. 25 out of 35 beats instead of the previously programmed 12 out of 16 beats), upon notification of the ICD) of the non-physiologic nature of the event, by the patient device. Other self programming options include one or more of (a) the reprogramming (shortening) of the time to redetect sinus rhythm (making it less likely that back-to-back flurries of make-break signals are inappropriately detected as a single longer event;

(b) changing the sensitivity for electrogram detection; and (c) changing other signal processing characteristics such as the filtering of the electrogram signals.

(In an ICD with multiple parallel analysis algorithms, each of the algorithms could process the electrogram signals differently (e.g. different filtering, different gain, etc.) and the outputs of the algorithms could be compared (as discussed in conjunction with FIG. 57).)

In the branch corresponding to Example B, the control hierarchy (e.g. as set up by the screen shown in FIG. 14) is such that the patient device may reprogram the ICD. In the example, the detect duration is increased to 25 out of 35 events. In addition, ICD notification of the patient device is reprogrammed so that only a shorter number of make-break signals (6 out of 9) is required to trigger notification of the patient device.

In both the Example A and Example 8, the next event is ICD detection of an even longer run of high rate electrograms—32 out of 37 beats—which is long enough to trigger MP notification by the ICD. Example C led to MP notification by the patient device without any patient device interaction with the ICD. All three examples converge following MP notification.

In the example, the MP consults the M.E. device, which searches its database for relevant information, i.e.

(a) information about this patient's medical (and ICD and lead) history;

(b) general product information about the patients ICD and lead;

(c) stored electrogram samples which may include [i] samples from this patient at prior times, [ii] samples from other patients who have experienced a lead malfunction (emphasizing cases of malfunction of the same lead and device combination), [iii] samples from other patients who have experienced header or other ICD malfunctions which may manifest in the generation of abnormal sensed signals, and [iv] samples from other patients experiencing known electromagnetic interference.

Based on the analysis of the aforementioned, the M.E. device concludes that the recorded electrograms have a high likelihood of being consistent with lead malfunction, and so informs the MP. The MP then:

(a) reprograms the ICD for a still longer VT detect period (35 out of 45 beats);

(b) reprograms a shorter sinus rhythm redetect time;

(c) reprograms a lesser degree of sensitivity on the ventricular electrogram channel of the ICD;

(d) reprograms ICD notification of the MP to have an identical duration as does ICD detection, and turns off patient device notification (preferring to handle the problem directly);

(e) informs the patient via the patient device; and (f) informs the patient's MD and any necessary quality control person(s).

Figure 82:
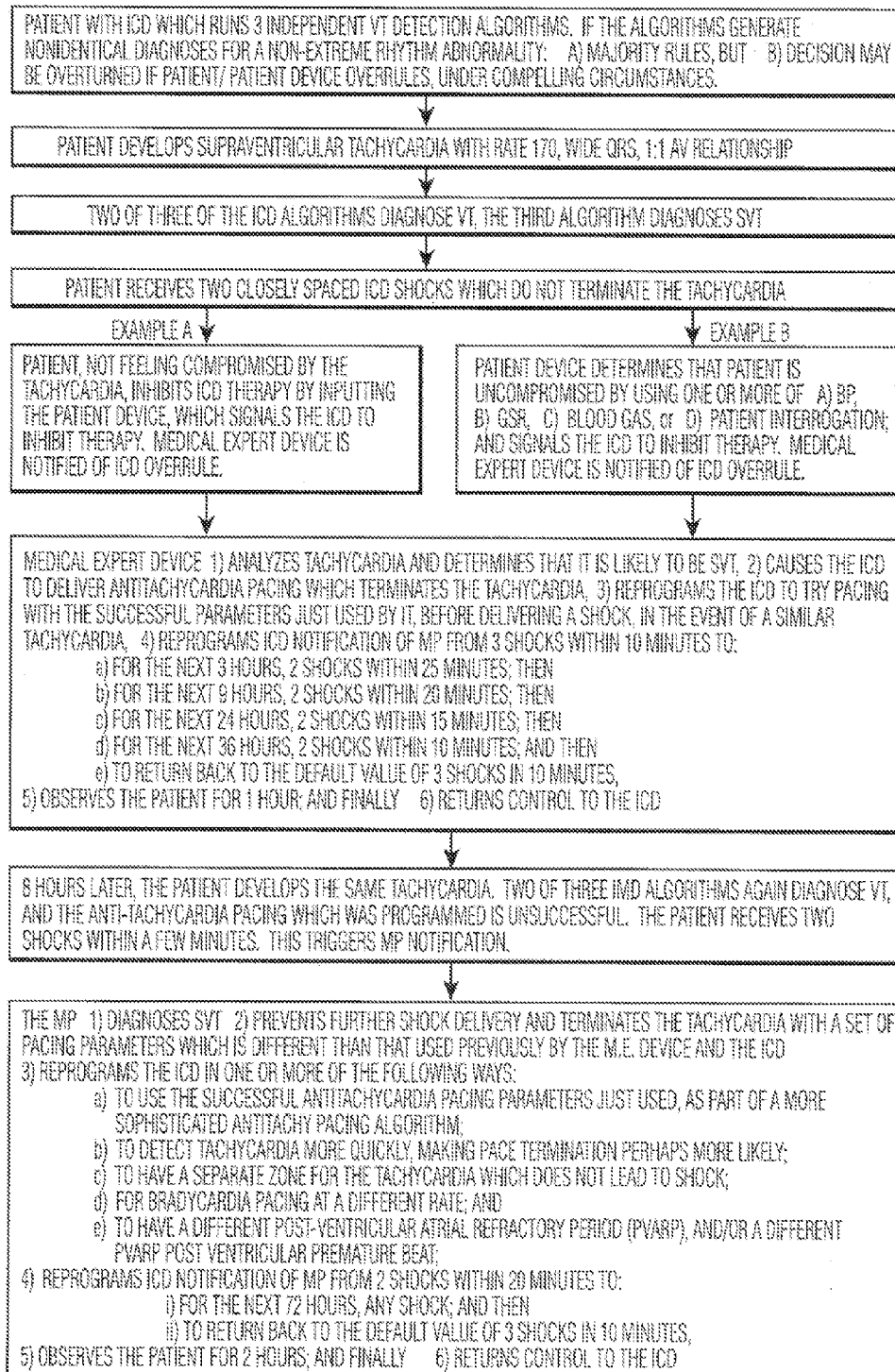
FIG. 82 is a block diagram illustrating examples of the interaction of an implantable cardioverter defibrillator, a patient device, a patient, a medical expert device, and a medical professional.

FIG. 82 shows an example of an ICD with three independent VT detection algorithms operating essentially simultaneously, in parallel. ICD programming is such that, for non-extreme rhythm abnormalities (e.g. rate less than 200 b.p.m.) the majority rules, i.e. if the algorithms do not agree as to whether an event is or is not VT, then the decision of the two algorithms which agree is accepted. The ICD is further programmed so that under certain compelling circumstances, either the patient or the patient device may overrule the ICD decision.

The patient, with ICD so programmed, develops a tachycardia characterized by rate 170 b.p.m., a prolonged QRS duration and an electrogram morphology suggestive of VT, and a 1:1 relationship between atrial and ventricular events, with AV timing not classic for supraventricular tachycardia. Two of the ICD algorithms diagnose VT, while the third diagnoses supraventricular tachycardia ("SVT"). The ICD accordingly treats the event as VT, and delivers two shocks, neither of which terminate the tachycardia. (In an alternate example, the initial majority diagnosis may be SVT, but after the programmed period of therapy inhibition for SVT elapses without SVT termination, VT therapy is delivered.)

In Example A, the patient, aware of the tachycardia but not feeling compromised by it inhibits ICD therapy by inputting a corresponding command to the patient device; This would be allowable if the previously programmed control hierarchy gave this power to the patient. The patient device then signals the ICD to inhibit therapy, and the M.E. device is notified.

In Example B, after the two patient shocks, the patient device determines that the patient is uncompromised:

(a) by utilizing information obtained from one or more physiologic sensors, e.g. [i] a blood pressure device (which the patient device might ask the patient to apply); [ii] a sensor for the determination of skin resistance (expected to be elevated if the patient is significantly compromised because of an increase in sympathetic tone associated with the compromised state) and/or [iii] a sensor for one or more of oxygen or carbon dioxide; and/or (b) by patient interrogation.

When the patient devices makes this determination it signals the ICD to inhibit therapy (the ICD having been programmed to allow such inhibition), and the M.E. device is notified.

At this point, Example A and Example B become identical. The M.E. device, (a) by analyzing signals from the ICD electrograms and/or the analyses of each of the ICD algorithms (transmitted as per FIG. 8), and/or (b) by consulting its event library (see FIG. 12), concludes that the tachycardia is supraventricular in origin, and that defibrillator shocks are inappropriate. It then causes the ICD to deliver antitachycardia pacing in the ventricle (the details of which are based on either (a) data from the M.E. device event database, (b) an algorithm available to the M.E. or (c) an algorithm resident in the ICD), which successfully terminates the SVT. The M.E. device may cause the ICD to deliver the ATP by (a) accessing control to the non-invasive electrophysiologic testing function, or (b) programming the ICD to deliver ATP for the SVT under consideration. The M.E. device will have been given the permission to control the ICD in this manner because of previous programming of the control hierarchy setup (see, for example, FIG. 14).

Following tachycardia termination, the M.E. device then reprograms the ICD to deliver ATP similar to that which terminated the tachycardia (if such programming was not performed prior to the tachycardia termination). The M.E. device may also reprogram a time dependent MP notification sequence, for enhanced MP notification over the following 72 hours (the baseline criterion having been 3 shocks in 10 minutes (see a similar algorithm for second takeover in FIG. 69), e.g. that MP notification (and hence possible MP takeover) is to be triggered:

(a) during the next 3 hours, by 2 shocks during a moving window of 25 minutes duration; then (b) during the following 9 hours, by 2 shocks during a moving window of 20 minutes duration; then (c) during the following 24 hours, by 2 shocks during a moving window of 15 minutes duration; then (d) during the following 36 hours, by 2 shocks during a moving window of 10 minutes duration; and followed then by (e) a return to the previously programmed format of MP notification by the IMD for 3 shocks during a moving window of 10 minutes duration.

The M.E. device then observes the patient continuously for the next hour to check for ongoing stability, and then returns control to the ICD.

In the last phase of the example, the supraventricular tachycardia recurs 8 hours later. The ICD, whose detection algorithm was not reprogrammed by the M.E. device, again diagnoses VT, but this time delivers the programmed ATP. However, the ATP is unsuccessful, and is again followed by two (CD shocks within a few minutes. This triggers MP notification.

The MP diagnoses SVT, as did the M.E. device. He/she access ICD control by (a) accessing control to the non-invasive electrophysiologic testing function, or (b) programming the ICD to deliver ATP for the SVT under consideration. The MP choice of the ATP parameters (and perhaps the site of stimulation [i.e. the atrium]) differ from that utilized successfully by the M.E. device but, later, unsuccessfully by the IC).

The MP inhibits autonomous ICD therapy and delivers his/her choice of ATP which successfully terminates the tachycardia. The MP then programs one or more of:

(a) the successful ATP format that was used to terminate the current SVT episode;

(b) a shorter tachycardia detect time, thereby hoping to further increase the likelihood of successful pacing termination;

(c) a separate detection and treatment zone/regime which encompasses the SVT in question, and which detection results only in ATP and not in a shock;

(d) bradycardia pacing at a different rate, hoping that such programming may lessen the likelihood of SVT recurrence; and (e) an altered value of post ventricular atrial refractory period ("PVARP"), or of PVARP extension post premature ventricular beat, also hoping to lessen the likelihood of SVT recurrence.

The MP also reprograms the criteria for ICD notification of the MP from the present setting of 2 shocks in 20 minutes to: (a) for the next 72 hours, any shock, and (b) thereafter to return to the default value of 3 shocks in 10 minutes. The MP observes the patient for 2 hours and then returns control to the ICD.

The aforementioned examples in described in FIGS. 78-82 are intended easily to illustrate various advantageous features of the current invention. The examples do not illustrate all of the features, and do not cover all of the many types of implantable medical devices which may be controlled by the system and methods described herein.

ABBREVIATIONS

ATP=antitachycardia pacing
BS=blood sugar
EEG=electroencephalogram
GSR=galvanic skin resistance
HR=heart rate
ICD=implantable cardioverter defibrillator
IMD=implanted medical device
M.E. device=M.E.D.=MEdev=medical expert device
MP=medical profession
PT=patient
PT device=PTdev=PT.D.=patient device
RR=respiratory rate
RS=remote station
SVT=supraventricular tachycardia
VT=ventricular tachycardia There has thus been shown and described novel apparatus and methodology for controlling an implantable medical device which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. Medical monitoring and treatment apparatus which may be controlled by a plurality of control sources, said apparatus comprising, in combination:

(a) a personal medical device (PMD) adapted to be carried by a patient, either internally or externally, said PMD being alternatively self-controlled and remotely controlled, said device comprising, in combination:
  (i) a first transmitting/receiving (T/R) device for transmitting at least one signal representing medical data of the patient to, and for receiving external control signals from external control stations;
  (ii) an electronic medical treatment device for treating the patient in response to treatment device signals applied thereto;
  (iii) a first sensor circuit, having a first sensor circuit output, for producing at least one first sensor circuit output signal at said first sensor circuit output in response to medical data sensed from the patient by said first sensor circuit; and
  (iv) a first processor, coupled to each of
    (1) said first sensor circuit output,
    (2) said first T/R device, and
    (3) said treatment device,
  for
    (1) analyzing said at least one first sensor circuit output signal and, based on the analysis, generating (A) at least one first medical information signal representing said medical data, and (B) an internal control signal for controlling said treatment device,
    (2) receiving at least one external control signal;
    (3) generating at least one treatment device signal; and
    (4) receiving at least one command-hierarchy setting signal; and
(b) at least two external control stations, each comprising, in combination:
  (i) a Pth transmitting/receiving (T/R) device for electronic communication with said first T/R device of said PMD; and
  (ii) a Pth processor, coupled to said Pth T/R device, for producing at least one external control signal for controlling said PMD;
wherein:
(1) said first T/R device transmits at least one first medical information signal to at least one of said external control stations;
(2) said first processor is operative to generate at least one treatment device signal in response to at least one of (a) said internal control signal, and (b) an external control signal received from at least one of a plurality of said external control stations by said first T/R device;
(3) in response to said command-hierarchy setting signal, said first processor is operative to assign a unique priority level to each of said internal and external control signals, wherein the values of said assigned priority levels indicate a control hierarchy among all such control signals and their sources,
wherein:
  a treatment device signal represented by a control signal assigned a given priority level overrides a treatment device signal represented by a control signal assigned a lower priority level;
whereby said PMD delivers the therapy represented by the control signal which has been assigned the highest priority level;
thereby to establish and maintain a hierarchy among the sources of control of said PMD.

2. The apparatus defined in claim 1, further comprising a command station for setting the operating state of said PMD, said command station including:
  (a) a command input device, for inputting a state setting command and for producing a command signal;
  (b) a second processor, coupled to said command input device, for generating a state control signal in response to said command signal;
  (c) a command transmitting device, coupled to said second processor, for transmitting a command-hierarchy setting signal to said first processor via said first T/R device, in response to said state control signal from said second processor;
thereby to set the operating state of said PMD.

3. The apparatus defined in claim 2, wherein:
  (i) said command input device is operative to input a biologic identifier prior to the inputting of said at least one hierarchy-setting command, for transmission by said command transmitting device to said first processor,
  (ii) said first processor is operative to store at least one biologic identifier;
  (iii) said first processor is operative to assign said priority levels indicating said control hierarchy only if said received biologic identifier matches the stored biologic identifier.

4. The apparatus defined in claim 2, wherein:
  (i) said command input device is operative to input a password prior to inputting of said at least one hierarchy-setting command, for transmission by said command transmitting device to said first processor,
  (ii) said first processor is operative to store at least one password; and
  (iii) said first processor is operative to assign said priority levels indicating said control hierarchy only if said received password matches the stored password;
whereby access to setting the control hierarchy is password restricted.

5. The apparatus defined in claim 1, wherein said PMD is an implanted medical device (IMD), implanted in a body of said patient.

6. The apparatus defined in claim 5, wherein said medical data is internal medical data, acquired within a body of said patient.

7. The apparatus defined in claim 6, further comprising a first sensor, implanted inside of said body, for sensing said internal medical data; and wherein said first sensor circuit further comprises a sensor circuit input, adapted to be coupled to said first sensor;
  whereby said IMD is operative to sense said internal medical data.

8. The apparatus defined in claim 6, further comprising a first sensing device, implanted inside of said body, comprising:
  (a) a second sensor, for sensing internal medical data of said patient;
  (b) a third processor, coupled to said second sensor, for producing a first sensing signal representing said internal medical data; and
  (c) a first sensor transmitting device, coupled to said third processor, for transmitting a first sensing output signal, representing said internal medical data, to said first T/R device;
  wherein said first sensor circuit is coupled to said first T/R device, for receipt of information representing said internal medical state, received by said first T/R device;
  whereby said IMD is operative to sense a representation of said internal medical data transmitted by said implanted first sensing device.

9. The apparatus defined in claim 6, wherein:
(A) one of said external control stations is a local external control station, located in the vicinity of said IMD, comprising, in combination:
  (i) a second transmitting/receiving (T/R) device for electronic communication with said first T/R device of said IMD; and
  (ii) a seventh processor, coupled to said second T/R device, for producing at least one local external control signal for controlling said IMD;
(B) another one of said external control stations is a remote external control station comprising, in combination:
  (i) a third transmitting/receiving (T/R) device for electronic communication with said first T/R device of said IMD; and
  (ii) an eighth processor, coupled to said third T/R device, for producing at least one remote external control signal for controlling said IMD; and
wherein:
(1) said first T/R device transmits at least one signal representing an internal medical state of said patient to at least one of said local and said remote external control stations;
(2) said first processor is operative to generate at least one treatment device control signal in response to at least one of (a) said internal control signal, and (b) an external control signal received from at least one of said local and said remote external control stations by said first T/R device;
(3) said first processor is operative to assign a priority level to each of (i) said internal control signal, (ii) said local external control signal and (iii) said remote external control signal,
thereby to establish and maintain a hierarchy among the sources of control of said IMD.

10. The apparatus defined in claim 9, wherein:
(i) said local external control station further comprises a first input device, coupled to said seventh processor, for inputting hierarchy-setting commands by at least one of (a) said patient, and (b) a medical professional;
(ii) said seventh processor is operative to produce a hierarchy-setting signal in response to an inputted hierarchy-setting command; and
(iii) said second T/R transmits said hierarchy setting signal to said first processor via said first T/R device;
thereby to allow at least one of said patient and a medical professional to set the control hierarchy of said apparatus, from said local external control station.

11. The apparatus defined in claim 10, wherein:
(i) said first input device is operative to input a biologic identifier prior to the inputting of said at least one hierarchy-setting command, for transmission by said seventh T/R device to said first processor,
(ii) said first processor is operative to store at least one biologic identifier;
(iii) said first processor is operative to assign said priority levels indicating said control hierarchy only if said received biologic identifier matches the stored biologic identifier.

12. The apparatus defined in claim 10, wherein:
(i) said first input device is operative to input a password prior to inputting of said at least one hierarchy-setting command, for transmission by said seventh T/R device to said first processor,
(ii) said first processor is operative to store at least one password; and
(iii) said first processor is operative to assign said priority levels indicating said control hierarchy only if said received password matches the stored password;
whereby access to setting the control hierarchy is password restricted.

13. The apparatus defined in claim 9, wherein:
(i) said remote external control station further comprises a second input device, coupled to said eighth processor, for inputting hierarchy-setting commands by a medical professional;
(ii) said eighth processor is operative to produce said hierarchy-setting signal in response to an inputted hierarchy-setting command; and
(iii) said third T/R transmits said hierarchy-setting signal to said first processor via said first T/R device;
thereby to allow a medical professional to set the control hierarchy of said apparatus, from said remote external control station.

14. The apparatus defined in claim 13, wherein:
(i) said second input device is operative to input a password prior to inputting of said at least one hierarchy-setting command, for transmission by said eighth T/R device to said first processor,
(ii) said first processor is operative to store at least one password; and
(iii) said first processor is operative to assign said priority levels indicating said control hierarchy only if said received password matches the stored password;
whereby access to setting the control hierarchy is password restricted.

15. The apparatus defined in claim 13, wherein:
(i) said second input device is operative to input a biologic identifier prior to the inputting of said at least one hierarchy-setting command, for transmission by said eighth T/R device to said first processor,
(ii) said first processor is operative to store at least one biologic identifier;
(iii) said first processor is operative to assign said priority levels indicating said control hierarchy only if said received biologic identifier matches the stored biologic identifier.

16. The apparatus defined in claim 9, wherein said internal control signal is assigned the highest priority;
thereby to give said internal control signal the highest priority for controlling said IMD.

17. The apparatus defined in claim 9, wherein said local external control station further comprises at least one first patient input device, coupled to the seventh processor, for inputting therapy commands from said patient; and wherein the inputted patient therapy command causes said seventh processor to produce a patient external control signal which indicates the therapy choice of said patient for controlling the IMD.

18. The apparatus defined in claim 17, wherein said patient external control signal is assigned the highest priority;
thereby to give the highest priority to said patient, for controlling the IMD.

19. The apparatus defined in claim 9, wherein:
(i) said local external control station further comprises a second sensor circuit, having a second sensor circuit output, for producing at least one second sensor circuit output signal at said second sensor circuit output in response to external medical data sensed from the patient by said second sensor circuit; and
(ii) the seventh processor is operative to analyze said at least one second sensor output signal to produce a patient device external control signal which indicates the therapy choice of said seventh processor, for controlling said IMD.

20. The apparatus defined in claim 19, wherein:
(i) said seventh processor is further operative to generate a first urgent command-hierarchy setting signal, in response to the analysis of at least one of (A) said at least one second sensor output signal, and (B) said signal representing medical data of the patient; and
(ii) said second T/R device is operative to transmit said first urgent hierarchy-setting signal to said first processor, via said first T/R device;
whereby the processor of said local external control station may reset the control hierarchy upon the detection of an urgent patient condition.

21. The apparatus defined in claim 20, wherein:
(i) said seventh processor is further operative to generate a first non-urgent command-hierarchy setting signal, in response to the analysis of at least one of (A) said at least one second sensor output signal, and (B) said signal representing medical data of the patient; and
(ii) said second T/R device is operative to transmit said first non-urgent hierarchy-setting signal to said first processor, via said first T/R device;
whereby the processor of said local external control station may further reset the control hierarchy upon the detection of a stable patient condition, after an urgent patient condition.

22. The apparatus defined in claim 19, wherein said patient device external control signal is assigned the highest priority;
thereby to give the highest priority to the therapy choice of the seventh processor, making therapy choices based on said external medical data sensed from the patient, for controlling said MD.

23. The apparatus defined in claim 19, wherein said local external control station further comprises at least one seventh sensor, placed external to and in proximity to said patient, and coupled to said second sensor circuit, for providing physiologic data about said patient.

24. The apparatus defined in claim 23, wherein said seventh sensor is selected from the group consisting of:
(i) an electrocardiogram electrode,
(ii) a blood pressure cuff,
(iii) an oxygen saturation sensor,
(iv) a carbon dioxide detector,
(v) an accelerometer,
(vi) a detector of body attitude,
(vii) a ketone detector,
(viii) a respiration detector,
(ix) an electroencephalogram electrode,
(x) an electrode for measuring skin resistance,
(xi) a video camera, and
(xii) a microphone.

25. The apparatus defined in claim 19 further comprising:
(a) an output device, coupled to said seventh processor, for providing at least one question to said patient, and
(b) a second input device, coupled to said seventh processor, for inputting at least one response from said patient;
wherein:
(i) said response, if any, to said at least one question indicates a degree of necessity of therapy for said patient;
(ii) said seventh processor is operative to determine said degree of necessity from the inputted response, if any;
(iii) said seventh processor utilizes the determination of said degree of necessity to select a therapy choice; and
(iv) said seventh processor produces a patient device external control signal which indicates said therapy choice of said local external control station based on said determination, for transmission to said first processor.

26. The apparatus defined in claim 9, wherein said remote external control station further comprises a medical professional input device, coupled to the eighth processor, for inputting therapy choices from a medical professional; and wherein an inputted medical professional therapy command causes the eighth processor to produce a medical professional external control signal which indicates the therapy choice of said medical professional for controlling the IMD.

27. The apparatus defined in claim 26, wherein said medical professional external control signal is assigned the highest priority;
thereby to give the highest priority to said medical professional, for controlling said IMD.

28. The apparatus defined in claim 9, wherein said remote external control station further comprises a database, coupled to said eighth processor, for storing information about at least one of:
(i) the patient,
(ii) the IMD,
(iii) the prior use of the IMD by the patient,
(iv) the prior use of other implanted medical devices (IMDs) by the patient,
(v) the prior use of the IMD by other patients, and
(vi) the prior use of other IMDs by other patients;
wherein said eighth processor is operative to select a therapy choice based on analysis by said eighth processor of:
(a) information obtained from said database, and
(b) said at least one signal representing an internal medical state of a patient; and
wherein said eighth processor produces a medical expert external control signal which indicates the therapy choice of said remote external control station based on said analysis, for transmission to said first processor.

29. The apparatus defined in claim 28, wherein:
(i) said eighth processor is further operative to generate a second urgent command-hierarchy setting signal, in response to the analysis of at least one of (A) the information obtained from said database, and (B) said signal representing medical data of the patient; and
(ii) said third T/R device is operative to transmit said second urgent hierarchy-setting signal to said first processor, via said first T/R device;
whereby the processor of said remote external control station may reset the control hierarchy upon the detection of an urgent patient condition.

30. The apparatus defined in claim 29, wherein:
(i) said eighth processor is further operative to generate a second non-urgent command-hierarchy setting signal, in response to the analysis of at least one of (A) the information obtained from said database, and (B) said signal representing medical data of the patient; and
(ii) said third T/R device is operative to transmit said second non-urgent hierarchy-setting signal to said first processor, via said first T/R device;
whereby the processor of said remote external control station may further reset the control hierarchy upon the detection of a stable patient condition, after an urgent patient condition.

31. The apparatus defined in claim 28, wherein said medical expert external control signal is assigned the highest priority;

thereby to give the highest priority to the therapy choice selected by the third processor performing the analysis which includes the database information, for controlling said IMD.

32. The apparatus defined in claim 28, wherein said analysis by said eighth processor comprises at least one of:
   (i) analyzing the results of the prior use of the IMD by the patient, at a time when internal medical data sensed from the patient was substantially similar to the current patient internal medical data;
   (ii) analyzing the results of the prior use of the IMD by the patient, at a time when internal medical data sensed from the patient was substantially different from the current patient internal medical data;
   (iii) analyzing the results of the prior use of another IMD by the patient, at a time when internal medical data sensed from the patient was substantially similar to the current patient internal medical data;
   (iv) analyzing the results of the prior use of another IMD by the patient, at a time when internal medical data sensed from the patient was substantially different from the current patient internal medical data;
   (v) analyzing the results of the prior use of substantially similar IMDs by other patients, at times when internal medical data sensed from said other patients was substantially similar to the current patient internal medical data;
   (vi) analyzing the results of the prior use of substantially similar IMDs by other patients, at times when internal medical data sensed from the other patients was substantially different from the current patient internal medical data;
   (vii) analyzing the results of the prior use of different IMDs by other patients, at times when internal medical data sensed from said other patients was substantially similar to the current patient internal medical data; and
   (viii) analyzing the results of the prior use of different IMDs by other patients, at a time when internal medical data sensed from said other patients was substantially different from the current patient internal medical data;
thereby to determine an optimal medical treatment based on information in said database.

33. The apparatus defined in claim 5, further comprising a second sensing device, located outside of said body, comprising:
   (a) a third sensor, for sensing external medical data of said patient;
   (b) a fourth processor, coupled to said third sensor, for producing a second sensing signal representing said external medical data; and
   (c) a second sensor transmitting device, coupled to said fourth processor, for transmitting a second sensing signal, representing said external medical data, to said first T/R device;
   wherein said first sensor circuit is coupled to said first T/R device, for receipt of information representing said external medical data, received by said first T/R device;
   whereby said IMD is operative to sense a representation of said external medical data transmitted by said external second sensing device.

34. The apparatus defined in claim 1, wherein said PMD is an external medical device (EMD), located external to the body of said patient.

35. The apparatus defined in claim 34, further comprising a third sensing device, located inside of said body, comprising:
   (a) a fourth sensor, for sensing internal medical data of said patient;
   (b) a fifth processor, coupled to said fourth sensor, for producing a third sensing signal representing said internal medical data; and
   (c) a third sensor transmitting device, coupled to said fifth processor, for transmitting a third sensing signal, representing said internal medical data, to said first T/R device;
   wherein said first sensor circuit is coupled to said first T/R device, for receipt of information representing said internal medical data, received by said first T/R device;
   whereby said EMD is operative to sense a representation of said internal medical data transmitted by said internal third sensing device.

36. The apparatus defined in claim 34, wherein said medical data is external medical data, acquired outside of a body of said patient.

37. The apparatus defined in claim 36, further comprising a fourth sensing device, located outside of said body, comprising:
   (a) a fifth sensor, for sensing external medical data of said patient;
   (b) a sixth processor, coupled to said fifth sensor, for producing a fourth sensing signal representing said external medical data; and
   (c) a fourth sensor transmitting device, coupled to said sixth processor, for transmitting a fourth sensing signal, representing said external medical data, to said first T/R device;
   wherein said first sensor circuit is coupled to said first T/R device, for receipt of information representing said external medical state, received by said first T/R device;
   whereby said EMD is operative to sense a representation of said external medical data transmitted by said external fourth sensing device.

38. The apparatus defined in claim 36, further comprising a sixth sensor, located outside of said body, for sensing external medical data; and wherein said first sensor circuit further comprises a sensor circuit input, adapted to be coupled to said sixth sensor;
   whereby said EMD is operative to sense said external medical data.

39. The apparatus defined in claim 1, wherein said first processor is operative to permanently assign at least one of said priority levels indicating said control hierarchy.

40. Medical monitoring and treatment apparatus which is controlled by a plurality of control sources, said system comprising, in combination:
   (a) an implantable medical device (IMD), which is alternatively self-controlled and remotely controlled, said device comprising, in combination:
      (i) a first transmitting/receiving (T/R) device for transmitting at least one signal representing an internal medical state of a patient to, and for receiving external control signals from, external locations;
      (ii) a medical treatment device for treating said patient in response to treatment device control signals applied thereto;
      (iii) a first sensor circuit, having a first sensor circuit output, for producing at least one first sensor circuit output signal at said first sensor circuit output in response to the internal medical data sensed from the patient by said first sensor circuit; and (iv) a first processor, coupled to each of
  (1) said first sensor circuit output,
  (2) said first T/R device, and
  (3) said treatment device,
for
  (1) analyzing said at least one first sensor circuit output signal;
  (2) generating an internal control signal, in response to said analysis, for controlling said treatment device; and
  (3) generating at least one treatment device control signal;
(b) a local external control station comprising, in combination:
  (i) a second transmitting/receiving (T/R) device for electronic communication with said first T/R device of said IMD; and
  (ii) a second processor, coupled to said second T/R device, for producing at least one local external control signal for controlling said IMD; and
(c) a remote external control station comprising, in combination:
  (i) a third transmitting/receiving (T/R) device for electronic communication with said first T/R device of said IMD; and
  (ii) a third processor, coupled to said third T/R device, for producing at least one remote external control signal for controlling said IMD;
wherein:
  (1) said first T/R device transmits at least one signal representing an internal medical state of said patient to at least one of said local and said remote external control stations; and
  (2) said first processor is operative to generate at least one treatment device control signal in response to at least one of:
    (a) said internal control signal, and
    (b) at least one external control signal received from at least one of:
      (i) said local external control station, and
      (ii) said remote external control station by said first T/R device;
whereby said IMD delivers therapy in response to at least one of:
the analysis of said at least one first sensor circuit output signal by said first processor,
said at least one local external control signal, and
said at least one remote external control signal.

41. The apparatus defined in claim 40, wherein, when both (i) a local external control signal is received by said first T/R device, and (ii) an internal control signal is generated, the response of said first processor to both signals is selected from the group consisting of:
  (a) the therapy choice indicated by said local external control signal takes priority over the therapy choice indicated by said internal control signal, for determining the treatment;
  (b) the therapy choice indicated by said internal control signal takes priority over the therapy choice indicated by said local external control signal, for determining the treatment; and
  (c) both of the therapy choices indicated by said local external control signal and said internal control signal determine the treatment.

42. The apparatus defined in claim 40, wherein, when both (i) a remote external control signal is received by said first T/R device, and (ii) an internal control signal is generated, the response of said first processor to both signals is selected from the group consisting of:
  (a) the therapy choice indicated by said remote external control signal takes priority over the therapy choice indicated by said internal control signal, for determining the treatment;
  (b) the therapy choice indicated by said internal control signal takes priority over the therapy choice indicated by said remote external control signal, for determining the treatment; and
  (c) both of the therapy choices indicated by said remote external control signal and said internal control signal determine the treatment.

43. The apparatus defined in claim 40, wherein, when both (i) a local external control signal is received by said first T/R device, and (ii) a remote external control signal is received by said first T/R device, the response of said first processor to both signals is selected from the group consisting of:
  (a) the therapy choice indicated by said local external control signal takes priority over the therapy choice indicated by said remote external control signal, for determining the treatment;
  (b) the therapy choice indicated by said remote external control signal takes priority over the therapy choice indicated by said local external control signal, for determining the treatment; and
  (c) both of the therapy choices indicated by said local external control signal and said remote external control signal determine the treatment.

44. The apparatus defined in claim 40, wherein, when:
  (i) a remote external control signal is received by said first T/R device,
  (ii) a local external control signal is received by said first T/R device, and
  (iii) an internal control signal is generated;
the response of said first processor to both signals is selected from the group consisting of:
  (a) the therapy choice indicated by said remote external control signal takes priority over both (1) the therapy choice indicated by said local external control signal, and (2) the therapy choice indicated by said internal control signal, for determining the treatment;
  (b) the therapy choice indicated by said local external control signal takes priority over both (1) the therapy choice indicated by said remote external control signal, and (2) the therapy choice indicated by said internal control signal, for determining the treatment;
  (c) the therapy choice indicated by said internal control signal takes priority over both (1) the therapy choice indicated by said local external control signal, and (2) the therapy choice indicated by said remote external control signal, for determining the treatment;
  (d) both of the therapy choices indicated by said local external control signal and said internal control signal determine the treatment;
  (e) both of the therapy choices indicated by said remote external control signal and said internal control signal determine the treatment;
  (f) both of the therapy choices indicated by said local external control signal and said remote external control signal determine the treatment; and
  (g) all three of the therapy choices indicated by said remote external control signal, said local external control signal, and said internal control signal determine the treatment.

45. The system defined in claim 40, wherein said local external control station further comprises a patient assessment device, coupled to said second processor, for assessing the physiologic state of said patient, and for generating an assessment signal in response thereto, and wherein:
  (i) said second processor is operative to analyze said assessment signal and, based on the analysis, to generate a first local processor signal indicating a therapy choice for said medical treatment device, and
  (ii) in response to said first local processor signal, said second T/R device is operative to transmit a local external control signal, indicating the therapy choice of said second processor, to said first T/R device;
  whereby said local external control station controls the therapy choice of said IMD.

46. The system defined in claim 45, wherein said patient assessment device is operative to analyze said signal representing an internal medical state of a patient and, based on the analysis, to cause said second processor to generate said first local processor signal indicating a therapy choice for said medical treatment device.

47. The system defined in claim 45, further comprising a patient communication device, coupled to said patient assessment device for exchanging information with the patient, wherein:
  (a) said patient communication device is operative to ask at least one question of said patient, and to receive a respective response, if any, inputted to said patient communication device;
  (b) said patient assessment device is operative to assess the response to said at least one question, and to generate a patient fitness signal, representing the physiologic state of said patient as assessed by said at least one question;
  (c) said second processor is operative to utilize said at least one response for additional analysis for the determination of the first local processor signal indicating a therapy choice for said medical treatment device.

48. The system defined in claim 45, wherein:
  (i) said local external control station further comprises a second sensor circuit, having a second sensor circuit output, for producing at least one second sensor circuit output signal at said second sensor circuit output in response to the external medical data sensed from the patient by said second sensor circuit; and
  (ii) said patient assessment device is coupled to said second sensor circuit output and is operative to utilize said at least one second sensor output signal for analysis of said external medical data, for the generation of an assessment signal representing the physiologic state of said patient as observed externally;
  thereby to utilize the signal representing the external medical state of the patient, in the therapy decision of said second processor.

49. The system defined in claim 48, wherein said patient assessment device is further operative to provide said second sensor output signal to said second processor, and wherein said second processor is operative to cause said second T/R device to transmit a representation of said second sensor output signal to at least one of:
  (a) said first T/R device, and
  (b) said third T/R device;
  thereby to allow for the use of information based on the second sensor output signal by at least one said first processor and said third processor.

50. The system defined in claim 45, wherein said second processor is further operative to cause said second T/R device to transmit a signal representing at least one of (i) the information in said assessment signal, and (ii) the analysis by said second processor of said assessment signal to at least one of:
  (a) said first T/R device, and
  (b) said third T/R device;
  thereby to allow for the use of information based on the patient assessment signal by at least one said first processor and said third processor.

51. The system defined in claim 45, further comprising a second input device, coupled to said second processor, for inputting a medical treatment device therapy selection, if any, by the patient;
  wherein:
  (i) if said patient does not input a medical therapy selection to said second input device, said first local processor signal, if any, causes said second T/R device to transmit a local external control signal representing the therapy choice indicated by said first local processor signal to said first T/R device, and
  (iii) if said patient does input a medical therapy selection to said second input device, said second processor causes said second T/R device to transmit a local external control signal representing the therapy choice indicated by said second input device to said first T/R device;
  thereby to establish a control hierarchy for treatment selection source in which the treatment selection by said patient takes priority over a treatment selection based on the analysis of said patient assessment signal.

52. The system defined in claim 51, further comprising a third command station for setting an operating state of said local external control station, said third command station including:
  (a) an eleventh input device, for inputting a third operating state command, and for producing a third command signal;
  (b) a sixth processor coupled to said eleventh input device, for generating a third state control signal in response to said third command signal;
  (c) a third command transmitting device, coupled to said sixth processor, for transmitting said third state control signal to said second processor via said second T/R device;
  wherein, in response to said third state control signal, said second processor is operative to determine which, if any, of a plurality of control sources takes priority;
  thereby to define a control hierarchy for treatment selection source at the local external control station.

53. The system defined in claim 45, further comprising a third input device, coupled to said second processor, for inputting a medical treatment device therapy selection, if any, by the patient;
  wherein:
  (i) if said second processor generates said first local processor signal, a local external control signal representing the therapy choice resulting from said second processor analysis is transmitted to said first T/R device, and
  (iii) if said second processor does not generate said first local processor signal, and if said patient does input a medical therapy selection to said third input device, a local external control signal representing the therapy choice indicated by said third input device is transmitted to said first T/R device;
  thereby to establish a control hierarchy for treatment selection source in which the treatment selection based on the analysis of said patient assessment signal takes priority over a treatment selection of said patient.

54. The system defined in claim 53, further comprising a fourth command station for setting an operating state of said local external control station, said fourth command station including:
(a) a twelfth input device, for inputting a fourth operating state command, and for producing a fourth command signal;
(b) a seventh processor coupled to said twelfth input device, for generating a fourth state control signal in response to said fourth command signal;
(c) a fourth command transmitting device, coupled to said seventh processor, for transmitting said fourth state control signal to said second processor via said second T/R device;
wherein, in response to said fourth state control signal, said second processor is operative to determine which, if any, of a plurality of control sources takes priority;
thereby to define a control hierarchy for treatment selection source at the local external control station.

55. The system defined in claim 45, further comprising a fourth input device, coupled to said second processor, for inputting a medical treatment device therapy selection, if any, by the patient;
wherein:
(i) if said second processor generates said first local processor signal, and if said patient does not input a medical treatment device therapy selection to said fourth input device, a local external control signal representing the therapy choice resulting from said second processor analysis of said patient assessment signal is transmitted to said first T/R device, and
(ii) if said second processor does not generate said first local processor signal, and if said patient does input a medical treatment device therapy selection to said fourth input device, a local external control signal representing the therapy choice of said patient is transmitted to said first T/R device, and
(iii) if said second processor generates said first local processor signal, and if said patient does input a medical treatment device therapy selection to said fourth input device, a local external control signal representing both (1) the therapy choice resulting from said second processor analysis of said patient assessment signal, and (2) the therapy choice indicated by said fourth input device, is transmitted to said first T/R device;
thereby to transmit the therapy choice of both the patient and the second processor.

56. The system defined in claim 40, wherein:
(i) said local external control station further comprises a first input device, coupled to said second processor, for inputting a medical treatment device therapy selection by said patient;
(ii) in response to said selection, said second processor is operative to generate a second local processor signal indicating a therapy choice of said patient, and
(iii) in response to said second local processor signal, said second T/R device is operative to transmit a local external control signal representing the patient choice to said first T/R device;
whereby said patient controls the therapy choice of said medical treatment device.

57. The system defined in claim 56, wherein said local external control station further comprises a first display device, coupled to said second processor, for display of information representing the medical state of said patient, based on said signal representing an internal medical state of a patient; thereby to provide internal medical information to the patient for patient decisions.

58. The system defined in claim 40, wherein said remote external control station further comprises a remote patient assessment device, coupled to said third processor, for remotely assessing the physiologic state of said patient, and for generating a remote assessment signal in response thereto, and wherein:
(i) said third processor is operative to analyze said remote assessment signal and, based on the analysis, to generate a first remote processor signal indicating a therapy choice for said medical treatment device, and
(ii) in response to said first remote processor signal, said third T/R device is operative to transmit a remote external control signal indicating the therapy choice of said third processor, to said first T/R device;
whereby said remote external control station controls the therapy choice of said IMD.

59. The system defined in claim 58, wherein said remote patient assessment device is operative to analyze said signal representing an internal medical state of a patient and, based on the analysis, to cause said third processor to generate said first remote processor signal indicating a therapy choice for said medical treatment device.

60. The system defined in claim 58, wherein:
(i) said third T/R device is operative to receive a signal transmitted by said second T/R device concerning the physiologic state of said patient as measured external to the body of said patient; and
(ii) said remote patient assessment device is operative to analyze such external medical signal and, based on the analysis, to cause said third processor to generate said first remote processor signal indicating a therapy choice for said medical treatment device.

61. The system defined in claim 58, further comprising a database, coupled to said remote patient assessment device, for storing and providing database information concerning at least one of:
(i) the patient using the IMD,
(ii) the IMD,
(iii) a prior use of the IMD by the patient,
(iv) a prior use of other implanted medical devices (IMDs) by the patient,
(v) a prior use of a substantially similar IMD by other patients, and
(vi) a prior use of different IMDs by other patients; and
wherein said third processor is further operative to utilize both (i) a received signal representing an internal medical state of the patient (ii) information obtained from said database for the determination of the first remote processor signal indicating a therapy choice for said medical treatment device.

62. The system defined in claim 61, wherein said third processor is further operative to cause said third T/R device to transmit a representation of said database information to at least one of:
(a) said first T/R device, and
(b) said second T/R device,
thereby to allow for the use of said database information by at least one said first processor and said second processor.

63. The system defined in claim 58, further comprising a sixth input device, coupled to said third processor, for inputting a medical treatment device therapy selection, if any, by a medical professional;

wherein:
(i) if the medical professional does not input a medical therapy selection to said sixth input device, said first remote processor signal, if any, causes said third T/R device to transmit a remote external control signal representing the therapy choice indicated by said first remote processor signal to said first T/R device, and
(iii) if the medical professional does input a medical therapy selection to said sixth input device, said third processor causes said third T/R device to transmit a remote external control signal representing the therapy choice indicated by said sixth input device to said first T/R device;
thereby to establish a control hierarchy for treatment selection source in which the treatment selection by said medical professional takes priority over a treatment selection based on the analysis of said remote patient assessment signal.

64. The system defined in claim 63, further comprising a fifth command station for setting an operating state of said remote external control station, said fifth command station including:
(a) a thirteenth input device, for inputting a fifth operating state command, and for producing a fifth command signal;
(b) an eighth processor coupled to said thirteenth input device, for generating a fifth state control signal in response to said fifth command signal;
(c) a fifth command transmitting device, coupled to said eighth processor, for transmitting said fifth state control signal to said third processor via said third T/R device;
wherein, in response to said fifth state control signal, said third processor is operative to determine which, if any, of a plurality of control sources takes priority;
thereby to define a control hierarchy for treatment selection source at the remote external control station.

65. The system defined in claim 58, further comprising a seventh input device, coupled to said third processor, for inputting a medical treatment device therapy selection, if any, by the medical professional;
wherein:
(i) if said third processor generates said first remote processor signal, a remote external control signal representing the therapy choice resulting from said third processor analysis is transmitted to said first T/R device, and
(iii) if said third processor does not generate said first remote processor signal, and if said medical professional does input a medical therapy selection to said seventh input device, a remote external control signal representing the therapy choice indicated by said seventh input device is transmitted to said first T/R device;
thereby to establish a control hierarchy for treatment selection source in which the treatment selection based on the analysis of said remote patient assessment signal takes priority over a treatment selection of said medical professional.

66. The system defined in claim 65, further comprising a sixth command station for setting an operating state of said remote external control station, said sixth command station including:
(a) a fourteenth input device, for inputting a sixth operating state command, and for producing a sixth command signal;
(b) an ninth processor coupled to said fourteenth input device, for generating a sixth state control signal in response to said sixth command signal;
(c) a sixth command transmitting device, coupled to said ninth processor, for transmitting said sixth state control signal to said third processor via said third T/R device;
wherein, in response to said sixth state control signal, said third processor is operative to determine which, if any, of a plurality of control sources takes priority;
thereby to define a control hierarchy for treatment selection source at the remote external control station.

67. The system defined in claim 58, further comprising an eighth input device, coupled to said third processor, for inputting a medical treatment device therapy selection, if any, by the medical professional;
wherein:
(i) if said third processor generates said first remote processor signal, and if said medical professional does not input a medical treatment device therapy selection, a remote external control signal representing the therapy choice resulting from said third processor analysis of said remote patient assessment signal is transmitted to said first T/R device, and
(ii) if said third processor does not generate said first remote processor signal, and if said medical professional does input a medical treatment device therapy selection, a remote external control signal representing the therapy choice of said medical professional is transmitted to said first T/R device, and
(iii) if said third processor generates said first remote processor signal, and if said medical professional does input a medical treatment device therapy selection, a remote external control signal representing both (1) the therapy choice resulting from said third processor analysis of said remote patient assessment signal, and (2) the therapy choice indicated by said eighth input device, is transmitted to said first T/R device;
thereby to transmit the therapy choice of both the medical professional and the third processor.

68. The system defined in claim 40, wherein said remote external control station further comprises:
(a) a second display device, coupled to said third processor, for display of information representing the medical state of said patient, based on said signal representing an internal medical state of a patient, and
(b) a fifth input device, coupled to said third processor, for inputting a medical treatment device therapy selection by a medical professional;
wherein:
(i) in response to said a therapy selection by said medical professional, said third processor is operative to generate a second remote processor signal indicating a therapy choice of said medical professional, and
(ii) in response to said second remote processor signal, said third T/R device is operative to transmit a remote external control signal representing the medical professional choice to said first T/R device;
whereby said medical professional controls the therapy choice of said medical treatment device.

69. The system defined in claim 40, further comprising at least one additional external control station comprising:
(i) a respective additional transmitting/receiving (T/R) device for electronic communication with said first T/R device of said IMD; and (ii) a respective processor, coupled to said respective T/R device, for producing at least one additional external control signal for controlling said IMD
whereby said IMD delivers therapy in response to at least one of:
the analysis of said at least one first sensor circuit output signal by said first processor,
said at least one local external control signal,
said at least one remote external control signal, and
said at least one additional external control signal.

70. The system defined in claim 40, further comprising a first command station for setting an operating state of said IMD, said first command station including:
   (a) a ninth input device, for inputting a first operating state command, and for producing a first command signal;
   (b) a fourth processor coupled to said ninth input device, for generating a first state control signal in response to said first command signal;
   (c) a first command transmitting device, coupled to said fourth processor, for transmitting said first state control signal to said first processor via said first T/R device;
   wherein, in response to said first state control signal, said first processor is operative to determine which, if any, of a plurality of control signals takes priority;
   thereby to define the operation of the IMD upon receipt by said IMD of at least two control signals each indicating a different therapy choice.

71. The system defined in claim 40, further comprising a second command station for setting an operating state of said IMD, said second command station including:
   (a) a tenth input device, for inputting a second operating state command, and for producing a second command signal;
   (b) a fifth processor coupled to said tenth input device, for generating a second state control signal in response to said second command signal;
   (c) a second command transmitting device, coupled to said fifth processor, for transmitting said second state control signal to said first processor via said first T/R device;
   wherein, in response to said second state control signal, said first processor is operative to determine which, if any, of a plurality of therapy choices, indicated by a control signal, takes priority;
   thereby to define the operation of the IMD upon receipt by said IMD of a control signal indicating a plurality of different therapy choices.

* * * * *